(12) United States Patent
Fuchs et al.

(10) Patent No.: US 11,707,442 B2
(45) Date of Patent: Jul. 25, 2023

(54) ANTIBACTERIAL AND ANTIFUNGAL COMPOUNDS

(71) Applicants: The General Hospital Corporation, Boston, MA (US); Rhode Island Hospital, A Lifespan-Partner, Providence, RI (US)

(72) Inventors: Helen Burgwyn Fuchs, Quincy, MA (US); Eleftherios Mylonakis, Providence, RI (US); Frederick M. Ausubel, Newton, MA (US); Raj Mohan Raja Muthiah, San Jose, CA (US); Wooseong Kim, Providence, RI (US)

(73) Assignees: The General Hospital Corporation, Boston, MA (US); Rhode Island Hospital, A Lifespan-Partner, Providence, RI (US)

( * ) Notice: Subject to any disclaimer, the term of this patent is extended or adjusted under 35 U.S.C. 154(b) by 0 days.

(21) Appl. No.: 15/763,023

(22) PCT Filed: Sep. 23, 2016

(86) PCT No.: PCT/US2016/053411
§ 371 (c)(1),
(2) Date: Jan. 14, 2019

(87) PCT Pub. No.: WO2017/053778
PCT Pub. Date: Mar. 30, 2017

(65) Prior Publication Data
US 2019/0054048 A1    Feb. 21, 2019

Related U.S. Application Data

(60) Provisional application No. 62/233,107, filed on Sep. 25, 2015.

(51) Int. Cl.
| | |
|---|---|
| *A61K 31/192* | (2006.01) |
| *A61K 31/7036* | (2006.01) |
| *A61P 31/04* | (2006.01) |
| *A61K 38/17* | (2006.01) |
| *A61K 45/06* | (2006.01) |
| *A61P 31/10* | (2006.01) |
| *A61K 9/00* | (2006.01) |
| *A61K 31/4196* | (2006.01) |
| *A61K 31/5383* | (2006.01) |
| *A61K 31/7048* | (2006.01) |
| *A61K 31/7135* | (2006.01) |

(52) U.S. Cl.
CPC .......... *A61K 31/192* (2013.01); *A61K 9/0014* (2013.01); *A61K 9/0019* (2013.01); *A61K 9/0053* (2013.01); *A61K 31/4196* (2013.01); *A61K 31/5383* (2013.01); *A61K 31/7036* (2013.01); *A61K 31/7048* (2013.01); *A61K 31/7135* (2013.01); *A61K 38/1729* (2013.01); *A61K 45/06* (2013.01); *A61P 31/04* (2018.01); *A61P 31/10* (2018.01); *Y02A 50/30* (2018.01)

(58) Field of Classification Search
CPC .. A61K 31/192; A61K 9/0014; A61K 9/0019; A61K 9/0053; A61K 31/4196; A61K 31/5383; A61K 31/7036; A61K 31/7048; A61K 31/7135; A61K 38/1729; A61K 45/06; A61P 31/04; A61P 31/10; Y02A 50/30
See application file for complete search history.

(56) References Cited

U.S. PATENT DOCUMENTS

| | | | |
|---|---|---|---|
| 4,200,738 A | 4/1980 | Hill et al. | |
| 5,602,104 A | 2/1997 | Shroot et al. | |
| 6,127,415 A | 10/2000 | Pfahl et al. | |
| 6,858,647 B2 * | 2/2005 | Voegel .................. | A61Q 15/00 514/458 |
| 6,905,670 B2 | 6/2005 | Ausubel et al. | |
| 8,101,793 B2 | 1/2012 | Merlini et al. | |

(Continued)

FOREIGN PATENT DOCUMENTS

| | | |
|---|---|---|
| EP | 0379367 | 7/1990 |
| WO | WO 97/02814 | 1/1997 |
| WO | 2015/062486 | 5/2015 |

OTHER PUBLICATIONS

Pan et al. Arch Dermatol Res (2009) 301:15-20 (Year: 2009).*

(Continued)

*Primary Examiner* — Jeffrey S Lundgren
*Assistant Examiner* — William Y Lee
(74) *Attorney, Agent, or Firm* — Fish & Richardson P.C.

(57) ABSTRACT

The present application provides that synthetic retinoid compounds are useful in methods of treating bacterial infections, such as a bacterial infection caused by *S. aureus*, methicillin-resistant *S. aureus* (MRSA), vancomycin-resistant *S. aureus* (VRSA), *E. faecalis*, *E. faecium*, *B. subtilis*, and *B. anthracis*. The present application also provides a tricyclic fluoroquinolone compound, Z3060, useful in methods of treating bacterial infections, such as a bacterial infection caused by *S. aureus*, methicillin-resistant *S. aureus* (MRSA), vancomycin-resistant *S. aureus* (VRSA), *E.* spp., *K. pneumoniae*, *P. aeruginosa*, *A. baumannii*, *E. faecium*, and *E. faecalis*. Also provided herein is a gold compound, auranofin, useful in treating bacterial and fungal infections, such as a fungal infection caused by *C. albicans*, *C. parapsilosis*, *C. tropicalis*, *C. glabrata*, and *C. neoformans*.

13 Claims, 79 Drawing Sheets
Specification includes a Sequence Listing.

(56) References Cited

U.S. PATENT DOCUMENTS

| | | | |
|---|---|---|---|
| 2003/0055110 A1 | 3/2003 | Voegel et al. | |
| 2006/0159638 A1* | 7/2006 | Segura | A61K 8/06 424/62 |
| 2011/0183943 A1* | 7/2011 | Dhuin | A61K 31/192 514/154 |
| 2012/0034270 A1 | 2/2012 | Grobelny et al. | |

OTHER PUBLICATIONS

International Search Report for International Application No. PCT/US2016/053411, dated Feb. 3, 2017.
Allison et al., "Metabolite-enabled eradication of bacterial persisters by aminoglycosides," Nature, 2011,473: 216-220.
Altucci et al., "RAR and RXR modulation in cancer and metabolic disease," Nat. Rev. Drug Discov, 2007, 6: 793-810.
Angelucci et al., "Inhibition of Schistosoma mansoni thioredoxin-glutathione reductase by auranofin: structural and kinetic aspects," J. Biol. Chem, Oct. 2009, 284(42), 28977-28985.
Baddour et al., "Infective endocarditis in adults: diagnosis, antimicrobial therapy, and management of complications: a scientific statement for healthcare professionals from the American Heart Association," Circulation, 2015, 132: 1435-1486.
Bicanic et al., "Symptomatic relapse of HIV-associated cryptococcal meningitis after initial fluconazole monotherapy: the role of fluconazole resistance and immune reconstitution," Clin. Infect. Dis, 2006, 43: 1069-1073.
Bii et al., "Antifungal drug susceptibility of Cryptococcus neoformans from clinical sources in Nairobi, Kenya," Mycoses, 50, 25-30 (2007).
Bonilla et al., "Platyhelminth mitochondrial and cytosolic redox homeostasis is controlled by a single thioredoxin glutathione reductase and dependent on selenium and glutathione," J. Biol. Chem, 2008, 283(26): 17898-907.
Breger et al., "Antifungal chemical compounds identified using a C. elegans pathogenicity assay," PLoS Pathog, 2007, 3(2): e18.
Buchholtz et al., "Severity of gentamicin's nephrotoxic effect on patients with infective endocarditis: a prospective observational cohort study of 373 patients," Clin, Infect. Dis, 2009, 48: 65-71.
Cassetta et al., Drug repositioning: auranofin as a prospective antimicrobial agent for the treatment of severe staphylococcal infections, Biometals, 2014, 27(4), 787-791.
Chambers and DeLeo, "Waves of resistance: *Staphylococcus aureus* in the antibiotic era," Nat. Rev. Microbiol, 2009, 7, 629-641.
Chen et al., "Interaction of daptomycin with lipid bilayers: a lipid extracting effect," Biochemistry, 2014,53: 5384-5392.
Cleveland et al., "Declining Incidence of Candidemia and the Shifting Epidemiology of Candida Resistance in Two US Metropolitan Areas, 2008-2013: Results from Population-Based Surveillance," PLoS One, Mar. 2015, 10: e0120452.
Conery et al., "High-throughput screening for novel anti-infectives using a C. elegans pathogenesis model," Curr. Protoc. Chem. Biol, 2014, 6: 25-37.
Conlon et al., "Activated ClpP kills persisters and eradicates a chronic biofilm infection," Nature, Nov. 2013, 503: 365-370.
Conlon et al., "Persister formation in *Staphylococcus aureus* is associated with ATP depletion," Nature Microbiology, 2016, 1: 16051.
Cosgrove et al., "Initial low-dose gentamicin for *Staphylococcus aureus* bacteremia and endocarditis is nephrotoxic," Clin. Infect. Dis, 2009, 48: 713-721.
Cuddy, "Methicillin resistant *Staphylococcus aureus*: a new pandemic?," Plast Surg, 2008, 28(4): 168-9.
Cuellar-Cruz et al., "Differential response of Candida albicans and Candida glabrata to oxidative and nitrosative stresses," Curr. Microbiol, 2014, 733-739.
Davies and Davies, "Origins and evolution of antibiotic resistance," Microbiol Mol Biol Rev, 2010, 74: 417 433.

Debnath et al., "A high-throughput dmg screen for Entamoeba histolytica identifies a new lead and target," Nature, 2012, 18(6): 956-960.
Denning, "Echinocandin antifungal drugs," Lancet, 2003, 362(9390): 1142-1151.
Dismukes, "Management of cryptococcosis," Clin. Infect. Dis, 1993, 17 Suppl 2: S507-12.
Elbaz et al., "The metabolic enzyme ManA reveals a link between cell wall integrity and chromosome morphology," PLoS Genet, 2010, 6: el001119.
Enjalbert,, "Stress-induced Gene Expression in Candida albicans: Absence of a General Stress Response," Mol. Biol. Cell, 2002, 14(4), 1460-1467.
Falord et al., "Investigation of the *Staphylococcus aureus* GraSR regulon reveals novel links to virulence, stress response and cell wall signal transduction pathways," PLoS ONE, 2011, 6: e21323.
Fey et al., "A genetic resource for rapid and comprehensive phenotype screening of nonessential *Staphylococcus aureus* genes," MBio, 2013, 4: e00537-12.
Fuchs et al., Inhibition of bacterial and fungal pathogens by the orphaned drug auranofin, Future Med. Chem., 2016, 8(2), 117-132.
Garsin et al., "A simple model host for identifying Gram-positive virulence factors," PNAS, 2001, 98(19), 10892-7.
Göhring et al., "New role of the disulfide stress effector YjbH in ß-lactam susceptibility of *Staphylococcus aureus*," Antimicrob. Agents Chemother, 2011, 55: 5452-5458.
Holland et al., "Clinical Management of *Staphylococcus aureus* Bacteremia," JAMA, 2014, 312(13), 1330-1341.
Holmgren, "Reduction of Disulfides by Thioredoxin," J. Biol. Chem, 1979, 254(18): 9113-9119.
Hurdle et al., "Targeting bacterial membrane function: an underexploited mechanism for treating persistent infections," Nat. Rev. Microbiol, 2011, 9: 62-75.
Ianiri and Indrum, "Essential Gene Discovery in the Basidiomycete Cryptococcus," MBio, 2015, 6(12),e02334-14.
International Preliminary Report on Patentability in International Application No. PCT/US2016/053411, dated Mar. 27, 2018, 9 pages.
Irby et al., "A review of adapalene in the treatment of acne vulgaris," J. Adolesc. Health, 2008, 43: 421-424.
Jackson-Rosario and Self, "Inhibition of selenium metabolism in the oral pathogen Treponema denticola," J. Bacteriol, 2009, 191(12), 4035-40.
Jackson-Rosario et al., "Auranofin disrupts selenium metabolism in Clostridium difficile by forming a stable Au—Se adduct," J Biol Inorg Chem, 2009, 14(4): 507-519.
Junqueira et al., "Oral Candida albicans isolates from HIV-positive individuals have similar in vitro biofilm-forming ability and pathogenicity as invasive Candida isolates," BMC Microbiol, 2011, 11: 247.
Kean et al., "Auranofin," Br. J. Rheumatol, 1997, 36(5): 560-72.
Keren et al., "Persister cells and tolerance to antimicrobials," FEMS Microbiol. Lett, 2004, 230: 13-18.
Kim et al., "Identification of an antimicrobial agent effective against methicillin-resistant *Staphylococcus aureus* persisters using a fluorescence-based screening strategy," PLoS ONE, 2015, 10:e0127640.
Kim et al., "NH125 kills methicillin-resistant *Staphylococcus aureus* persisters by lipid bilayer disruption," Future Med. Chem, 2016, 8: 257-269.
Lew and Waldvogel, "Osteomyelitis," The Lancet, 2004, 364: 369-379.
Lewis, "Persister cells," Annu. Rev. Microbiol, 2010, 64: 357-372.
Liu et al., "Clinical practice guidelines by the Infectious Diseases Society of America for the treatment of methicillin-resistant *Staphylococcus aureus* infections in adults and children," Clin. Infect. Dis, 2011, 52: el8-e55.
Lu and Holmgren, "The thioredoxin antioxidant system," Free Radic. Biol. Med, 2014, 66: 75-87.
Lu et al., "Inhibition of bacterial thioredoxin reductase: An antibiotic mechanism targeting bacteria lacking glutathione," FASEB J, 2013, 27: 1394 1403.
Mdodo et al., cerebrospinal fluid isolates from AIDS patients in Kenya, 2012, 54(5): 1-7.

(56) References Cited

OTHER PUBLICATIONS

Meehl et al., "Interaction of the GraRS two-component system with the VraFG ABC transporter to support vancomycin-intermediate resistance in *Staphylococcus aureus*," Antimicrob. Agents Chemother, 2007, 51: 2679-2689.
Missall and Lodge, "Thioredoxin reductase is essential for viability in the fungal pathogen Cryptococcus neoformans," Eukaryot. Cell, 2005, 4(2): 487-489.
Mutters et al., "Control of the spread of vancomycin-resistant enterococci in hospitals," 2013, 110(43): 725-31.
Newton et al., "Distribution of thiols in microorganisms: Mycothiol is a major thiol in most actinomycetes," J. Bacteriol, 1996, 178(7): 1990-1995.
Nobile et al., "Critical role of Bcr1-dependent adhesins in *C. albicans* biofilm formation in vitro and in vivo" PLoS Pathog, 2006, 2(7): e63.
Orhan et al., "Synergy tests by E test and checkerboard methods of antimicrobial combinations against Brucella melitensis," J. Clin, Microbiol, 2005, 43(1): 140-3.
Pan et al., "Resistance of Asian Cryptococcus neoformans serotype a is confined to few microsatellite genotypes," PLoS One, 2012, 7(3): e32868.
Pfaller et al., "Antifungal susceptibility of Candida, Cryptococcus neoformans, and Aspergillus fumigatus from the Asia and Western Pacific region: data from the SENTRY antifungal surveillance program (2010-2012)," J Antiobiot, 2015, 68: 556-561.
Rajamuthiah et al., "A defensin from the model beetle Tribolium castaneum acts synergistically with telavancin and daptomycin against multidrug resistant *Staphylococcus aureus*," PLoS ONE, 2015, 10: e0128576.
Rajamuthiah et al., "Whole animal automated platform for drug discovery against multi-drug resistant *Staphylococcus aureus*," Plos One, 2014, 9(2):e89189.
Rajput and Karuppayil, "Small molecules inhibit growth, viability and ergosterol biosynthesis in Candida albicans," Springerplus, 2013, 2(1): 26.
Rhodes et al., "Effects of Gold(I) antiarthritic drugs and related compounds on Pseudomonas putida," J. Inorg, Chem, 1992, 46: 129-142.
Rice et al., "Enterococcus faecium Low-Affinity pbp5 Is a Transferable Determinant," Antimicrob. Agents Chemother, 2005, 49(12): 5007-5012.

Shimono et al., "Potent inhibition of heterotopic ossification by nuclear retinoic acid receptor-γagonists," Nat. Med., 2011, 17: 454-460.
Tang et al., "Combination of bexarotene and the retinoid CD1530 reduces murine oral-cavity carcinogenesis induced by the carcinogen 4-nitroquinoline 1-oxide," PNAS, 2014, 111: 8907-8912.
Tejman-Yarden et al., "A reprofiled drug, auranofin, is effective against etronidazole-resistant Giardia lamblia," Antimicrob. Agents Chemother, 2013, 57(5): 2029-35.
Tong et al., "*Staphylococcus aureus* infections: epidemiology, pathophysiology, clinical manifestations, and management," Clin. Microbiol. Rev, 2015, 28: 603-661.
Uziel et al., "Transcriptional Regulation of the *Staphylococcus aureus* Thioredoxin and Thioredoxin Reductase Genes in Response to Oxygen and Disulfide Stress Transcriptional Regulation of the *Staphylococcus aureus* Thioredoxin and Thioredoxin Reductase Genes in Response," J. Bacteriol., 2004, 186(2): 2004, 186(2): 326-34.
Valli et al., "Atypical retinoids ST1926 and CD437 are S-phase-specific agents causing DNA double-strand breaks: significance for the cytotoxic and antiproliferative activity," Mol. Cancer Ther, 2008, 7: 2941-2954.
Yang et al., "The *Staphylococcus aureus* two-component regulatory system, GraRS, senses and confers resistance to selected cationic antimicrobial peptides," Infect. Immun., 2012. 80: 74-81.
Bernard et al., "Abstract: Identification of synthetic retinoids with selectivity for human nuclear retinoic acid receptor gamma," Biochem, Biophys. Res. Commun., 1992, 186(2):977-983, 1 page.
Cincinelli et al., "Abstract: A novel atypical retinoid endowed with proapoptotic and antitumor activity," Journal of Medicinal Chemistry, 2003, 46(6):909-912, 1 page.
Giannini et al., "New retinoid derivatives as back-ups of Adarotene," Bioorg. Med. Chem., 2012, 20(7)2405-2415.
Piskin and Uzunali, "A review of the use of adapalene for the treatment of acne vulgaris," Therapeutics and Clinical Risk Management, 2007, 3(4):621-624.
Thacher et al., "Therapeutic applications for ligands of retinoid receptors," Curr. Pharm. Des., 2000, 6(1):25-58.
Valins et al., "The expression of Toll-like receptors in dermatalogical diseases and the therapeutic effect of current and newer topical toll-like receptor modulators," Clinical and Asthetic Dermatology, 2010, 3(9):20-29.

* cited by examiner

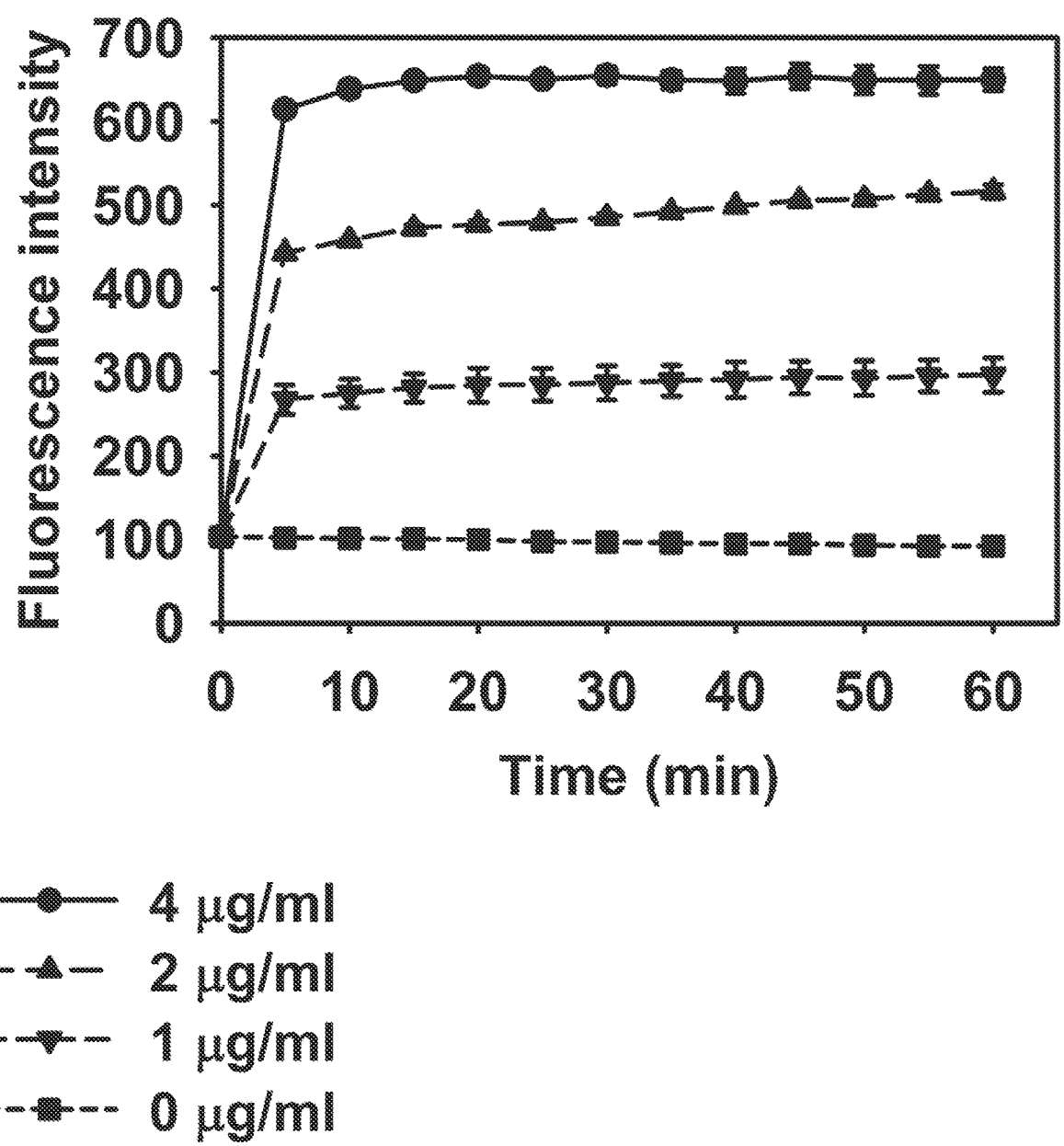

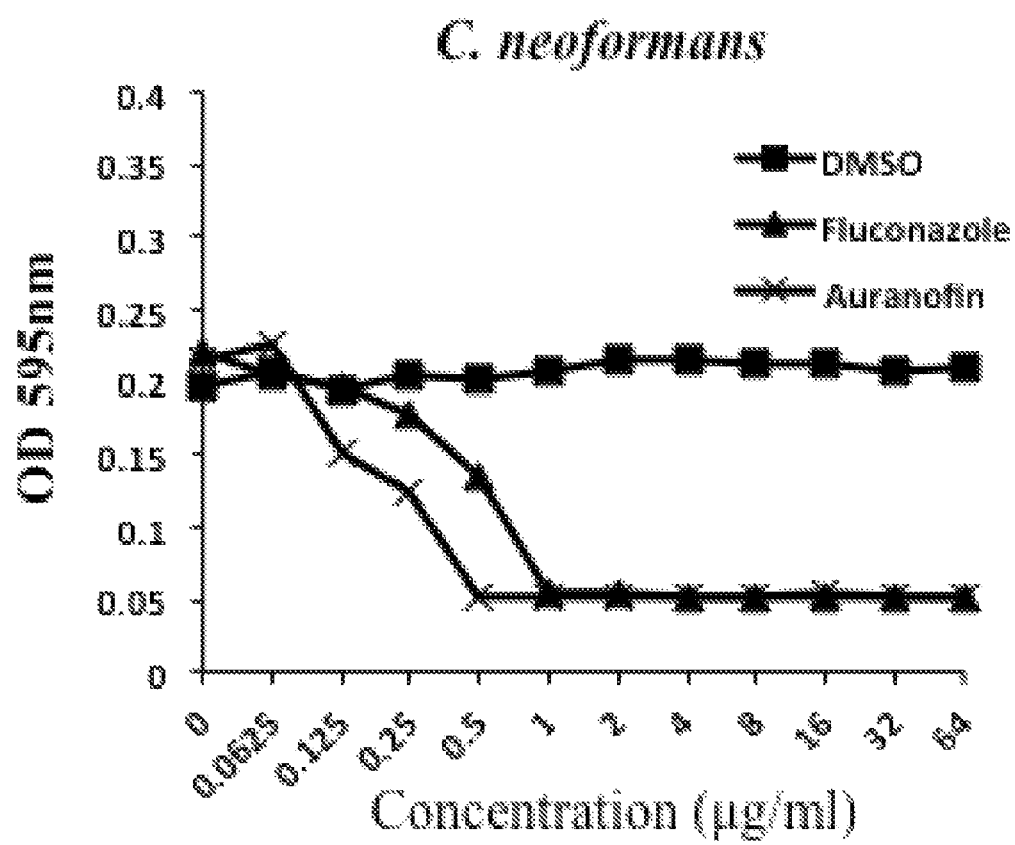

*B. subtilis*

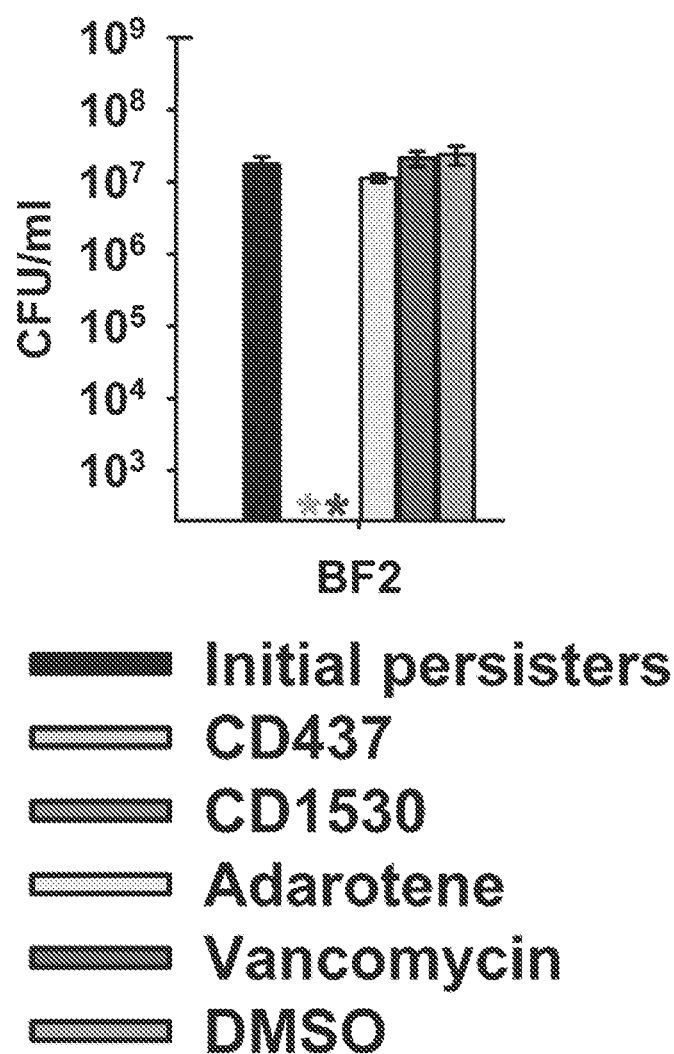

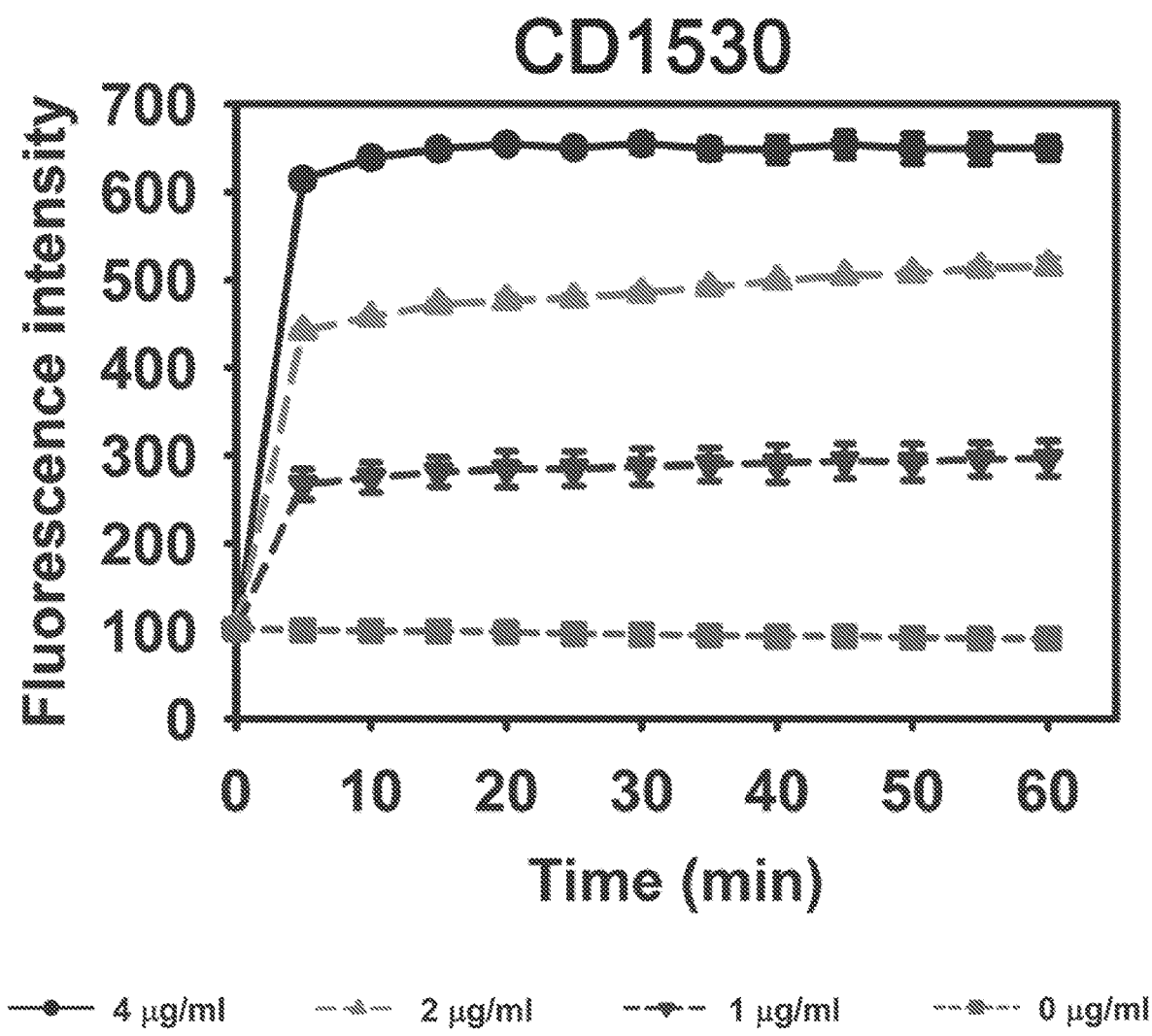

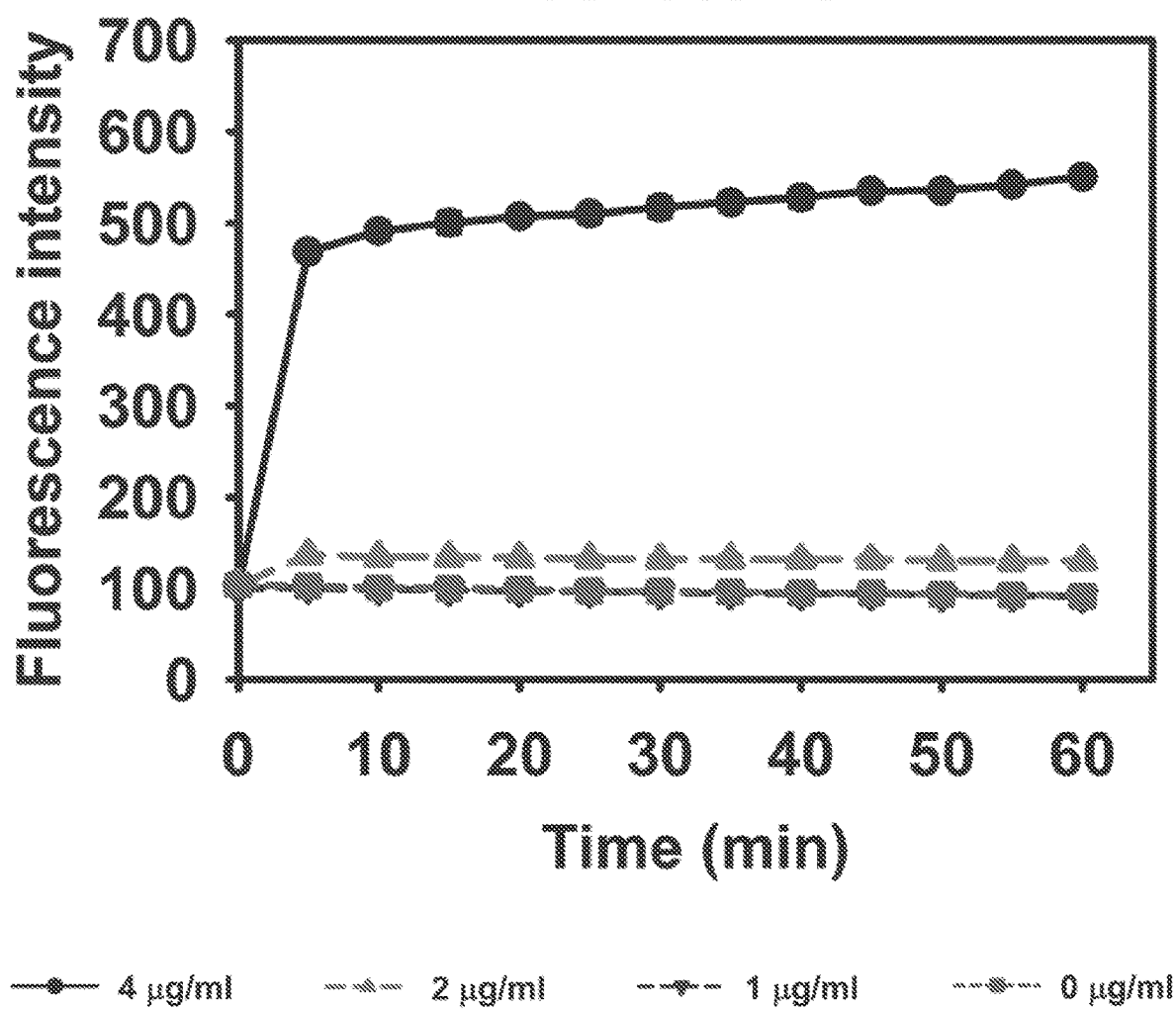

OD600

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: synthetic nucleic acid

```
<400> SEQUENCE: 1
acacctgtga cagccatgaa                                               20

<210> SEQ ID NO 2
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 2
acagtcgacg tgacttgcag                                               20

<210> SEQ ID NO 3
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 3
aaaattatgg ggcggtcaac                                               20

<210> SEQ ID NO 4
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 4
cgattgcatc gtttcgtatg                                               20

<210> SEQ ID NO 5
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 5
aagcattgtc gagtagcttg c                                             21

<210> SEQ ID NO 6
<211> LENGTH: 19
<212> TYPE: DNA
<213> ORGANISM: Artificial Sequence
<220> FEATURE:
<223> OTHER INFORMATION: synthetic nucleic acid

<400> SEQUENCE: 6
cccaggccag tcaattttt                                                19

<210> SEQ ID NO 7
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 7
aaatcgaaca agccccttct                                               20

<210> SEQ ID NO 8
<211> LENGTH: 21
```

<212> TYPE: DNA
<213> ORGANISM: Artificial Sequence
<220> FEATURE:
<223> OTHER INFORMATION: synthetic nucleic acid

<400> SEQUENCE: 8
cgaactggtt aaattcggaa a                                     21

<210> SEQ ID NO 9
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 9
tgccaacgac tgaagttacg                                       20

<210> SEQ ID NO 10
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 10
tctgatgtcc acctaaccat gt                                    22

<210> SEQ ID NO 11
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 11
atcatgttca acacggaacg                                       20

<210> SEQ ID NO 12
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 12
tgaaatcgcc ttcaaagaca                                       20

<210> SEQ ID NO 13
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 13
cgcattttta caaattgaac ca                                    22

<210> SEQ ID NO 14
<211> LENGTH: 20
<212> TYPE: DNA
<213> ORGANISM: Artificial Sequence
<220> FEATURE:

```
<223> OTHER INFORMATION: synthetic nucleic acid

<400> SEQUENCE: 14
atcataccgc ttgaggcaac                                          20
```

ANTIBACTERIAL AND ANTIFUNGAL COMPOUNDS

CLAIM OF PRIORITY

This application is a 371 U.S. National Phase Application of PCT/US2016/053411, filed on Sep. 23, 2016, which claims the benefit of U.S. Provisional Application No. 62/233,107, filed Sep. 25, 2015. The entire contents of the foregoing are hereby incorporated by reference.

FEDERALLY SPONSORED RESEARCH OR DEVELOPMENT

This invention was made with Government support under Grant No. P01AI0843214, awarded by the NIH. The Government has certain rights in the invention.

SEQUENCE LISTING

This application contains a Sequence Listing that has been submitted electronically as an ASCII text file named "29539-0185US1_SL_ST25.txt." The ASCII text file, created on Mar. 31, 2023, is 3,102 bytes in size. The material in the ASCII

TECHNICAL FIELD

This invention relates to organic and organometallic compounds, and more particularly to compounds useful in treating bacterial and fungal infections.

BACKGROUND

With the continual emergence of drug resistant strains of bacteria and fungi, additional therapy options are needed. Bacterial Pathogens: *S. aureus* and *Enterococcus* species have emerged as significant Gram-positive bacterial pathogens, presenting drug resistant strains such as methicillin resistant *S. aureus* (MRSA), vancomycin resistant *S. aureus* (VRSA), and vancomycin resistant *Enterococcus* (VRE). In 2005, 94,000 life-threating infections were attributed to *S. aureus* (Cuddy S M. Methicillin resistant *Staphylococcus aureus*: a new pandemic?Plast Surg 2008; 28(4): 168-9.). Like MRSA, VRE has also become an important nosocomial pathogen, causing outbreaks in hospitals all over the world. VRE has been documented to colonize patients in dialysis units, neonatal units, hematology/oncology wards, and liver transplant units (Mutters N T, Mersch-Sundermann V, Mutters R, Brandt C, Schneider-Brachert W, Frank U. Control of the spread of vancomycin-resistant enterococci in hospitals. 2013; 110(43):725-31.). The current arsenal of drugs is not sufficient to treat these infections.
Fungal Pathogens: The increased prevalence of anti-microbial resistance is not just restricted to bacterial pathogens; it can also be found among fungal microbes. 496 clinical isolates of fungi were collected and evaluated for antifungal resistance. Among the pathogens evaluated fluconazole resistance was found among *Candida glabrata* (6.8%), *Candida parapsilosis* (5.7%), and *Candida tropicalis* (3.6%) (Pfaller M, Messer S, Jones R N, Castanheira M. Antifungal susceptibility of *Candida, Cryptococcus neoformans*, and *Aspergillus fumigatus* from the Asia and Western Pacific region: data from the SENTRY antifungal surveillance program (2010-2012). J Antiobiot (Tokyo). 2015.).
*C. neoformans* is a significant fungal pathogen to susceptible patients, mostly immunocompromised individuals. Although there are drugs to treat *C. neoformans*, they can require prolonged use and can lead to toxic effects. *C. albicans* is a diploid fungus that grows both as yeast and filamentous cells and a causal agent of opportunistic oral and genital infections in humans. *C. glabrata* is highly opportunistic pathogen of the urogenital tract, and of the bloodstream. *C. parapsilosis* is a fungal species of the yeast family that has become a significant cause of sepsis and of wound and tissue infections in immuno-compromised patients. *C. tropicalis* is a common medical yeast pathogen.

Accordingly, there is a need for compounds that can be used for killing or inhibiting growth of bacterial and fungal pathogens, and in methods of treatment of bacterial and fungal infections. Therefore, the present application provides compounds useful for killing or inhibiting growth of bacterial and fungal pathogens, in addition to methods of treatment of bacterial and fungal infections.

SUMMARY

The present application provides, inter alia, a method of killing or inhibiting growth of Gram-positive bacteria, the method comprising contacting the bacteria with an effective amount of a compound of Formula I:

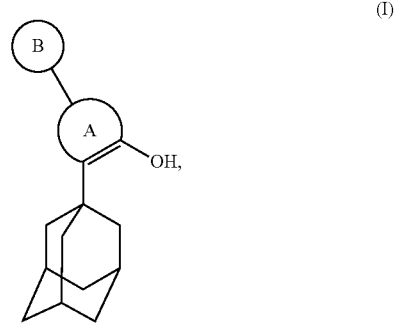

(I)

or a pharmaceutically acceptable salt thereof, wherein:
ring A is selected from the group consisting of phenyl and naphthyl, each of which is optionally substituted by 1, 2, or 3 independently selected $R^A$ groups;
each $R^A$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, HO—$C_{1-3}$ alkylene, $NH_2$, $C_{1-4}$alkylamino, and di($C_{1-4}$ alkyl)amino;
ring B is selected from the group consisting of phenyl and naphthyl, each of which is optionally substituted by 1, 2, 3, or 4 independently selected $R^B$ groups; and
each $R^B$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, HO—$C_{1-3}$ alkylene, $NH_2$, $C_{1-4}$alkylamino, di($C_{1-4}$ alkyl)amino, thio, —C(=O)N(di-$C_{1-4}$ alkyl), —C(=O)NH($C_{1-4}$ alkyl), —C(=O)—$C_{1-4}$ alkyl, —OC(=O)—$C_{1-4}$ alkyl, —NHC(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, each $R^A$ is independently selected from the group consisting of halo, OH, $NO_2$, CN, $C_{1-3}$ alkyl, $C_{1-3}$ haloalkyl, $C_{1-3}$ alkoxy, and $NH_2$.

In some embodiments, each $R^B$ is independently selected from the group consisting of halo, OH, $NO_2$, CN, $C_{1-3}$ alkyl, $C_{1-3}$ haloalkyl, $C_{1-3}$ alkoxy, $NH_2$, —C(=O)—$C_{1-4}$ alkyl, —C(═O)NH(C$_{1-4}$ alkyl), —C(═O)—C$_{1-4}$ alkoxy, —C(═O)OH, —(CH═CH)—C(═O)OH, and —(CH═CH)—C(═O)—C$_{1-4}$ alkoxy.

In some embodiments, each R$^B$ is independently selected from the group consisting of OH, C$_{1-3}$ alkoxy, —C(═O)—C$_{1-4}$ alkyl, —C(═O)—C$_{1-4}$ alkoxy, —C(═O)OH, —(CH═CH)—C(═O)OH, and —(CH═CH)—C(═O)—C$_{1-4}$ alkoxy.

In some embodiments, each R$^B$ is independently selected from the group consisting of —C(═O)OH and —(CH═CH)—C(═O)OH.

In some embodiments, ring A is phenyl and ring B is phenyl.

In some embodiments, ring A is phenyl and ring B is naphthyl.

In some embodiments, ring A is naphthyl and ring B is phenyl.

In some embodiments, the compound of Formula I is selected from the group consisting of:

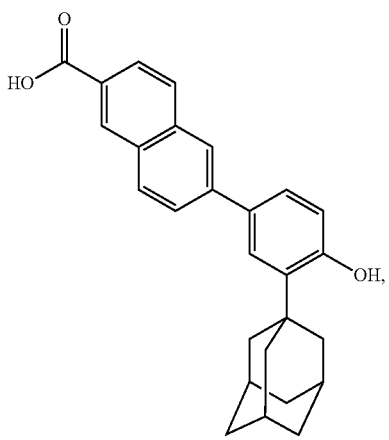

Ia

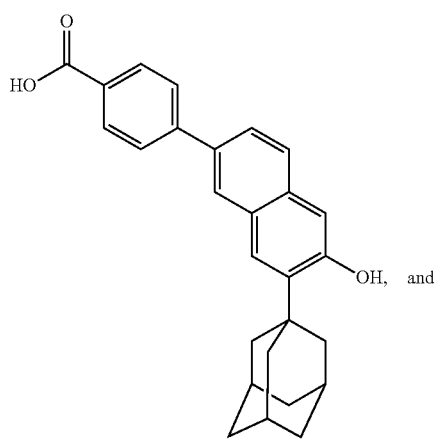

Ib

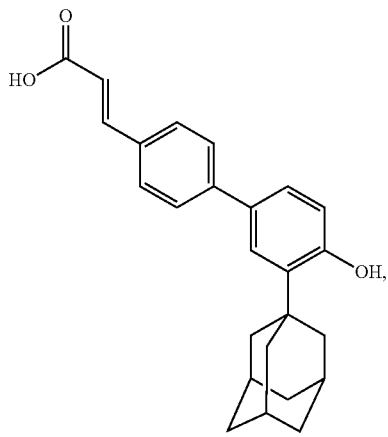

Ic or a pharmaceutically acceptable salt thereof.

In some embodiments, the bacteria is a member of a genus selected from the group consisting of *Staphylococcus, Streptococcus, Peptococcus, Enterococcus,* and *Bacillus*.

In some embodiments, the bacteria is a member of a genus selected from the group consisting of *Staphylococcus, Enterococcus,* and *Bacillus*.

In some embodiments, the bacteria is a member of a species selected from the group consisting of *S. aureus*, methicillin-resistant *S. aureus* (MRSA), vancomycin-resistant *S. aureus* (VRSA), *E. faecalis, E. faecium, B. subtilis,* and *B. anthracis*.

The present application also provides a method of treating a bacterial infection caused by Gram-positive bacteria in a subject, the method comprising administering to the subject in need thereof a therapeutically effective amount of a compound of Formula I:

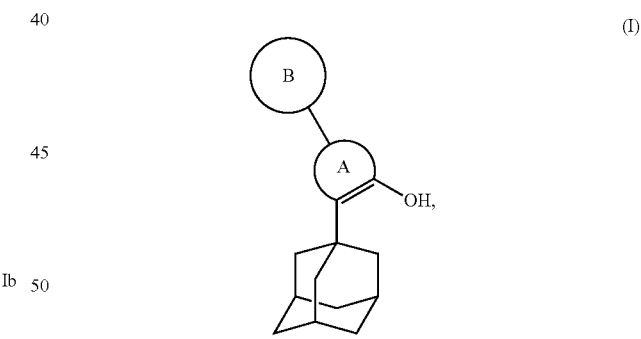

(I)

or a pharmaceutically acceptable salt thereof, wherein:
ring A is selected from the group consisting of phenyl and naphthyl, each of which is optionally substituted by 1, 2, or 3 independently selected R$^A$ groups;
each R$^A$ is independently selected from the group consisting of halo, OH, NO$_2$, CN, C$_{1-4}$ alkyl, C$_{1-4}$ haloalkyl, C$_{1-4}$ alkoxy, C$_{1-4}$ haloalkoxy, cyano-C$_{1-3}$ alkylene, HO—C$_{1-3}$ alkylene, NH$_2$, C$_{1-4}$alkylamino, and di(C$_{1-4}$ alkyl)amino;
ring B is selected from the group consisting of phenyl and naphthyl, each of which is optionally substituted by 1, 2, 3, or 4 independently selected R$^B$ groups; and
each R$^B$ is independently selected from the group consisting of halo, OH, NO$_2$, CN, C$_{1-4}$ alkyl, C$_{1-4}$ haloalkyl, $C_{1-4}$ alkoxy, $C_{1-4}$ haloalkoxy, cyano-$C_{1-3}$ alkyene, HO—$C_{1-3}$ alkylene, $NH_2$, $C_{1-4}$alkylamino, di($C_{1-4}$ alkyl)amino, thio, —C(=O)N(di-$C_{1-4}$ alkyl), —C(=O)NH($C_{1-4}$ alkyl), —C(=O)—$C_{1-4}$ alkyl, —OC(=O)—$C_{1-4}$ alkyl, —NHC(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^A$ is selected from the group consisting of halo, OH, $NO_2$, CN, $C_{1-3}$ alkyl, $C_{1-3}$ haloalkyl, $C_{1-3}$ alkoxy, and $NH_2$.

In some embodiments, $R^B$ is selected from the group consisting of halo, OH, $NO_2$, CN, $C_{1-3}$ alkyl, $C_{1-3}$ haloalkyl, $C_{1-3}$ alkoxy, $NH_2$, —C(=O)—$C_{1-4}$ alkyl, —C(=O)NH($C_{1-4}$ alkyl), —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^B$ is selected from the group consisting of OH, $C_{1-3}$ alkoxy, —C(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^B$ is selected from the group consisting of —C(=O)OH and —(CH=CH)—C(=O)OH.

In some embodiments, ring A is phenyl and ring B is phenyl.

In some embodiments, ring A is phenyl and ring B is naphthyl.

In some embodiments, ring A is naphthyl and ring B is phenyl.

In some embodiments, the compound of Formula I is selected from the group consisting of:

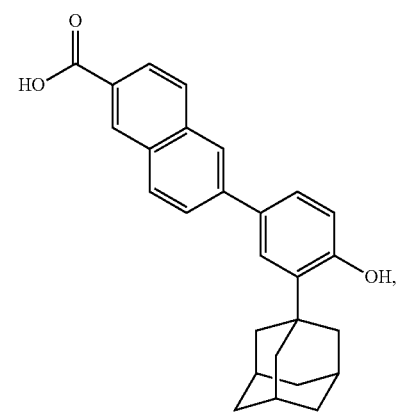

Ia

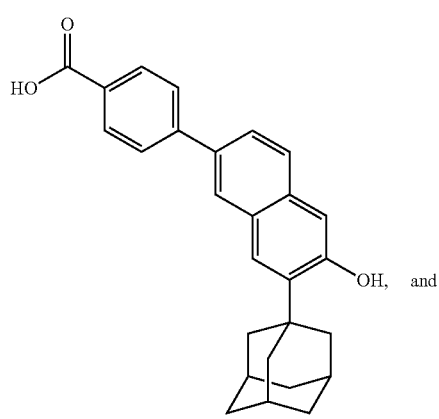

Ib and

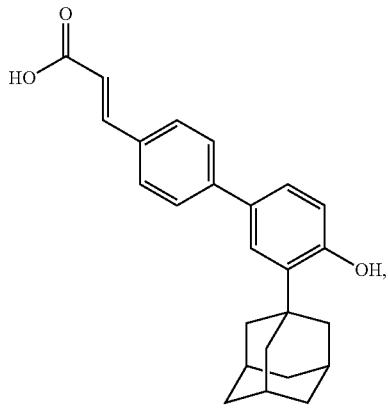

Ic or a pharmaceutically acceptable salt thereof.

In some embodiments, the bacterial infection is caused by the bacteria of a genus selected from the group consisting of *Staphylococcus, Streptococcus, Peptococcus, Enterococcus*, and *Bacillus*.

In some embodiments, the bacterial infection is caused by the bacteria selected from the group consisting of *Staphylococcus, Enterococcus*, and *Bacillus*.

In some embodiments, the bacterial infection is caused by the bacteria of a species selected from the group consisting of *S. aureus*, methicillin-resistant *S. aureus* (MRSA), vancomycin-resistant *S. aureus* (VRSA), *E. faecalis, E. faecium, B. subtilis*, and *B. anthracis*.

In some embodiments, the bacterial infection is selected from the group consisting of nosocomial infection, skin infection, respiratory infection, wound infection, endovascular infection, CNS infection, abdominal infection, blood stream infection, urinary tract infection, pelvic infection, invasive systemic infection, gastrointestinal infection, dental infection, zoonotic infection, and connective tissue infection.

In some embodiments, the bacterial infection is selected from the group consisting of atopic dermatitis, sinusitis, food poisoning, abscess, pneumonia, meningitis, osteomyelitis, endocarditis, bacteremia, sepsis, and urinary tract infection.

In some embodiments, the compound of Formula I is administered to the subject by a route selected from the group consisting of oral, sublingual, gastrointestinal, rectal, topical, intradermal, subcutaneous, nasal, intravenous, and intramuscular.

In some embodiments, the compound of Formula I is administered to the subject in combination with at least one therapeutic agent.

In some embodiments, the therapeutic agent is antibiotic.

In some embodiments, the antibiotic is selected from the group consisting of a quinolone, a β-lactam, a cephalosporin, a penicillin, a carbapenem, a lipopetide, an aminoglycoside, a glycopeptide, a macrolide, an ansamycin, a sulfonamide, and combinations of two or more thereof.

The present application also provides a method of killing or inhibiting growth of bacteria, the method comprising contacting the bacteria with an effective amount of a compound of Formula II:

(II)

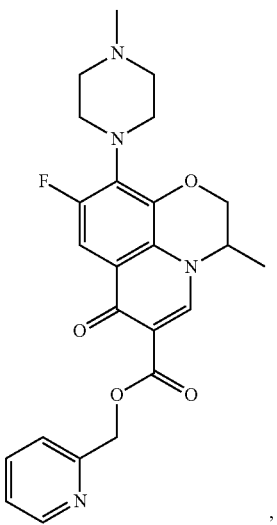

or a pharmaceutically acceptable salt thereof.

In some embodiments, the bacteria is a member of a genus selected from the group consisting of *Staphylococcus, Enterococcus, Enterobacter Klebsiella, Pseudomonas,* and *Acinetobacter.*

In some embodiments, the bacteria is a member of a species selected from the group consisting of *S. aureus,* methicillin-resistant *S. aureus* (MRSA), vancomycin-resistant *S. aureus* (VRSA), *E.* spp., *K. pneumoniae, P aeruginosa, A. baumannii, E. faecium,* and *E. faecalis.*

The present application also provides a method of treating a bacterial infection in a subject, the method comprising administering to the subject in need thereof a therapeutically effective amount of a compound of Formula II:

(II)

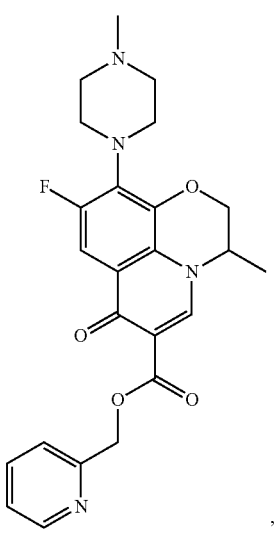

or a pharmaceutically acceptable salt thereof.

In some embodiments, the bacterial infection is caused by the bacteria of a genus selected from the group consisting of *Staphylococcus, Enterococcus, Enterobacter Klebsiella, Pseudomonas,* and *Acinetobacter.*

In some embodiments, the bacterial infection is caused by the bacteria of a species selected from the group consisting of *S. aureus,* methicillin-resistant *S. aureus* (MRSA), vancomycin-resistant *S. aureus* (VRSA), *E.* spp., *K. pneumoniae, P aeruginosa, A. baumannii, E. faecium,* and *E. faecalis.*

In some embodiments, the bacterial infection is selected from the group consisting of nosocomial infection, skin infection, respiratory infection, wound infection, endovascular infection, CNS infection, abdominal infection, blood stream infection, urinary tract infection, pelvic infection, invasive systemic infection, gastrointestinal infection, dental infection, zoonotic infection, and connective tissue infection.

In some embodiments, the bacterial infection is selected from the group consisting of abscess, sinusitis, food poisoning, pneumonia, meningitis, osteomyelitis, endocarditis, bacteremia, sepsis, bronchitis, thrombophlebitis, urinary tract infection, cholecystitis, diarrhea, septicemia, gastrointestinal infection, and endocarditis.

In some embodiments, the compound of Formula II is administered to the subject by a route selected from the group consisting of oral, sublingual, gastrointestinal, rectal, topical, intradermal, subcutaneous, nasal, intravenous, and intramuscular.

In some embodiments, the compound of Formula II is administered to the subject in combination with at least one therapeutic agent.

In some embodiments, the therapeutic agent is antibiotic.

In some embodiments, the antibiotic is selected from the group consisting of a quinolone, a β-lactam, a cephalosporin, a penicillin, a carbapenem, a lipopetide, an aminoglycoside, a glycopeptide, a macrolide, an ansamycin, a sulfonamide, and combinations of two or more thereof.

The present application also provides a method of killing or inhibiting the growth of a fungal pathogen, the method comprising contacting the fungal pathogen with an effective amount of a compound of Formula III:

(III)

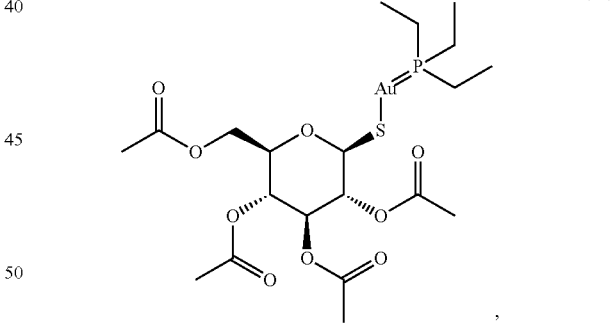

or a pharmaceutically acceptable salt thereof.

In some embodiments, the fungal pathogen is a member of a genus selected from the group consisting of *Candida, Aspergillus, Blastomyces, Cryptococcus, Histoplasma,* and *Pneumocystis.*

In some embodiments, the fungal pathogen is a member of a genus selected from the group consisting of *Candida* and *Cryptococcus.*

In some embodiments, the fungal pathogen is a member of a species selected from the group consisting of *C. albicans, C. parapsilosis, C. tropicalis, C. glabrata,* and *C. neoformans.*

The present application also provides a method of treating a fungal infection in a subject comprising administering to the subject in need thereof a therapeutically effective amount of a compound of Formula III:

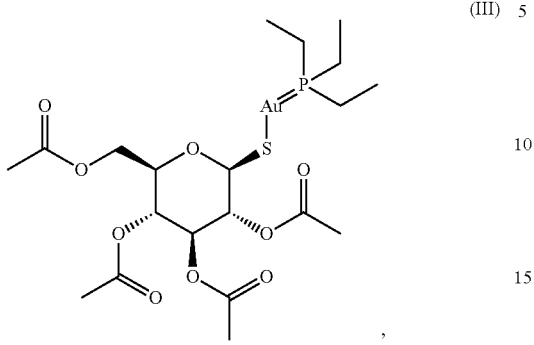
(III)

or a pharmaceutically acceptable salt thereof.

In some embodiments, the fungal infection is caused by a fungal pathogen of a genus selected from the group consisting of *Candida, Aspergillus, Blastomyces, Cryptococcus, Histoplasma*, and *Pneumocystis*.

In some embodiments, the fungal infection is caused by a fungal pathogen of a genus selected from the group consisting of *Candida* and *Cryptococcus*.

In some embodiments, the fungal infection is caused by a fungal pathogen of a species selected from the group consisting of *C. albicans, C. parapsilosis, C. tropicalis, C. glabrata*, and *C. neoformans*.

In some embodiments, the fungal infection is selected from the group consisting of skin infection, mucous membrane infection, blood stream infection, deep organ infection, respiratory infection, and oral infection.

In some embodiments, the fungal infection is selected from the group consisting of seborrhoeic dermatitis, dandruff, tinea nigra, tinea unguium, tinea corporis, tinea cruris, tinea capitis, tinea corpus, cryptococcal meningitis, cryptococcosis, aspergillosis, candidemia, histoplasmosis, candidosis, moniliasis, keratitis, mucormycosis, zygomycosis and thrush.

In some embodiments, the compound of Formula III is administered to the subject by the route selected from the group consisting of oral, sublingual, gastrointestinal, rectal, topical, intradermal, subcutaneous, nasal, intravenous, and intramuscular.

In some embodiments, the compound of Formula III is administered to the subject by a route selected from the group consisting of oral, topical, and intravenous.

In some embodiments, the compound of Formula III is administered to the subject in combination with at least one therapeutic agent.

In some embodiments, the therapeutic agent is antifungal.

In some embodiments, the antifungal is selected from the group consisting of a polyene, an imidazole, a triazole, a thiazole, an allylamine, a thiocarbamate, an echinocandin, and combinations of two or more thereof.

In some embodiments, the antifungal is fluconazole.

The present application provides, inter alia, a method of killing or inhibiting growth of Gram-positive bacteria which is resistant to one or more other antibiotic agents, the method comprising contacting the bacteria with an effective amount of a compound of Formula I:

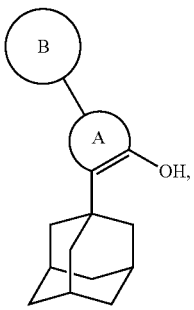
(I)

or a pharmaceutically acceptable salt thereof, wherein:

ring A is selected from the group consisting of phenyl and naphthyl, each of which is optionally substituted by 1, 2, or 3 independently selected $R^A$ groups;

each $R^A$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, HO—$C_{1-3}$ alkylene, $NH_2$, $C_{1-4}$alkylamino, and di($C_{1-4}$ alkyl)amino;

ring B is selected from the group consisting of phenyl and naphthyl, each of which is optionally substituted by 1, 2, 3, or 4 independently selected $R^B$ groups; and each $R^B$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, HO—$C_{1-3}$ alkylene, $NH_2$, $C_{1-4}$alkylamino, di($C_{1-4}$ alkyl) amino, thio, —C(=O)N(di-$C_{1-4}$ alkyl), —C(=O)NH($C_{1-4}$ alkyl), —C(=O)—$C_{1-4}$ alkyl, —OC(=O)—$C_{1-4}$ alkyl, —NHC(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, each $R^A$ is independently selected from the group consisting of halo, OH, $NO_2$, CN, $C_{1-3}$ alkyl, $C_{1-3}$ haloalkyl, $C_{1-3}$ alkoxy, and $NH_2$.

In some embodiments, each $R^B$ is independently selected from the group consisting of halo, OH, $NO_2$, CN, $C_{1-3}$ alkyl, $C_{1-3}$ haloalkyl, $C_{1-3}$ alkoxy, $NH_2$, —C(=O)—$C_{1-4}$ alkyl, —C(=O)NH($C_{1-4}$ alkyl), —C(=O)—$C_{1-4}$ alkoxy, —C(=O)OH, —(CH=CH)—C(=O)OH, and —(CH=CH)—C(=O)—$C_{1-4}$ alkoxy.

In some embodiments, each $R^B$ is independently selected from the group consisting of OH, $C_{1-3}$ alkoxy, —C(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, each $R^B$ is independently selected from the group consisting of —C(=O)OH and —(CH=CH)—C(=O)OH.

In some embodiments, ring A is phenyl and ring B is phenyl.

In some embodiments, ring A is phenyl and ring B is naphthyl.

In some embodiments, ring A is naphthyl and ring B is phenyl.

In some embodiments, the compound of Formula I is selected from the group consisting of:

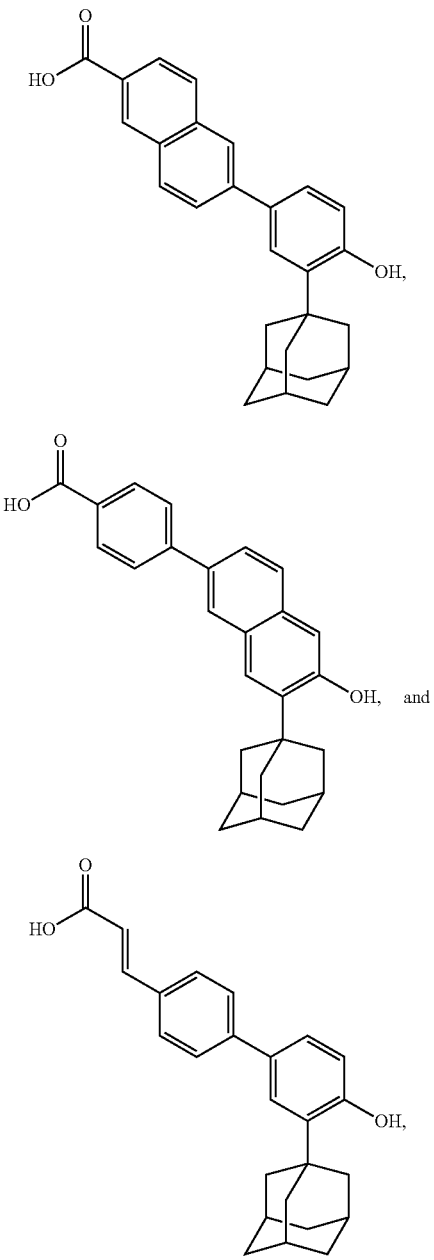

or a pharmaceutically acceptable salt thereof.

In some embodiments, the bacteria is a member of a genus selected from the group consisting of *Staphylococcus, Streptococcus, Peptococcus, Enterococcus*, and *Bacillus*.

In some embodiments, the bacteria is a member of a genus selected from the group consisting of *Staphylococcus, Enterococcus*, and *Bacillus*.

In some embodiments, the bacteria is a member of a species selected from the group consisting of *S. aureus*, methicillin-resistant *S. aureus* (MRSA), vancomycin-resistant *S. aureus* (VRSA), *E. faecalis, E. faecium, B. subtilis*, and *B. anthracis*.

In some embodiments, the bacteria is resistant to one or more antibiotic agents selected from methicillin, vancomycin, rifampicin, gentamicin and ciprofloxacin.

In some embodiments, the bacteria is resistant to methicillin, vancomycin, rifampicin, gentamicin and ciprofloxacin.

The present application also provides a method of treating a bacterial infection caused by Gram-positive bacteria which is resistant to treatment with one or more other antibiotic agents in a subject, the method comprising administering to the subject in need thereof a therapeutically effective amount of a compound of Formula I:

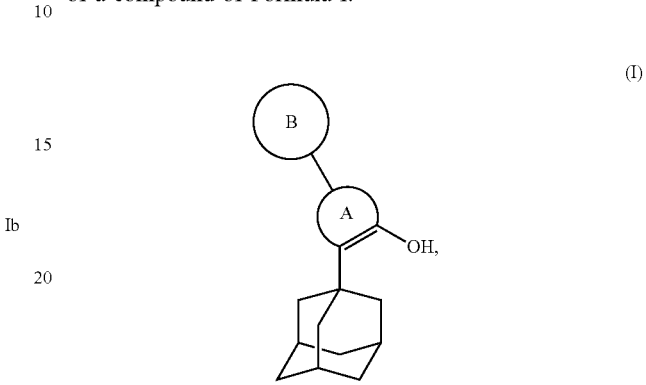

or a pharmaceutically acceptable salt thereof, wherein:

ring A is selected from the group consisting of phenyl and naphthyl, each of which is optionally substituted by 1, 2, or 3 independently selected $R^A$ groups;

each $R^A$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, HO—$C_{1-3}$ alkylene, $NH_2$, $C_{1-4}$alkylamino, and di($C_{1-4}$ alkyl)amino;

ring B is selected from the group consisting of phenyl and naphthyl, each of which is optionally substituted by 1, 2, 3, or 4 independently selected $R^B$ groups; and each $R^B$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkyene, HO—$C_{1-3}$ alkylene, $NH_2$, $C_{1-4}$alkylamino, di($C_{1-4}$ alkyl)amino, thio, —C(=O)N(di-$C_{1-4}$ alkyl), —C(=O)NH($C_{1-4}$ alkyl), —C(=O)—$C_{1-4}$ alkyl, —OC(=O)—$C_{1-4}$ alkyl, —NHC(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^A$ is selected from the group consisting of halo, OH, $NO_2$, CN, $C_{1-3}$ alkyl, $C_{1-3}$ haloalkyl, $C_{1-3}$ alkoxy, and $NH_2$.

In some embodiments, $R^B$ is selected from the group consisting of halo, OH, $NO_2$, CN, $C_{1-3}$ alkyl, $C_{1-3}$ haloalkyl, $C_{1-3}$ alkoxy, $NH_2$, —C(=O)—$C_{1-4}$ alkyl, —C(=O)NH($C_{1-4}$ alkyl), —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^B$ is selected from the group consisting of OH, $C_{1-3}$ alkoxy, —C(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^B$ is selected from the group consisting of —C(=O)OH and —(CH=CH)—C(=O)OH.

In some embodiments, ring A is phenyl and ring B is phenyl.

In some embodiments, ring A is phenyl and ring B is naphthyl.

In some embodiments, ring A is naphthyl and ring B is phenyl.

In some embodiments, the compound of Formula I is selected from the group consisting of:

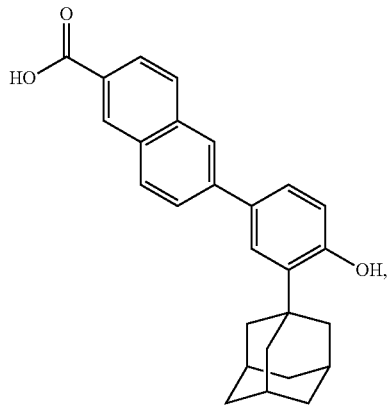

Ia

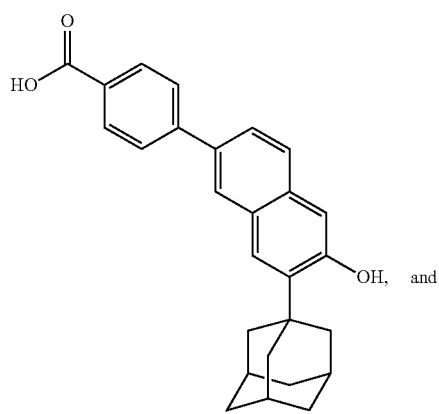

Ib

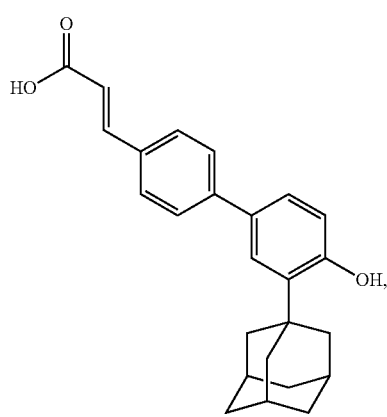

Ic or a pharmaceutically acceptable salt thereof.

In some embodiments, the bacterial infection is caused by the bacteria of a genus selected from the group consisting of *Staphylococcus, Streptococcus, Peptococcus, Enterococcus,* and *Bacillus.*

In some embodiments, the bacterial infection is caused by the bacteria selected from the group consisting of *Staphylococcus, Enterococcus,* and *Bacillus.*

In some embodiments, the bacterial infection is caused by the bacteria of a species selected from the group consisting of *S. aureus*, methicillin-resistant *S. aureus* (MRSA), vancomycin-resistant *S. aureus* (VRSA), *E. faecalis, E. faecium, B. subtilis,* and *B. anthracis.*

In some embodiments, the bacterial infection is resistant to treatment with one or more antibiotic agents selected from methicillin, vancomycin, rifampicin, gentamicin and ciprofloxacin.

In some embodiments, the bacterial infection is resistant to treatment with methicillin, vancomycin, rifampicin, gentamicin and ciprofloxacin.

In some embodiments, the bacterial infection is selected from the group consisting of nosocomial infection, skin infection, respiratory infection, wound infection, endovascular infection, CNS infection, abdominal infection, blood stream infection, urinary tract infection, pelvic infection, invasive systemic infection, gastrointestinal infection, dental infection, zoonotic infection, and connective tissue infection.

In some embodiments, the bacterial infection is selected from the group consisting of atopic dermatitis, sinusitis, food poisoning, abscess, pneumonia, meningitis, osteomyelitis, endocarditis, bacteremia, sepsis, and urinary tract infection.

In some embodiments, the compound of Formula I is administered to the subject by a route selected from the group consisting of oral, sublingual, gastrointestinal, rectal, topical, intradermal, subcutaneous, nasal, intravenous, and intramuscular.

In some embodiments, the compound of Formula I is administered to the subject in combination with at least one additional therapeutic agent.

In some embodiments, the additional therapeutic agent is antibiotic.

In some embodiments, the additional therapeutic agent is an aminoglycoside antibiotic.

In some embodiments, the additional therapeutic agent is gentamicin.

In some embodiments, the additional therapeutic agent is cationic antimicrobial peptide (CAMP).

In some embodiments, the cationic antimicrobial peptide is defensin 1.

In some embodiments, the compound of Formula I and the additional therapeutic agent are administered consecutively.

In some embodiments, the compound of Formula I and the additional therapeutic agent are administered simultaneously.

The present disclosure also provides a pharmaceutical composition comprising:
(i) a compound of Formula I:

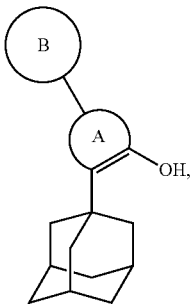

(I)

or a pharmaceutically acceptable salt thereof, wherein:
ring A is selected from the group consisting of phenyl and naphthyl, each of which is optionally substituted by 1, 2, or 3 independently selected $R^4$ groups;

each $R^A$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, HO—$C_{1-3}$ alkylene, $NH_2$, $C_{1-4}$alkylamino, and di($C_{1-4}$ alkyl)amino;

ring B is selected from the group consisting of phenyl and naphthyl, each of which is optionally substituted by 1, 2, 3, or 4 independently selected $R^B$ groups; and each $R^B$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, HO—$C_{1-3}$ alkylene, $NH_2$, $C_{1-4}$alkylamino, di($C_{1-4}$ alkyl)amino, thio, —C(=O)N(di-$C_{1-4}$ alkyl), —C(=O)NH($C_{1-4}$ alkyl), —C(=O)—$C_{1-4}$ alkyl, —OC(=O)—$C_{1-4}$ alkyl, —NHC(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy;

(ii) at least one additional therapeutic agent, and (iii) a pharmaceutically acceptable carrier.

In some embodiments, $R^A$ is selected from the group consisting of halo, OH, $NO_2$, CN, $C_{1-3}$ alkyl, $C_{1-3}$ haloalkyl, $C_{1-3}$ alkoxy, and $NH_2$.

In some embodiments, $R^B$ is selected from the group consisting of halo, OH, $NO_2$, CN, $C_{1-3}$ alkyl, $C_{1-3}$ haloalkyl, $C_{1-3}$ alkoxy, $NH_2$, —C(=O)—$C_{1-4}$ alkyl, —C(=O)NH($C_{1-4}$ alkyl), —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^B$ is selected from the group consisting of OH, $C_{1-3}$ alkoxy, —C(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^B$ is selected from the group consisting of —C(=O)OH and —(CH=CH)—C(=O)OH.

In some embodiments, ring A is phenyl and ring B is phenyl.

In some embodiments, ring A is phenyl and ring B is naphthyl.

In some embodiments, ring A is naphthyl and ring B is phenyl.

In some embodiments, the compound of Formula I is selected from the group consisting of:

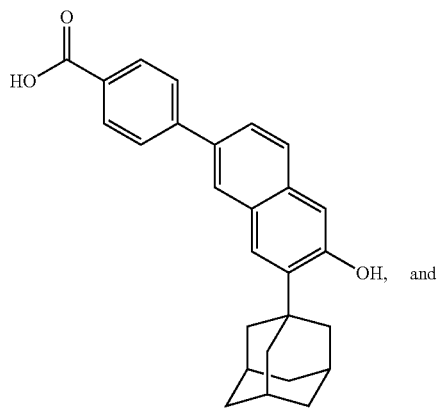

Ia

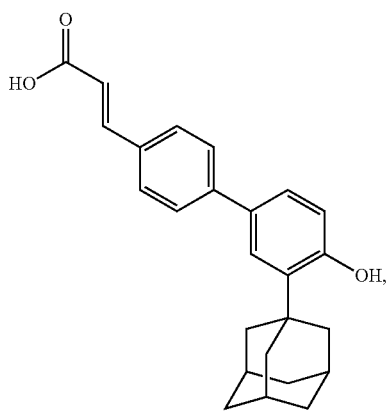

Ib

Ic or a pharmaceutically acceptable salt thereof.

In some embodiments, the additional therapeutic agent is selected from aminoglycoside antibiotic and cationic antimicrobial peptide (CAMP).

In some embodiments, the additional therapeutic agent is selected from gentamicin and defensin 1.

The present disclosure also provides a method of killing or inhibiting growth of Gram-positive bacteria, the method comprising contacting the bacteria with an effective amount of a compound of Formula IV:

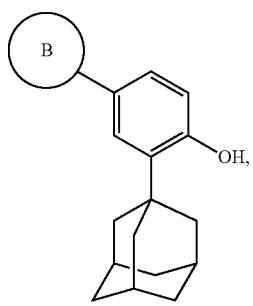

(IV)

or a pharmaceutically acceptable salt thereof, wherein:

ring B is selected from the group consisting of phenyl and naphthyl, each of which is optionally substituted by 1, 2, 3, or 4 independently selected $R^B$ groups; and each $R^B$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, $NH_2$, $C_{1-4}$alkylamino, di($C_{1-4}$ alkyl)amino, thio, —C(=O)N(di-$C_{1-4}$ alkyl), —C(=O)NH($C_{1-4}$ alkyl), —C(=O)—$C_{1-4}$ alkyl, —OC(=O)—$C_{1-4}$ alkyl, —NHC(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, ring B is phenyl.

In some embodiments, ring B is naphthyl.

In some embodiments, ring B is substituted with one $R^B$ group.

In some embodiments, $R^B$ is selected from the group consisting of OH, $C_{1-3}$ alkoxy, —C(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^B$ is selected from the group consisting of —C(=O)OH and —(CH=CH)—C(=O)OH.

In some embodiments, the compound of Formula IV is selected from:

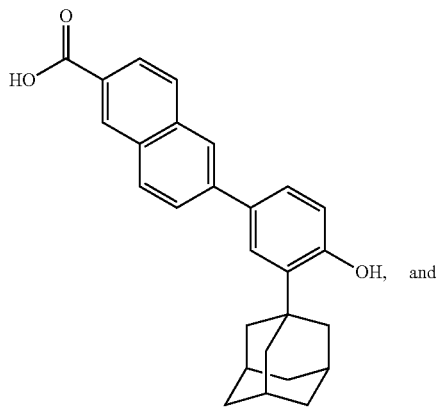
(Ia)

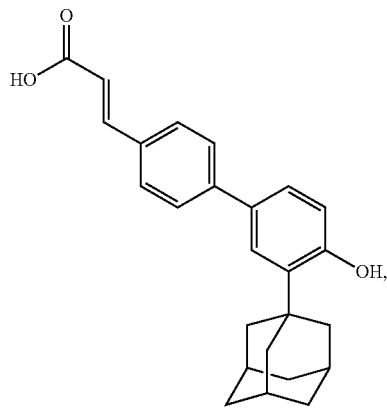
(Ic)

or a pharmaceutically acceptable salt thereof.

In some embodiments, the bacteria is a member of a genus selected from the group consisting of *Staphylococcus, Streptococcus, Peptococcus, Enterococcus,* and *Bacillus*.

In some embodiments, the bacteria is a member of a genus selected from the group consisting of *Staphylococcus, Enterococcus,* and *Bacillus*.

In some embodiments, the bacteria is a member of a species selected from the group consisting of *S. aureus*, methicillin-resistant *S. aureus* (MRSA), vancomycin-resistant *S. aureus* (VRSA), *E. faecalis, E. faecium, B. subtilis,* and *B. anthracis*.

The present disclosure also provides a method of treating a bacterial infection caused by Gram-positive bacteria, the method comprising administering to the subject in need thereof a therapeutically effective amount of a compound of a compound of Formula IV:

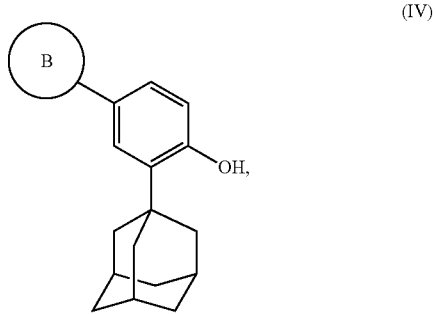
(IV)

or a pharmaceutically acceptable salt thereof, wherein:

ring B is selected from the group consisting of phenyl and naphthyl, each of which is optionally substituted by 1, 2, 3, or 4 independently selected $R^B$ groups; and each $R^B$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, $NH_2$, $C_{1-4}$alkylamino, di($C_{1-4}$ alkyl)amino, thio, —C(=O)N(di-$C_{1-4}$ alkyl), —C(=O)NH($C_{1-4}$ alkyl), —C(=O)—$C_{1-4}$ alkyl, —OC(=O)—$C_{1-4}$ alkyl, —NHC(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, ring B is phenyl.

In some embodiments, ring B is naphthyl.

In some embodiments, ring B is substituted with one $R^B$ group.

In some embodiments, $R^B$ is selected from the group consisting of OH, $C_{1-3}$ alkoxy, —C(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^B$ is selected from the group consisting of —C(=O)OH and —(CH=CH)—C(=O)OH.

In some embodiments, the compound of Formula IV is selected from:

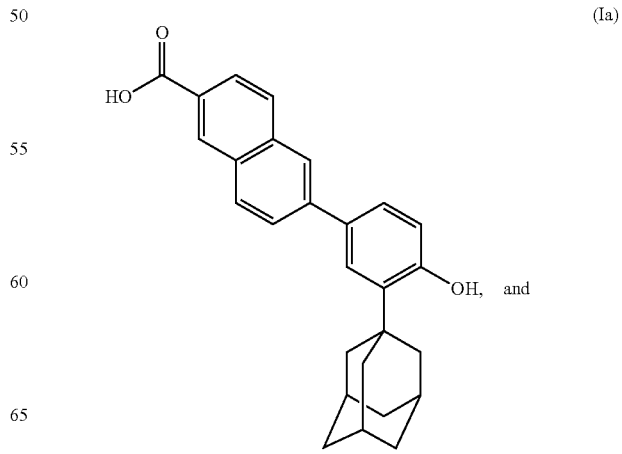
(Ia)

-continued

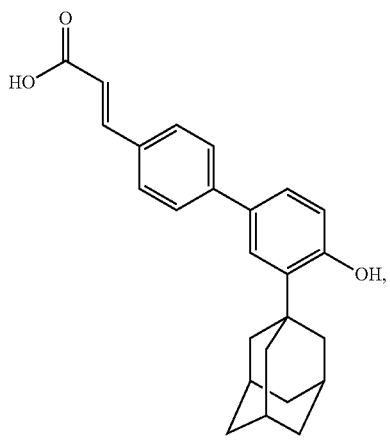

(Ic)

or a pharmaceutically acceptable salt thereof.

In some embodiments, the bacterial infection is caused by the bacteria of a genus selected from the group consisting of *Staphylococcus, Streptococcus, Peptococcus, Enterococcus*, and *Bacillus*.

In some embodiments, the bacterial infection is caused by the bacteria selected from the group consisting of *Staphylococcus, Enterococcus*, and *Bacillus*.

In some embodiments, the bacterial infection is caused by the bacteria of a species selected from the group consisting of *S. aureus*, methicillin-resistant *S. aureus* (MRSA), vancomycin-resistant *S. aureus* (VRSA), *E. faecalis, E. faecium, B. subtilis*, and *B. anthracis*.

In some embodiments, the bacterial infection is selected from the group consisting of nosocomial infection, skin infection, respiratory infection, wound infection, endovascular infection, CNS infection, abdominal infection, blood stream infection, urinary tract infection, pelvic infection, invasive systemic infection, gastrointestinal infection, dental infection, zoonotic infection, and connective tissue infection.

In some embodiments, the bacterial infection is selected from the group consisting of atopic dermatitis, sinusitis, food poisoning, abscess, pneumonia, meningitis, osteomyelitis, endocarditis, bacteremia, sepsis, and urinary tract infection.

In some embodiments, the compound of Formula IV is administered to the subject by a route selected from the group consisting of oral, sublingual, gastrointestinal, rectal, topical, intradermal, subcutaneous, nasal, intravenous, and intramuscular.

In some embodiments, the compound of Formula IV is administered to the subject in combination with at least one additional therapeutic agent.

In some embodiments, the additional therapeutic agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, and combinations of two or more thereof.

In some embodiments, the additional therapeutic agent is an aminoglycoside antibiotic.

In some embodiments, the aminoglycoside antibiotic is gentamicin.

In some embodiments, the additional therapeutic agent is cationic antimicrobial peptide (CAMP).

In some embodiments, the cationic antimicrobial peptide is defensin 1.

In some embodiments, the compound of Formula IV and the additional therapeutic agent are administered consecutively.

In some embodiments, the compound of Formula IV and the additional therapeutic agent are administered simultaneously.

In some embodiments, the additional therapeutic agent is selected from the group consisting of a quinolone, a β-lactam, a cephalosporin, a penicillin, a carbapenem, a lipopetide, an aminoglycoside, a glycopeptide, a macrolide, an ansamycin, a sulfonamide, and combinations of two or more thereof.

The present application also provides a method of killing or inhibiting growth of bacteria, the method comprising contacting the bacteria with an effective amount of a compound of Formula II:

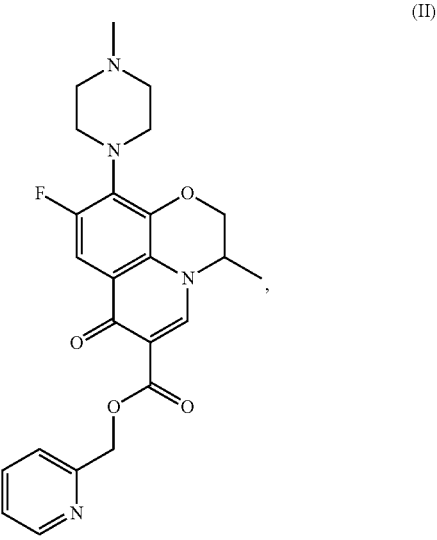 [SMILES: CC1COc2c(N3CCN(C)CC3)c(F)cc3c(=O)c(C(=O)OCc4ccccn4)cn1c23]

(II)

or a pharmaceutically acceptable salt thereof.

In some embodiments, the bacteria is a member of a genus selected from the group consisting of *Staphylococcus, Enterococcus, Enterobacter Klebsiella, Pseudomonas*, and *Acinetobacter*.

In some embodiments, the bacteria is a member of a species selected from the group consisting of *S. aureus*, methicillin-resistant *S. aureus* (MRSA), vancomycin-resistant *S. aureus* (VRSA), *E.* spp., *K. pneumoniae, P. aeruginosa, A. baumannii, E. faecium*, and *E. faecalis*.

The present application also provides a method of treating a bacterial infection in a subject, the method comprising administering to the subject in need thereof a therapeutically effective amount of a compound of Formula II:

(II)

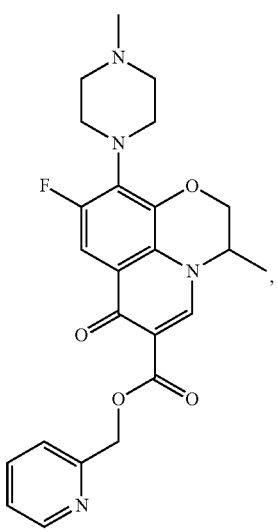

or a pharmaceutically acceptable salt thereof.

In some embodiments, the bacterial infection is caused by the bacteria of a genus selected from the group consisting of Staphylococcus, Enterococcus, Enterobacter Klebsiella, Pseudomonas, and Acinetobacter.

In some embodiments, the bacterial infection is caused by the bacteria of a species selected from the group consisting of S. aureus, methicillin-resistant S. aureus (MRSA), vancomycin-resistant S. aureus (VRSA), E. spp., K. pneumoniae, P aeruginosa, A. baumannii, E. faecium, and E. faecalis.

In some embodiments, the bacterial infection is selected from the group consisting of nosocomial infection, skin infection, respiratory infection, wound infection, endovascular infection, CNS infection, abdominal infection, blood stream infection, urinary tract infection, pelvic infection, invasive systemic infection, gastrointestinal infection, dental infection, zoonotic infection, and connective tissue infection.

In some embodiments, the bacterial infection is selected from the group consisting of abscess, sinusitis, food poisoning, pneumonia, meningitis, osteomyelitis, endocarditis, bacteremia, sepsis, bronchitis, thrombophlebitis, urinary tract infection, cholecystitis, diarrhea, septicemia, gastrointestinal infection, and endocarditis.

In some embodiments, the compound of Formula II is administered to the subject by a route selected from the group consisting of oral, sublingual, gastrointestinal, rectal, topical, intradermal, subcutaneous, nasal, intravenous, and intramuscular.

In some embodiments, the compound of Formula II is administered to the subject in combination with at least one additional therapeutic agent.

In some embodiments, the additional therapeutic agent is antibiotic.

In some embodiments, the antibiotic is selected from the group consisting of a quinolone, a β-lactam, a cephalosporin, a penicillin, a carbapenem, a lipopetide, an aminoglycoside, a glycopeptide, a macrolide, an ansamycin, a sulfonamide, and combinations of two or more thereof.

The present application also provides a method of killing or inhibiting the growth of a fungal pathogen, the method comprising contacting the fungal pathogen with an effective amount of a compound of Formula III:

(III)

or a pharmaceutically acceptable salt thereof.

In some embodiments, the fungal pathogen is a member of a genus selected from the group consisting of Candida, Aspergillus, Blastomyces, Cryptococcus, Histoplasma, and Pneumocystis.

In some embodiments, the fungal pathogen is a member of a genus selected from the group consisting of Candida and Cryptococcus.

In some embodiments, the fungal pathogen is a member of a species selected from the group consisting of C. albicans, C. parapsilosis, C. tropicalis, C. glabrata, and C. neoformans.

In some embodiments, the fungal pathogen is resistant to one or more antifungal agents selected from amphotericin B and fluconazole.

In some embodiments, the fungal pathogen is resistant to amphotericin B and fluconazole.

The present application also provides a method of treating a fungal infection in a subject comprising administering to the subject in need thereof a therapeutically effective amount of a compound of Formula III:

(III)

or a pharmaceutically acceptable salt thereof.

In some embodiments, the fungal infection is caused by a fungal pathogen of a genus selected from the group consisting of Candida, Aspergillus, Blastomyces, Cryptococcus, Histoplasma, and Pneumocystis.

In some embodiments, the fungal infection is caused by a fungal pathogen of a genus selected from the group consisting of Candida and Cryptococcus.

In some embodiments, the fungal infection is caused by a fungal pathogen of a species selected from the group consisting of C. albicans, C. parapsilosis, C. tropicalis, C. glabrata, and C. neoformans.

In some embodiments, the fungal infection is selected from the group consisting of skin infection, mucous membrane infection, blood stream infection, deep organ infection, respiratory infection, and oral infection.

In some embodiments, the fungal infection is selected from the group consisting of seborrhoeic dermatitis, dandruff, tinea nigra, tinea unguium, tinea corporis, tinea cruris, tinea capitis, tinea corpus, cryptococcal meningitis, cryptococcosis, aspergillosis, candidemia, histoplasmosis, candidosis, moniliasis, keratitis, mucormycosis, zygomycosis and thrush.

In some embodiments, the compound of Formula III is administered to the subject by the route selected from the group consisting of oral, sublingual, gastrointestinal, rectal, topical, intradermal, subcutaneous, nasal, intravenous, and intramuscular.

In some embodiments, the compound of Formula III is administered to the subject by a route selected from the group consisting of oral, topical, and intravenous.

In some embodiments, the compound of Formula III is administered to the subject in combination with at least one additional therapeutic agent.

In some embodiments, the additional therapeutic agent is antifungal.

In some embodiments, the antifungal is selected from the group consisting of a polyene, an imidazole, a triazole, a thiazole, an allylamine, a thiocarbamate, an echinocandin, and combinations of two or more thereof.

In some embodiments, the antifungal is selected from amphotericin B and fluconazole.

In some embodiments, the compound of Formula III and the additional therapeutic agent are administered consecutively.

In some embodiments, the compound of Formula III and the additional therapeutic agent are administered simultaneously.

The present disclosure also provides a pharmaceutical composition comprising:
(i) a compound of Formula III:

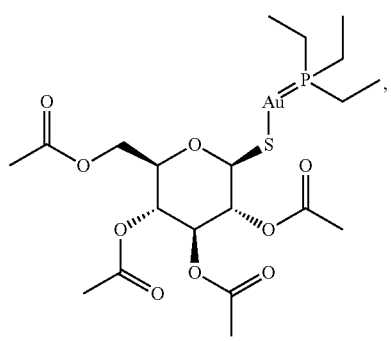

(III)

(ii) at least one additional therapeutic agent, and
(iii) a pharmaceutically acceptable carrier.

In some embodiments, the additional therapeutic agent is an antigungal.

In some embodiments, the antifungal is selected from the group consisting of a polyene, an imidazole, a triazole, a thiazole, an allylamine, a thiocarbamate, an echinocandin.

In some embodiments, the antifungal is selected from amphotericin B and fluconazole.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

FIG. 4B is a line graph showing toxicity testing of CD1530 against human erythrocytes at increasing concentrations.

FIG. 7C is a line graph showing MIC of auranofon for inhibition of *C. neoformans*.

FIG. 26C is a bar graph showing viability of *S. aureus* clinical isolate BF2 after treatment with CD437, CD1530, adarotene or vancomycin.

FIG. 28B is a line graph showing uptake of SYTOX Green (Ex=485 nm, Em=525 nm) over time measured spectrophotometrically by exponential-phase MRSA cells treated with the indicated concentrations of CD1530.

FIG. 28C is a line graph showing uptake of SYTOX Green (Ex=485 nm, Em=525 nm) over time measured spectrophotometrically by exponential-phase MRSA cells treated with the indicated concentrations of adarotene.

DETAILED DESCRIPTION

Compounds

Figure 1:
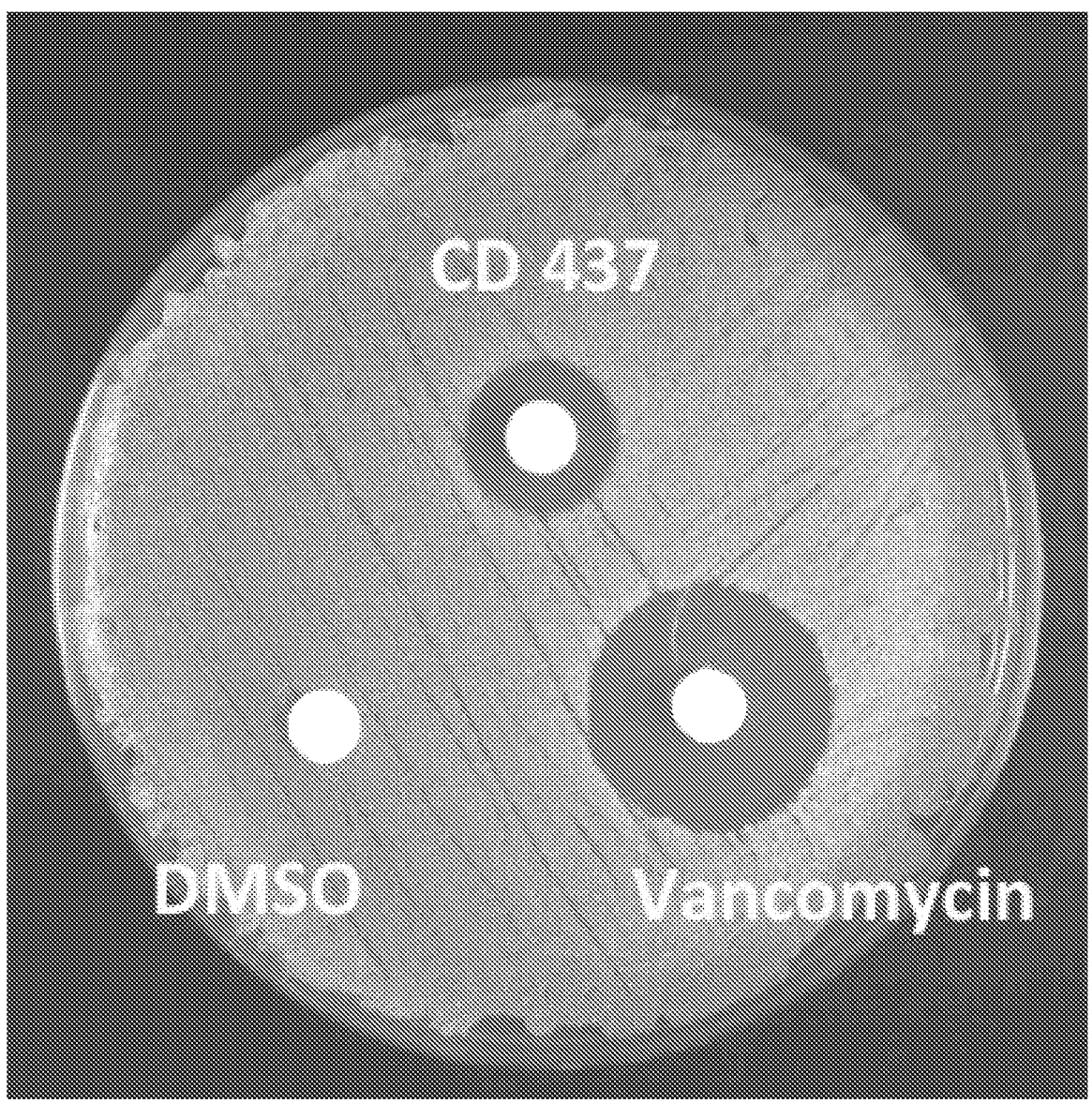
FIG. 1 is an image showing direct inhibition of *S. aureus* by CD 437 using a disk clearing assay.

In some embodiments, the present application is directed to methods of using a compound of Formula (I):

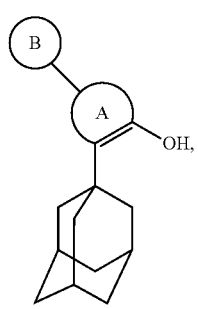

or a pharmaceutically acceptable salt thereof, wherein:

ring A is selected from the group consisting of phenyl and naphthyl, each of which is optionally substituted by 1, 2, or 3 independently selected $R^A$ groups;

each $R^A$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, HO—$C_{1-3}$ alkylene, $NH_2$, $C_{1-4}$alkylamino, and di($C_{1-4}$ alkyl)amino;

ring B is selected from the group consisting of phenyl and naphthyl, each of which is optionally substituted by 1, 2, 3, or 4 independently selected $R^B$ groups; and each $R^B$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, HO—$C_{1-3}$ alkylene, $NH_2$, $C_{1-4}$alkylamino, di($C_{1-4}$ alkyl)amino, thio, —C(=O)N(di-$C_{1-4}$ alkyl), —C(=O)NH($C_{1-4}$ alkyl), —C(=O)—$C_{1-4}$ alkyl, —OC(=O)—$C_{1-4}$ alkyl, —NHC(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, each $R^A$ is independently selected from the group consisting of halo, OH, $NO_2$, CN, $C_{1-3}$ alkyl, $C_{1-3}$ haloalkyl, $C_{1-3}$ alkoxy, and $NH_2$.

In some embodiments, each $R^B$ is independently selected from the group consisting of halo, OH, $NO_2$, CN, $C_{1-3}$ alkyl, $C_{1-3}$ haloalkyl, $C_{1-3}$ alkoxy, $NH_2$, —C(=O)—$C_{1-4}$ alkyl, —C(=O)NH($C_{1-4}$ alkyl), —C(=O)—$C_{1-4}$ alkoxy, —C(=O)OH, —(CH=CH)—C(=O)OH, and —(CH=CH)—C(=O)—$C_{1-4}$ alkoxy.

In some embodiments, each $R^B$ is independently selected from the group consisting of OH, $C_{1-3}$ alkoxy, —C(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, each $R^B$ is independently selected from the group consisting of —C(=O)OH and —(CH=CH)—C(=O)OH.

In some embodiments, ring A is phenyl and ring B is phenyl.

In some embodiments, ring A is phenyl and ring B is naphthyl.

In some embodiments, ring A is naphthyl and ring B is phenyl.

In some embodiments, when ring A is naphthyl and ring B is phenyl, $R^B$ is not —C(=O)OH.

In some embodiments, the compound of Formula (I) is a compound of Formula Ia:

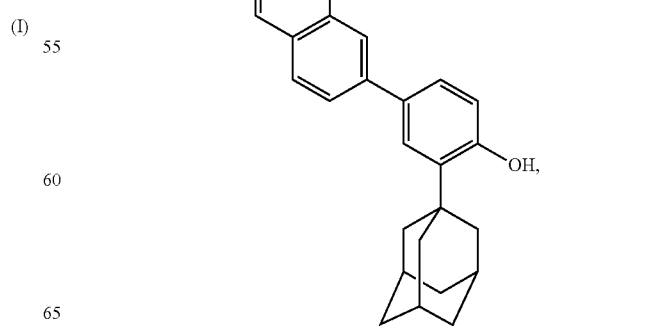

also known as CD 437 (CAS registry number 125316-60-1), and 6-(4-hydroxy-3-tricyclo[3.3.1.13,7]dec-1-ylphenyl)-2-naphthalenecarboxylic acid. CD 437 is a third generation RARγ-selective retinoid.

In some embodiments, the compound of Formula (I) is a compound of Formula Ib:

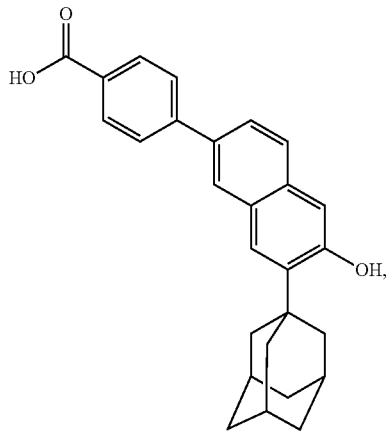

(Ib)

or a pharmaceutically acceptable salt thereof. The compound of Formula (Ib) is also known as CD 1530 (CAS registry number 107430-66-0), and 4-(6-hydroxy-7-tricyclo[3.3.1.13,7]dec-1-yl-2-naphthalenyl)-benzoic acid. CD 1530 is a third generation retinoid and a retinoic acid receptor gamma (RARγ) agonist.

In some embodiments, the compound of Formula (I) is a compound of Formula (Ic):

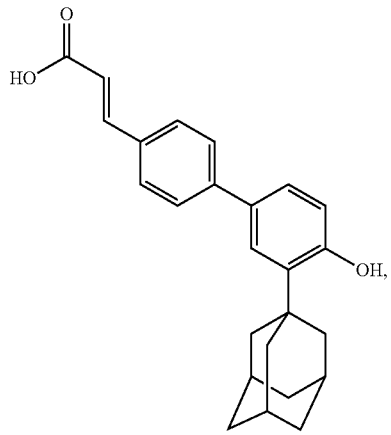

(Ic)

or a pharmaceutically acceptable salt thereof. The compound of Formula (Ic) is also known as Adarotene (CAS registry number 496868-77-0), also known as (2E)-3-(4'-Hydroxy-3'-tricyclo[3.3.1.13,7]dec-1-yl[1,1'-biphenyl]-4-yl)-2-propenoic acid, and ST 1926. Adarotene is an atypical retinoid due to the phenolic hydroxyl group that has lost the ability to activate retinoic acid receptors (RARs), it exhibits antiproliferative activity on human cancer cells, functioning as an apoptosis inducer and damaging DNA.

Synthetic retinoids, such as CD 437, CD 1530, Adarotene, and Adapalene, are ligands for the RAR and RXR nuclear receptors, and are known to be used for the treatment of psoriasis, photoaging, and cancer.

In some embodiments, the compound of Formula (I) is a compound of Formula (IV):

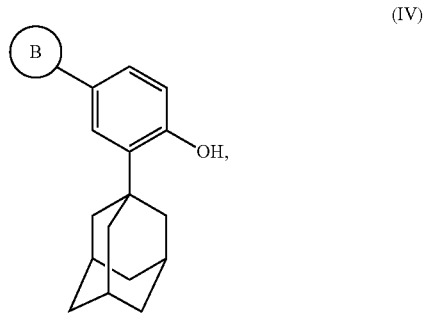

(IV)

or a pharmaceutically acceptable salt thereof, wherein:

ring B is selected from the group consisting of phenyl and naphthyl, each of which is optionally substituted by 1, 2, 3, or 4 independently selected $R^B$ groups; and each $R^B$ is independently selected from the group consisting of halo, OH, $NO_2$, CN, $C_{1-4}$ alkyl, $C_{1-4}$ haloalkyl, $C_{1-4}$ alkoxy, $C_{1-4}$ haloalkoxy, cyano-$C_{1-3}$ alkylene, $NH_2$, $C_{1-4}$alkylamino, di($C_{1-4}$ alkyl)amino, thio, —C(=O)N(di-$C_{1-4}$ alkyl), —C(=O)NH($C_{1-4}$ alkyl), —C(=O)—$C_{1-4}$ alkyl, —OC(=O)—$C_{1-4}$ alkyl, —NHC(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, ring B is phenyl.

In some embodiments, ring B is naphthyl.

In some embodiments, ring B is substituted with one $R^B$ group.

In some embodiments, $R^B$ is selected from the group consisting of OH, $C_{1-3}$ alkoxy, —C(=O)—$C_{1-4}$ alkyl, —C(=O)—$C_{1-4}$ alkoxy, —C(=O)OH, —(CH=CH)—C(=O)OH, and —(CH=CH)—C(=O)—$C_{1-4}$ alkoxy.

In some embodiments, $R^B$ is selected from the group consisting of —C(=O)OH and —(CH=CH)—C(=O)OH.

In some embodiments, the compound of Formula IV is selected from:

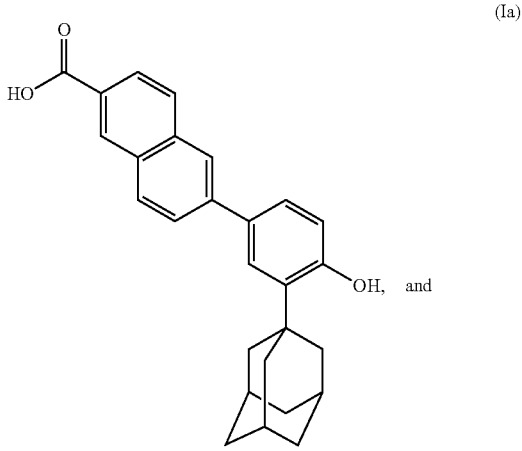

(Ia)

OH, and

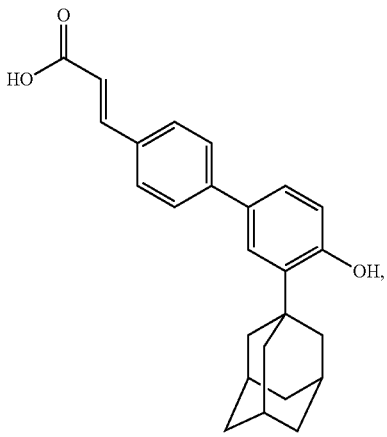

(Ic)

or a pharmaceutically acceptable salt thereof.

In some embodiments, the present application is directed to methods of using a compound of Formula (II):

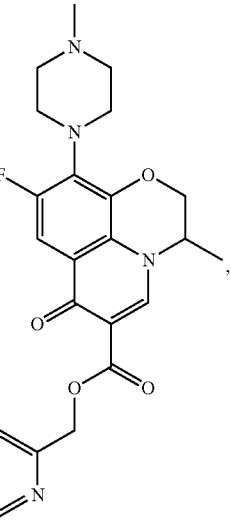

(II)

or a pharmaceutically acceptable salt thereof, also known as Z3060, and pyridin-2-ylmethyl 9-fluoro-3-methyl-10-(4-methylpiperazin-1-yl)-7-oxo-3,7-dihydro-2H-[1,4]oxazino[2,3,4-ij]quinoline-6-carboxylate (available from Enamine, catalog number T5415579, product ID Z30609449, $C_{24}H_{25}FN_4O_4$).

In some embodiments, the present application is directed to methods of using a compound of Formula (III):

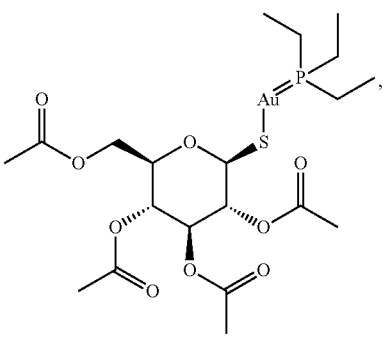

(III)

or a pharmaceutically acceptable salt thereof. The compound of Formula (III) is also known as auranofin (CAS registry number 34031-32-8), NSC 321521, SKF 39162; 2,3,4,6-tetra-o-acetyl-1-thio-D-glucanpyranosato-S-(triethyl-phosphine)-gold, and [1-(thio-κS)—β-D-glucopyranose-2,3,4,6-tetraacetato](triethylphosphine)-gold. Auranofin is a monomeric gold(I) species where the triethylphosphine group stabilizes the gold thiol complex. As an anti-inflammatory compound, auranofin has been used to treat arthritic conditions. Auranofin is approved by FDA since 1985. Auranofin can be taken orally, in contrast to many of the current therapeutic options that require intravenous delivery.

In some embodiments, a salt of a compound of Formulae I, Ia, Ib, Ic, IV, II, and III is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formulae I, Ia, Ib, Ic, IV, II, and III include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formulae I, Ia, Ib, Ic, IV, II, and III include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of Formulae I, Ia, Ib, Ic, IV, II, and III, or pharmaceutically acceptable salts thereof, are substantially isolated.

Synthesis of Compounds

Compounds of Formulae I, Ia, Ib, Ic, IV, II, and III, including salts thereof, can be prepared using known organic synthesis techniques and can be synthesized according to any of numerous possible synthetic routes. In some cases, compounds as provided herein are commercially available.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: Advances in Heterocyclic Chemistry, Vols. 1-107 (Elsevier, 1963-2012); *Journal of Heterocyclic Chemistry* Vols. 1-49 (*Journal of Heterocyclic Chemistry,* 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, $4^{th}$ Ed., Wiley & Sons, Inc., New York (2006).

The compound of Formula Ia can be synthesized according to the methods and procedures described, for example, in U.S. Pat. No. 6,127,415. The compound of Formula Ib can be synthesized according to the methods and procedures described, for example, in U.S. Pat. No. 5,602,104. The compound of Formula Ic can be synthesized according to the methods and procedures described, for example, in U.S. Pat. No. 8,101,793. The compound of Formula III can be synthesized according to the methods and procedures described, for example, in U.S. Pat. No. 4,200,738.

Compounds of Formula I can be synthesized according to methods and procedures analogous to those described in U.S. Pat. Nos. 6,127,415; 5,602,104; and 8,101,793; or compounds of Formula I can be readily prepared according to numerous methods and procedures available to one of ordinary skill in the art. Such methods and procedures can be found, for example, in Smith et al., March's Advanced Organic Chemistry: Reactions, Mechanisms, and Structure, 6th Ed. (Wiley, 2007). Suitable starting materials and intermediates are readily available from various commercial sources.

Methods

Inhibition of Bacterial Pathogens

The present application is directed to a method of killing or inhibiting growth of bacteria, the method comprising contacting the bacteria with an effective amount of a compound of Formulae I, Ia, Ib, Ic, IV, Formula II or Formula III described herein.

In some embodiments, the minimal inhibitory concentration (MIC) of a compound of any one of Formulae I, Ia, Ib, Ic or IV for killing or inhibiting growth of bacteria (e.g, any one of bacteria described herein) is from about 0.1 µg/ml to about 4 g/ml, from about 0.1 µg/ml to about 3 µg/ml, from about 0.1 µg/ml to about 4 µg/ml, from about 2 µg/ml, from about 0.25 µg/ml to about 4 µg/ml, from about 0.5 µg/ml to about 3 µg/ml, from about 0.5 µg/ml to about 2 µg/ml, or from about 1 µg/ml to about 2 µg/ml. In some embodiments, the minimal inhibitory concentration (MIC) of a compound of any one of Formulae I, Ia, Ib or Ic for killing or inhibiting growth of bacteria is about 0.25 µg/ml, about 0.5 µg/ml, about 1 µg/ml, about 1.5 µg/ml, about 2 µg/ml, about 3 µg/ml, or about 4 µg/ml.

In some embodiments, the minimal inhibitory concentration (MIC) of a compound of Formula III for killing or inhibiting growth of bacteria (e.g., any one of bacteria described herein) is from about 0.1 µg/ml to about 2 µg/ml, from about 0.25 µg/ml to about 1.5 µg/ml, or from about 0.25 µg/ml to about 1 µg/ml. In some embodiments, the minimal inhibitory concentration (MIC) of a compound of Formula III for killing or inhibiting growth of bacteria (e.g., any one of bacteria described herein) is about 0.25 µg/ml, about 0.5 µg/ml, about 1 µg/ml, about 1.5 µg/ml or about 2 µg/ml.

In some embodiments, the bacteria (e.g., any one of bacteria described herein) is resistant to one or more of other antibiotic agents (e.g., antibiotic agents disclosed herein). In some embodiments, the bacteria (e.g., any one of bacteria described herein) is at least 2-fold, 4-fold, 8-fold, 10-fold, 24-fold, 48-fold, 100-fold, 256-fold, 512-fold or 1000-fold resistant to one or more of other antibiotic agents (e.g., antibiotic agents disclosed herein). In some embodiments, the bacteria is multi-drug resistant (MDR). In some embodiments, any one of bacteria described herein is resistant to methicillin, vancomycin, rifampicin, linezolid, daptomycin, gentamicin and/or ciprofloxacin. In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to methicillin, vancomycin, rifampicin, linezolid, daptomycin, gentamicin and/or ciprofloxacin. In some embodiments, any one of bacteria described herein is resistant to an antibiotic selected from methicillin, vancomycin, rifampicin, gentamicin and ciprofloxacin. In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to an antibiotic selected from methicillin, vancomycin, rifampicin, gentamicin and ciprofloxacin. In some embodiments, any one of bacteria described herein is resistant to methicillin, vancomycin, rifampicin, gentamicin and ciprofloxacin. In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to methicillin, vancomycin, rifampicin, gentamicin and ciprofloxacin.

In some embodiments, the bacteria (e.g., any one of bacteria described herein) is not resistant to a compound of Formulae I, Ia, Ib, Ic, IV, Formula II or Formula III. In some embodiments, the bacteria (e.g., any one of bacteria described herein) is at most 1.5-fold resistant to a compound of Formulae I, Ia, Ib, Ic, IV, Formula II or Formula III. In some embodiments, the bacteria (e.g., any one of bacteria described herein) is at most 2-fold resistant to a compound of Formulae I, Ia, Ib, Ic, IV, Formula II or Formula III.

In some embodiments, any one of bacteria described herein is resistant to one or more of other antibiotic agents (e.g., antibiotic agents disclosed herein) and is not resistant to a compound of Formulae I, Ia, Ib, Ic, IV, Formula II or Formula III.

In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to one or more of other antibiotic agents (e.g., antibiotic agents disclosed herein) and at most 1.5-fold or at most 2-fold resistant to a compound of Formulae I, Ia, Ib, Ic, IV, Formula II or Formula III. In some embodiments, the bacteria is Gram-positive bacteria.

In some embodiments, the bacteria is a member of a genus selected from the group consisting of *Staphylococcus, Streptococcus, Peptococcus, Enterococcus*, and *Bacillus*.

In some embodiments, the bacteria is a member of *Staphylococcus* genus and the species of bacteria is selected from the group consisting of *S. aureus*, methicillin-resistant *S. aureus* (MRSA), vancomycin-resistant *S. aureus* (VRSA), *S. arlettae, S. agnetis, S. auricularis, S. capitis, S. caprae, S. carnosus, S. caseolyticus, S. chromogenes, S. cohnii, S. condimenti, S. delphini, S. devriesei, S. epidermidis, S. equorum, S. felis, S. fleurettii, S. gallinarum, S. haemolyticus, S. hominis, S. hyicus, S. intermedius, S. kloosii, S. leei, S. lentus, S. lugdunensis, S. lutrae, S. massiliensis, S. microti, S. muscae, S. nepalensis, S. pasteuri, S. pettenkoferi, S. piscifermentans, S. pseudintermedius, S. pseudolugdunensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus*.

In some embodiments, the bacteria is *S. aureus* which is resistant to an antibiotic selected from methicillin, vancomycin, rifampicin, linezolid, daptomycin, gentamicin and ciprofloxacin. In some embodiments, the bacteria is *S. aureus* which is at least 2-fold, at least 4-fold, at least 8-fold, at least 10-fold, at least 24-fold, at least 48-fold, at least 100-fold, at least 256-fold, at least 512-fold, or at least 1000-fold resistant to an antibiotic selected from methicillin, vancomycin, rifampicin, linezolid, daptomycin, gentamicin and ciprofloxacin.

In some embodiments, the bacteria is *S. aureus* which is resistant to an antibiotic selected from methicillin, vancomycin, rifampicin, gentamicin and ciprofloxacin. In some embodiments, the bacteria is *S. aureus* which is at least 2-fold, at least 4-fold, at least 8-fold, at least 10-fold, at least 24-fold, at least 48-fold, at least 100-fold, at least 256-fold, at least 512-fold, or at least 1000-fold resistant to an antibiotic selected from methicillin, vancomycin, rifampicin, gentamicin and ciprofloxacin.

In some embodiments, the bacteria is *S. aureus* which is resistant to methicillin, vancomycin, rifampicin, linezolid, daptomycin, gentamicin and ciprofloxacin. In some embodiments, the bacteria is *S. aureus* which is at least 2-fold, at least 4-fold, at least 8-fold, at least 10-fold, at least 24-fold, at least 48-fold, at least 100-fold, at least 256-fold, at least 512-fold, or at least 1000-fold resistant to methicillin, vancomycin, rifampicin, linezolid, daptomycin, gentamicin and ciprofloxacin.

In some embodiments, the bacteria is *S. aureus* which is resistant to methicillin, vancomycin, rifampicin, gentamicin and ciprofloxacin. In some embodiments, the bacteria is *S. aureus* which is at least 2-fold, at least 4-fold, at least 8-fold, at least 10-fold, at least 24-fold, at least 48-fold, at least 100-fold, at least 256-fold, at least 512-fold, or at least 1000-fold resistant to methicillin, vancomycin, rifampicin, gentamicin and ciprofloxacin.

In some embodiments, the bacteria is *S. aureus* which is resistant to an antibiotic selected from methicillin, vancomycin, rifampicin, linezolid, daptomycin, gentamicin and ciprofloxacin and not resistant to a compound of Formulae I, Ia, Ib, Ic, Formula II or Formula III. In some embodiments, the bacteria is *S. aureus* which is at least 2-fold, at least 4-fold, at least 8-fold, at least 10-fold, at least 24-fold, at least 48-fold, at least 100-fold, at least 256-fold, at least 512-fold, or at least 1000-fold resistant to an antibiotic selected from methicillin, vancomycin, rifampicin, linezolid, daptomycin, gentamicin and ciprofloxacin, and at most 2-fold resistant to a compound of Formulae I, Ia, Ib, Ic, Formula II or Formula III.

In some embodiments, the bacteria is *S. aureus* which is resistant to an antibiotic selected from methicillin, vancomycin, rifampicin, gentamicin and ciprofloxacin, and not resistant to a compound of Formulae I, Ia, Ib, Ic, Formula II or Formula III. In some embodiments, the bacteria is *S. aureus* which is at least 2-fold, at least 4-fold, at least 8-fold, at least 10-fold, at least 24-fold, at least 48-fold, at least 100-fold, at least 256-fold, at least 512-fold, or at least 1000-fold resistant to an antibiotic selected from methicillin, vancomycin, rifampicin, gentamicin and ciprofloxacin, and at most 2-fold resistant to a compound of Formulae I, Ia, Ib, Ic, IV, Formula II or Formula III.

In some embodiments, the bacteria is *S. aureus* which is resistant to methicillin, vancomycin, rifampicin, linezolid, daptomycin, gentamicin and ciprofloxacin, and not resistant to a compound of Formulae I, Ia, Ib, Ic, IV, Formula II or Formula III. In some embodiments, the bacteria is *S. aureus* which is at least 2-fold, at least 4-fold, at least 8-fold, at least 10-fold, at least 24-fold, at least 48-fold, at least 100-fold, at least 256-fold, at least 512-fold, or at least 1000-fold resistant to methicillin, vancomycin, rifampicin, linezolid, daptomycin, gentamicin and ciprofloxacin, and at most 2-fold resistant to a compound of Formulae I, Ia, Ib, Ic, IV, Formula II or Formula III.

In some embodiments, the bacteria is *S. aureus* which is resistant to methicillin, vancomycin, rifampicin, gentamicin and ciprofloxacin, and not resistant to a compound of Formulae I, Ia, Ib, Ic, IV, Formula II or Formula III. In some embodiments, the bacteria is *S. aureus* which is at least 2-fold, at least 4-fold, at least 8-fold, at least 10-fold, at least 24-fold, at least 48-fold, at least 100-fold, at least 256-fold, at least 512-fold, or at least 1000-fold resistant to methicillin, vancomycin, rifampicin, gentamicin and ciprofloxacin, and at most 2-fold resistant to a compound of Formulae I, Ia, Ib, Ic, IV, Formula II or Formula III.

In some embodiments, the bacteria is *S. aureus* which is at least 256-fold resistant to ciprofloxacin and at most 2-fold resistant to CD437. In some embodiments, the bacteria is methicillin-resistant *S. aureus* (MRSA) which is at least 256-fold resistant to ciprofloxacin and at most 2-fold resistant to CD437.

In some embodiments, the bacteria is a member of Peptococcus genus and the species of bacteria is *P. magnus*.

In some embodiments, the bacteria is a member of *Streptococcus* genus and the species of bacteria is selected from the group consisting of *S. agalactiae, S. anginosus, S. bovis, S. canis, S. constellatus, S. dysgalactiae, S. equinus, S. iniae, S. intermedius, S. milleri, S. mitis, S. mutans, S. oralis, S. parasanguinis, S. peroris, S. pneumoniae, S. pseudopneumoniae, S. pyogenes, S. ratti, S. salivarius, S. tigurinus, S. thermophilus, S. sanguinis, S. sobrinus, S. suis, S. uberis, S. vestibularis, S. viridans,* and *S. zooepidemicus*.

In some embodiments, the bacteria is a member of *Enterococcus* genus and the species of bacteria is selected from the group consisting of *E. avium, E. durans, E. faecalis, E. gallinarum, E. haemoperoxidus, E. hirae, E. malodoratus, E. moraviensis, E. mundtii, E. pseudoavium, E. raffinosus, E. solitaries,* and *E. faecium*.

In some embodiments, the bacteria is Gram-negative bacteria.

In some embodiments, the bacteria is a member of a family selected from the group consisting of Enterobacteriaceae, Helicobacteraceae, Campylobacteraceae, Neisseriaceae, Pseudomonadaceae, Moraxellaceae, Xanthomonadaceae, Pasteurellaceae, and Legionellaceae.

In some embodiments, the bacteria is a member of a genus selected from the group consisting of *Citrobacter, Enterobacter, Escherichia, Klebsiella, Pantoea, Proteus, Salmonella, Serratia, Shigella, Yersinia, Helicobacter, Wolinella, Campylobacter, Arcobacter, Neisseria, Francisella, Pseudomonas, Acinetobacter, Moraxella, Stenotrophomonas, Haemophilus, Pasteurella,* and *Legionella*.

In some embodiments, the bacteria is a member of *Citrobacter* genus and the species of bacteria is selected from the group consisting of *C. amalonaticus, C. braakii, C. diversus, C. farmer, C. freundii, C. gillenii, C. koseri, C. murliniae, C. rodentium, C. sedlakii, C. werkmanii,* and *C. youngae*.

In some embodiments, the bacteria is a member of *Enterobacter* genus and the species of bacteria is selected from the group consisting of *E. aerogenes, E. amnigenus, E. agglomerans, E. arachidis, E. asburiae, E. cancerogenous, E. cloacae, E. cowanii, E. dissolvens, E. gergoviae, E. helveticus, E. hormaechei, E. intermedius, E. kobei, E. ludwigii, E. mori, E. nimipressuralis, E. oryzae, E. pulveris, E. pyrinus, E. radicincitans, E. taylorae, E. turicensis, E. sakazakii,* and *E.* spp.

In some embodiments, the bacteria is a member of *Escherichia* genus and the species of bacteria is selected from the group consisting of *E. albertii, E. blattae, E. coli, E. fergusonii, E. hermannii,* and *E. vulneris*.

In some embodiments, the bacteria is a member of *Klebsiella* genus and the species of bacteria is selected from the group consisting of *K. granulomatis, K. oxytoca, K. pneumoniae, K. terrigena,* and *K. planticola*.

In some embodiments, the bacteria is a member of *Pantoea* genus and the species of bacteria is selected from the group consisting of *P. agglomerans, P. ananatis, P. citrea, P. dispersa, P. punctata, P. stewartii, P. terrea,* and *P. vagans*.

In some embodiments, the bacteria is a member of *Proteus* genus and the species of bacteria is selected from the group consisting of *P. hauseri, P. mirabilis, P. myxofaciens, P. penneri,* and *P. vulgaris*.

In some embodiments, the bacteria is a member of *Salmonella* genus and the species of bacteria is selected from the group consisting of *S. bongori,* and *S. enterica*.

In some embodiments, the bacteria is a member of *Serratia* genus and the species of bacteria is selected from the group consisting of *S. entomophila, S. ficaria, S. fonticola, S. grimesii, S. liquefaciens, S. marcescens, S. odorifera, S. plymuthica, S. proteamaculans, S. quinivorans, S. rubidaea,* and *S. symbiotica*.

In some embodiments, the bacteria is a member of *Shigella* genus and the species of bacteria is selected from the group consisting of *S. boydii, S. dysenteriae, S. flexneri,* and *S. sonnei*.

In some embodiments, the bacteria is a member of *Yersinia* genus and the species of bacteria is selected from the group consisting of *Y. pestis, Y. pseudotuberculosis,* and *Y. enterocolitica*.

In some embodiments, the bacteria is a member of *Helicobacter* genus and the species of bacteria is selected from the group consisting of *H. acinonychis, H. anseris, H. aurati, H. baculiformis, H. bilis, H. bizzozeronii, H. brantae, H. canadensis, H. canis, H. cetorum, H. cholecystus, H. cinaedi, H. cynogastricus, H. equorum, H. felis, H. fennelliae, H. ganmani, H. heilmannii, H. hepaticus, H. mesocricetorum, H. macacae, H. marmotae, H. mastomyrinus, H. mesocricetorum, H. muridarum, H. mustelae, H. pametensis, H. pullorum, H. pylori, H. rappini, H. rodentium, H. salomonis, H. suis, H. trogontum, H. typhlonius,* and *H. winghamensis*.

In some embodiments, the bacteria is a member of *Campylobacter* genus and the species of bacteria is selected from the group consisting of *C. avium, C. butzleri, C. canadensis, C. cinaedi, C. coli, C. concisus, C. corcagiensis, C. cryaerophilus, C. cuniculorum, C. curvus, C. fennelliae, C. fetus, C. gracilis, C. helveticus, C. hominis, C. hyoilei, C. hyointestinalis, C. insulaenigrae, C. jejuni, C. lanienae, C. lari, C. mucosalis, C. mustelae, C. nitrofigilis, C. peloridis, C. pylori, C. rectus, C. showae, C. sputorum, C. subantarcticus, C. upsaliensis, C. ureolyticus,* and *C. volucris*.

In some embodiments, the bacteria is a member of Arcobacter genus and the species of bacteria is selected from the group consisting of *A. bivalviorum, A. butzleri, A. cibarius, A. cryaerophilus, A. defluvii, A. ellisii, A. halophilus, A. marinus, A. molluscorum, A. mytili, A. nitrofigilis, A. skirrowii, A. thereius, A. trophiarum,* and *A. venerupis*.

In some embodiments, the bacteria is a member of *Neisseria* genus and the species of bacteria is selected from the group consisting of *N. bacilliformis, N. cinerea, N. denitriicans, N. elongata, N. flavescens, N. gonorrhoeae, N. lactamica, N. macacae, N. meningitidis, N. mucosa, N. pharyngis, N. polysaccharea, N. sicca, N. subflava,* and *N. weaver*.

In some embodiments, the bacteria is a member of *Francisella* genus and the species of bacteria is selected from the group consisting of *F. tularensis, F. novicida, F. hispaniensis, W. persica, F. noatunensis, F. philomiragia, F. halioticida, F. endociliophora,* and *F. guangzhouensis*.

In some embodiments, the bacteria is a member of *Pseudomonas* genus and the species of bacteria is selected from the group consisting of *P. aeruginosa, P. oryzihabitans,* and *P. plecoglossicida*.

In some embodiments, the bacteria is a member of *Acinetobacter* genus and the species of bacteria is *A. baumannii*.

In some embodiments, the bacteria is a member of *Moraxella* genus and the species of bacteria is selected from the group consisting of *M. catarrhalis, M. lacunata*, and *M. bovis*.

In some embodiments, the bacteria is a member of *Stenotrophomonas* genus and the species of bacteria is *S. maltophilia*.

In some embodiments, the bacteria is a member of *Haemophilus* genus and the species of bacteria is selected from the group consisting of *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, Haemophilus segnis*, and *H. somnus*.

In some embodiments, the bacteria is a member of *Pasteurella* genus and the species of bacteria is selected from the group consisting of *P. multocida, P. stomatis, P. dagmatis, P. canis, P. bettyae*, and *P. anatis*.

In some embodiments, the bacteria is a member of *Legionella* genus and the species of bacteria is selected from the group consisting of *L. pneumophila, L. anisa, L. bozemanae, L. cincinnatiensis, L. gormanii, L. jordani, L. longbeachae, L. maceachernii, L. micdadei, L. sainthelensi, L. wadsworthii*, and *L. waltersii*.

In some embodiments, the bacteria is a member of *Mycobacterium* genus and the species of bacteria is selected from a group consisting of *M. tuberculosis* and *M. smegmatic*.

The present application is also directed to a method of killing or inhibiting growth of bacteria (e.g., any bacteria described herein), the method comprising the steps of:

(i) determining that the bacteria is resistant (e.g., least 2-fold, at least 4-fold, at least 8-fold, at least 10-fold, at least 24-fold, at least 48-fold, at least 100-fold, at least 256-fold, at least 512-fold, or at least 1000-fold resistant) to one or more other antibiotic agents (e.g., any one of antibiotic agents described herein); and (ii) contacting the bacteria with an effective amount of a compound of Formulae I, Ia, Ib, Ic, IV, Formula II or Formula III described herein.

In some embodiments, the present application is directed to a method of killing or inhibiting growth of bacteria, the method comprising contacting the bacteria with an effective amount of a compound of Formulae I, Ia, Ib, Ic or IV described herein. In some aspects of these embodiments, the bacteria is a member of a genus selected from the group consisting of *Staphylococcus, Streptococcus, Peptococcus, Enterococcus*, and *Bacillus*. In some aspects of these embodiments, the bacteria is a member of a genus selected from the group consisting of *Staphylococcus, Enterococcus*, and *Bacillus*. In some aspects of these embodiments, the bacteria is a member of a species selected from the group consisting of *S. aureus*, methicillin-resistant *S. aureus* (MRSA), vancomycin-resistant *S. aureus* (VRSA), *E. faecalis, E. faecium, B. subtilis*, and *B. anthracis*.

In some embodiments, the present application is directed to a method of killing or inhibiting growth of bacteria, the method comprising contacting the bacteria with an effective amount of a compound of Formula II described herein. In some aspects of these embodiments, the bacteria is a member of a genus selected from the group consisting of *Staphylococcus, Enterococcus, Enterobacter, Klebsiella, Pseudomonas*, and *Acinetobacter*. In some aspects of these embodiments, the bacteria is a member of a species selected from the group consisting of *S. aureus*, methicillin-resistant *S. aureus* (MRSA), vancomycin-resistant *S. aureus* (VRSA), *E.* spp., *K. pneumoniae, P. aeruginosa, A. baumannii, E. faecium*, and *E. faecalis*.

In some embodiments, the present application is directed to a method of killing or inhibiting growth of bacteria, the method comprising contacting the bacteria with an effective amount of a compound of Formula III as described herein. In some aspects of these embodiments, the bacteria is any one of family, genus or species of bacteria described herein. In some aspects of these embodiments, the bacteria is *S. aureus*, methicillin-resistant *S. aureus* (MRSA), *S. epidermidis*, or *E. coli*. In some aspects of these embodiments, the bacteria is any one of bacteria described, for example, in Cassetta et al., Drug repositioning: auranofin as a prospective antimicrobial agent for the treatment of severe staphylococcal infections, Biometals, 2014, 27(4), 787-791, the disclosure of which is incorporated herein by reference in its entirety. In other aspects of these embodiments, the bacteria is any one of bacteria described, for example, in Fuchs et al., Inhibition of bacterial and fungal pathogens by the orphaned drug auranofin, *Future Med. Chem.*, 2016, 8(2), 117-132, the disclosure of which is incorporated herein by reference in its entirety. In other aspects of these embodiments, the bacteria is resistant to vancomycin and/or oxacillin; or the bacteria is resistant to chloramphenicol and/or vancomycin. In other aspects of these embodiments, the bacteria is resistant to vancomycin, oxacillin, and/or chloramphenicol. In other aspects of these embodiments, the bacteria is *S. aureus* that is resistant to vancomycin and/or oxacillin. In other aspects of these embodiments, the bacteria is methicillin-resistant *S. aureus* (MRSA) that is also resistant to vancomycin and/or oxacillin. In other aspects of these embodiments, the bacteria is *E. faeicium* (that may be resistant to chloramphenicol and/or oxacillin). In other aspects of these embodiments, the bacteria is *A. baumannii*. In other aspects of these embodiments, the bacteria is *E. faeicium*. In other aspects of these embodiments, the bacteria is *B. subtilis, K. pneumonia, P. aeruginosa*, or *Enterobacter*. In yet other aspects of these embodiments, the bacteria is a member of a species selected from the group consisting of *S. aureus*, methicillin-resistant *S. aureus* (MRSA), vancomycin-resistant *S. aureus* (VRSA), *E.* spp., *K. pneumoniae, P. aeruginosa, A. baumannii, E. faecium*, and *E. faecalis*.

The present application is also directed to a method of treating a bacterial infection in a subject, the method comprising administering to the subject in need thereof a therapeutically effective amount of a compound of Formulae I, Ia, Ib, Ic, Formula II or Formula III as described herein. In some embodiments, the bacterial infection is resistant to treatment by one or more other antibiotic agents (e.g., any one of antibiotic agents described herein).

The present application is also directed to a method of treating a bacterial infection in a subject, the method comprising the steps of:

(i) determining that the bacterial infection is resistant (e.g., least 2-fold, at least 4-fold, at least 8-fold, at least 10-fold, at least 24-fold, at least 48-fold, at least 100-fold, at least 256-fold, at least 512-fold, or at least 1000-fold resistant) to treatment with one or more other antibiotic agents (e.g., any one of antibiotic agents described herein); and (ii) administering to the subject (e.g., in need of such treatment) a therapeutically effective amount of a compound of Formulae I, Ia, Ib, Ic, IV, Formula II or Formula III as described herein.

In some embodiments, the bacterial infection is caused by any bacteria disclosed herein (e.g., bacteria of any family, genus, or species described herein).

In some embodiments, the bacterial infection resistant (e.g., least 2-fold, at least 4-fold, at least 8-fold, at least 10-fold, at least 24-fold, at least 48-fold, at least 100-fold, at least 256-fold, at least 512-fold, or at least 1000-fold resistant) to treatment by an antibiotic selected from methicillin, vancomycin, rifampicin, linezolid, daptomycin, gentamicin and ciprofloxacin.

In some embodiments, the bacterial infection is resistant (e.g., at least 2-fold, at least 4-fold, at least 8-fold, at least 10-fold, at least 24-fold, at least 48-fold, at least 100-fold, at least 256-fold, at least 512-fold, or at least 1000-fold resistant) to treatment by an antibiotic selected from methicillin, vancomycin, rifampicin, gentamicin and ciprofloxacin.

In some embodiments, the bacterial infection resistant (e.g., at least 2-fold, at least 4-fold, at least 8-fold, at least 10-fold, at least 24-fold, at least 48-fold, at least 100-fold, at least 256-fold, at least 512-fold, or at least 1000-fold resistant) to treatment with methicillin, vancomycin, rifampicin, linezolid, daptomycin, gentamicin and ciprofloxacin.

In some embodiments, the bacterial infection is resistant (e.g., at least 2-fold, at least 4-fold, at least 8-fold, at least 10-fold, at least 24-fold, at least 48-fold, at least 100-fold, at least 256-fold, at least 512-fold, or at least 1000-fold resistant) to treatment with methicillin, vancomycin, rifampicin, gentamicin and ciprofloxacin.

In some embodiments, the bacterial infection is caused by *S. aureus* and is resistant (e.g., least 2-fold, at least 4-fold, at least 8-fold, at least 10-fold, at least 24-fold, at least 48-fold, at least 100-fold, at least 256-fold, at least 512-fold, or at least 1000-fold resistant) to treatment with an antibiotic selected from methicillin, vancomycin, rifampicin, linezolid, daptomycin, gentamicin and ciprofloxacin.

In some embodiments, the bacterial infection is caused by *S. aureus* and is resistant (e.g., at least 2-fold, at least 4-fold, at least 8-fold, at least 10-fold, at least 24-fold, at least 48-fold, at least 100-fold, at least 256-fold, at least 512-fold, or at least 1000-fold resistant) to treatment with an antibiotic selected from methicillin, vancomycin, rifampicin, gentamicin and ciprofloxacin.

In some embodiments, the bacterial infection is caused by *S. aureus* and is resistant (e.g., at least 2-fold, at least 4-fold, at least 8-fold, at least 10-fold, at least 24-fold, at least 48-fold, at least 100-fold, at least 256-fold, at least 512-fold, or at least 1000-fold resistant) to treatment with methicillin, vancomycin, rifampicin, linezolid, daptomycin, gentamicin and ciprofloxacin.

In some embodiments, the bacterial infection is caused by *S. aureus* and is resistant (e.g., at least 2-fold, at least 4-fold, at least 8-fold, at least 10-fold, at least 24-fold, at least 48-fold, at least 100-fold, at least 256-fold, at least 512-fold, or at least 1000-fold resistant) to treatment with methicillin, vancomycin, rifampicin, gentamicin and ciprofloxacin.

In some embodiments, the bacterial infection is a skin infection. In some aspects of these embodiments, the skin infection is selected from the group consisting of pimples, impetigo, boils, cellulitis, folliculitis, carbuncles, scalded skin syndrome, skin abscesses, atopic dermatitis, and typhoid fever.

In some embodiments, the bacterial infection is a respiratory infection. In some aspects of these embodiments, the respiratory infection is selected from the group consisting of upper respiratory tract infection, bronchopneumonia, atypical pneumonia, tuberculosis, *Mycobacterium tuberculosis*, pneumonia, anaerobic pleuropulmonary infection, ventilator-associated pneumonia, aspiration pneumonia, lung abscess, bronchitis, chronic obstructive pulmonary disease, obstructive pulmonary disease, Pontiac fever, and legionellosis.

In some embodiments, the bacterial infection is a wound infection. In some aspects of these embodiments, the wound infection is a postsurgical wound infection.

In some embodiments, the bacterial infection is a blood stream infection. In some aspects of these embodiments, the blood stream infection is bacteremia.

In some embodiments, the bacterial infection is a pelvic infection. In some aspects of the embodiments, the pelvic infection is bacterial vaginosis.

In some embodiments, the bacterial infection is a gastrointestinal infection. In some aspects of these embodiments, the gastrointestinal infection is selected from the group consisting of peptic ulcer, chronic gastritis, duodenitis, gastroenteritis, diarrhea, dysentery, diphtheria, and foodborne illness.

In some embodiments, the bacterial infection is a bone, joint or muscle infection.

In some aspects of these embodiments, the bone, joint or muscle infection is selected from the group consisting of tetanus, secondary meningitis, meningitis, neonatal meningitis, sinusitis, laryngitis, arthritis, septic arthritis, Bartholin gland abscess, chancroid, osteomyelitis, endocarditis, mediastinitis, pericarditis, peritonitis, otitis media, blepharoconjunctivitis, keratoconjunctivitis, and conjunctivitis.

In some embodiments, the bacterial infection is selected from the group consisting of a dental infection, a zoonotic infection, an invasive systemic infection, a urinary tract infection, an abdominal infection, a CNS infection, an endovascular infection, and a nosocomial infection.

In some embodiments, the bacterial infection is selected from the group consisting of syphilis, leprosy, abscesses, sepsis, empyema, and tularemia.

In some embodiments, the bacterial infection is characterized as persistent to treatment with one or more other antibiotic agents.

In some embodiments, the bacterial infection is associated with implanted devices (e.g., catheter, ballon catheter, stent, pacer etc) In some embodiments, the bacterial infection is osteomyelitis, endocarditis, or an infection associated with an implanted device, which is caused by a *S. aureus* persister.

In some embodiments, the present application is directed to a method of treating a bacterial infection in a subject, the method comprising administering to the subject in need thereof a therapeutically effective amount of a compound of Formulae I, Ia, Ib, Ic or IV described herein. In some aspects of these embodiments, wherein the bacterial infection is caused by the bacteria of a genus selected from the group consisting of *Staphylococcus, Streptococcus, Peptococcus, Enterococcus*, and *Bacillus*. In some aspects of these embodiments, the bacteria selected from the group consisting of *Staphylococcus, Enterococcus*, and *Bacillus*. In some aspects of these embodiments, the bacterial infection is caused by the bacteria of a species selected from the group consisting of *S. aureus*, methicillin-resistant *S. aureus* (MRSA), vancomycin-resistant *S. aureus* (VRSA), *E. faecalis, E. faecium, B. subtilis*, and *B. anthracis*. In some aspects of these embodiments, the bacterial infection is selected from the group consisting of nosocomial infection, skin infection, respiratory infection, wound infection, endovascular infection, CNS infection, abdominal infection, blood stream infection, urinary tract infection, pelvic infection, invasive systemic infection, gastrointestinal infection, dental infection, zoonotic infection, and connective tissue infection.

In some embodiments, the present application is directed to a method of treating a bacterial infection in a subject, the method comprising administering to the subject in need thereof a therapeutically effective amount of a compound of Formula II described herein. In some aspects of these embodiments, the bacterial infection is caused by the bacteria of a genus selected from the group consisting of *Staphylococcus, Enterococcus, Enterobacter, Klebsiella, Pseudomonas*, and *Acinetobacter*. In some aspects of these embodiments, the bacterial infection is caused by the bacteria of a species selected from the group consisting of *S. aureus*, methicillin-resistant *S. aureus* (MRSA), vancomycin-resistant *S. aureus* (VRSA), *E.* spp., *K. pneumoniae, P. aeruginosa, A. baumannii, E. faecium*, and *E. faecalis*. In some aspects of these embodiments, the bacterial infection is selected from the group consisting of nosocomial infection, skin infection, respiratory infection, wound infection, endovascular infection, CNS infection, abdominal infection, blood stream infection, urinary tract infection, pelvic infection, invasive systemic infection, gastrointestinal infection, dental infection, zoonotic infection, and connective tissue infection.

Inhibition of Fungal Pathogens

The present application is also directed to a method of killing or inhibiting the growth of a fungal pathogen, the method comprising contacting the fungal pathogen with an effective amount of a compound of Formula III described herein.

In some embodiments, the fungal pathogen is a member of a family selected from the group consisting of Saccharomycetaceae, Trichocomaceae, Arthrodermataceae, Ajellomycetaceae, Pneumocystidaceae, Incertce sedis, Tremellaceae, Onygenaceae, Herpotrichiellaceae, Cunninghamellaceae, Teratosphaeriaceae, Herpotrichiellaceae, Malasseziaceae, and Microascaceae.

In some embodiments, the fungal pathogen is a member of a genus selected from the group consisting of *Candida, Trichophyton, Aspergillus, Microsporum, Blastomyces, Histoplasma, Pneumocystis, Rhodotorula, Madurella, Cryptococcus, Coccidioides, Cladophialophora, Cunninghamella, Hortaea, Fonsecaea, Malassezia, Scedosporium*, and *Scopulariopsis*.

In some embodiments, the fungal pathogen is a member of *Candida* genus and the species of a fungal pathogen is selected from the group consisting of *C. albicans, C. ascalaphidarum, C. amphixiae, C. antarctica, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermedia, C. jeffresii, C. kefyr, C. keroseneae, C. krusei, C. lusitaniae, C. lyxosophila, C. maltosa, C. marina, C. membranifaciens, C. milleri, C. mogii, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis, C. ubatubensis*, and *C. zemplinina*.

In some embodiments, the fungal pathogen is a member of *Candida* genus and the species of a fungal pathogen is selected from the group consisting of *C. albicans, C. krusei, C. glabrata, C. parapsilosis, C. tropicalis, C. pseudotropicalis, C. guilliermondii, C. dubliniensis*, and *C. lusitaniae*.

In some embodiments, the fungal pathogen is a member of *Trichophyton* genus and the species of a fungal pathogen is selected from the group consisting of *T. ajelloi, T. concentricum, T. equinum, T. flavescens, T. gloriae, T. megnini, T. mentagrophytes, T. mentagrophytes, T. onychocola, T. phaseoliforme, T. redellii, T. rubrum, T. rubrum* downy strain, *T. rubrum* granular strain, *T. schoenleinii, T. simii, T. soudanense, T. terrestre, T. tonsurans, T. vanbreuseghemii, T. verrucosum, T. violaceum*, and *T. yaoundei*.

In some embodiments, the fungal pathogen is a member of *Aspergillus* genus and the species of a fungal pathogen is selected from the group consisting of *A. fumigatus, A. flavus*, and *A.* spp.

In some embodiments, the fungal pathogen is a member of *Microsporum* genus and the species of a fungal pathogen is selected from the group consisting of *M. amazonicum, M. audouinii, M. boullardii, M. canis, M. canis, M. cookei, M. distortum, M. duboisii, M. equinum, M. ferrugineum, M. fulvum, M. gallinae, M. gypseum, M. langeronii, M. nanum, M. persicolor, M. praecox, M. ripariae*, and *M. rivalieri*.

In some embodiments, the fungal pathogen is a member of *Epidermophyton* genus and the species of a fungal pathogen is selected from the group consisting of *E. floccosum* and *E. stockdaleae*.

In some embodiments, the fungal pathogen is a member of *Blastomyces* genus and the species of a fungal pathogen is *B. dermatitidis*.

In some embodiments, the fungal pathogen is a member of *Histoplasma* genus and the species of a fungal pathogen is selected from the group consisting of *H. capsulatum* and *H. duboisii*.

In some embodiments, the fungal pathogen is a member of *Pneumocystis* genus and the species of a fungal pathogen is *P. jirovecii*.

In some embodiments, the fungal pathogen is a member of *Rhodotorula* genus and the species of a fungal pathogen is selected from the group consisting of *R. glutinis, R. minuta*, and *R. mucilaginosa*

In some embodiments, the fungal pathogen is a member of Madurella genus and the species of a fungal pathogen is *M. grisea*.

In some embodiments, the fungal pathogen is a member of *Cryptococcus* genus and the species of a fungal pathogen is selected from the group consisting of *C. neoformans, C. gattii, C. albidus*, and *C. uniguttulatus*.

In some embodiments, the fungal pathogen is a member of *Coccidioides* genus and the species of a fungal pathogen is selected from the group consisting of *C. immitis*, and *C. posadasii*.

In some embodiments, the fungal pathogen is a member of *Cladophialophora* genus and the species of a fungal pathogen is selected from the group consisting of *C. bantiana*.

In some embodiments, the fungal pathogen is a member of Cunninghamella genus and the species of a fungal pathogen is *C. africana*.

In some embodiments, the fungal pathogen is a member of *Hortaea* genus and the species of a fungal pathogen is *H. werneckili*.

In some embodiments, the fungal pathogen is a member of *Fonsecaea* genus and the species of a fungal pathogen is *F. pedrosoi*.

In some embodiments, the fungal pathogen is a member of *Malassezia* genus and the species of a fungal pathogen is selected from the group consisting of *M. restricta, M. globose, M. dermatis*, and *M. pachydermatis*.

In some embodiments, the fungal pathogen is a member of *Scedosporium* genus and the species of a fungal pathogen is *S. prolificans*.

In some embodiments, the fungal pathogen is a member of *Microascus* genus and the species of a fungal pathogen is *M. brevicaulis*.

In some embodiments, the present application is directed to a method of killing or inhibiting the growth of a fungal pathogen, the method comprising contacting the fungal pathogen with an effective amount of a compound of Formula III described herein. In some aspects of these embodiments, the fungal pathogen is a member of a genus selected from the group consisting of *Candida, Aspergillus, Blastomyces, Cryptococcus, Histoplasma*, and *Pneumocystis*. In some aspects of these embodiments, the fungal pathogen is a member of a genus selected from the group consisting of *Candida* and *Cryptococcus*. In some aspects of these embodiments, the fungal pathogen is a member of a species selected from the group consisting of *C. albicans, C. parapsilosis, C. tropicalis, C. glabrata*, and *C. neoformans*.

In some embodiments, the minimal inhibitory concentration (MIC) of a compound of Formula III for inhibiting growth of a fungal pathogen (e.g., *C. neoformans, C. albicans, C. glabrata, C. tropicalis*) is from about 0.1 µg/ml to about 50 µg/ml, from about 0.25 µg/ml to about 16 µg/ml, from about 0.25 µg/ml to about 32 µg/ml, from about 0.5 µg/ml to about 20 µg/ml, from about 0.5 µg/ml to about 12 µg/ml, from about 1 µg/ml to about 20 µg/ml, or from about 2 µg/ml to about 8 µg/ml. In some embodiments, the minimal inhibitory concentration (MIC) of a compound of Formula III for inhibiting growth of a fungal pathogen (e.g., *C. neoformans, C. albicans, C. glabrata, C. tropicalis*) is about 0.1 µg/ml, 0.125 µg/ml, about 0.25 µg/ml, about 0.5 µg/ml, about 1 µg/ml, about 2 µg/ml, about 4 µg/ml, about 8 µg/ml, about 16 µg/ml, or about 32 µg/ml.

In some embodiments, fungal pathogen is resistant to amphotericin B and/or azole drugs. In some embodiments, the fungal pathogen is resistant to fluconazole (e.g., fluconazole-resistant strains of *C. glabrata, C. parapsilosis, C. tropicalis*). In some embodiments, the fungal pathogen is at least 2-fold-resistant to fluconazole and/or amphotericin B (e.g., 4-fold, 8-fold, 10-fold, 24-fold, 48-fold, 100-fold, 256-fold or 1000-fold resistant to fluconazole and/or amphotericin B). The present application is also directed to a method of treating a fungal infection in a subject, the method comprising administering to the subject in need thereof a therapeutically effective amount of a compound of Formula III described herein.

In some embodiments, the fungal infection is caused by any one of the fungal pathogens disclosed herein (e.g., fungal pathogen of any family, genus, or species described herein).

In some embodiments, the fungal infection is a skin infection. In some aspects of these embodiments, the skin infection is selected from the group consisting of intertrigo, balanitis, seborrhoeic dermatitis, dandruff and generalized candidiasis.

In some embodiments, the fungal infection is an infection of a mucous membrane.

In some aspects of these embodiments, the infection of a mucous membrane is selected from the group consisting of thrush, esophagitis, and vaginitis.

In some embodiments, the fungal infection is a blood stream infection. In some aspects of the embodiments, the blood stream infection is candidemia.

In some embodiments, the fungal infection is a deep organ infection. In some aspects of these embodiments, the deep organ infection is selected from the group consisting of hepatosplenic candidiasis, urinary tract candidiasis, arthritis, endocarditis, and endophthamitis.

In some embodiments, the fungal infection is selected from the group consisting of candidosis, moniliasis, oidiomycosis, sporotrichosis, pneumocystis pneumonia, mucormycosis, histoplasmosis, fungal eye infections, keratitis, endophthalmitis, allergic bronchopulmonary aspergillosis, allergic aspergillus sinusitis, aspergillus sinusitis, bronchopulmonary aspergillosis, aspergilloma, chronic pulmonary aspergillosis, invasive aspergillosis, cutaneous aspergillosis, coccidioidomycosis, cryptococcal meningitis, *C. gattii* cryptococcosis, histoplasmosis, zygomycosis, tinea capitis, tinea corpus, dermatophytoses, athlete's foot, ringworm, jock itch, tinea corporis, onychomycosis, tinea unguium, blastomycosis, tinea nigra, chromoblastomycosis, and eumycetoma.

In some embodiments, the compound of Formula III is effective at inhibiting laboratory reference strains. In some embodiments, the compound of Formula III is effective at inhibiting clinical isolates of *C. tropicalis, C. glabrata*, and *C. neoformans*.

In some embodiments, a compound of any one of Formulae I, Ia, Ib, Ic, II or III is effective at killing or inhibiting bacterial growth on a surface. In some aspects of these embodiments, the surface is a floor, a table, a kitchen counter, a cutting board, or a medical instrument. In some embodiments, a compound of Formula III is effective at killing or inhibiting growth of a fungal pathogen on a surface. In some aspects of these embodiments, the surface is a floor, a table, a kitchen counter, a cutting board, or a medical instrument.

Compositions and Formulations

The present application also provides pharmaceutical compositions comprising an effective amount of a compound of any one of Formulae I, Ia, Ib, Ic, IV, II, and III, or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

If required, the solubility and bioavailability of the compounds of the present application in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of the present application optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the present application include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, the compound any one of Formulae I, Ia, Ib, Ic, IV, II, and III is administered orally. Compositions of the present application suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031.

Topical administration of the pharmaceutical compositions of the present application is especially useful when the desired treatment involves areas or organs readily accessible by topical application.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form.

In some embodiments, the topical composition comprises a combination of a compound of any one of Formulae I, Ia, Ib, Ic, IV, II, and III, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

Lists of ingredients, which are well known in the art, are disclosed, for example, in "Cosmetics: Science and Technology," edited by M. S. Balsam and E. Sagarin, 2nd Edition, 1972, Wiley Pub. Co.; "The Chemistry and Manufacture of Cosmetics" by M. G. DeNavasse; and "Harry's Cosmeticology," J. B. Wilkinson et al., 7th Edition, 1982, Chem. Pub. Co.; the disclosures of each of the above being incorporated herein by reference in their entirety. In some embodiments, diluents, carriers, and excipients may include, but are not limited to, polyethylene glycols (such as PEG200, PEG300, PEG400, PEG540, PEG600, PEG1450 or mixtures thereof) and coconut oils (such as propylene glycol dicaprate, coco-caprylate/caprate, propylene glycol dicaprylate/dicaprate, caprylic/capric triglyceride, caprylic/capric/lauric triglyceride, caprylic/capric/linoleic triglyceride, tricaprin, tricaprylin, glyceryl trioleate, neopentyl glycol dicaprylate/dicaprate, caprylic/capric/palmitic/stearic triglceride, or mixtures thereof). In some embodiments, suitable carriers include, but are not limited to, mineral oil, sorbitan monostearate, polysorbate 60, cetyl esters wax, cetearyl alcohol, 2-octyldodecanol, benzyl alcohol, and water. In some embodiments, preservatives may include, but are not limited to, 1,2-hexanediol, benzoic acid, benzothonium chloride, borax, bronopol, butylparaben, caprylyl glycol, chlorophene, chloroxylenol, chlorphenesin, dehydroacetic acid, diazolidinyl urea, DMDM hydantoin, ethylhexylglycerin, ethylparaben, formaldehyde-releasing preservative, Germaben II, hoelen, imidazolidinyl urea, iodopropynyl butylcarbamate, isobutylparaben, methylchloroisothiazolinone, methyldibromo glutaronitrile, Methylisothiazolinone, methylparaben, o-cymen-5-ol, phenoxyethanol, phenoxyisopropanol, phytosphingosine, polyaminopropyl biguanide, potassium sorbate, propylparaben, quaternium-15, sodium benzoate, sodium citrate, sodium dehydroacetate, sodium hexametaphosphate, sodium hydroxymethylglycinate, sodium lactobionate, sodium metabisulfite, sodium sulfite, sorbic acid, and styrax benzoin. In some embodiments, slip agents may include, but are not limited to, amodimethicone, bis-PEG-18 methyl ether dimethyl silane, bis-phenylpropyl dimethicone, butylene glycol, cetyl dimethicone, cetyl dimethicone copolyol, cetyl PEG/PPG-10/1-dimethicone, cyclohexasiloxane, cyclomethicone, cyclopentasiloxane, cyclotetrasiloxane, decylene glycol, diisostearoyl trimethylolpropane siloxy silicate, dimethicone, dimethicone copolyol, dimethicone crosspolymer, dimethiconol, dipropylene glycol, hexylene glycol, hydrolyzed silk, isododecane, methicone, methyl trimethicone, methylsilanol mannuronate, methylsilanol PEG-7 glyceryl cocoate, PEG-10 dimethicone, PEG-10 dimethicone/vinyl dimethicone crosspolymer, PEG-12 dimethicone, PEG/PPG-18/18 dimethicone, PEG/PPG-20/15 dimethicone, pentylene glycol, phenyl trimethicone, polymethylsilsesquioxane, PPG-3 benzyl ether myristate, silica dimethyl silylate, silk powder, siloxane, simethicone, sorbitol, stearyl dimethicone, stearyl methicone, triethoxycaprylylsilane, trimethylsiloxysilicate, xylitol, and zinc stearate. In some embodiments, sunscreen actives may include, but are not limited to, avobenzone, benzephenone-3, benzophenones, bumetrizole, butyl methoxydibenzoylmethane, ecamsule, ensulizole, ethylhexyl methoxycinnamate, homosalate, menthyl anthranilate, meradmiate, Mexoryl SX, octinoxate, octisalate, octocrylene, octyl methoxycinnamate, octyl salicylate, oxybenzone, padimate 0, para-aminobenzoic acid (PABA), Parsol 1789, terephthalylidine dicamphor sulfonic acid, Tinosorb M, Tinosorb S, and titanium dioxide. In some embodiments, emulsifiers, surfactants, and detergents may include, but are not limited to, ammonium laureth sulfate, ammonium lauryl sulfate, arachidyl glucoside, behenic acid, bis-PEG-18 methyl ether dimethyl silane, $C_{20-40}$ pareth-40, cocamidopropyl betaine, cocamidopropyl dimethylamine, cocamidopropyl hydroxysultaine, coco-glucoside, coconut oil, decyl glucoside, dicetyl phosphate, dihydrocholeth-30, disodium cocoamphodiacetate, disodium cocoyl glutamate, disodium lauraminopropionate, glyceryl behanate, hydrogenated vegetable glycerides citrate, isohexadecane, isostearamide DEA, lauramphocarboxyglycinate, laureth-23, laureth-4, laureth-7, lauryl PEG-9 polydimethylsiloxyethyl dimethicone, lauryl alcohol, lauryl glucoside, magnesium laureth sulfate, magnesium oleth sulfate, myristic acid, nonoxynols, oleic acid, oleth 10, palm kernel acid, palmitic acid, PEG-60 almond glycerides, PEG-75 shea butter glycerides, PEG 90M, PEG-10 dimethicone, PEG-10 dimethicone/vinyl dimethicone crosspolymer, PEG-10 rapeseed sterol, PEG-100 stearate, PEG-12 dimethicone, PEG-120 methyl glucose dioleate, PEG-20 methyl glucose sesquistearate, PEG-40 stearate, PEG-60 hydrogenated castor oil, PEG-7 glyceryl cocoate, PEG-8, PEG-80 sorbitan laurate, PEG/PPG-17/6 copolymer (polyethylene glycol/polypropylene glycol-17/6 copolymer), PEG/PPG-18/18 dimethicone, PEG/PPG-20/15 dimethicone, poloxamer 184, Poloxamer 407, poloxamers, polyglyceryl-3 beeswax, polyglyceryl-4 isostearate, polyglyceryl-6 isostearate, polysorbate 20, polysorbate 60, polysorbate 80, potassium cetyl phosphate, potassium hydroxide, potassium myristate, PPG-12 buteth-16, PPG-26-Buteth-26, *Salvia officinalis, Saponaria officinalis* extract, soapwort, sodium $C_{14-16}$ olefin sulfonate, sodium cetearyl sulfate, sodium cocoamphoacetate, sodium cocoate, sodium cocoyl glutamate, sodium cocoyl isethionate, sodium dilauramidoglutamide lysine, sodium hexametaphosphate, sodium hydroxide, sodium laureth sulfate, sodium laureth-13 carboxylate, sodium lauroamphoacetate, sodium lauroyl lactylate, sodium lauroyl sarcosinate, sodium lauryl glucose carboxylate, sodium lauryl sulfate, sodium methyl cocoyl taurate, sodium methyl taurate, sodium myreth sulfate, sodium palm kernelate, sodium palmate, sodium PEG-7 olive oil carboxylate, sodium trideceth sulfate, steareth-20, TEA-lauryl sulfate (triethanolamine-lauryl sulfate), and tribehenin PEG-20 esters.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides a method of coating an implantable medical device comprising the step of contacting said device with the coating composition described above. It will be obvious to those skilled in the art that the coating of the device will occur prior to implantation into a mammal.

According to another embodiment, the present application provides a method of impregnating an implantable drug release device comprising the step of contacting said drug release device with a compound or composition of the present application. Implantable drug release devices include, but are not limited to, biodegradable polymer capsules or bullets, non-degradable, diffusible polymer capsules and biodegradable polymer wafers.

According to another embodiment, the present application provides an implantable medical device coated with a compound or a composition comprising a compound of the present application, such that said compound is therapeutically active.

According to another embodiment, the present application provides an implantable drug release device impregnated with or containing a compound or a composition comprising a compound of the present application, such that said compound is released from said device and is therapeutically active.

Where an organ or tissue is accessible because of removal from the subject, such organ or tissue may be bathed in a medium containing a composition of the present application, a composition of the present application may be painted onto the organ, or a composition of the present application may be applied in any other convenient way.

In the pharmaceutical compositions of the present application, a compound of any one of Formulae I, Ia, Ib, Ic, IV, II, and III is present in an effective amount (e.g., a therapeutically effective amount).

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y, 1970, 537.

In some embodiments, an effective amount of a compound of any one of Formulae I, Ia, Ib, Ic, IV, II, and III can range, for example, from about 1 mg to about 200 mg, from about 1 to about 100 mg, from about 1 to about 50 mg, from about 1 mg to about 30 mg, from about 1 mg to about 15 mg, from about 10 mg to about 2000 mg, from about 10 mg to about 1900 mg, from about 10 mg to about 1800 mg, from about 10 mg to about 1700 mg, from about 10 mg to about 1600 mg, from about 10 mg to about 1500 mg, from about 10 mg to about 1400 mg, from about 10 mg to about 1300 mg, from about 10 mg to about 1200 mg, from about 10 mg to about 1100 mg, from about 10 mg to about 1000 mg, from 10 mg about to about 900 mg, from about 10 mg to about 800 mg, from about 10 mg to about 700 mg, from about 10 mg to about 600 mg, from about 10 mg to about 500 mg, from about 10 mg to about 400 mg, from about 10 mg to about 300 mg, from about 10 mg to about 200 mg, from about 10 mg to about 100 mg, and from about 10 mg to about 50 mg. In some embodiments, an effective amount of a compound of any one of Formulae I, Ia, Ib, Ic, IV, II, and III is 1 mg, 2 mg, 3 mg, 4 mg, 5 mg, 6 mg, 7 ng, 8 mg, 9 mg, or 10 mg. In some aspects of these embodiments, the composition containing an effective amount of a compound of any one of Formulae I, Ia, Ib, Ic, IV, II, and III is administered once daily. In some aspects of these embodiments, the composition containing an effective amount of a compound of any one of Formulae I, Ia, Ib, Ic, IV, II, and III is administered twice daily. In some aspects of these embodiments, the composition containing an effective amount of a compound of any one of Formulae I, Ia, Ib, Ic, IV, II, and III is administered thrice daily.

In some embodiments, an effective amount of a compound of any one of Formulae I, Ia, Ib, Ic, IV, II, and III can range, for example, from about 0.01 mg/kg to about 0.5 mg/kg, from about 0.01 mg/kg to about 0.4 mg/kg, from about 0.01 mg/kg to about 0.3 mg/kg, from about 0.01 mg/kg to about 0.2 mg/kg, from about 0.01 mg/kg to about 0.1 mg/kg, from about 0.1 mg/kg to about 0.5 mg/kg, from about 0.2 mg/kg to about 0.5 mg/kg, from about 1 mg/kg to about 500 mg/kg, from about 1 mg/kg to about 200 mg/kg, from about 1 mg/kg to about 100 mg/kg, from about 1 mg/kg to about 50 mg/kg, from about 1 mg/kg to about 40 mg/kg, from about 1 mg/kg to about 30 mg/kg, from about 1 mg/kg to about 20 mg/kg, from about 1 mg/kg to about 10 mg/kg, from about 2 mg/kg to about 400 mg/kg, from about 3 mg/kg to about 300 mg/kg, from about 4 mg/kg to about 200 mg/kg, from about 5 mg/kg to about 100 mg/kg, from about 10 mg/kg to about 500 mg/kg, from about 10 mg/kg to about 400 mg/kg, from about 10 mg/kg to about 300 mg/kg, from about 10 mg/kg to about 200 mg/kg, from about 10 mg/kg to about 100 mg/kg, and from about 10 mg/kg to about 50 mg/kg. In some aspects of these embodiments, the composition containing an effective amount of a compound of any one of Formulae I, Ia, Ib, Ic, IV, II, and III is administered once daily. In some aspects of these embodiments, the composition containing an effective amount of a compound of any one of Formulae I, Ia, Ib, Ic, IV, II, and III is administered twice daily. In some aspects of these embodiments, the composition containing an effective amount of a compound of any one of Formulae I, Ia, Ib, Ic, IV, II, and III is administered thrice daily.

In some embodiments, an effective amount of a compound of any one of Formulae I, Ia, Ib, Ic, IV, II, and III can be, for example, 0.01 mg/kg, 0.02 mg/kg, 0.03 mg/kg, 0.05 mg/kg, 0.1 mg/kg, 0.2 mg/kg, 0.3 mg/kg, 0.5 mg/kg, 1 mg/kg, 5 mg/kg, 10 mg/kg, 20 mg/kg, 30 mg/kg, 40 mg/kg, 50 mg/kg, or 100 mg/kg. In some aspects of these embodiments, the composition containing an effective amount of a compound of any one of Formulae I, Ia, Ib, Ic, IV, II, and III is administered once daily. In some aspects of these embodiments, the composition containing an effective amount of a compound of any one of Formulae I, Ia, Ib, Ic, IV, II, and III is administered twice daily. In some aspects of these embodiments, the composition containing an effective amount of a compound of any one of Formulae I, Ia, Ib, Ic, IV, II, and III is administered thrice daily.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

The present application also provides cleaning compositions comprising an effective amount of a compound of any one of Formulae I, Ia, Ib, Ic, IV, II, and III, or a salt thereof; and an acceptable carrier. The carrier(s) are "acceptable" in the sense of being compatible with the other ingredients of the composition. Acceptable carriers that may be used in a cleaning composition of the present application include, but are not limited to, alcohols, water, surfactants, emollients, stabilizers, thickeners, and essential oils.

Combination Therapies

In some embodiments, a composition of the present application further comprises one or more additional therapeutic agents. The additional therapeutic agent may be selected from any compound or therapeutic agent known to have or that demonstrates advantageous properties when administered with a compound of any one of Formulae I, Ia, Ib, Ic, IV, II, and III.

In some embodiments, a method of treating a subject in need thereof as disclosed herein comprises administering to the subject one or more additional therapeutic agents.

In some embodiments, a compound of any one of Formula I, Ia, Ib, Ic, IV, II and III can be used in combination with an antibiotic.

In some embodiments, a compound of any one of Formula I, Ia, Ib, Ic, IV, II and III can be used in combination with a cationic antimicrobial peptide (CAMP). In some aspects of these embodiments, the cationic antimicrobial peptide is a defensin peptide (e.g., defensin 1 such as beta-defensin 1 or alpha-defensin 1), or cecropin, andropin, moricin, ceratotoxin, melittin, magainin, dermaseptin, bombinin, brevinin (e.g., brevinin-1), esculentin, buforin II (e.g., from amphibians), CAP18 (e.g., from rabbits), LL37 (e.g., from humans), abaecin, apidaecins (e.g., from honeybees), prophenin (e.g., from pigs), indolicidin (e.g., from cattle), brevinins, protegrin (e.g., from pig), tachyplesins (e.g., from horseshoe crabs), or drosomycin (e.g., from fruit flies).

In some embodiments, the antibiotic is selected from the quinolone class of antibiotic compounds. In some aspects of these embodiments, the antibiotic is selected from the group consisting of levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, rufloxacin, temafloxacin, tosufloxacin, trovafloxacin, and besifloxacin.

In some embodiments, the antibiotic is selected from the β-lactam class of antibiotic compounds.

In some embodiments, the antibiotic is selected from the cephalosporin class of antibiotic compounds. In some aspects of these embodiments, the antibiotic is selected from the group consisting of cefazolin, cefuroxime, ceftazidime, cephalexin, cephaloridine, cefamandole, cefsulodin, cefonicid, cefoperazine, cefoprozil, and ceftriaxone.

In some embodiments, the antibiotic is selected from the penicillin class of antibiotic compounds. In some aspects of these embodiments, the antibiotic is selected from the group consisting of penicillin G, penicillin V, procaine penicillin, and benzathine penicillin, ampicillin, and amoxicillin, benzylpenicillin, phenoxymethylpenicillin, oxacillin, methicillin, dicloxacillin, flucloxacillin, temocillin, azlocillin, carbenicillin, ricarcillin, mezlocillin, piperacillin, apalcillin, hetacillin, bacampicillin, sulbenicillin, mecicilam, pevmecillinam, ciclacillin, talapicillin, aspoxicillin, cloxacillin, nafcillin, and pivampicillin.

In some embodiments, the antibiotic is selected from the carbapenem class of antibiotic compounds. In some aspects of these embodiments, the antibiotic is selected from the group consisting of thienamycin, tomopenem, lenapenem, tebipenem, razupenem, imipenem, meropenem, ertapenem, doripenem, panipenem (betamipron), and biapenem.

In some embodiments, the antibiotic is selected from the lipopeptide class of antibiotic compounds. In some aspects of these embodiments, the antibiotic is selected from the group consisting of polymyxin B, colistin (polymyxin E), and daptomycin.

In some embodiments, the antibiotic is selected from the aminoglycoside class of antibiotic compounds. In some aspects of these embodiments, the antibiotic is selected from the group consisting of gentamicin, amikacin, tobramycin, debekacin, kanamycin, neomycin, netilmicin, paromomycin, sisomycin, spectinomycin, and streptomycin.

In some embodiments, the antibiotic is selected from the glycopeptide class of antibiotic compounds. In some aspects of these embodiments, the antibiotic is selected from the group consisting of vancomycin, teicoplanin, telavancin, ramoplanin, daptomycin, decaplanin, and bleomycin.

In some embodiments, the antibiotic is selected from the macrolide class of antibiotic compounds. In some aspects of these embodiments, the antibiotic is selected from the group consisting of azithromycin, clarithromycin, erythromycin, fidaxomicin, telithromycin, carbomycin A, josamycin, kitasamycin, midecamycin/midecamycinacetate, oleandomycin, solithromycin, spiramycin, troleandomycin, tylosin/tylocine, roxithromycin, dirithromycin, troleandomycin, spectinomycin, methymycin, neomethymycin, erythronolid, megalomycin, picromycin, narbomycin, oleandomycin, triacetyl-oleandomycin, laukamycin, kujimycin A, albocyclin and cineromycin B.

In some embodiments, the antibiotic is selected from the ansamycin class of antibiotic compounds. In some aspects of these embodiments, the antibiotic is selected from the group consisting of streptovaricin, geldanamycin, herbimycin, rifamycin, rifampin, rifabutin, rifapentine and rifamixin.

In some embodiments, the antibiotic is selected from the sulfonamide class of antibiotic compounds. In some aspects of these embodiments, the antibiotic is selected from the group consisting of sulfanilamide, sulfacetarnide, sulfapyridine, sulfathiazole, sulfadiazine, sulfamerazine, sulfadimidine, sulfasomidine, sulfasalazine, mafenide, sulfamethoxazole, sulfamethoxypyridazine, sulfadimethoxine, sulfasymazine, sulfadoxine, sulfametopyrazine, sulfaguanidine, succinylsulfathiazole and phthalylsulfathiazole.

In some embodiments, the antibiotic is selected from the group consisting of quinolones, fluoroquinolones, β-lactams, cephalosporins, penicillins, carbapenems, lipopeptide antibiotics, glycopeptides, macrolides, ansamycins, sulfonamides, and combinations of two or more thereof.

In some embodiments, a compound of Formula III can be used in combination with an antifungal.

In some embodiments, the antifungal is selected from the polyene class of antifungal compounds. In some aspects of these embodiments, the antifungal is selected from the group consisting from Amphotericin B, Candicidin, Filipin, Hamycin, Natamycin, Nystatin, and Rimocidin.

In some embodiments, the antifungal is selected from the imidazole class of antifungal compounds. In some aspects of these embodiments, the antifungal is selected from the group consisting of Butoconazole, Clotrimazole, Econazole, Fenticonazole, Isoconazole, Ketoconazole, Luliconazole, Miconazole, Omoconazole, Oxiconazole, Sertaconazole, Sulconazole, and Tioconazole.

In some embodiments, the antifungal is selected from triazole class of antifungal compounds. In some aspects of these embodiments, the antifungal is selected from the group consisting of Albaconazole, Efinaconazole, Epoxiconazole, Fluconazole, Isavuconazole, Itraconazole, Posaconazole, Propiconazole, Ravuconazole, Terconazole, and Voriconazole.

In some embodiments, the antifungal is selected from thiazole class of antifungal compounds. In some aspects of these embodiments, the antifungal is Abafungin.

In some embodiments, the antifungal is selected from Allylamine class of antifungal compounds.

In some embodiments, the antifungal is selected from Echinocandin class of antifungal compounds. In some aspects of these embodiments, the antifungal is selected from the group consisting of anidulafungin, caspofungin, and micafungin.

In some embodiments, the antifungal is selected from the group consisting of a polyene, an imidazole, a triazole, a thiazole, an allylamine, a thiocarbamate, an echinocandin, and combinations of two or more thereof.

In some embodiments, the antifungal is fluconazole.

In some embodiments, the present application provides separate dosage forms of a compound of any one of Formulae I, Ia, Ib, Ic, IV, II, and III and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

For pharmaceutical compositions that comprise an additional therapeutic agent, or for methods that comprise using an additional therapeutic agent, an effective amount of the additional therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these additional therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety. In some embodiments, when the additional therapeutic agent is gentamicin, the effective amount of gentamicin is lower than the amount that causes nephrotoxicity in a subject.

In some embodiments, the present disclosure is directed to a pharmaceutical composition comprising:
(i) a compound of Formula I (as described herein)
(ii) at least one additional therapeutic agent (e.g., any one of therapeutic agents described herein, for example aminoglycoside antibiotic such as gentamicin and cationic antimicrobial peptide such as defensin 1), and
(iii) a pharmaceutically acceptable carrier as described herein.

In some embodiments, the present disclosure is directed to a pharmaceutical composition comprising:
(i) a compound of Formula III:
(ii) at least one additional therapeutic agent (e.g., an antifungal such as a polyene, an imidazole, a triazole, a thiazole, an allylamine, a thiocarbamate, or echinocandin; e.g., antifungal is amphotericin B or fluconazole), and
(iii) a pharmaceutically acceptable carrier as described herein.

Some of the second therapeutic agents referenced above will act synergistically with the compounds of the present application. In some embodiments, some of the second therapeutic agents referenced above will show additive effect. When this occurs, it will allow the effective dosage of the second therapeutic agent and/or the compound of the present application to be reduced from that required in a monotherapy. This has the advantage of minimizing toxic side effects of either the second therapeutic agent of a compound of the present application, synergistic improvements in efficacy, improved ease of administration or use and/or reduced overall expense of compound preparation or formulation.

Definitions

At various places in the present specification, substituents of compounds of the present application are disclosed in groups or in ranges. It is specifically intended that various embodiments of the present application include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. Alkylene groups can be saturated or unsaturated (e.g., containing —C═C— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms).

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and iso-propoxy), butoxy (e.g., n-butoxy and tert-butoxy), and the like. In some embodiments, the alkyl group has 1 to 6, 1 to 4, or 1 to 3 carbon atoms.

As used herein, "halo" refers to F, Cl, Br, or I. In some embodiments, a halo is F, Cl, or Br. In other embodiments, halo is F, Cl, or I. In other embodiments, halo is F, I, or Br.

As used herein, the term "$C_{n-m}$ haloalkyl", employed alone or in combination with other terms, refers to an alkyl group having from one halogen atom to 2 s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl) amino and N-isopropylamino), N-butylamino (e.g., N-(n-butyl)amino and N-(tert-butyl)amino), and the like.

As used herein, the term "di $C_{n-m}$ alkylamino" refers to a group of formula —$N(alkyl)_2$, wherein each alkyl group independently has n to m carbon atoms. In some embodiments, each alkyl group has 1 to 6, 1 to 4, or 1 to 3 carbon atoms. Examples of dialkylamino groups include, but are not limited to, N,N-methylehtylamino, N,N-diethylamino, N,N-propylethylamino, N,N-butylisopropylamino, and the like.

As used herein, the term "cyano-$C_{1-3}$ alkylene" refers to a group of formula —($C_{1-3}$ alkylene)-CN.

As used herein, the term "HO—$C_{1-3}$ alkylene" refers to a group of formula —($C_{1-3}$ alkylene)-OH.

As used herein, the term "thio" refers to a group of formula —SH.

As used herein, the term "cyano" refers to a group of formula —CN.

As used herein, the term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

As used herein, the term "tautomer" refers to compounds which are capable of existing in a state of equilibrium between two isomeric forms. Such compounds may differ in the bond connecting two atoms or groups and the position of these atoms or groups in the compound.

As used herein, the term "isomer" refers to structural, geometric and stereo isomers. As the compound of the present application may have one or more chiral centers, it is capable of existing in enantiomeric forms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the terms "resistant" and "persistent" (or "persister") refer to bacterial strains that exhibit a high level of tolerance to one or more antibiotics. In some embodiments, the bacterial strain is resistant when the MIC of the bacterial strain is at least 2× (2-fold) of the MIC for the non-resistant strain. The x-fold resistant bacterial strain may be determined by the following steps: (i) MIC is determined for a non-resistant bacterial strain; (ii) the non-resistant bacterial strain is treated in a multi-well plate with an antibiotic at 2×, 5×, 10× etc, of the minimal inhibitory concentration (MIC); (iii) bacterial culture treated with the highest concentration that permitted bacterial growth is taken for serial passage for 100 days; and (iv) MIC of the bacterial culture after 100 days of serial passage is determined. If MIC of the bacterial culture after 100 days of serial passage is at least 2× of the MIC of the non-resistant strain, then the bacterial culture is at least 2× resistant to the antibiotic.

As used herein, the term "pharmaceutical carrier", or "pharmaceutically acceptable carrier" refers to a pharmaceutically acceptable solvent, suspending agent or vehicle for delivering the compound of the present application to the subject. The carrier may be liquid or solid and is selected with the planned manner of administration in mind. Each carrier must be pharmaceutically "acceptable" in the sense of being compatible with other ingredients of the composition and non-injurious to the subject.

As used herein, "topical use", "topical route" and "topically applying" means directly laying on or spreading on the skin, hair, mucous membrane (e.g., oral or vaginal mucous membrane), or nail, e.g., by use of the hands or an applicator such as a wipe.

The term "topical composition" as used herein refers to any composition suitable for the topical application to mammalian keratinous tissue such as in particular to human skin. In particular, the topical compositions according to the present disclosure are cosmetic compositions that can be topically applied to mammalian keratinous tissue, particularly to human skin.

EXAMPLES

Materials.

Bacterial and fungal reference strains used in the described studies are listed in Table 1. Bacterial strains were grown at 37° C. and fungal cultures were grown at 30° C., unless otherwise stated. All bacterial and fungal cells were stored at −80 OC until needed.

The clinical isolates were derived from the U.S. (Massachusetts General Hospital, Boston, Mass.) and China (made available by BEI Resources).

TABLE 1

Microbial strains

| Name (genus, species) | Strain |
|---|---|
| Bacteria | |
| Staphylococcus aureus | MW2 |
| Enterococcus faecium | 2421 |
| Klebsiella pneumoniae | 77326 |
| Acinetobacter baumannii | ATCC 17978 |
| Pseudomonas aeruginosa | PA14 |
| Enterobacter sp. | KCTC 2625 |
| Bacillus subtilis | PY 79 |
| Enterococcus faecalis | MMH 594 |
| Fungi | |
| Candida albicans | SC5314 (CAN14) |
| Candida glabrata | ATCC 90030 |
| Candida parapsilosis | ATCC 22019 |
| Candida tropicalis | ATCC 13803 |
| Cryptococcus neoformans | KN99α |

Bacterial strains and growth conditions and persister isolation: methicillin-resistant *S. aureus* (MRSA) strain MW2 BAA-1707, vancomycin-resistant *S. aureus* strain VRS 1, 11 clinical *S. aureus* isolates, 8 clinical *Enterococcus faecium* isolates, *Klebsiella pneumoniae* WGLW2 (BEI Resources, Manassas, Va., USA), *Acinetobacter baumannii* ATCC 17978, *Pseudomonas aeruginosa* PA14, and *Enterobacter aerogenes* ATCC 13048 were used to test antimicrobial activity (See Table 1a). *S. aureus* and *E. faecium* strains were grown in tryptic soy broth (TSB) (BD, Franklin Lakes, N.J., USA) or brain-heart infusion (BHI) broth (BD, Franklin Lakes, N.J., USA), respectively at 37° C. at 225 rpm. *K. pneumoniae, A. baumannii, P. aeruginosa*, and *E. aerogenes* were grown in Luria Bertani (LB) broth (BD, Franklin Lakes, N.J., USA).

Antimicrobial agents and chemicals: vancomycin, oxacillin, gentamicin, ciprofloxacin, rifampicin, and adapalene were purchased from Sigma-Aldrich (St Louis, Mo., USA). CD437, CD1530, linezolid, and daptomycin were purchased from R&D Systems (Minneapolis, Minn., USA) and adarotene was purchased from MedChem Express (Monmouth Junction, N.J., USA). 10 mg/ml stocks of all antibiotics were made in DMSO or ddH$_2$O. For assays with daptomycin, media or buffer were supplemented with 50 μg/ml CaCl$_2$.

Dioleoyl-glycero-phosphocholine (DOPC), Dioleoyl-glycero-phosphoglycerol (DOPG) and Dioleoyl-glycero-phosphoethanolamine-N-lissamine rhodamine B sulfonyl (18:1 Liss Rhod PE) were purchased from Avanti Polar Lipids (Alabaster, Ala., USA)

Analytical Methods.

Disc clearing assay: The disc diffusion test was performed on Mueller Hinton (MH) agar plates for bacterial cultures and yeast extract, peptone, dextrose (YPD) for fungal cultures. The assay was repeated 3 times. Discs were soaked in 10 μl of either DMSO or 10 mg/ml compound stock solution and air-dried. Three hundred microliters of an overnight culture of bacteria or fungi were spread on plates. After completely drying the agar plate in a laminar flow hood, DMSO or compound impregnated discs were overlaid on the plate and incubated at 35° C. for 18 hrs. Antimicrobial susceptibly was determined by presence of a zone of inhibition.

Minimal bacterial inhibitory concentrations (MIC): Compounds (10 mg/ml stock solution in DMSO) were tested by broth microdilution, in triplicate, in 96-well plates. To test the bacterial MICs for compounds described herein, the total volume in each well was 100 μl of test compounds and bacterial cells in MH broth. Two-fold serial dilutions were carried out to get compounds in the concentration range 0.0625-64 μg/ml. The bacterial concentration was adjusted to an initial OD$_{600}$ of 0.03. After incubation at 35° C. for 18 hrs, the absorbance was measured at 595 nm in accordance with CLSI document M07-A8. The MICs of antibiotics were determined by the standard microdilution method recommended by the Clinical and Laboratory Standards Institute.

Killing kinetics assay. An *S. aureus* overnight culture was diluted 1:10,000 in 25 ml fresh TSB in a 250 ml flask. In order to obtain exponential-phase cells, the diluted cell suspension was incubated at 37° C., with shaking at 225 rpm for 4 h until the OD$_{600\ nm}$ was 0.4 (~2×10$^7$ CFU/ml). 0.5 ml of the exponential phase cell culture was added to the wells of a 2 ml deep well assay block (Corning Costar 3960) containing 0.5 ml of pre-warmed TSB with twice the desired concentrations of compounds. The assay block was sealed with a gas-permeable Breathe-Easy membrane and incubated at 37° C. shaking at 225 rpm. At specific times, 50 μl samples were removed, serially diluted and spot-plated onto tryptic soy agar (TSA, BD) plates to enumerate the number of cells. These experiments were conducted in triplicate.

Resistance selection: to attempt to select bacterial mutants that are resistant to compounds disclosed herein, ~10$^{10}$ CFU *S. aureus* MW2 were plated onto TSA plates containing 2.5×, 5×, or 10×MICs of the compounds (e.g., CD437, CD1530, or adarotene). Development of resistant mutants by serial passage was conducted as previously described (Friedman, L. et al. Genetic changes that correlate with reduced susceptibility to daptomycin in *Staphylococcus aureus*. Antimicrob. Agents Chemother. 2006, 50, 2137-2145). Briefly, 50 μl of ~10$^6$ CFU *S. aureus* MW2 were added into the wells of a 96-well plate containing 50 μl of an extended gradient of the compound (e.g., CD437). The extended gradient was created by 2-fold serial dilutions with cation-adjusted Muller-Hinton media (CaMH) from three different starting concentrations: 80, 96, and 128 μg/ml. The plate contained final antibiotic concentrations of 0, 0.375, 0.5, 0.625, 0.75, 1, 1.25, 1.5, 2, 2.5, 3, 4, 5, 6, 8, 10, 12, 16, 20, 24, 32, 40, 48, and 64 μg/ml. After incubating the plate at 37° C. for 24 h, OD$_{600}$ nm was measured by a spectrophotometer (SpectraMax M2, Molecular Devices). Bacterial growth was defined as OD$_{600\ nm}$≥0.1. Two μl of the bacterial culture at the highest drug concentration that permitted bacterial growth was diluted 1,000-fold in CaMH, and the diluted culture was used as inoculum for the next passage. The rest of the culture was stored in 16% glycerol at −80° C. Serial passage was performed on two independent cultures (SP1 and SP2) for 100 days, and a separate ciprofloxacin selection served as a control. Confirmation of decreased susceptibility to the compound (e.g. retinoid) was conducted by re-measuring MICs of the compound against the resistant mutants from each glycerol freezer stock.

Genomic DNA extraction, library preparation, and genome sequencing: genomic DNAs from days 1, 75, and 100 from SP1 and days 1, 55, and 100 from SP2 were isolated using a DNeasy kit (Qiagen, Valencia, Calif., USA). The standard Gram-positive bacteria protocol was preceded by treatment of the bacterial pellet with 10 mg/ml lysozyme and 5 ng/ml lysostaphin and incubation at 37° C. for 30 min. Genomic DNA was quantified using a Qubit fluorometric assay (Invitrogen, Carlsbad, Calif., USA), and a paired-end sequencing library (2×250 bp) was prepared for each sample using a Nexttera XT DNA sample preparation kit (Illumina, San Diego, Calif., USA). The quality and quantity of each sequencing library were determined using an Agilent 2100 Bioanalyzer (Santa Clara, Calif., USA), and libraries were pooled and sequenced using an Illumina MiSeq (MEEI Ocular Genomics Institute, Boston, Mass., USA).

Genome assembly, annotation, and variant calling: genomes of the starting strain for each selection were assembled de novo using CLC Genomics Workbench version 7.0 (CLC bio, Cambridge, Mass., USA). Assemblies were annotated using RAST, and the annotated assembly of each starting strain was used as a reference to call genetic variants in subsequent samples. Single nucleotide polymorphisms (SNPs) and insertion/deletion (indel) variants were identified by mapping sequencing reads to the annotated reference assembly using default parameters. Variants supported by at least 50 sequencing reads and present at >50% frequency were examined further.

Identification of mutated genes related to the decreased susceptibility to retinoids: mutations causing amino acid changes were confirmed by sequencing of PCR amplified regions (~500 bp) surrounding each altered nucleotide. The primers are shown in Table M1.

TABLE M1

Primers used in this study

| Primer | 5'-3' sequence |
|---|---|
| graS-F | ACACCTGTGACAGCCATGAA |
| graS-R | ACAGTCGACGTGACTTGCAG |
| manA-F (for CD1) | AAAATTATGGGCGGTCAAC |
| manA-R (for CD1) | CGATTGCATCGTTTCGTATG |
| MW2474-F | AAGCATTGTCGAGTAGCTTGC |
| MW2472-R | CCCAGGCCAGTCAATTTTT |
| yjbH-F | AAATCGAACAAGCCCCTTCT |
| yjbH-R | CGAACTGGTTAAATTCGGAAA |
| dltB-F | TGCCAACGACTGAAGTTACG |
| dltB-R | TCTGATGTCCACCTAACCATGT |
| manA-F (for CD2) | ATCATGTTCAACACGGAACG |
| manA-R (for CD2) | TGAAATCGCCTTCAAAGACA |
| MW1685-F | CGCATTTTTACAAATTGAACCA |
| MW1685-R | ATCATACCGCTTGAGGCAAC |

Sequencing of PCR products were conducted by GENEWIZ (South Plainfield, N.J., USA). The passage day when the mutations occurred was identified by colony PCR using three colonies from each glycerol freezer stock, followed by sequencing of the PCR products. The passage day when the susceptibility to the retinoids changed was identified by repeating MIC determinations using overnight cultures from three colonies from each glycerol freezer stock. The altered genes causing decreased susceptibility to the retinoids were identified by comparing the day of mutation with the day of change in retinoids susceptibility. The correlation between mutations in graS, manA, and yjbH and decreased susceptibility to retinoids was confirmed by comparing the susceptibility of S. aureus JE2 (wild-type, parent strain) to mutant strains, NE1756 (graS::ΦNΣ), NE1645 (manA::ΦNΣ), and NE896 (yjbH::ΦNΣ) from the Nebraska Transposon Mutant Library (Fey, P. D. et al. A genetic resource for rapid and comprehensive phenotype screening of nonessential Staphylococcus aureus genes. MBio 4, e00537-12-e00537-12 (2013)).

SYTOX Green membrane permeability assay: black, clear-bottom, 96-well plates (Corning no. 3904) were filled with 50 µl of phosphate buffered saline (PBS)/well containing the indicated concentration of antibiotics. Exponential-phase S. aureus MW2 prepared as described in Killing kinetics assay were then washed 3 times with the same volume of PBS. The washed cells were adjusted to $OD_{600}=0.4$ (~$2\times10^7$ CFU/ml) with PBS. SYTOX Green (Molecular Probes, Waltham, Mass., USA) was added to 10 ml of the diluted bacterial suspension to a final concentration of 5 µM and incubated for 30 min at room temperature in the dark. 50 µl of the bacteria/SYTOX Green mixture was added to each well of the 96-well plates containing antibiotics and fluorescence was measured at room temperature using a spectrophotometer (SpectraMax M2, Molecular Devices), with excitation and emission wavelengths of 485 nm and 525 nm, respectively. All experiments were conducted in triplicate.

Preparation of giant unilamellar vesicles (GUVs) and observation of effects of compounds on GUVs: GUVs were prepared by the electroformation method described previously (Kim, W. et al. NH125 kills methicillin-resistant Staphylococcus aureus persisters by lipid bilayer disruption. Future Med. Chem. 8, 257-269 (2016)). 4 mM of a lipid mixture consisting of DOPC/DOPG/18:1 Liss Rhod PE (7:3:0.005) was dissolved in chloroform. 40 µl of the lipid mixture was then spread onto indium tin oxide (ITO)-coated slides (50×75×1.1 mm, Delta Technologies, Loveland, Colo., USA). In order to remove chloroform, the ITO slides were dried in a vacuum chamber for 2 h. To make an elecroformation chamber, a 2 mm thick Teflon spacer was inserted between the lipid-applied surfaces of two ITO slides. 2 ml of 100 mM sucrose was added into the electroformation chamber, followed by sealing with binder clips. The swelling of the lipid bilayers was facilitated by applying an electric AC-field (10 Hz). The field strength was gradually increased from 0 to 0.5 kV/m for 30 min, and then was maintained constantly for 30 min. Detachment of GUVs from surfaces was conducted by reducing the AC-field from 10 Hz to 5 Hz for 20 min. The GUV suspension was diluted (1:30) in a 100 mM glucose solution. 49 µl of the diluted GUV suspension (~100 vesicles) was transferred to a black, clear-bottom 384-well plate (Corning no. 3712). The plate was left in the dark at room temperature for 30 min until all GUVs settled on the bottom of the plates. After adding 1 µl of compound solution to a well (final compound concentration: 10×MIC or 1×MIC), the GUVs were observed and imaged with an optical microscope equipped with fluorescence contrast and a digital camera (40× or 63× objectives, Axio Observer. A1 & AxioCam MRm, Zeiss, Germany).

All-atom molecular dynamics simulations: all-atom molecular dynamics (MD) simulations based on the GROMACS package (version 4.6.7) (Hess, B. et al. GROMACS 4: algorithms for highly efficient, load-balanced, and scalable molecular Simulation. J. Chem. Theory Comput. 4, 435-447 (2008)) were performed to investigate the interactions between the selected retinoids (CD437, CD1530, adarotene and adapalene) and plasma membrane of S. aureus. The GROMOS 54A7 force field (See, e.g., Schmid, N. et al. Definition and testing of the GROMOS force-field versions 54A7 and 54B7. Eur Biophys J 40, 843-856 (2011))

with Automated Topology Builder (See, e.g., Malde, A. K. et al. An automated force field topology builder (ATB) and repository: version 1.0. *J. Chem. Theory Comput.* 7, 4026-4037 (2011)) was employed for the retinoid molecules in the simulations. The plasma membrane of *S. aureus* was represented by a mixed lipid bilayer composed of 88 neutral-charged DOPC and 40 negatively-charged DOPG lipids (~7:3 ratio) with dimensions of 5.96 nm×5.96 nm. This mixture of lipids is known to form stable anionic liposomes and considered appropriate as a mimic of the lipid composition of bacterial plasma membranes[45]. Lipid bilayers at other lipid mixture ratios of 6:4 (80 DOPC and 48 DOPG lipids) and 5:5 (64 DOPC and 64 DOPG lipids) were also constructed to study the effects of membrane surface charges on the antimicrobial activity of retinoids. Sodium ions were added to neutralize the simulation system. The DOPC and DOPG lipids were modeled with Berger's lipid force field (Berger, et al. Molecular dynamics simulations of a fluid bilayer of dipalmitoylphosphatidylcholine at full hydration, constant pressure, and constant temperature. *Biophys. J.* 72, 2002-2013 (1997)), which is an extensively validated all-atom lipid model for membrane-related simulations (See, e.g., Céline Anezo, Alex H de Vries, Hans-Dieter Holtje, D Peter Tieleman, A.Siewert-Jan Marrink. Methodological issues in lipid bilayer simulations. *J. Phys. Chem. B* 107, 9424-9433 (2003); Benz, R. W., Castro-Roman, F., Tobias, D. J. & White, S. H. Experimental validation of molecular dynamics simulations of lipid bilayers: a new approach. *Biophys. J.* 88, 805-817 (2005); and Kandt, C., Ash, W. L. & Peter Tieleman, D. Setting up and running molecular dynamics simulations of membrane proteins. *Methods* 41, 475-488 (2007)). For enhanced computational efficiency, water molecules were represented by a polarization corrected simple point-charge SPC/E model (See, e.g., Berendsen, et al The missing term in effective pair potentials. *J. Phys. Chem.* 91, 6269-6271 (1987)). A geometric combining rule of Lennard-Jones potential was adopted for non-bonded interactions of retinoid molecules with lipids, ions and water. The fast smooth particle-mesh Ewald (Essmann, U. et al. A smooth particle mesh Ewald method. *J Chem Phys* 103, 8577-8593 (1995)) was used to calculate the long-rang electrostatic interactions. The system was modeled as an NPT ensemble, with periodic boundary conditions in all directions, under constant pressure P (1 atm) and constant temperature T (300 K). The simulation box had an initial height of 12.3 nm, which was large enough to prevent the membrane and retinoid molecules from interacting with their periodic images. The time step was fixed at 2 fs. After a 500 ns initial equilibration of solvated lipid systems, four retinoid molecules were introduced into the water phase above the membrane. After 100 ns of re-equilibration, the retinoid molecules were released and their interactions with the membrane including attachments, penetrations and equilibrium configurations were further simulated for 500 ns, similar to the previous study (Creighton, M. A. et al. Three-dimensional graphene-based microbarriers for controlling release and reactivity in colloidal liquid phases. *ACS Nano* 10, 2268-2276 (2016)). The free energy profiles for the translocations of retinoid molecules were calculated by steered molecular dynamics (See, e.g., Isralewitz, B., et al. Steered molecular dynamics and mechanical functions of proteins. *Curr. Opin. Struct. Biol.* 11, 224-230 (2001)), umbrella sampling and weighted histogram analysis method (See, e.g., Kumar, S., et al. A. The weighted histogram analysis method for free-energy calculations on biomolecules. I. The method. *J Comput Chem* 13, 1011-1021 (1992); and Hub, J. S., et al. g_wham—a free weighted histogram analysis implementation including robust error and autocorrelation estimates. *J. Chem. Theory Comput.* 6, 3713-3720 (2010)), with results giving the transfer energies and energy barriers associated with membrane penetration.

Human blood hemolysis. Hemolytic activity of retinoids on human erythrocytes was evaluated using a previously described method with modifications (Rajamuthiah, R. et al. A defensin from the model beetle *Tribolium castaneum* acts synergistically with telavancin and daptomycin against multidrug resistant *Staphylococcus aureus*. *PLoS ONE* 10, e0128576 (2015)). 10% human erythrocytes were purchased from Rockland Immunochemicals (Limerick, Pa., USA). The erythrocytes were diluted to 4% with PBS, and 100 µl was added to 100 µl of two-fold serial dilutions of compounds in PBS, 0.2% DMSO (negative control), or 2% Triton-X 100 (positive control) in a 96-well plate. The 96-well plate was incubated at 37° C. for 1 h and then centrifuged at 500×g for 5 min. 100 µl of the supernatant was transferred to a fresh 96-well plate, and absorbance of supernatants was measured at 540 nm. Percent hemolysis was calculated using the following equation: (A540 nm of compound treated sample—$A_{540nm}$ of 0.1% DMSO treated sample)/(A540 nm of 1% Triton X-100 treated sample—$A_{540nm}$ of 0.1% DMSO treated sample)×100. $HC_{50}$ (concentration of a compound causing 50% hemolysis) was determined using SigmaPlot 10.0 (Systat Software Inc., San Jose, Calif., USA).

Hepatotoxicity. Cryopreserved primary human hepatocytes were purchased from Cell Resource Core at Massachusetts General Hospital (Boston, Mass., USA). The hepatocytes were cultured in collagen sandwiched configuration in 24-well plates, as described previously (See, e.g., Dunn, J. C., et al. Hepatocyte function and extracellular matrix geometry: long-term culture in a sandwich configuration. *FASEB J.* 3, 174-177 (1989); Dunn, J. C., et al. Hepatocytes in collagen sandwich: evidence for transcriptional and translational regulation. *J. Cell Biol.* 116, 1043-1053 (1992); and Sharma, N. S. et al. Metabolic profiling based quantitative evaluation of hepatocellular metabolism in presence of adipocyte derived extracellular matrix. *PLoS ONE* 6, e20137 (2011)). Briefly, 0.4×10⁶ live cells were seeded in 24-well plates coated with rat tail collagen type I. In order for cells to attach onto collagen gel, the 24-well plates were incubated in a humidified 5% $CO_2$ incubator at 37° C. for 4 hours. The cells were washed and then cultured in 0.5 ml standard hepatocyte culture medium consisting of pre-warmed DMEM media supplemented with 10% FBS, 0.5 U/ml insulin, 14 ng/ml glucagon, 20 ng/ml EGF, 7.5 µg/ml hydrocortisone and 200 U/ml penicillin-streptomycin. The cell cultures were incubated in a humidified 5% $CO_2$ incubator at 37° C. At 24 h after seeding, a top layer of collagen gel was deposited on the hepatocytes attached to the bottom collagen layer and incubated for another 24 h, then the hepatocytes were treated with a range of concentrations of retinoids for 24 h. 50 µl of WST-1 (Roche, Mannheim, Germany) was added per well for the last 4 h of the 24 h period. WST-1 reduction was measured at absorbance 450 nm. The percent fluorescence relative to that of the no-treatment control was calculated. The assay was done in triplicate.

Evaluation of human ether-a-go-go-related gene (hERG) potassium channel inhibition potential. The inhibitory potential of CD437, CD1530, and adarotene on the cardiac voltage-gated potassium channel hERG was evaluated by Cyprotex (Macclefield, UK). Electrophysiology measurement was conducted using an IonWorks™ HT instrument (Molecular Devices Corporation, Sunnyvale, Calif., USA)

and 384-well planar PatChPlate™ (Molecular Devices Corporation). Briefly, Chinese hamster ovary (CHO) cells expressing the hERG potassium channel were dispensed into 384-well planar arrays, and hERG tail currents were measured by whole-cell voltage clamping. A range of concentrations (0.008 µM to 25 µM) of each retinoid were then added to the cells, and a second recording of the hERG current was made. The percent change in the hERG current was calculated. Quinidine, an established hERG inhibitor was used as a positive control, and 0.25% DMSO was used as a negative control.

Genotoxicity: the mutagenic potentials of CD437, CD1530, and adarotene were evaluated by the Ames test (See, e.g, Maron, D. M. et al. Revised methods for the Salmonella mutagenicity test. Mutat. Res. 113, 173-215 (1983)). The Ames test was conducted using histidine auxotroph Salmonella typhimurium strains TA1535 and TA1538. To test mutagenic potential of the synthetic retinoids themselves and their metabolic products, the assay was conducted both with and without rat liver S9 fraction (Moltox, Boone, N.C., USA). Briefly, 100 µl of bacterial overnight cultures was added into 500 µl of phosphate buffer containing a range of amounts of the retinoids dissolved in 10 µl DMSO and with or without 4% S9. After incubation at 37° C. for 1 h, the samples were added into 2 ml of soft agar including 0.5 mM of histidine/biotin, mixed, and poured onto minimal glucose agar plates. The plates were incubated at 37° C. for 48 h, and the revertant colonies were counted. 10 µl DMSO was used as a negative control. 5 Gig/plate sodium azide for TA1535 and 5 µg/plate 4-nitro-o-phenylenediamine (4NOP) for TA1538 were used as a positive control in the non-metabolic activation system. 5 µg/plate 2-aminoanthracene was used as a positive control for both strains in the metabolic activation system. The test was performed in triplicate.

Persister killing assay. As has been previously demonstrated, stationary-phase cells of *S. aureus* can be used to model persister cells (See, e.g., Keren, I., et al. Persister cells and tolerance to antimicrobials. *FEMS Microbiol. Lett.* 230, 13-18 (2004); Conlon, B. P. et al. Persister formation in *Staphylococcus aureus* is associated with ATP depletion. *Nature Microbiology* 1, 16051 (2016); Allison, K. R., et al. Metabolite-enabled eradication of bacterial persisters by aminoglycosides. *Nature* 473, 216-220 (2011); and Conlon, B. P. et al. Activated ClpP kills persisters and eradicates a chronic biofilm infection. *Nature* 503, 365-370 (2013)). It was shown previously that MW2 and the 11 clinical *S. aureus* isolates become persisters when grown to stationary phase and are tolerant to conventional antibiotics such as gentamicin, ciprofloxacin and vancomycin (See, e.g., Kim, W. et al. NH125 kills methicillin-resistant *Staphylococcus aureus* persisters by lipid bilayer disruption. *Future Med. Chem.* 8, 257-269 (2016); and Kim, W. et al. Identification of an antimicrobial agent effective against methicillin-resistant *Staphylococcus aureus* persisters using a fluorescence-based screening strategy. *PLoS ONE* 10, e0127640 (2015)). Persistency of station-phase *S. aureus* VRS 1 was evaluated by treating with 100×MIC daptomycin and linezolid due to its resistance to vancomycin, gentamicin, ciprofloxacin, and rifampicin. Persister cells of these 13 *S. aureus* strains were developed by growing cultures overnight to stationary phase at 37° C. at 225 rpm. The overnight cultures were washed three times with PBS and diluted to ~$10^7$ CFU/ml with the same buffer, which is the same concentration as used in the killing kinetics assay described herein. 1 ml of the persister suspension containing appropriate concentrations of antibiotics was added to the wells of a 2 ml deep well assay block (Corning Costar 3960) and incubated at 37° C., with shaking at 225 rpm. At specific times, 50 µl samples were removed, serially diluted and spot-plated on TSA plates to enumerate the number of live cells. These experiments were conducted in triplicate.

Deep-seated mouse thigh infection model for evaluating drug efficacy. A previously described protocol to mimic a chronic, deep-tissue infection was used with modifications (See, e.g., Conlon, B. P. et al. Activated ClpP kills persisters and eradicates a chronic biofilm infection. *Nature* 503, 365-370 (2013)). Six-week-old female CD1 ICR outbred mice (20-25 g) were obtained from Charles River Laboratories. To make mice neutropenic, 150 mg/kg and 100 mg/kg of cyclophosphamide were administered intraperitoneally (i.p.) at 4 days and 1 day before infection, respectively. On the day of infection, ~$10^7$ cells of stationary-phase *S. aureus* MW2 resuspended in 50 µl saline were injected to the right thigh of each mouse. CD437 was dissolved in Kolliphor EL (Sigma-Aldrich, St Louis, Mo., USA)/ethanol 1:1 and then diluted 1:10 in saline to a final concentration of 20 mg/kg. At 24 h post-infection, groups of mice (n=10) were treated with 30 mg/kg gentamicin subcutaneously (s.c.), 25 mg/kg vancomycin i.p., 20 mg/kg CD437 i.p., or the combination of 20 mg/kg CD437 i.p. and 30 mg/kg gentamicin s.c. every 12 h for 3 days. Control mice were injected with 200 µl of 10% Kolliphor EL/ethanol in saline i.p. every 12 h for 3 days. After euthanizing mice at 96 h post-infection, blood was collected by cardiac puncture and the infected thighs were aseptically excised. All samples were stored at 4° C. until use. Serum was analyzed for alanine aminotransferase and urea nitrogen content with commercially available kits, following the manufacturer's protocol (Pointe Scientific, Canton, Mich., USA). Thighs were homogenized in PBS and the number of MRSA in homogenates was enumerated by serial dilution and spot-plating on TSA plates, and bacterial load was recorded as CFU/g thigh tissue. This study and all experiments were performed in accordance with guidelines approved by Rhode Island Hospital Institutional Animal Care and Use Committee (RIH IACUC). Statistical significance among each group was analyzed by one-way ANOVA with post-hoc Tukey test using PASW Statistics 18 (SPSS Inc. Chicago, Ill., USA).

MIC against fungal cultures: Colonies of *C. neoformans* (strain KN99a) and *C. albicans* (strain CAN14) were inoculated in 5 ml of YPD media overnight at 30° C. The cells were harvested by centrifugation at 4000 RPM for 5 minutes and washed with PBS; the cell pellets were resuspended in RPMI 1640 medium. The cell count was calculated with a hemocytometer and adjusted to be between $5.0×10^4$ to $2.5×10^6$ cells/ml. A tested compound was prepared and added to RPMI 1640 medium at 2× the final concentration. MIC was determined in 96-well plates, working volume per well was 100 µl (50 µl compound+50 µl cells). For *C. albicans*, $OD_{595}$ was read after incubating the plate at 35° C. for 24 hrs. For KN99α, $OD_{595}$ was read after incubating the plate at 35° C. for 70 hrs in accordance with CLSI document M27-A2.

Static versus cidal assessment: The minimum bactericidal concentration (MBC) was determined as follows: 10 µl of bacterial culture from each micro-well of the MIC assay was plated on MH agar and incubated at 35° C. overnight. The lowest compound concentration at which there was no bacterial colony growth was considered the MBC.

The minimum fungicidal concentration was (MFC) was determined as follows: 10 µl of yeast culture from each micro-well of the MIC assay was plated on YPD agar and incubated at 35° C. overnight. The lowest compound concentration at which there was no fungal colony growth was considered the MFC.

Checkerboard assay (e.g., antibiotic synergy test): The antimicrobial or antifungal activity of a combination of a compound of present application with other agents was determined through a checkerboard assay. The checkerboard method for determining synergy of synthetic retinoids with conventional antibiotics can be conducted, for example, as previously described (See, e.g., Rajamuthiah, R. et al. A defensin from the model beetle *Tribolium castaneum* acts synergistically with telavancin and daptomycin against multidrug resistant *Staphylococcus aureus*. PLoS ONE 10, e0128576 (2015)) The compounds whose combinations were being tested were arrayed in serial concentrations, vertically for one compound and horizontally for the other compound in the same 96 well microplate. 2-fold serial dilutions of each retinoid were combined with 2-fold serial dilutions of each conventional antibiotic, which created an 8×8 matrix in a 96-well microtiter plate. The rest of the procedure involving addition of pathogen and measurement of growth was carried out as described for measurement of MIC.

The Fractional Inhibitory Concentration (FIC) index for two compounds, A and B, is defined by the following equation: $FIC=((A/MIC^A)+(B/MIC^B))$. $MIC^A$ and $NIC^B$ are MICs of compound A or B respectively. (A) is the lowest concentration of compound A in combination with compound B that inhibits growth of a pathogen and (B) is the lowest concentration of compound B that inhibits growth of a pathogen. An FIC<0.5 indicates synergism between the compounds being tested, greater than 2 suggest antagonism.

Example 1a. Antibacterial Activity of Synthetic Retinoids CD 437, CD 1530, Adarotene, and Adapalene FIG. 1 shows direct inhibition of *S. aureus* strain MW2 by CD 437 in a disk clearing assay. The disc diffusion test was carried out in triplicate on cation-adjusted Miller-Hinton agar. 6 mm discs were impregnated with 50 µg of compounds and air-dried. Three hundred microliters of an overnight *S. aureus* MW2 culture was spread on an agar plate and air-dried. The antimicrobial discs were overlaid on the plate and incubated at 37° C. for 20 hrs. Antimicrobial susceptibility was determined by measuring the diameter of the zone of inhibition. Large clear zones around a disc including CD 437 are observed, which indicates that CD 437 inhibits the growth of *S. aureus* MW2.

Figure 2A:
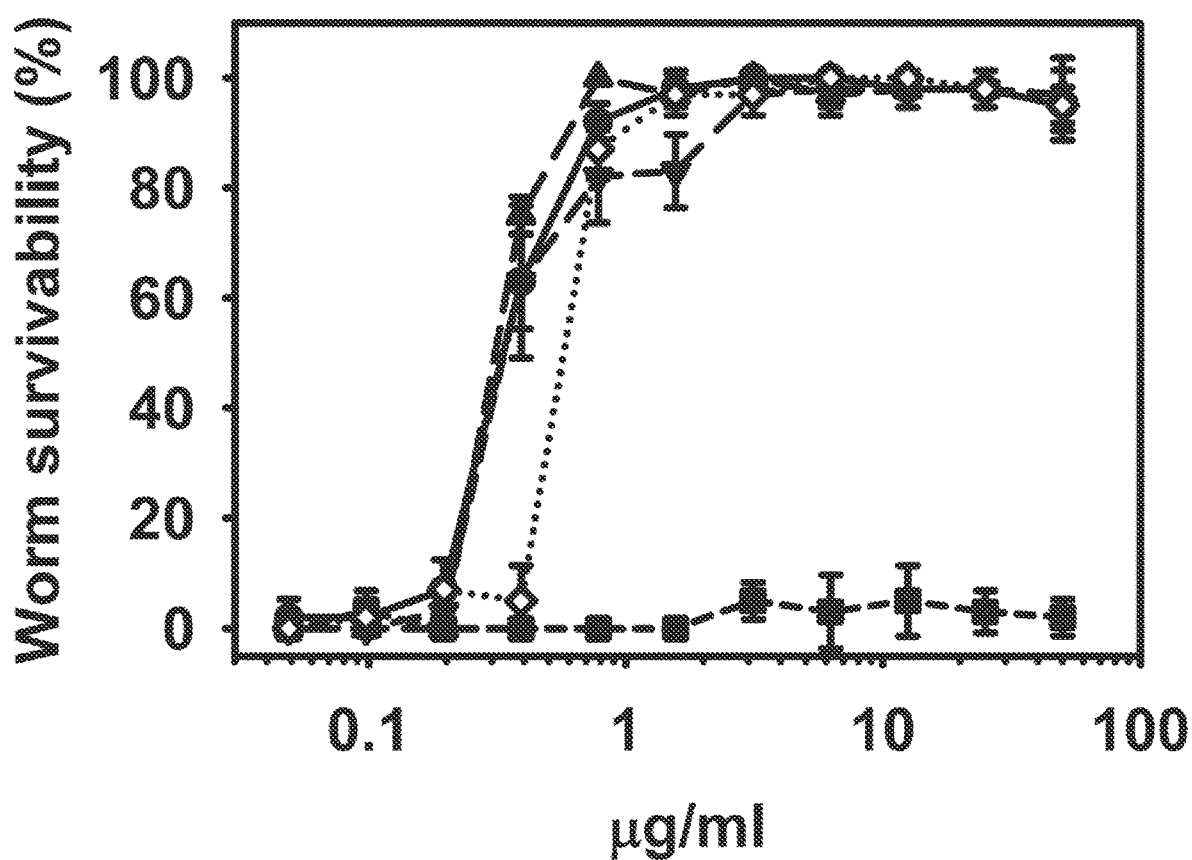
FIG. 2A is a line graph showing inhibition of MRSA by CD 437, CD 1530, adapalene and adarotene.
Figure 2B:
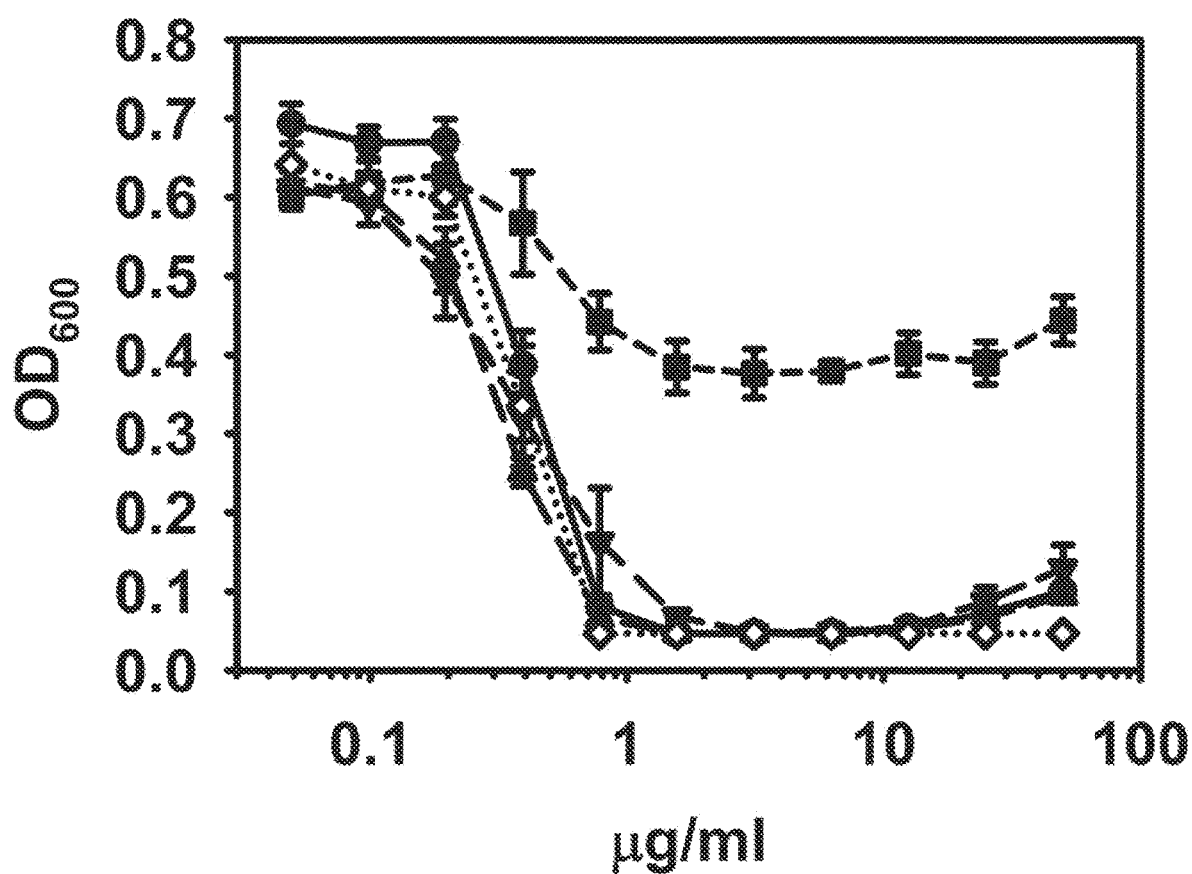
FIG. 2B is a line graph showing the prolonged survival of *C. elegans* worms infected with *S. aureus* and treated with CD437, CD1530.

FIG. 2A shows MIC of CD 437, CD 1530, adarotene, and adapalene, for methicillin resistant *S. aureus* (MRSA). FIG. 2B shows that CD 437 prolongs the survival of *C. elegans* infected with *S. aureus* in a dose response assay. The MIC of CD 437 and CD 1530 were 1 µg/ml, and adarotene was 2 µg/ml. CD 437, CD 1530, and adarotene all rescue *C. elegans* from MRSA infection and are nontoxic to *C. elegans* up to 50 µg/ml.

The compounds (CD 437, CD 1530, and adarotene) have also been shown to inhibit clinical isolates of *S. aureus*, all methicillin resistant *S. aureus* (MRSA) strains, testing 28 strains. For CD 437 and CD 1530, 28/28 isolates exhibit sensitivity to the compound with MICs≤2 µg/ml. In the case of adarotene, 27/28 strain had an MIC of ≤2 g/ml and 1 strain had an MIC of 4 µg/ml.

Both *E. faecium* and *E. faecalis* were susceptible to CD 437 and CD 1530 but were not inhibited by adapalene. The MICs for CD 437 and CD 1530 were 2 to 4 µg/ml. The Gram-negative bacteria *E. coli* and *P. aeruginosa* were resistant to the retinoids.

Adapalene (CAS registry number 106685-40-9), also known as CD 271, and 6-(4-methoxy-3-tricyclo[3.3.1.13,7] dec-1-ylphenyl)-2-naphthalenecarboxylic acid, has the following Formula:

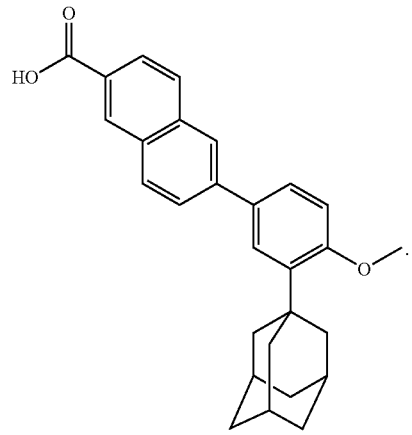 [SMILES: COc1ccc(-c2ccc3cc(C(=O)O)ccc3c2)cc1C12CC3CC(CC(C3)C1)C2]

Adapalene did not inhibit the bacteria directly (FIG. 2A).

The same group of compounds (CD 437, CD 1530, adarotene) showed dose dependent rescue of worm survival after infection with *S. aureus* with the exception of adapalene (FIG. 2B). The *C. elegans*-MRSA liquid infection assay has been described (Rajamuthiah et al. Plos One. 2014; 9(2):e89189). In brief, 4,500 glp-4 (bn2); sek-1(km4) L1 hatchlings were grown on SK-HB101 agar plates for 52 hours at the restrictive temperature of 25° C. until animals became sterile young adults and later harvested with M9 buffer. *S. aureus* MW2 was grown overnight at 37° C. in TSB, first under aerobic conditions and later shifted to anaerobic growth conditions at 37° C. The infection assay was performed in standard 384-well assay plates, in the presence of the compound being tested or 1% dimethyl sulfoxide (DMSO) as a control. Bacteria were added to the wells at a final $OD_{600}$ of 0.06, followed by the use of a Complex Object Parametric Analyzer and Sorter (COPAS) large particle sorter (Union Biometrica, Holliston, Mass., USA) to transfer 15 adult worms to each well of an assay plate. After 5 days of incubation in a humidified chamber at 25° C., the bacteria and other debris were washed from the wells with a microplate washer and the worms were stained with the vital dye Sytox Orange (Life Technologies). After overnight incubation at 25° C. in a humidified chamber, the plates were imaged using an Image Xpress Micro automated microscope (Molecular Devices, Sunnyvale, Calif., USA), capturing both transmitted light and TRITC (535 nm excitation, 610 nm emission) fluorescent images with a 2× objective. The images from the infection assay were processed using the open source image analysis software Cell-Profiler and analysis modules as described previously. The ratio of Sytox worm area to bright field worm area, and the resultant percentage survival data, is calculated by the software for each well of the assay plates. The assay was performed in triplicate comparing the survival of worms at various concentrations of drugs.

CD437 and CD1530 exhibit potent in vitro bactericidal activity against MRSA strain MW2 at MIC of 1 µg/ml and MRSA persisters at 8 µg/ml. See, e.g., FIGS. 22 (A-G), 23 and Table 1a.

FIG. 22(A-G) shows (A) Brightfield and fluorescence microscopy images of MRSA-infected *C. elegans*. Killing assays were carried out as described in Methods using *S. aureus* MRSA MW2 and 10 µg/ml retinoids, 10 µg/ml vancomycin (positive control), or 1% DMSO (negative control) at 25° C. for 5 days. Data are representative of three independent experiments. (B) Chemical structures of synthetic retinoids. (C) Growth of MRSA strain MW2 exposed to the indicated concentrations of compounds was quantified by measuring $OD_{600}$ after 18 h in tryptic soy broth (TSB). (D) *C. elegans* infected with MRSA strain MW2 was treated with indicated concentrations of compounds. Percent survival of *C. elegans* was normalized to *C. elegans* treated with DMSO. (E-F) MRSA persisters prepared as described in Methods were treated with the indicated concentrations of each retinoid. Viability was measured by serial dilution and plating on TSA plates. The data points on the x-axis are below the level of detection ($2 \times 10^2$ CFU/ml). (E,F) Results are shown as means±s.d.; n=3.

Figure 23:
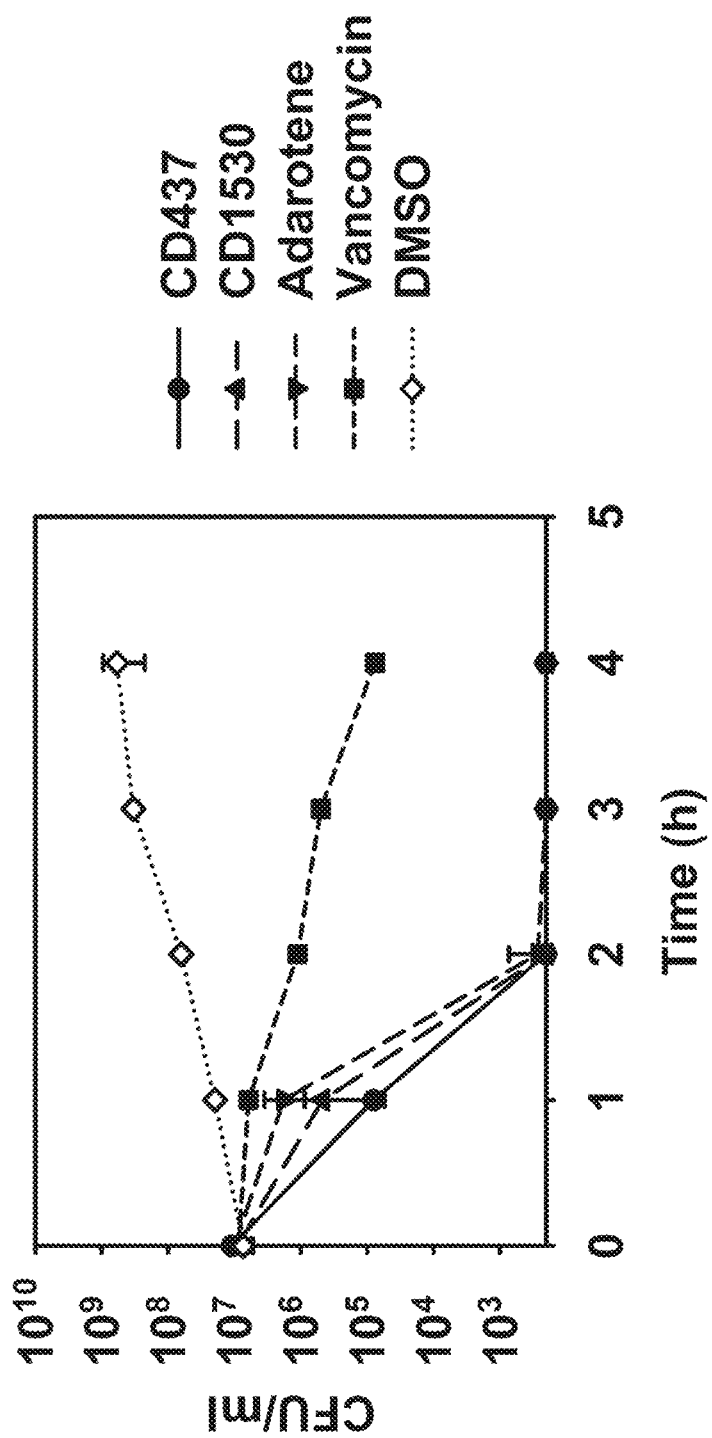
FIG. 23 is a line graph showing CD437, CD1530, and adarotene MRSA killing kinetics.
Figure 24:
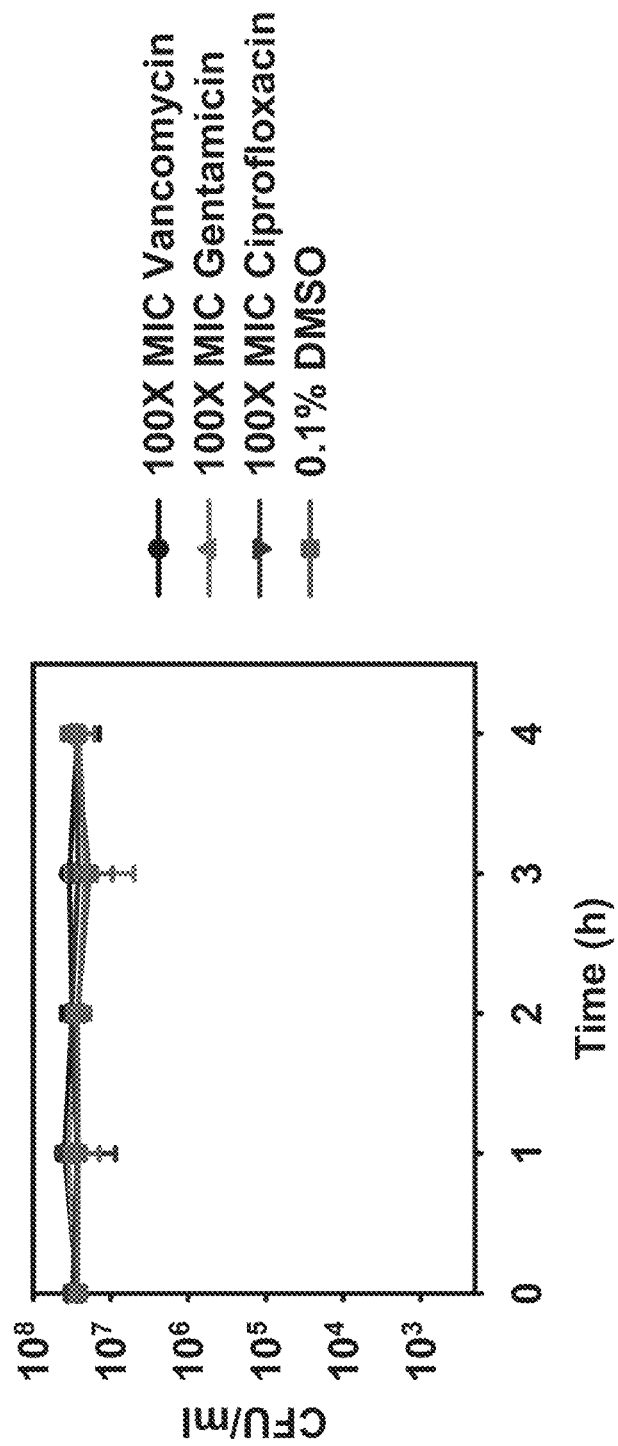
FIG. 24 is a line graph showing tolerance of stationary-phase cells of *S. aureus* MW2 to 100×MICs of conventional antibiotics.

FIG. 23 shows that CD437, CD1530, and adarotene exhibit fast killing kinetics. Exponential-phase MRSA cells were treated with 10×MIC of CD437, CD1530, adarotene, or vancomycin or 0.1% DMSO (negative control). Colony forming unit counts of cells were measured by serial dilution and plating on TSA plates. The data points on the x-axis are below the level of detection ($2 \times 10^2$ CFU/mL). Results are shown as means±s.d.; n=3.

rescued *C. elegans* from MRSA infection at concentrations higher than its MIC (FIG. 22(A-G)). Moreover, CD437, CD1530 and adarotene exhibited comparable antimicrobial activity against a panel of clinical *S. aureus* strains and *Enterococcus faecium* strains (clinically relevant Gram-positive pathogen), including multi-drug resistant (MDR) strains, see Table 1a. Adapalene did not have significant antimicrobial activity nor did it protect *C. elegans* from MRSA infection (FIG. 22(A-G)). CD437, CD1530, and adarotene contain a common hydroxyl group, whereas adapalene has a methoxy group instead. 8×MIC of CD437 or CD1530 completely eradicated *S. aureus* strain MW2 persisters within 1 h, whereas treatment with 8×MIC of adarotene did not (FIG. 22(A-G) and FIG. 24). 10×MIC of CD437 and CD1530, but not adarotene, also annihilated persisters formed by multi-drug resistant *S. aureus* strain VRS1 and 11 clinical *S. aureus* strains. See FIGS. 25 and 26(A-L).

Figure 25:
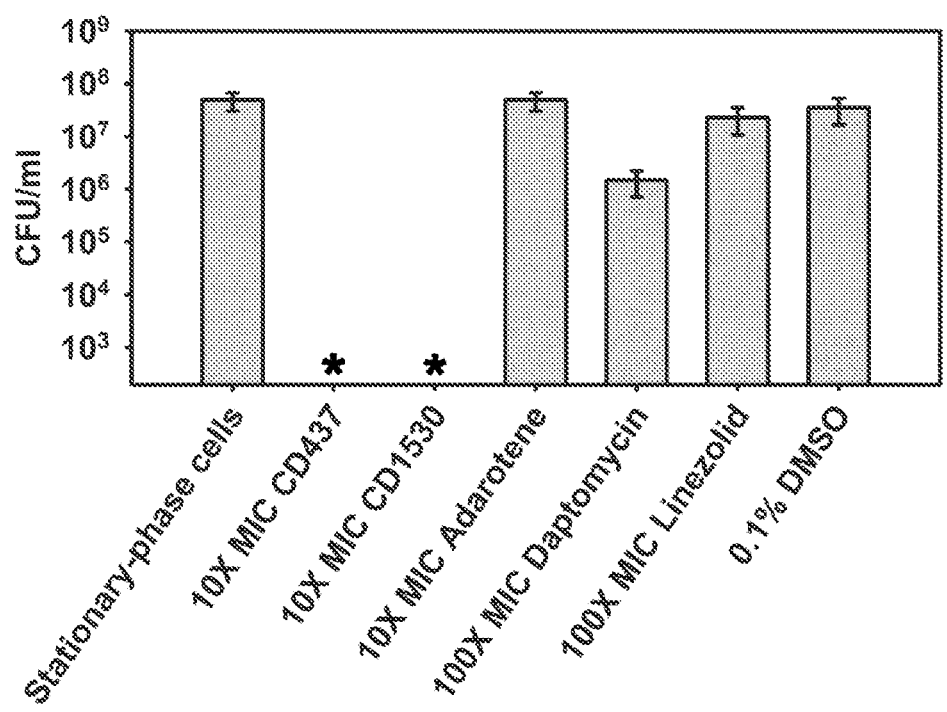
FIG. 25 is a bar graph showing that CD437 and CD1530 eradicate persisters formed by multidrug-resistant *S. aureus* VSR1.
Figure 26A:
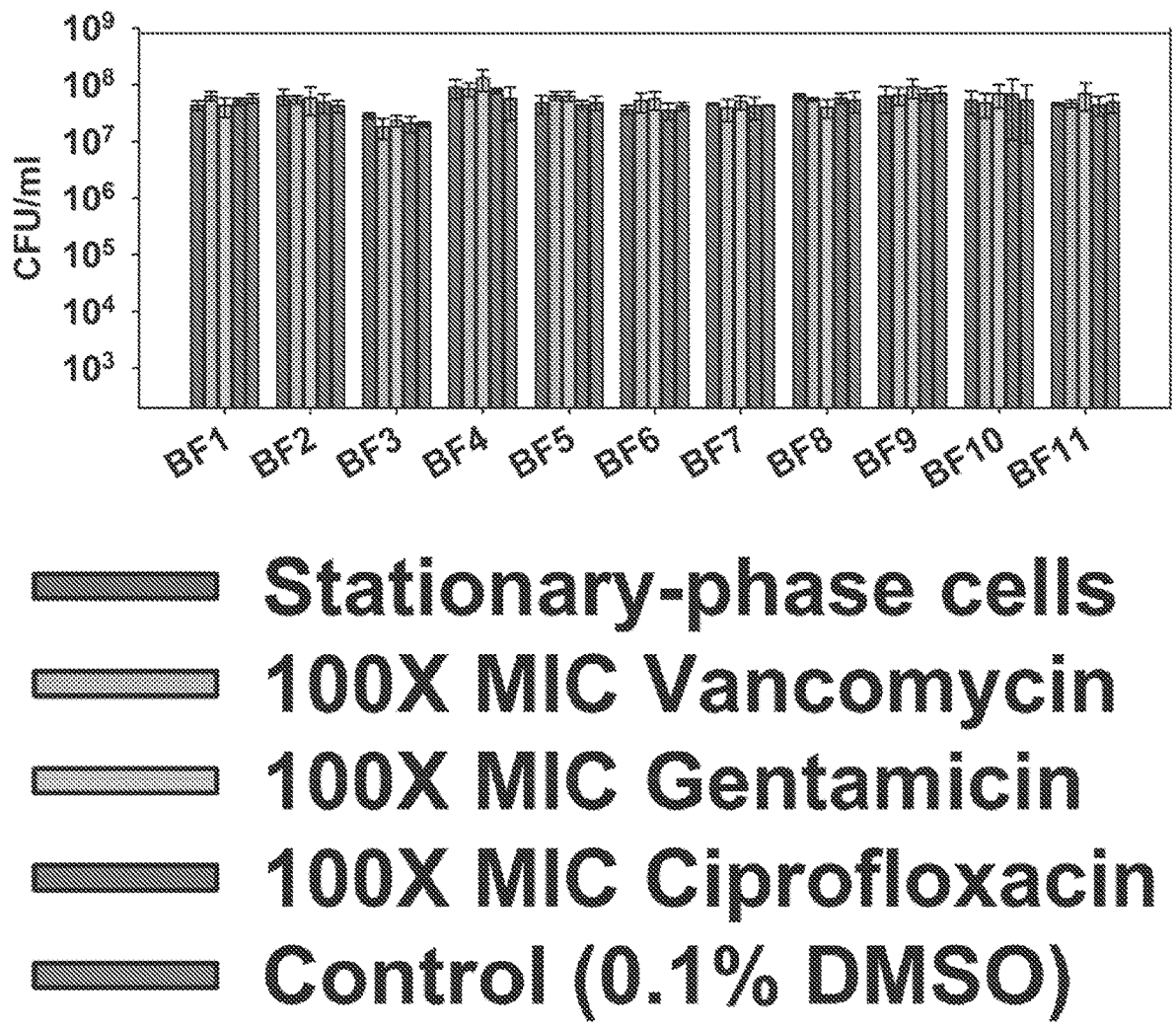
FIG. 26A is a bar graph showing that 11 clinical *S. aureus* isolates show tolerance to 100×MICs of conventional antibiotics.
Figure 26B:
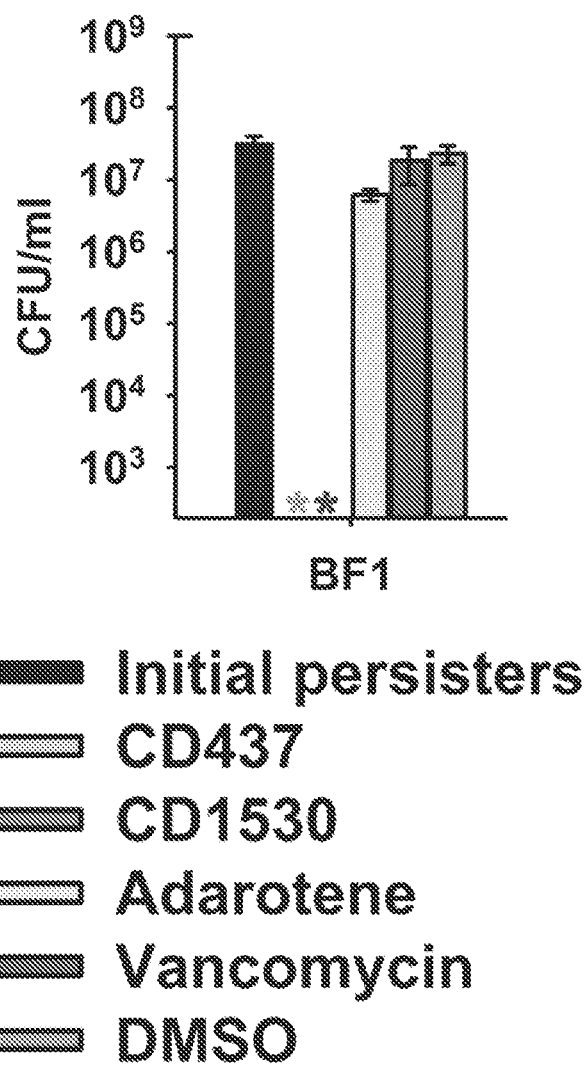
FIG. 26B is a bar graph showing viability of *S. aureus* clinical isolate BF1 after treatment with CD437, CD1530, adarotene or vancomycin.
Figure 26D:
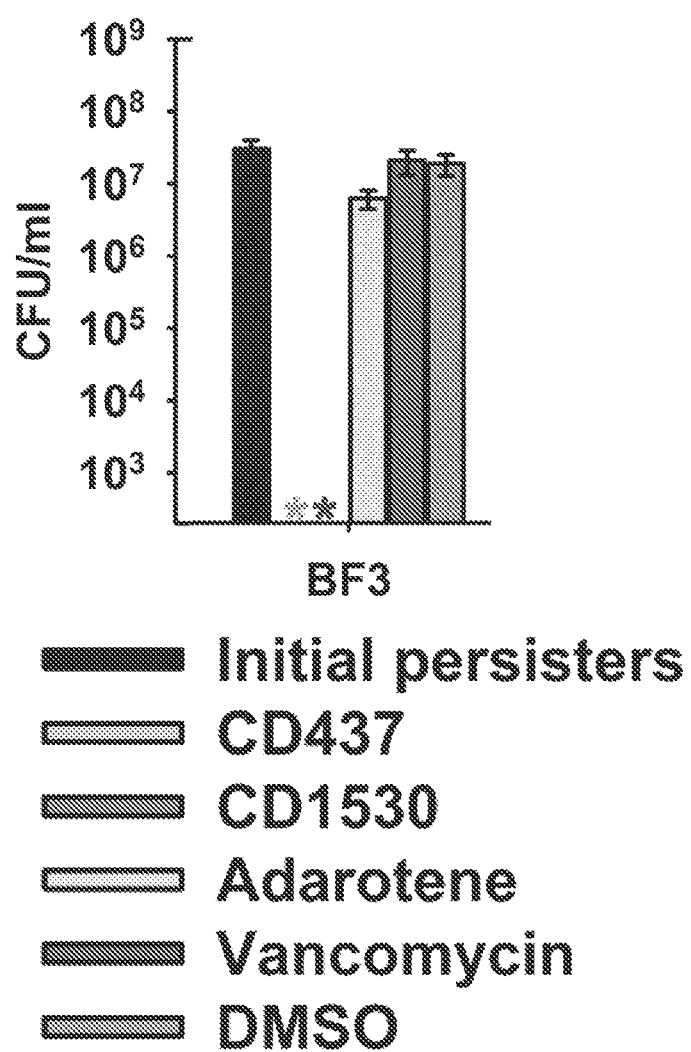
FIG. 26D is a bar graph showing viability of *S. aureus* clinical isolate BF3 after treatment with CD437, CD1530, adarotene or vancomycin
Figure 26E:
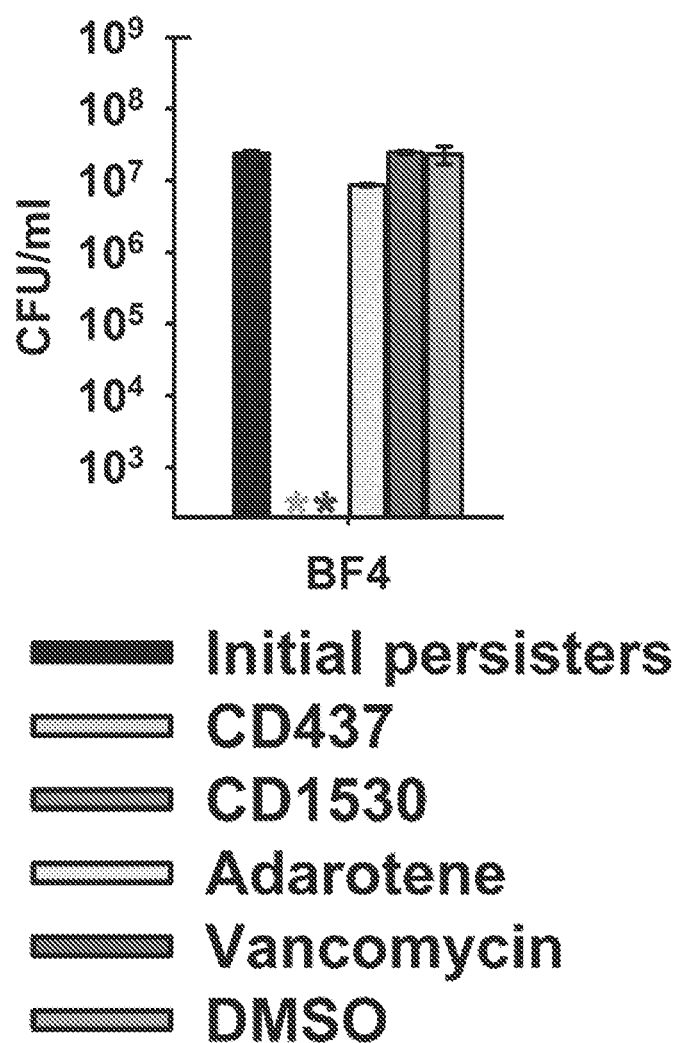
FIG. 26E is a bar graph showing viability of *S. aureus* clinical isolate BF4 after treatment with CD437, CD1530, adarotene or vancomycin.
Figure 26F:
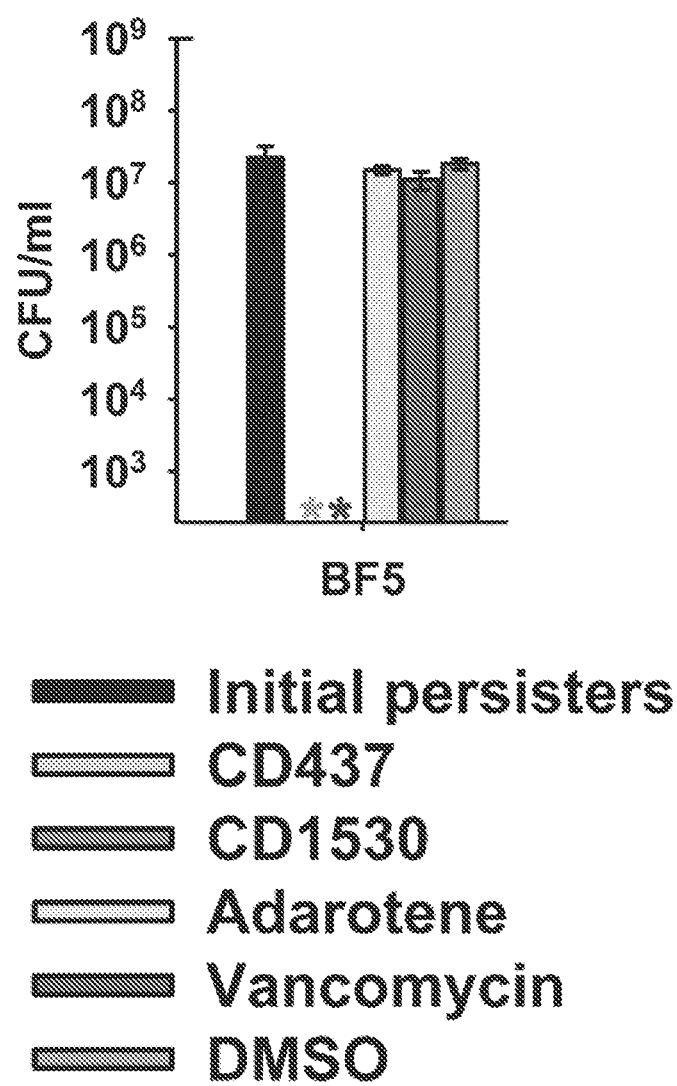
FIG. 26F is a bar graph showing viability of *S. aureus* clinical isolate BF5 after treatment with CD437, CD1530, adarotene or vancomycin
Figure 26G:
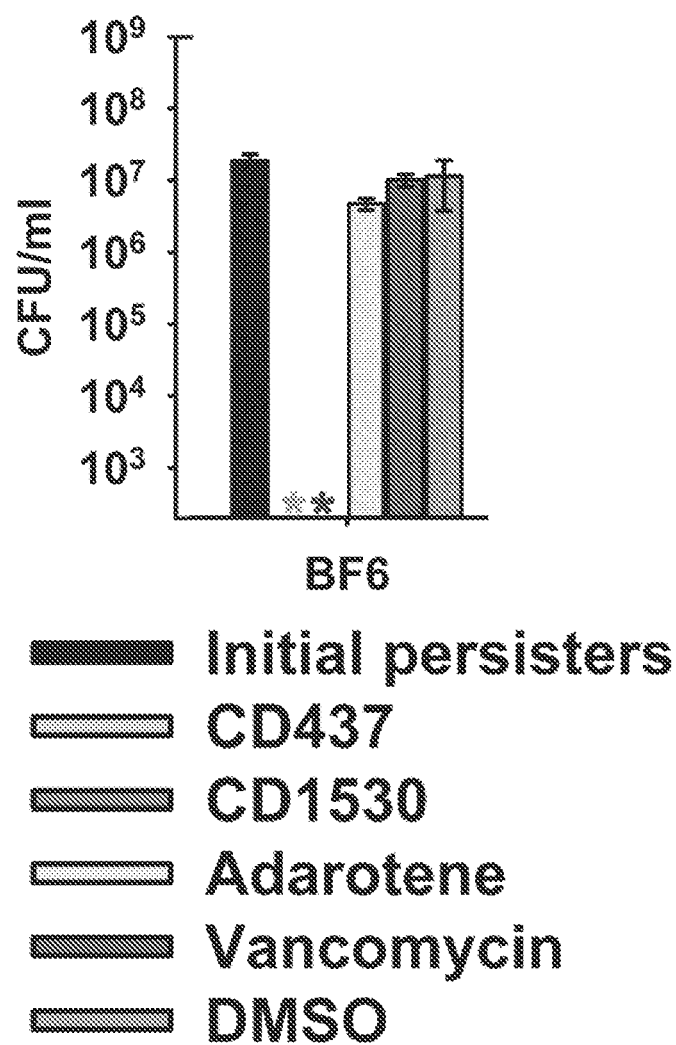
FIG. 26G is a bar graph showing viability of *S. aureus* clinical isolate BF6 after treatment with CD437, CD1530, adarotene or vancomycin.
Figure 26H:
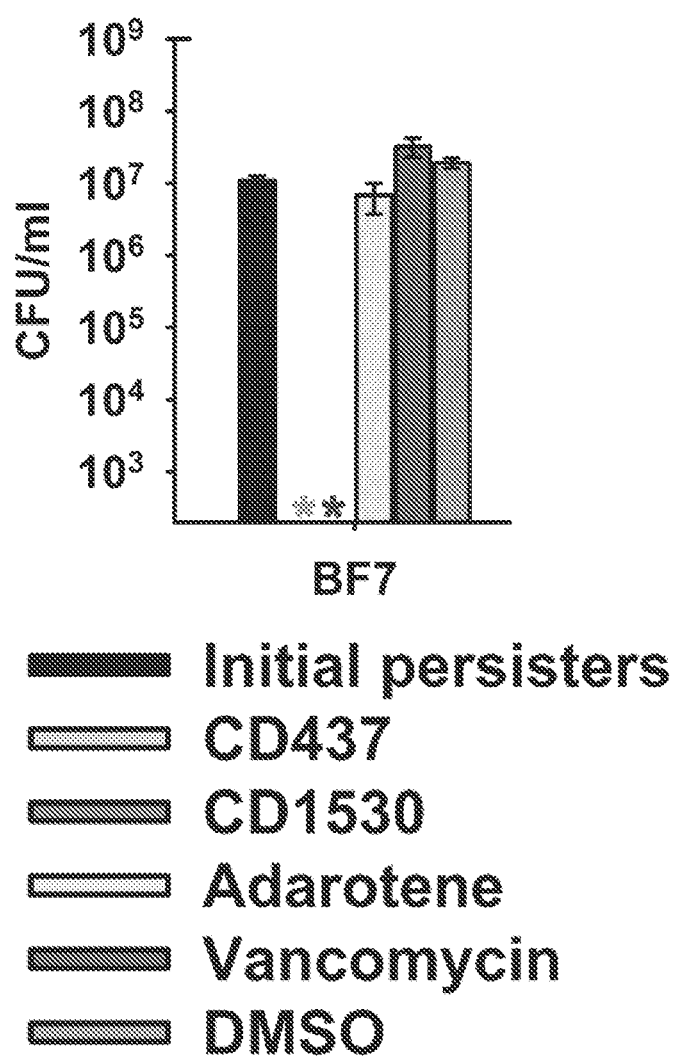
FIG. 26H is a bar graph showing viability of *S. aureus* clinical isolate BF7 after treatment with CD437, CD1530, adarotene or vancomycin
Figure 26I:
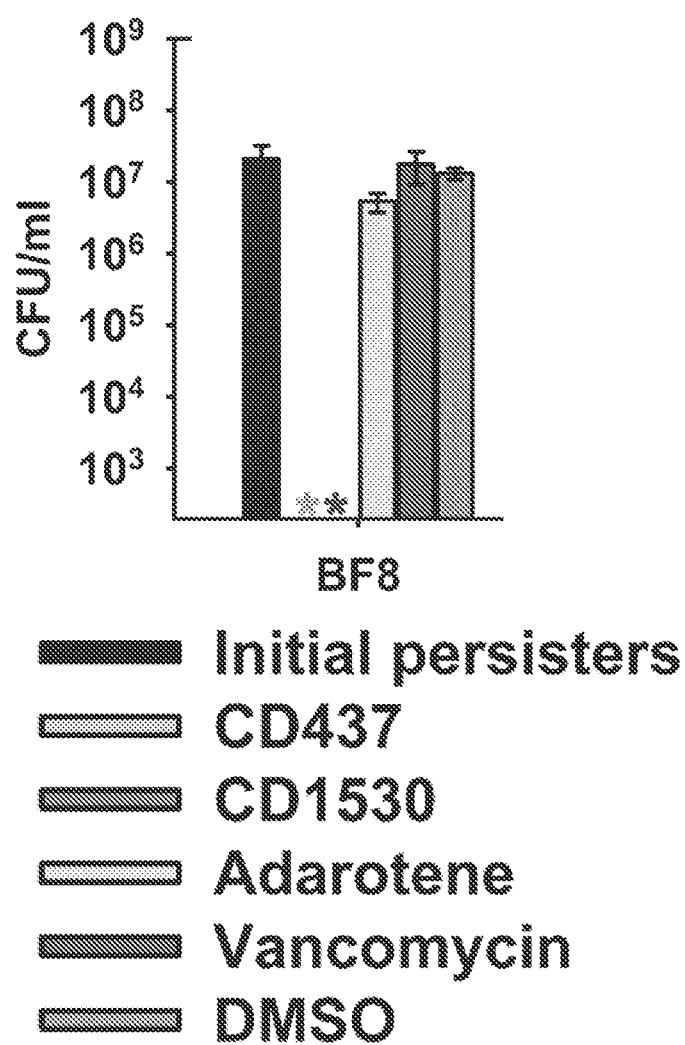
FIG. 26I is a bar graph showing viability of *S. aureus* clinical isolate BF8 after treatment with CD437, CD1530, adarotene or vancomycin
Figure 26J:
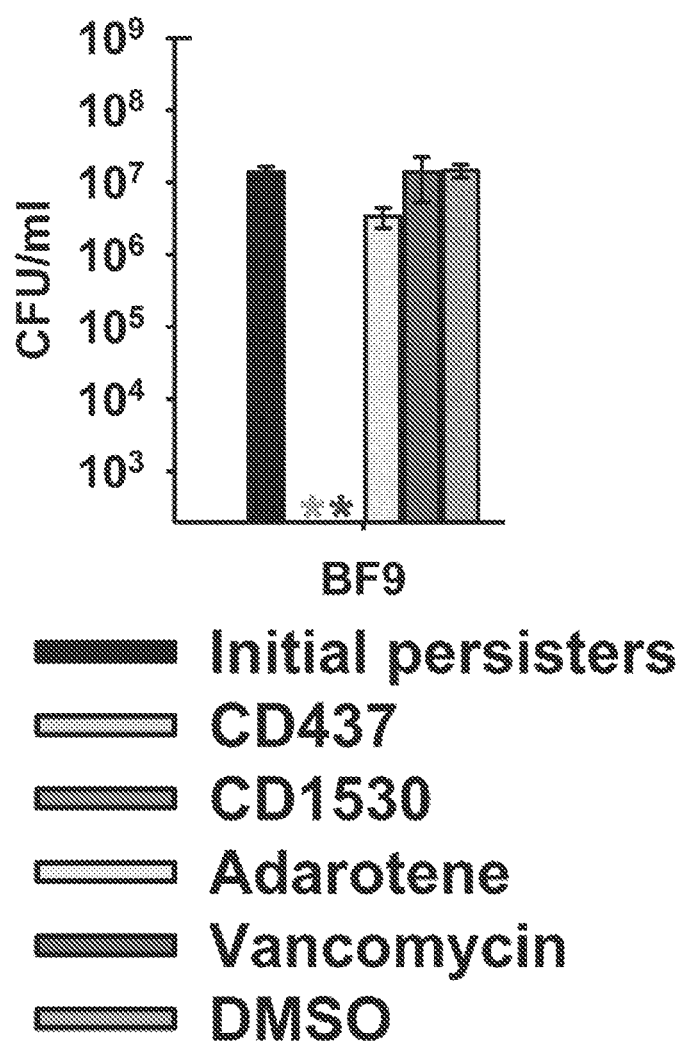
FIG. 26J is a bar graph showing viability of *S. aureus* clinical isolate BF9 after treatment with CD437, CD1530, adarotene or vancomycin
Figure 26K:
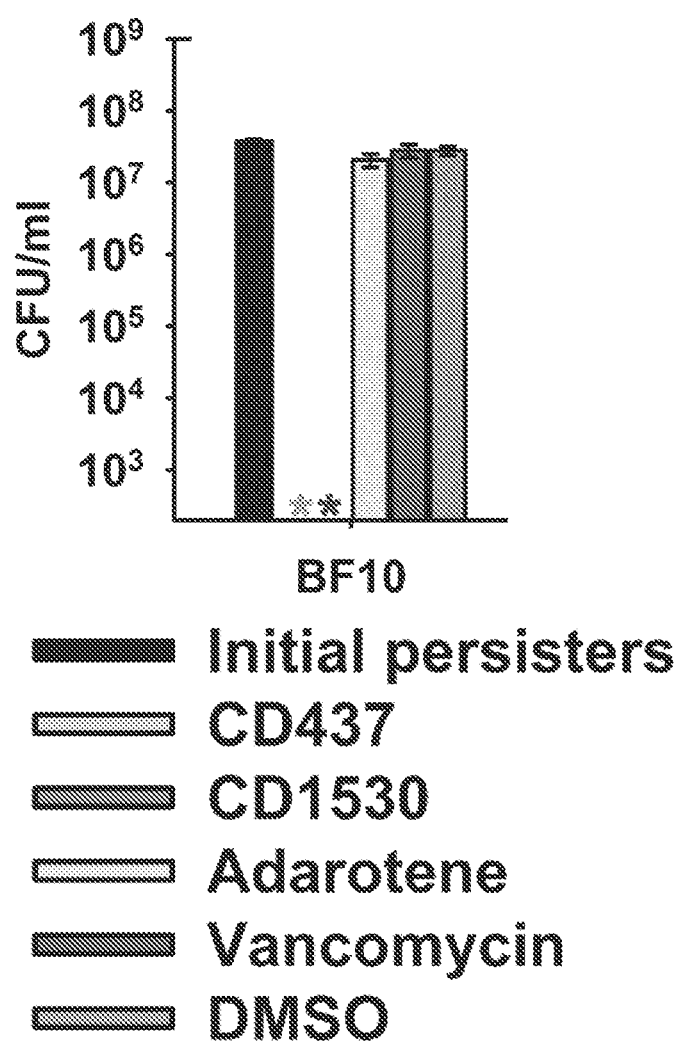
FIG. 26K is a bar graph showing viability of *S. aureus* clinical isolate BF10 after treatment with CD437, CD1530, adarotene or vancomycin
Figure 26L:
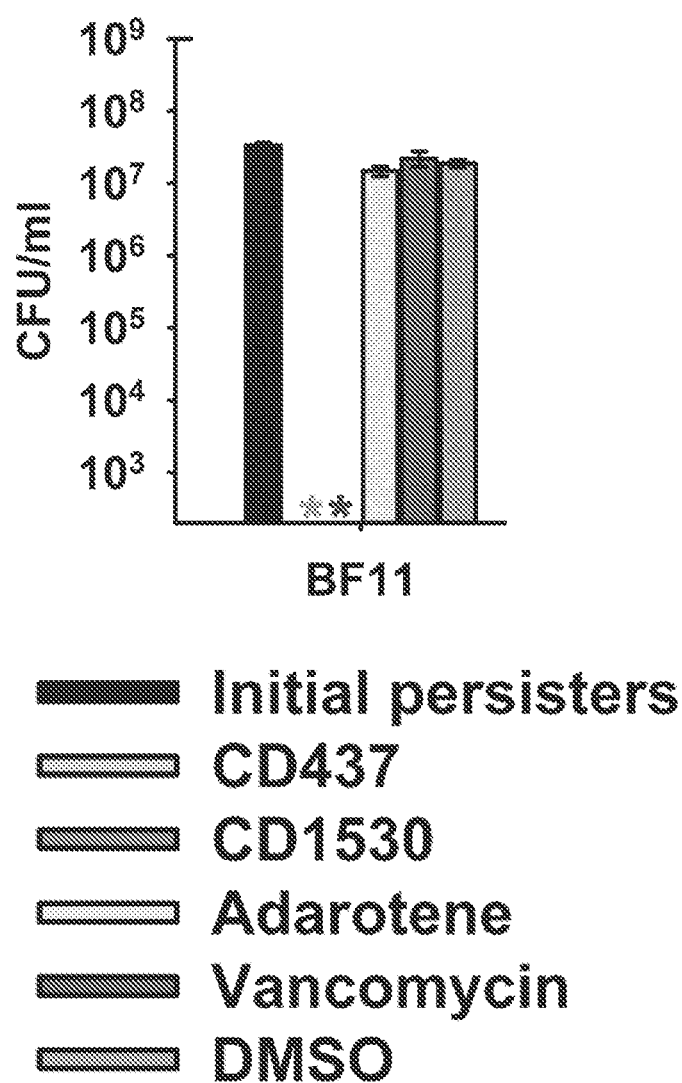
FIG. 26L is a bar graph showing viability of *S. aureus* clinical isolate BF11 after treatment with CD437, CD1530, adarotene or vancomycin

FIG. 25 shows CD437 and CD1530 eradicate persisters formed by multidrug-resistant *S. aureus* VSR1. Stationary-phase cultures of *S. aureus* VRS 1 were treated with 10×MIC of CD437 (10 µg/ml), CD1530 (10 µg/ml), or adarotene (20 µg/ml) and 100×MIC of linezolid (100 µg/ml) or daptomycin (100 µg/ml), and 0.1% DMSO (control) for 4 h. Viability was measured by serial dilution and plating on TSA plates. The asterisks on the x-axis are below the level of detection ($2 \times 10^2$ CFU/ml). Results are shown as means±s.d.; n=3.

TABLE 1a

Minimum inhibitory concentration (µg/ml) of synthetic retinoids against a panel of bacterial strains.

| Strains | CD437 | CD1530 | Adar[1] | Van[1] | Dap[1] | Oxa[1] | Gm[1] | Cipro[1] |
|---|---|---|---|---|---|---|---|---|
| *S. aureus* MW2 | 1 | 1 | 2 | 1 | 1 | 64 | 1 | 0.25 |
| *S. aureus* BF1 | 2 | 2 | 4 | 1 | 2 | >64 | 1 | 0.5 |
| *S. aureus* BF2 | 1 | 1 | 2 | 1 | 8 | >64 | 1 | 1 |
| *S. aureus* BF3 | 1 | 1 | 2 | 1 | 8 | 32 | 1 | 1 |
| *S. aureus* BF4 | 2 | 1 | 2 | 0.5 | 0.5 | 16 | 1 | 0.5 |
| *S. aureus* BF5 | 1 | 1 | 2 | 0.5 | 0.5 | >64 | 1 | 0.5 |
| *S. aureus* BF6 | 1 | 1 | 2 | 0.5 | 0.5 | 1 | 1 | 0.5 |
| *S. aureus* BF7 | 1 | 1 | 2 | 0.5 | 1 | >64 | 1 | 0.5 |
| *S. aureus* BF8 | 1 | 1 | 2 | 0.5 | 0.5 | >64 | 1 | 0.5 |
| *S. aureus* BF9 | 1 | 2 | 2 | 0.5 | 0.5 | 0.25 | 1 | 0.5 |
| *S. aureus* BF10 | 1 | 1 | 2 | 0.5 | 2 | >64 | 1 | 0.25 |
| *S. aureus* BF11 | 1 | 1 | 2 | 1 | 0.5 | >64 | 1 | 0.25 |
| *S. aureus* VRS1 | 1 | 1 | 1 | >64 | 1 | >64 | >64 | 64 |
| *E. faecium* E007 | 2 | 2 | 4 | 1 | 16 | >64 | >64 | 64 |
| *E. faecium* C68 | 2 | 2 | 4 | 64 | 8 | >64 | >64 | >64 |
| *E. faecium* D14 | 2 | 2 | 4 | 2 | 16 | >64 | 32 | 4 |
| *E. faecium* D24 | 1 | 1 | 2 | 1 | 32 | >64 | >64 | 1 |
| *E. faecium* D25 | 1 | 1 | 4 | 1 | 16 | >64 | 32 | 1 |
| *E. faecium* D29 | 1 | 1 | 2 | 2 | 16 | >64 | 64 | 0.5 |
| *E. faecium* WB213 | 1 | 1 | 2 | 16 | 16 | >64 | 32 | 32 |
| *E. faecium* WC176 | 2 | 2 | 4 | 64 | 16 | >64 | 64 | 1 |
| *K. pneumonia* WGLW2 | >64 | >64 | >64 | >64 | >64 | >64 | 1 | 0.063 |
| *A. baumannii* ATCC 17978 | >64 | >64 | >64 | >64 | >64 | >64 | 1 | 0.25 |
| *P. aeruginosa* PA14 | >64 | >64 | >64 | >64 | >64 | >64 | 2 | 0.063 |
| *E. aerogenes* ATCC 13048 | >64 | >64 | >64 | >64 | >64 | >64 | 2 | 0.031 |

[1]Adar: Adarotene, Van: vancomycin, Dap: Daptomycin, Oxa: Oxacillin, Gm: gentamicin, Cipro: ciprofloxacin CD437 or CD1530 are killing the bacteria to the limit of detection ($2 \times 10$ CFU/ml) within 3 h, faster than the killing kinetics of vancomycin, an antibiotic of "last resort", that is widely used for acute *S. aureus* infections (See FIG. 23). 100% of *C. elegans* animals survived MRSA infections when treated with CD437 or CD1530 at concentrations above their MICs (FIG. 22(A-G)), suggesting that they protect *C. elegans* from MRSA infection by functioning as traditional antibiotics that block bacterial growth. Adarotene, also exhibited bactericidal activity against MRSA MW2 (MIC 2 g/ml, FIG. 22(A-G), FIG. 23, Table 1a) and FIG. 26(A-L) shows CD437 and CD1530 eradicate persisters formed by a broad spectrum of *S. aureus* strains. (A) Stationary-phase cells of 11 clinical *S. aureus* isolates show tolerance to 100×MICs of conventional antibiotics, confirming they are persister cells. Stationary-phase cultures were treated with 0.1% DMSO (control), 100×MIC gentamicin, 100×MIC vancomycin, and 100×MIC ciprofloxacin for 4 h. (B-L) Persisters formed by 11 clinical *S. aureus* isolates were treated with 0.1% DMSO (control), 10×MICs of CD437, CD1530, adarotene or vancomycin for 4 h. Viability was measured by serial dilution and plating on TSA plates.

The asterisks on the x-axis are below the level of detection (2×10² CFU/ml). Results are shown as means±s.d.; n=3.

Example 1b. Study to Obtain Bacterial Mutants Resistant to of CD437, CD1530, or Adarotene Resistant mutants were not obtained by plating on TSB agar containing 2.5×, 5×, or 1 OX MIC of CD437, CD 1530, or adarotene (spontaneous mutation frequency of <10-10) (for details of the experiment, see the methods section). Similarly, serial passage of two independent *S. aureus* MW2 cultures (SP1 and SP2) for 100 days in sub-MIC levels of CD437 only yielded presumptive mutants with 2-fold more resistance to CD437, whereas serial passage of MW2 in ciprofloxacin generated strains that were 256-fold more resistant (see FIG. 27(A-C)).

in the MIC of CD437 against MRSA during serial passage was confirmed by re-measuring MICs using three colonies from aliquots of all 100 passages that had been stored in −80° C. Mutated genes are indicated on the day when the mutations were first detected.

The presumptive CD437-resistant mutants also exhibited 2-fold increased resistance to CD1530 and adarotene. To identify mutations in the CD437-resistant SP1 and SP2 cultures, whole genome sequences of day 100 cultures to day 1 cultures were compared and 36 and 38 mutations in the SP1 and SP2 cultures were identified, respectively. A limited number of these mutations caused amino acid changes in the corresponding proteins, including mutations in MW0622 (graS), MW2067 (manA), and MW2474 in SP1, and in MW0883 (yjbH), MW0815 (dltB), MW2067 (manA), and MW1685 in SP2 (See, e.g, Table 1b).

TABLE 1b

Amino acid changes located in open reading frames after in vitro selection with CD437

| Strain | Day of passage | Mutated gene | Function | Base change | Amino acid change |
|---|---|---|---|---|---|
| SP1 | 8 | MW0622 (graS) | Two-component sensor histidine kinase, GraS | 851C > T | Ser284Leu[1] |
| SP1 | 48 | MW2067 (manA) | Mannose-6-phosphate isomerase, ManA | 182G > A | Trp61Stop codon |
| SP1 | 74 | MW2474 | Hypothetical protein, TetR family regulatory protein | 347G > A | Cys116Tyr |
| SP2 | 13 | MW0883 (yjbH) | Hypothetical protein, YjbH | 730Cdeletion | Gln244frame shift |
| SP2 | 52 | MW0815 (dltB) | D-alanyl transfer protein | Insertion of TTAATTGCT between 30 T and 31 T | Insertion of LeuIleAla between Phe10 and Leu11 |
| SP2 | 59 | MW2067 (manA) | Mannose-6-phosphate isomerase, ManA | 777G > T | Lys259Asn |
| SP2 | 65 | MW1685 | Hypothetical protein, tRNA-binding protein | 359A > G | Asp120Gly |

[1]Ser284 is located in the C-terminal ATP-binding domain.

Figure 27A:
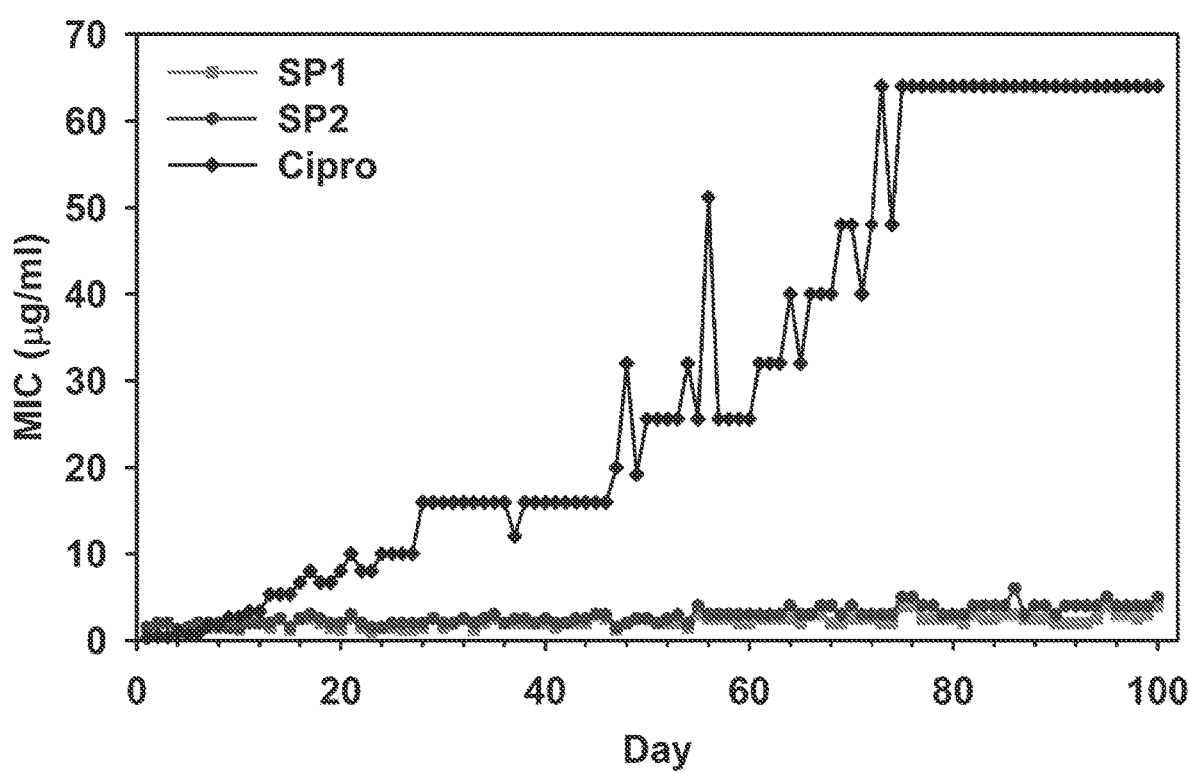
FIG. 27A is a line plot showing appearance of spontaneous CD437-resistant mutants over the course of 100 days during serial passage in duplicate.
Figure 27B:
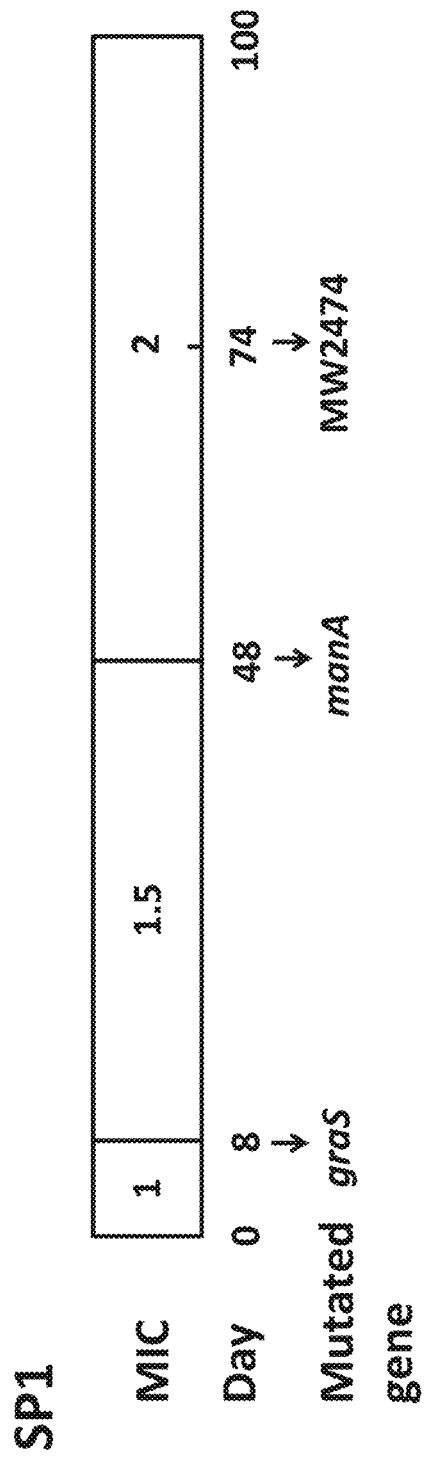
FIG. 27B is a plot showing time course of appearance of mutation in SP1 that affect the amino acid sequences of the corresponding genes as determined by PCR.
Figure 27C:
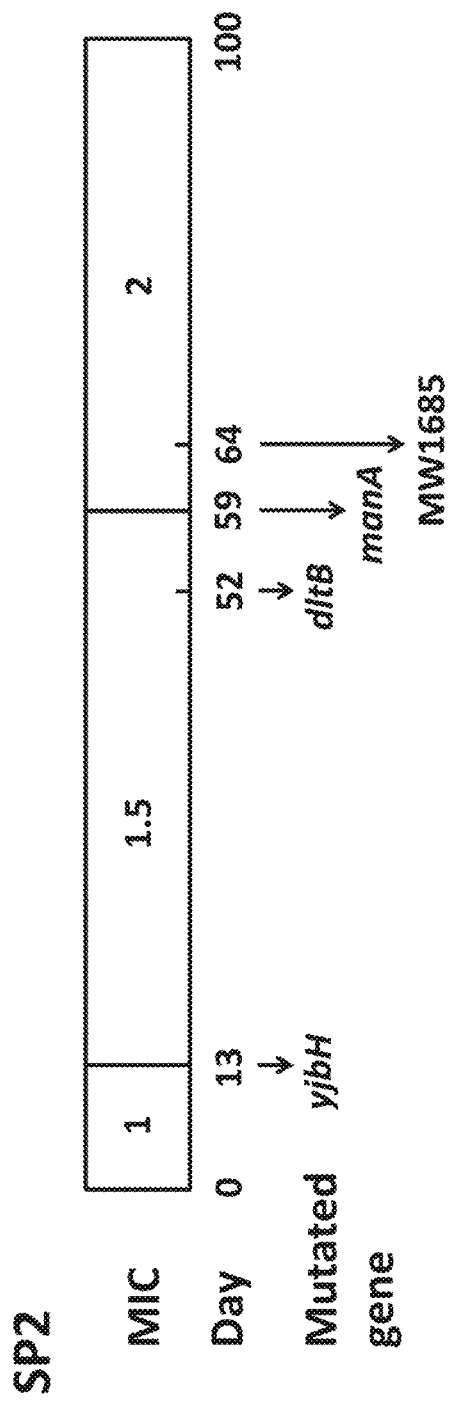
FIG. 27C is a plot showing time course of appearance of mutation in SP2 that affect the amino acid sequences of the corresponding genes as determined by PCR.

FIG. 27(A-C) shows isolation of *S. aureus* MW2 mutants resistant to CD437 by daily serial passage for 100 days. FIG. 27A shows the appearance of spontaneous CD437-resistant mutants exhibiting only 2-fold increase in MIC over the course of 100 days during serial passage in duplicate (SP1 and SP2) as described in Methods. This is a small increase in the MIC and suggests that resistance is not developed. Ciprofloxacin (Cipro) was used as a positive control for developed resistance during continuous exposure. FIG. 27B shows the time course of appearance of mutations in SP1 and SP2 that affect the amino acid sequences of the corresponding genes as determined by PCR. The modest increase PCR analysis showed that the mutations in graS and yjbH in SP1 and SP2 appeared at an early stage of the serial transfer experiment and resulted in a 1.5 fold increase in resistance to CD437 (FIG. 27(A-C)). Two independent mutations in manA in SP1 and SP2 were correlated with an increase in resistance to 2-fold above the MIC about halfway through the experiment (FIG. 27(A-C)). The mutations in graS, yjbH, and manA also resulted in a 1.5-fold increase in resistance to CD1530 and adarotene (See, e.g., Table Ic).

TABLE 1c

Antimicrobial susceptibility of S. aureus MW2 mutants isolated by serial passage for 100 days

| Mutant "strain"[1] | Mutated gene | MIC (µg/ml) | | | | |
|---|---|---|---|---|---|---|
| | | CD1530 | Adarotene | Vancomycin | Gentamicin | Defensin 1 |
| SP1-1 | | 1 | 2 | 1 | 1 | 16 |
| SP1-8 | graS | 1.5 | 3 | 0.5 | 0.25 | 8 |
| SP1-48 | graS, manA | 2 | 4 | 0.5 | 0.25 | 8 |
| SP1-74 | graS, manA, MW2474 | 2 | 4 | 0.5 | 0.25 | 8 |
| SP1-100 | graS, manA, MW2474 | 2 | 4 | 0.5 | 0.25 | 8 |
| SP2-1 | | 1 | 2 | 1 | 1 | 16 |
| SP2-13 | yjbH | 1.5 | 3 | 1 | 1 | 16 |
| SP2-52 | yjbH, dltB | 1.5 | 3 | 0.5 | 0.25 | 8 |
| SP2-59 | yjbH, dltB, manA | 2 | 4 | 0.5 | 0.25 | 8 |
| SP2-65 | yjbH, dltB, manA, MW1685 | 2 | 4 | 0.5 | 0.25 | 8 |
| SP2-100 | yjbH dltB, manA, MW1685 | 2 | 4 | 0.5 | 0.25 | 8 |

[1]The culture from each day during serial passage was named as 'the replicate number - day of passage.' For example, SP1-100 refers to the culture from the first biological replicate on day 100.

The correlation between mutations in graS, yjbH and manA and increased resistance to retinoids was also observed in S. aureus strain JE2 mutants containing transposon insertion in these 3 genes (See, e.g., Fey, P. D. et al. A genetic resource for rapid and comprehensive phenotype screening of nonessential Staphylococcus aureus genes. MBio 4, e00537-12-e00537-12 (2013)) (See, e.g., Table 1d)

TABLE 1d

MIC of graS, manA, or yjbH transposon insertion mutants in S. aureus JE2 background.

| S. aureus strain | CD437 (µg/ml) | CD1530 (µg/ml) | Adarotene (µg/ml) |
|---|---|---|---|
| JE2 (wild-type) | 1.5 | 1.5 | 2.5 |
| NE1756 (JE2 graS::φNΣ) | 2 | 2 | 4 |
| NE1645 (JE2 manA::φNΣ) | 3 | 3 | 4 |
| NE896 (JE2 yjbH::φNΣ) | 2 | 2 | 4 | manA, MW2474 and dltB are part of the GraSR regulon, a two-component regulatory system known to play an important role in resistance to cationic antimicrobial peptides (CAMPs) (See, e.g., Meehl, M. et al. Interaction of the GraRS two-component system with the VraFG ABC transporter to support vancomycin-intermediate resistance in Staphylococcus aureus. Antimicrob. Agents Chemother. 51, 2679-2689 (2007); Yang, S.-J. et al. The Staphylococcus aureus two-component regulatory system, GraRS, senses and confers resistance to selected cationic antimicrobial peptides. Infect. Immun. 80, 74-81 (2012); and Falord, M. et al. Investigation of the Staphylococcus aureus GraSR regulon reveals novel links to virulence, stress response and cell wall signal transduction pathways. PLoS ONE 6, e21323 (2011)), although mutations in MW2474 and dltB did not appear to result in a measurable increase in resistance to CD437 (FIG. 27(A-C)).

Example 1c. CD437, CD1530, and Adarotene Disrupt Membrane Lipid Bilayers

Figure 3:
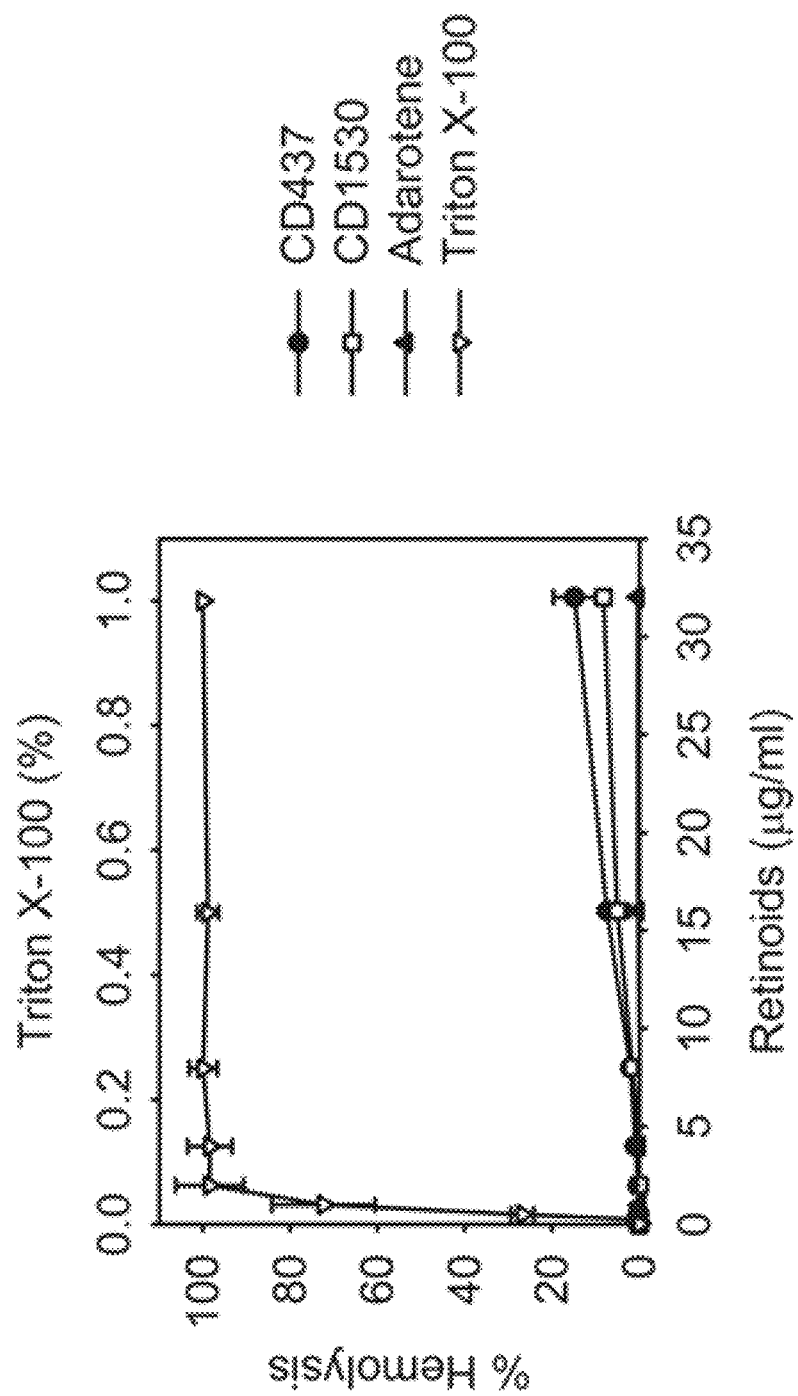
FIG. 3 is a line graph showing alterations in bacterial membrane permeability caused by synthetic retinoids (CD437 and CD1530) using a Sytox assay.

FIG. 3 shows that the compounds were tested against S. aureus in the presence of Sytox to evaluate membrane permeability. Damaged cell membrane integrity resulted in the admittance of Sytox stain. In an assay using Sytox to evaluate cell permeabilization in the presence of retinoid compound, higher fluorescence indicative of cell permeabilization by CD 437 and CD 1530 was observed (FIG. 3). By contrast, adarotene, did not show permeabilization at lower concentrations but was achieved at 4 µg/ml, in line with the higher MIC of this compound compared to CD 437 and CD 1530. The membrane permeabilization suggests the compounds disrupt the bacterial membrane.

Mutations in graS, manA, and yjbH affect cell envelope physiology (See, e.g., Meehl, M. et al. Interaction of the GraRS two-component system with the VraFG ABC transporter to support vancomycin-intermediate resistance in Staphylococcus aureus. Antimicrob. Agents Chemother. 51, 2679-2689 (2007); Yang, S.-J. et al. The Staphylococcus aureus two-component regulatory system, GraRS, senses and confers resistance to selected cationic antimicrobial peptides. Infect. Immun. 80, 74-81 (2012); and Falord, M. et al. Investigation of the Staphylococcus aureus GraSR regulon reveals novel links to virulence, stress response and cell wall signal transduction pathways. PLoS ONE 6, e21323 (2011); Elbaz, M. et al. The metabolic enzyme ManA reveals a link between cell wall integrity and chromosome morphology. PLoS Genet. 6, e1001119 (2010); and Gohring, N. et al. New role of the disulfide stress effector YjbH in β-lactam susceptibility of Staphylococcus aureus. Antimicrob. Agents Chemother. 55, 5452-5458 (2011)), suggesting that CD437, CD1530, and adarotene target the bacterial cell membrane. Deletion of graS results in an increase in the net bacterial surface negative charge, which increases susceptibility to positively charged antimicrobials, such as vancomycin and CAMPs, consistent with results showing that culture SP1 exhibited increased susceptibility to vancomycin and the CAMP defensin 1 after the graS mutation appeared on day 8 (See, e.g., Table 1c). Deletion of manA leads to decreased cell wall integrity and inactivation of YjbH results in increased peptidoglycan cross-linking and moderately increased resistance to beta-lactam antibiotics (See, e.g., Elbaz, M. et al. The metabolic enzyme ManA reveals a link between cell wall integrity and chromosome morphology. *PLoS Genet.* 6, e1001119 (2010); and Gohring, N. et al. New role of the disulfide stress effector YjbH in β-lactam susceptibility of *Staphylococcus aureus*. *Antimicrob. Agents Chemother.* 55, 5452-5458 (2011)). As shown in FIG. 28(A-M), CD437, CD1530, and adarotene, but not adapalene, induced MW2 membrane permeabilization in a dose-dependent manner, with significant permeabilization occurring at approximately their MICs.

FIG. 28(A-M) shows that CD437, CD1530, and adarotene disrupt membrane lipid bilayers. (A-D). Exponential-phase MRSA cells were treated with the indicated concentrations of retinoids. Membrane permeability was measured spectrophotometrically by monitoring the uptake of SYTOX Green (Ex=485 nm, Em=525 nm) over time. Results are shown as means±s.d.; n=3. (E,F) Giant unilamellar vesicles (GUVs) consisting of DOPC/DOPG (7:3) labeled with 18:1 Liss Rhod PE (0.05%) were treated with 10× or 1×MICs of CD437, CD1530, and adarotene, 20 μg/ml adapalene or 0.1% DMSO. Changes in GUVs were monitored over time using fluorescence microscopy (40× objective, Ex=460 nm, Em=483 nm). (G-J) Representative configurations of the synthetic retinoids at the onset of simulation, membrane attachment, membrane penetration and equilibrium state. (K) The side view and (L) the top view of configurations of nearest neighboring lipids around an embedded CD437 molecule. The retinoids and sodium ions are highlighted as large spheres. Phospholipids are shown as chains of atoms colored to identify hydrophilic and hydrophobic regions (hydrogen, white; oxygen, red; nitrogen, light blue; carbon, cyan; phosphorus, orange; sodium, dark blue). Water molecules are set to be transparent for clarity. (M) The free energy profile of the four retinoids penetrating into the membrane as a function of the distance between the center-of-mass (COM) of a retinoid and the bilayer. The dot-dashed line marks the averaged COM location of phosphate groups in lipids, indicative of the membrane surface. The membrane penetration of CD437, CD1530, adarotene, and adapalene are spontaneous with transfer energies of −8.92 $k_BT$, −7.14 $k_BT$, −1.45 $k_BT$, and 18.76 $k_BT$ and energy barriers of 1.42 $k_BT$, 1.12 $k_BT$, 2.03 $k_BT$, and 26.13 $k_BT$, respectively.

Disruption of the Integrity of Biomembrane-Mimicking Giant Unilamellar Vesicles (GUVs)

Additional evidence that CD437, CD1530, and adarotene target membranes was obtained by showing that the 3 retinoids disrupt the integrity of biomembrane-mimicking giant unilamellar vesicles (GUVs), consisting of a DOPC/DOPG lipid bilayer at a ratio of 7:3, which mimics the *S. aureus* membrane (Chen, Y.-F. et al. Interaction of daptomycin with lipid bilayers: a lipid extracting effect. *Biochemistry* 53, 5384-5392 (2014)). When GUVs were exposed to 1×MIC of CD437, CD1530, or adarotene, lipid aggregates formed on the surface of the GUVs, but they did not burst, even though the GUVs appeared to be damaged (FIG. 28(A-M)). At 10×MIC of all 3 retinoids, more surface aggregates formed than at 1×MIC and in the case of CD437, there was a transient expansion of the GUVs (FIG. 28(A-M)).

Figure 28A:
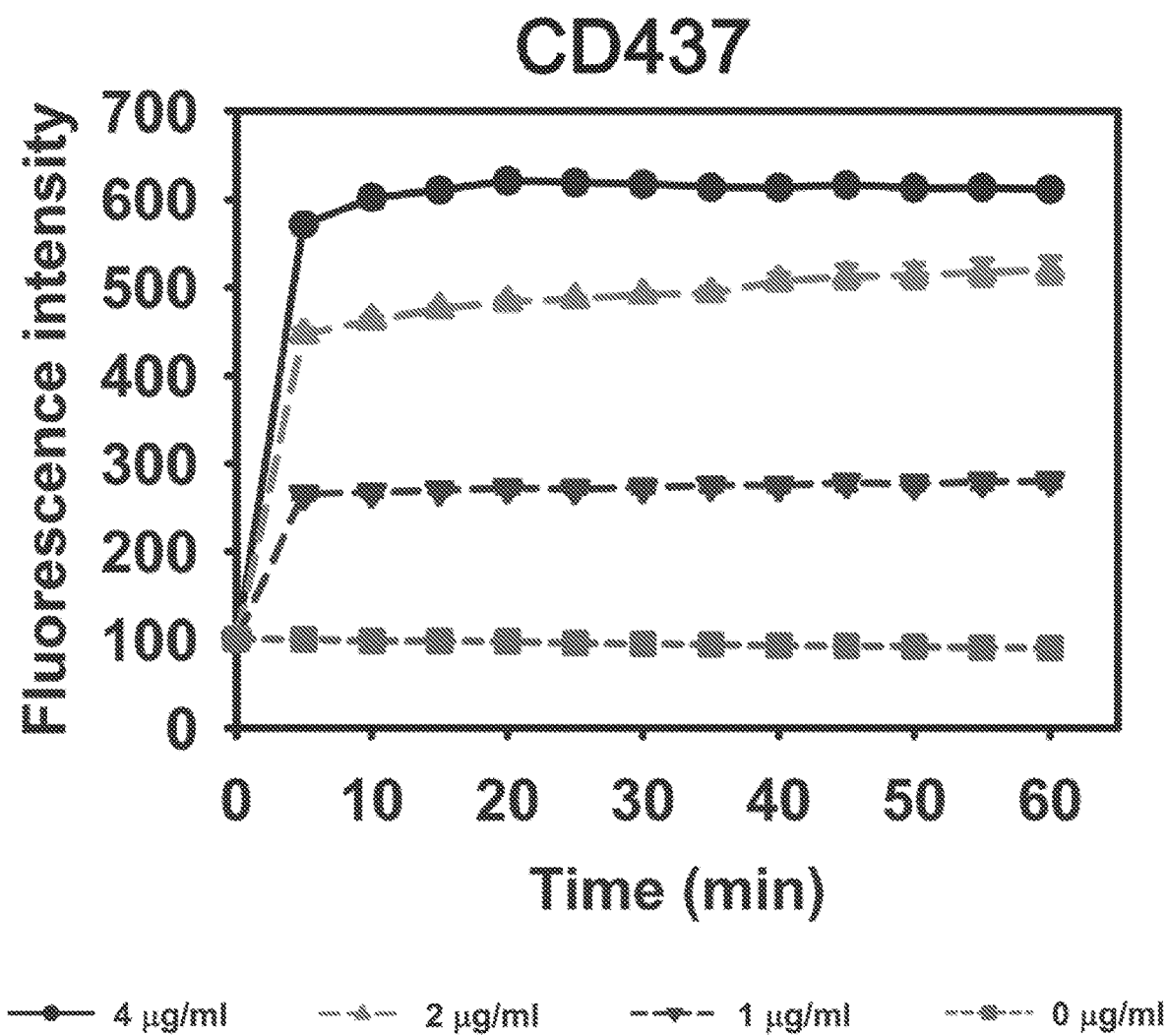
FIG. 28A is a line graph showing uptake of SYTOX Green (Ex=485 nm, Em=525 nm) over time measured spectrophotometrically by exponential-phase MRSA cells treated with the indicated concentrations of CD437.
Figure 28D:
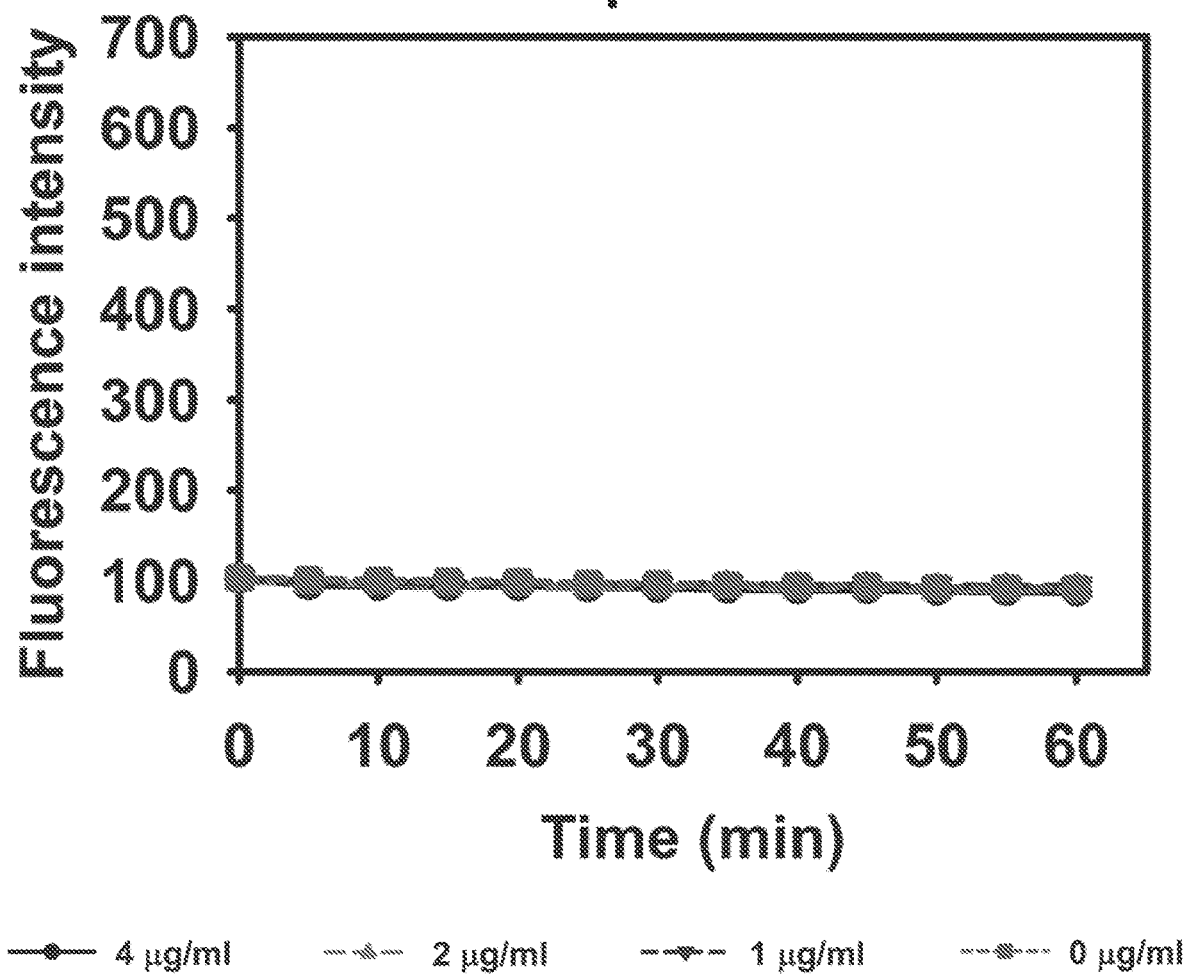
FIG. 28D is a line graph showing uptake of SYTOX Green (Ex=485 nm, Em=525 nm) over time measured spectrophotometrically by exponential-phase MRSA cells treated with the indicated concentrations of adapalene.
Figure 28E:
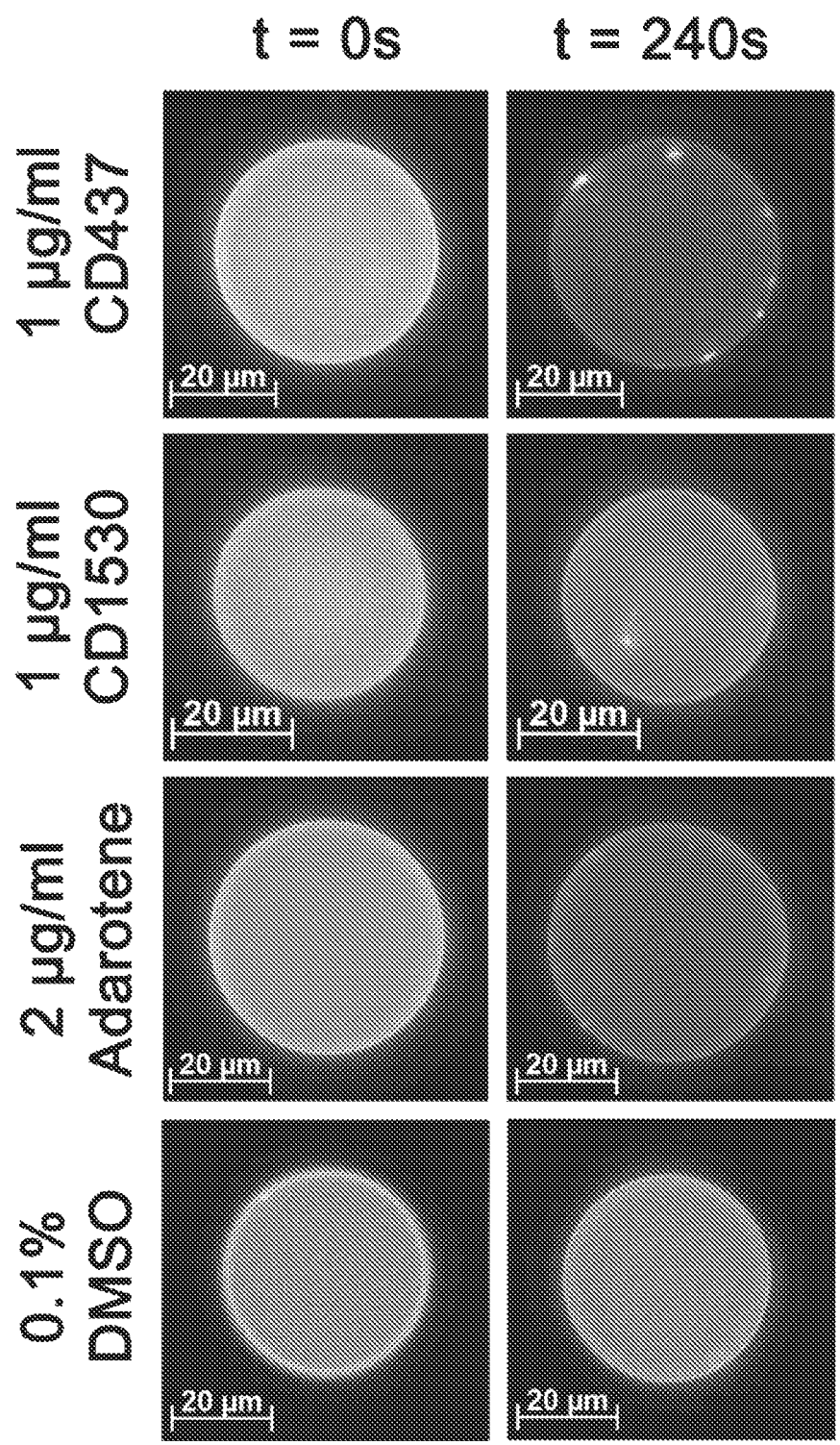
FIG. 28E contains images of giant unilamellar vesicles (GUVs) consisting of DOPC/DOPG (7:3) labeled with 18:1 Liss Rhod PE (0.05%) that were treated with 1×MICs of CD437, CD1530, and adarotene.
Figure 28F:
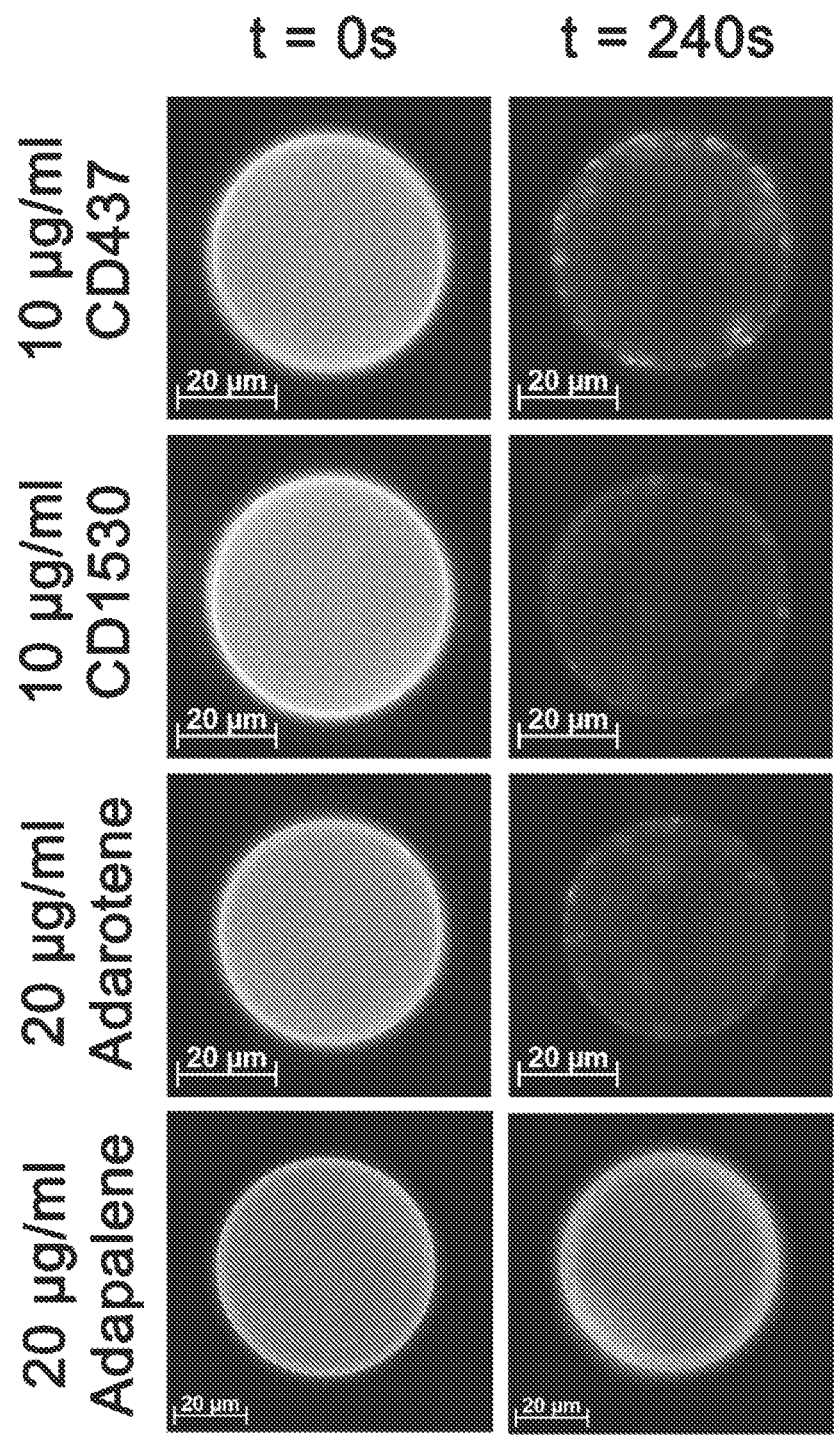
FIG. 28F contains images of giant unilamellar vesicles (GUVs) consisting of DOPC/DOPG (7:3) labeled with 18:1 Liss Rhod PE (0.05%) that were treated with 10×MICs of CD437, CD1530, and adarotene, 20 µg/ml adapalene or 0.1% DMSO
Figure 28G:
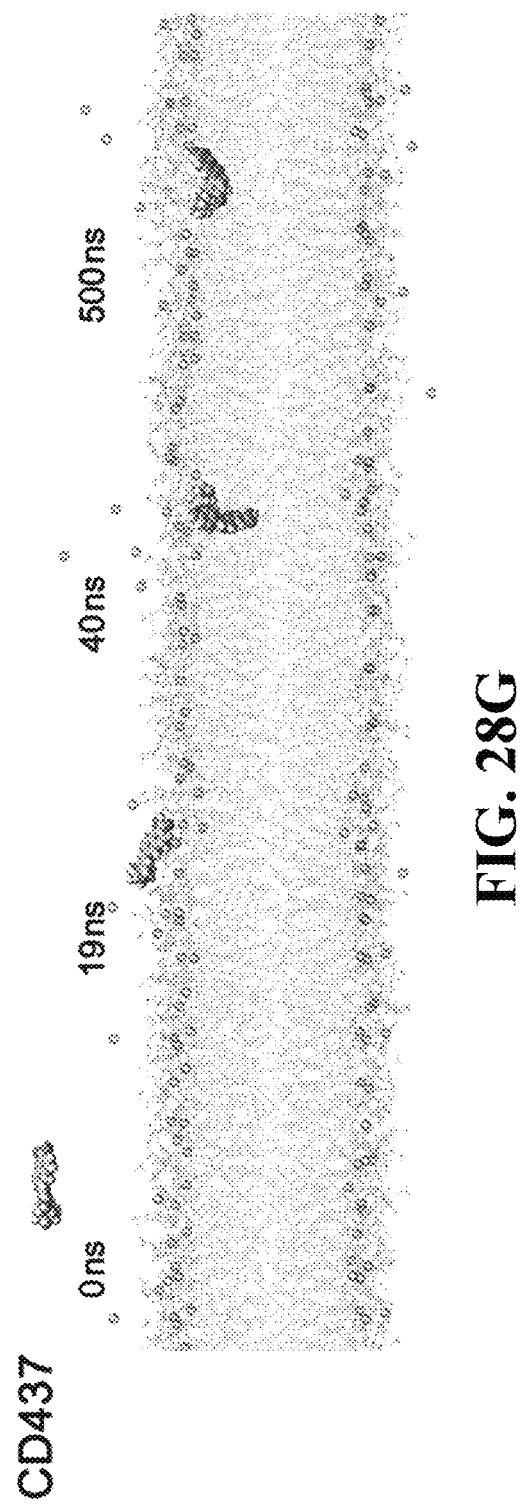
FIG. 28G is an image of representative configurations of CD437 at the onset of simulation, membrane attachment, membrane penetration and equilibrium state.
Figure 28H:
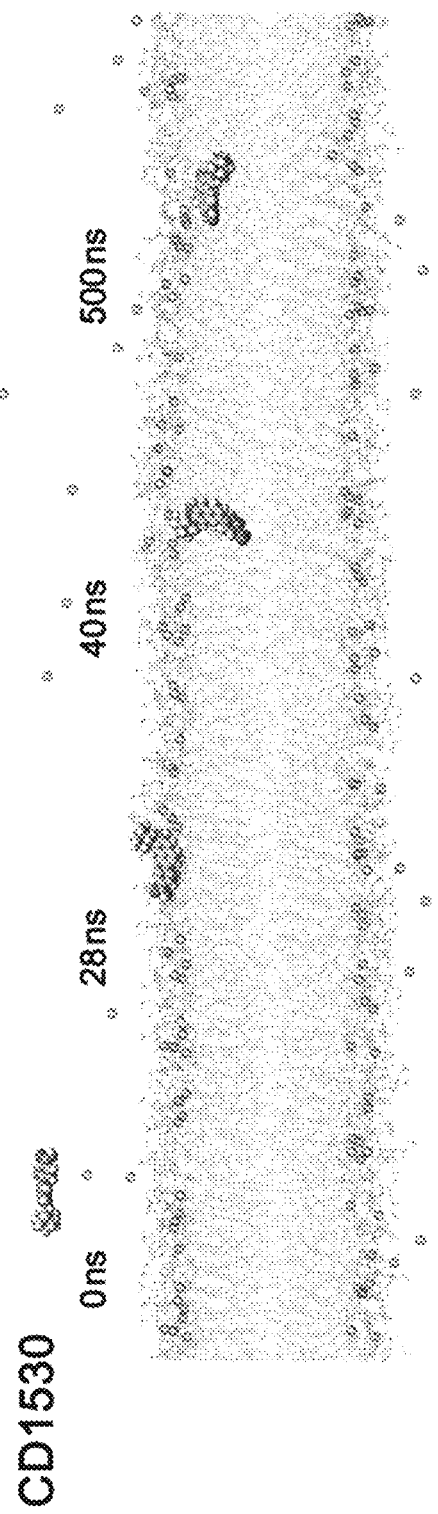
FIG. 28H is an image of representative configurations of CD1530 at the onset of simulation, membrane attachment, membrane penetration and equilibrium state
Figure 28I:
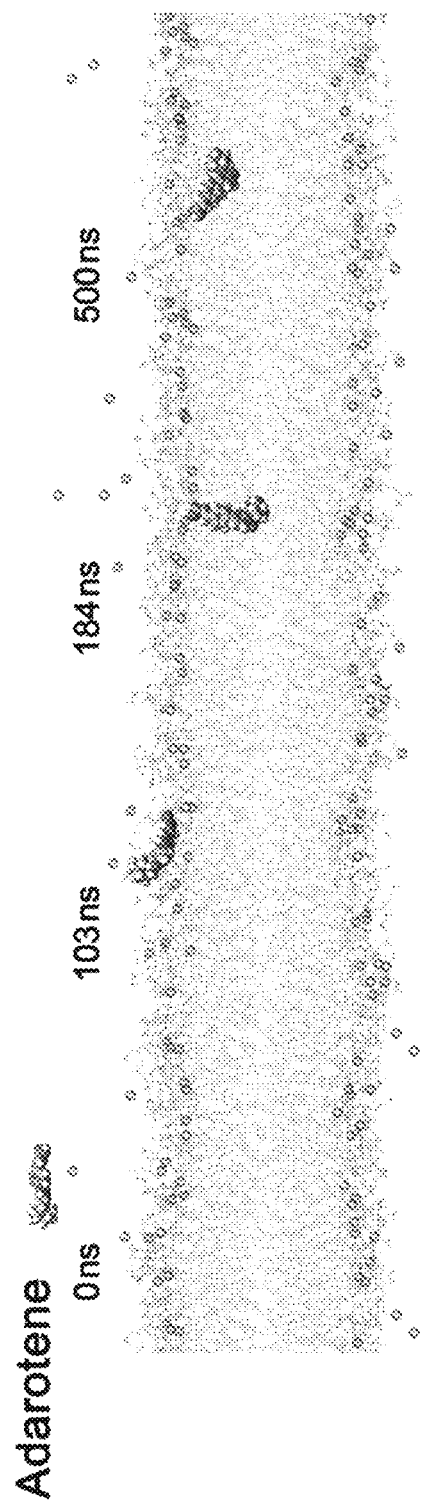
FIG. 28I is an image showing representative configurations of adarotene at the onset of simulation, membrane attachment, membrane penetration and equilibrium state
Figure 28J:
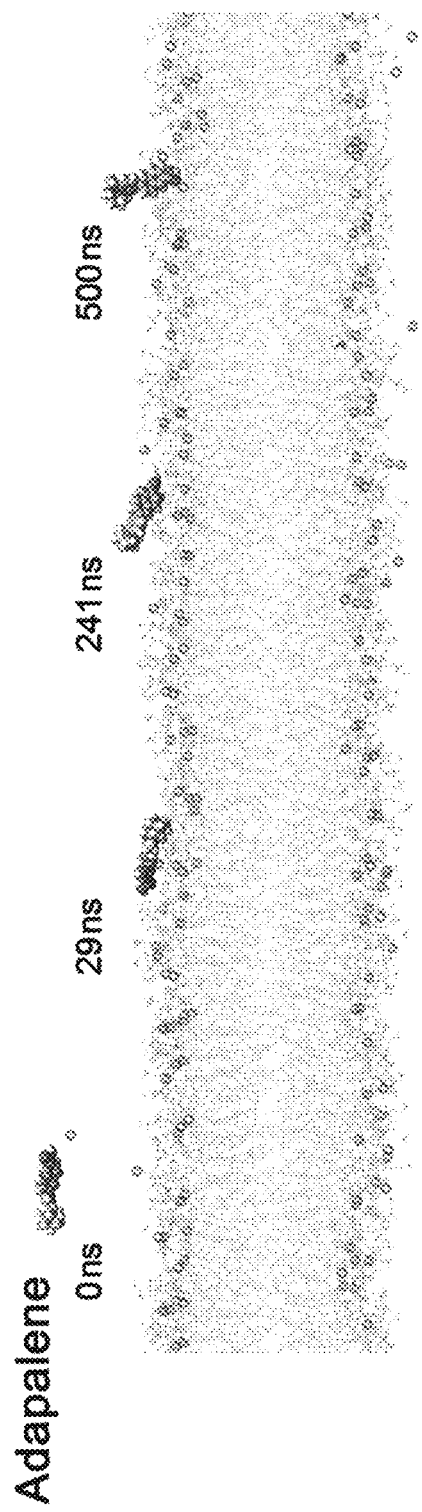
FIG. 28J is an image showing representative configurations of adapalene at the onset of simulation, membrane attachment, membrane penetration and equilibrium state
Figure 28K:
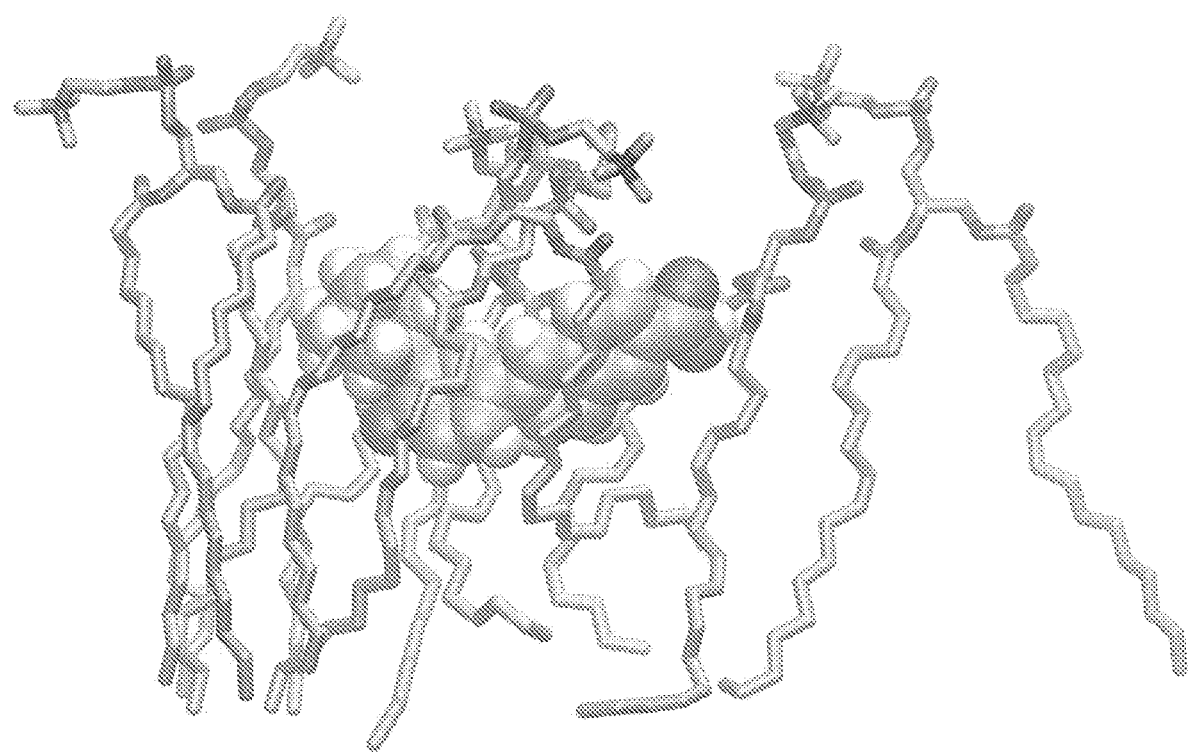
FIG. 28K is an image showing the side view of configurations of nearest neighboring lipids around an embedded CD437 molecule.
Figure 28L:
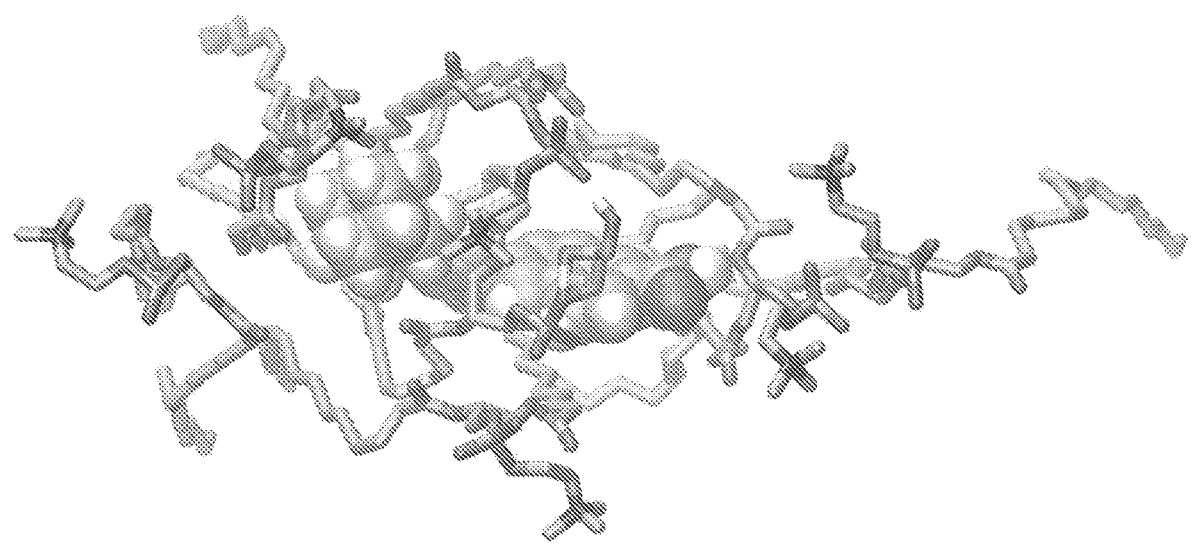
FIG. 28L is an image showing the top view of configurations of nearest neighboring lipids around an embedded CD437 molecule.
Figure 28M:
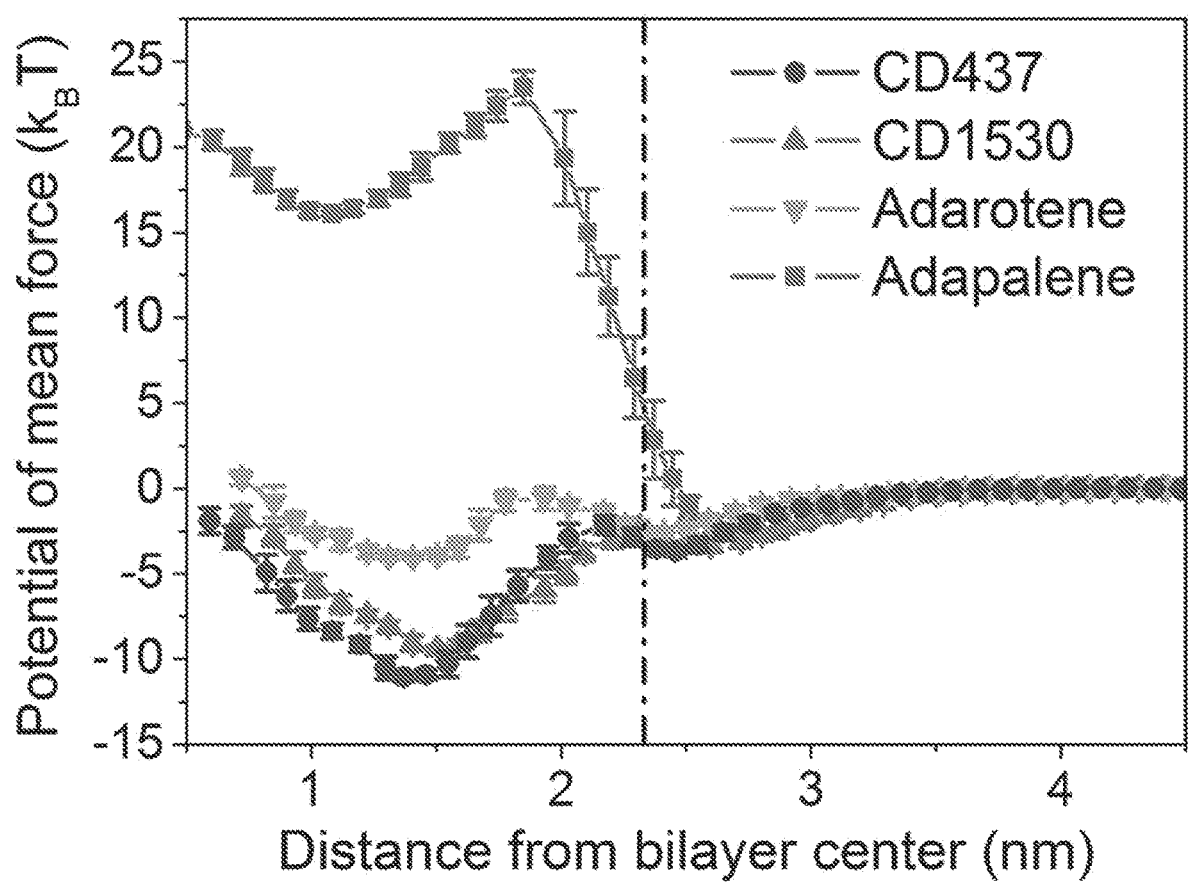
FIG. 28M is a line graph showing free energy profile of the four retinoids penetrating into the membrane as a function of the distance between the center-of-mass (COM) of a retinoid and the bilayer.

Molecular Dynamics (MD) Simulations to Model CD437, CD1530 and Adarotene Interacting with a DOPC/DOPG (7:3) Lipid Bilayer All-atom molecular dynamics (MD) simulations were used to model CD437, CD1530 and adarotene interacting with a DOPC/DOPG (7:3) lipid bilayer. These 3 retinoids are recruited to and anchored in the membrane surface by the carboxyl and hydroxyl groups that bind strongly to the hydrophilic lipid heads (FIG. 28(G-I)), thereby enabling penetration into the bilayer and maximizing interactions of hydrophobic regions. At equilibrium, CD437, CD1530, and adarotene become embedded and orthogonal to the lipid molecules in the outer membrane leaflet, inducing significant membrane perturbations (FIG. 28(K-L)). The energy evolution curves in FIG. 28(M) show that energy barriers of CD437, CD1530 and adarotene for membrane penetration are low enough for spontaneous membrane penetration. In contrast, adapalene, lacking the phenolic hydroxyl group, dangled from the membrane due to entropic repulsion (FIG. 28(J-M)), and could not penetrate due to an exceptional high energy barrier (26.13 $k_BT$) and an unfavorable transfer energy (18.76 $k_BT$) (FIG. 28(M)).

Figure 29:
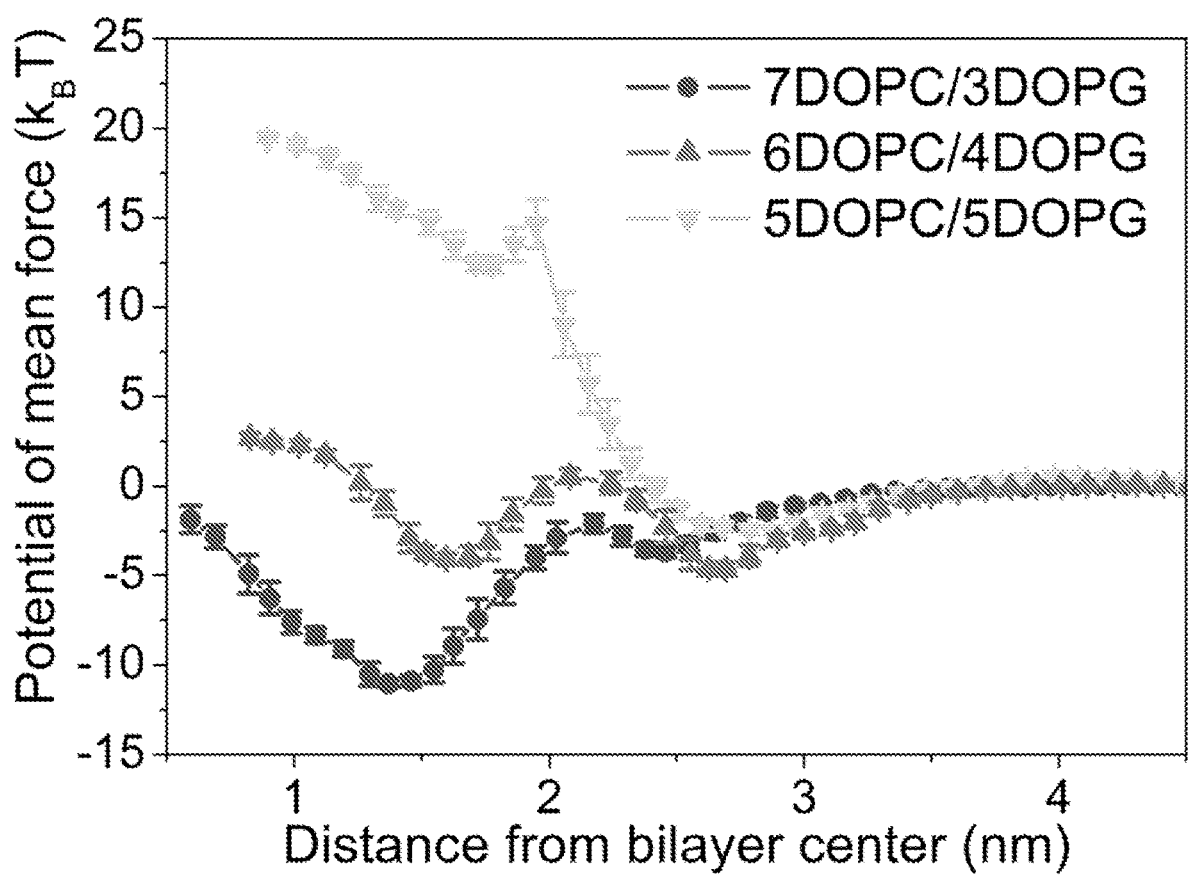
FIG. 29 is a line graph showing the free energy profiles of CD437 penetrating into mixed lipid bilayers at different DOPC:DOPG ratios of 7:3, 6:4 and 5:5.

To model mutations in graS, which causes an increase of net negative charge of the *S. aureus* envelope (See e.g., Tong, S. Y. C., Davis, J. S., Eichenberger, E., Holland, T. L. & Fowler, V. G. *Staphylococcus aureus* infections: epidemiology, pathophysiology, clinical manifestations, and management. *Clin. Microbiol. Rev.* 28, 603-661 (2015)), all-atom MD simulations were used to calculate energy profiles of the interaction between CD437 and lipid bilayers with an increasing proportion of negatively charged lipids (DOPG). A higher proportion of negative lipids lead to a higher energy barrier for CD437 penetration into the lipid bilayer (e.g., due to electrostatic repulsion between the carboxyl group of CD437 and the negatively-charged DOPG head groups, See FIG. 29). FIG. 29 shows the free energy profiles of CD437 penetrating into mixed lipid bilayers at different DOPC:DOPG ratios of 7:3, 6:4 and 5:5. This simulation suggests that resistance to retinoids is opposite to the resistance mechanism for cationic antimicrobials. An increase in the net positive surface charge that repels cationic antimicrobials attracts retinoid class antibiotics. All 3 retinoids show excellent antimicrobial activities against vancomycin- or daptomycin-resistant *S. aureus* or *E. faecium* strains (See Table 1a).

Example 2a. Toxicity of Synthetic Retinoids CD 437, CD 1530, and Adarotene

Figure 4A:
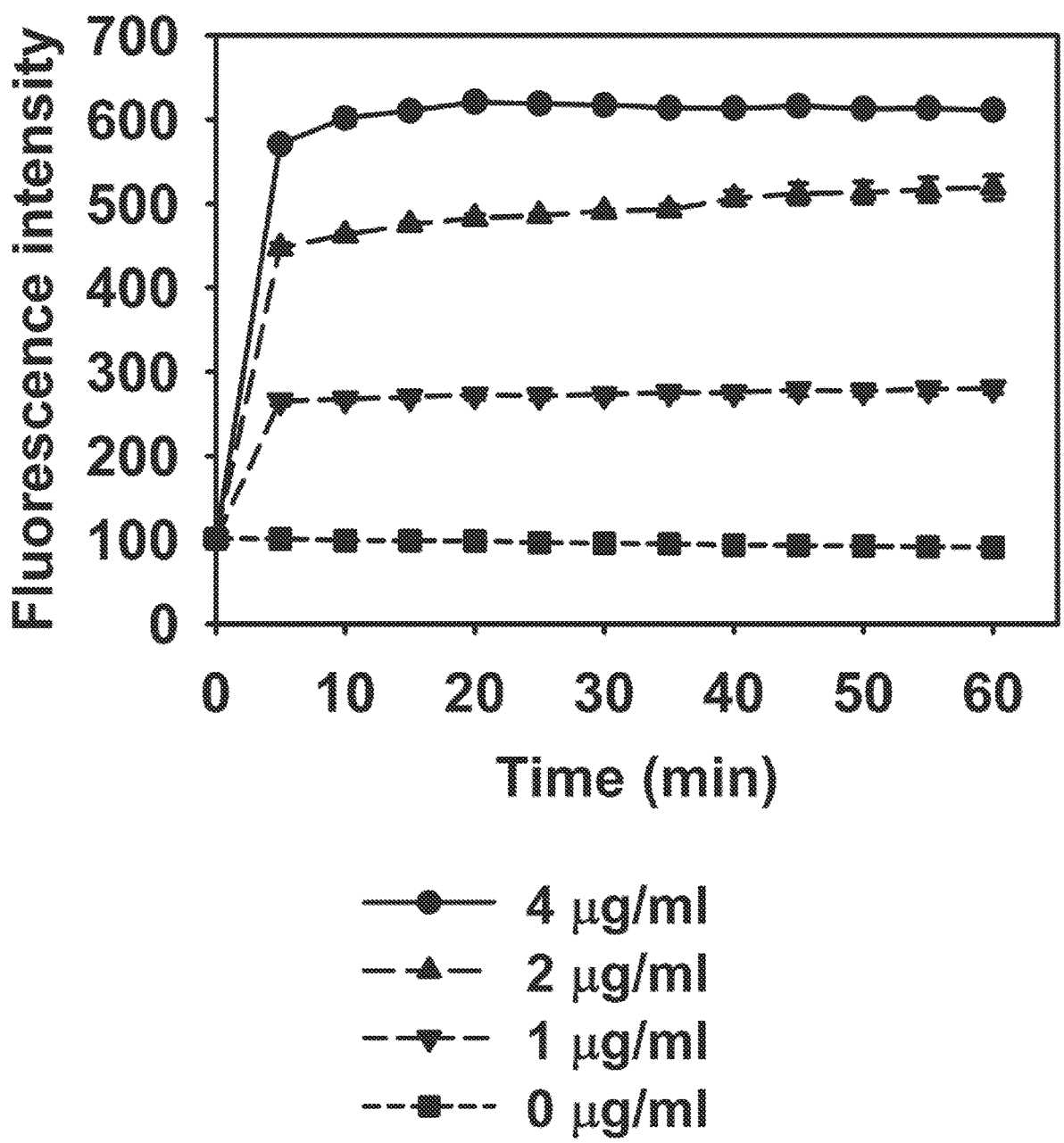
FIG. 4A is a line graph showing toxicity testing of CD437 against human erythrocytes at increasing concentrations.
Figure 4C:
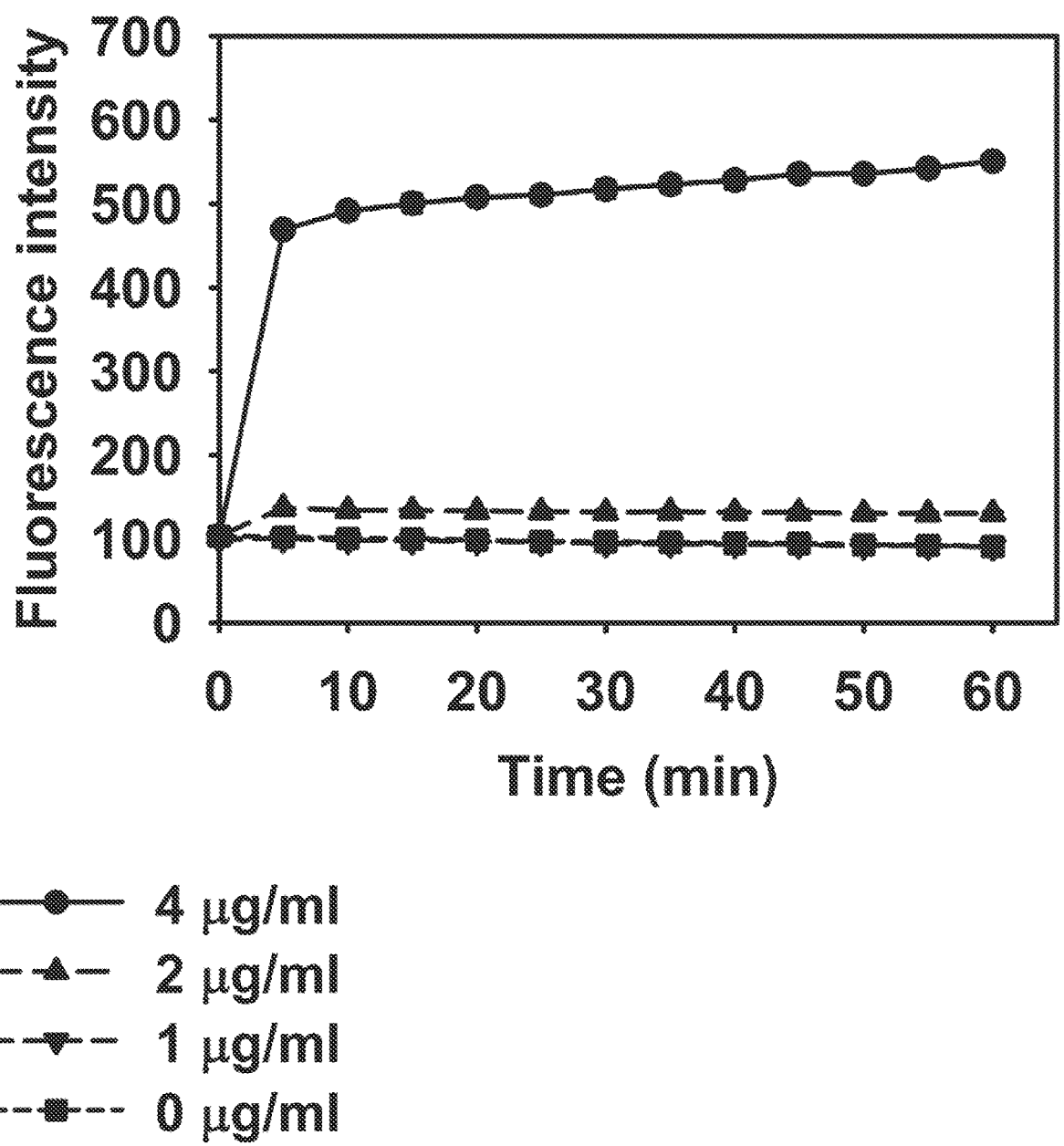
FIG. 4C is a line graph showing toxicity testing of adarotene against human erythrocytes at increasing concentrations.

Although these compounds act on the membrane (for discussion of membrane-active agents causing toxicity in mammals see, e.g., Hurdle, J. G. et al. Targeting bacterial membrane function: an underexploited mechanism for treating persistent infections. *Nat. Rev. Microbiol.* 9, 62-75 (2011)), FIG. 4(A-C) shows that CD 437, CD 1530, and adarotene were not toxic. FIG. 4(A-C) shows that increasing concentrations were tested and were not toxic to human erythrocytes. The protocol to test the ability of compounds to cause hemolysis used sheep red blood cells (RBCs). In a 96 well plate, 50 μl of 2% human erythrocytes suspended in PBS was added to 50 μl of compounds serially diluted in PBS and incubated at 37° C. for 1 hour. The plate was then centrifuged at 500 G for 5 minutes and 50 μl of the supernatant from each well of the assay plate was transferred to a fresh 96 well plate. Hemolysis was confirmed by both visual observation and measuring absorbance at 540 nm. Treatment was conducted in triplicate.

CD 437, CD 1530, and Adarotene exhibited 50% hemolytic concentrations only at >32 μg/ml (See, e.g., FIG. 30) and did not cause significant toxicity to primary human hepatocytes at 32 μg/ml (See, e.g., FIG. 31), did not inhibit the human ether-a-go-go related gene (hERG) potassium channels that are critical for cardiac action potential repolarization at 25 µM (See, e.g., FIG. 32), and did not show significant genotoxic potential (See, e.g., Table 1e).

TABLE 1e

Ames test for evaluating genotoxicity of synthetic retinoids

| | Without S9 | | With S9 | |
|---|---|---|---|---|
| Compound[1] (µg/plate) | Number of revertants (T1535) | Number of revertants (T1538) | Number of revertants (T1535) | Number of revertants (T1538) |
| NaN$_3$ (5) | 2010 ± 395 | N.D. | N.D. | N.D. |
| 4NOP (5) | N.D. | 231 ± 22 | N.D. | N.D. |
| 2AA (5) | N.D. | N.D. | 263 ± 15 | 2568 ± 108 |
| DMSO | 11 ± 1 | 5 ± 1 | 6 ± 2 | 7 ± 3 |
| CD437 (5) | 6 ± 2 | 5 ± 2 | 6 ± 3 | 9 ± 3 |
| CD437 (25) | 5 ± 2 | 4 ± 1 | 8 ± 3 | 10 ± 2 |
| CD437 (100) | 8 ± 2 | 3 ± 3 | 8 ± 3 | 6 ± 1 |
| CD1530 (5) | 7 ± 3 | 3 ± 3 | 7 ± 3 | 7 ± 3 |
| CD1530 (25) | 7 ± 2 | 4 ± 2 | 7 ± 2 | 10 ± 4 |
| CD1530 (100) | 8 ± 4 | 4 ± 2 | 8 ± 2 | 8 ± 2 |
| Adarotene (5) | 6 ± 1 | 6 ± 1 | 6 ± 2 | 8 ± 4 |
| Adarotene (25) | 7 ± 3 | 4 ± 3 | 7 ± 3 | 8 ± 1 |
| Adarotene (100) | 6 ± 2 | 5 ± 2 | 7 ± 1 | 7 ± 3 |

[1]NaN3: sodium azide, 4NOP: 4-nitro-o-phenylenediame, 2AA: 2-Aminoanthracene. All values are means ± s.d. of triplicate.

Figure 30:
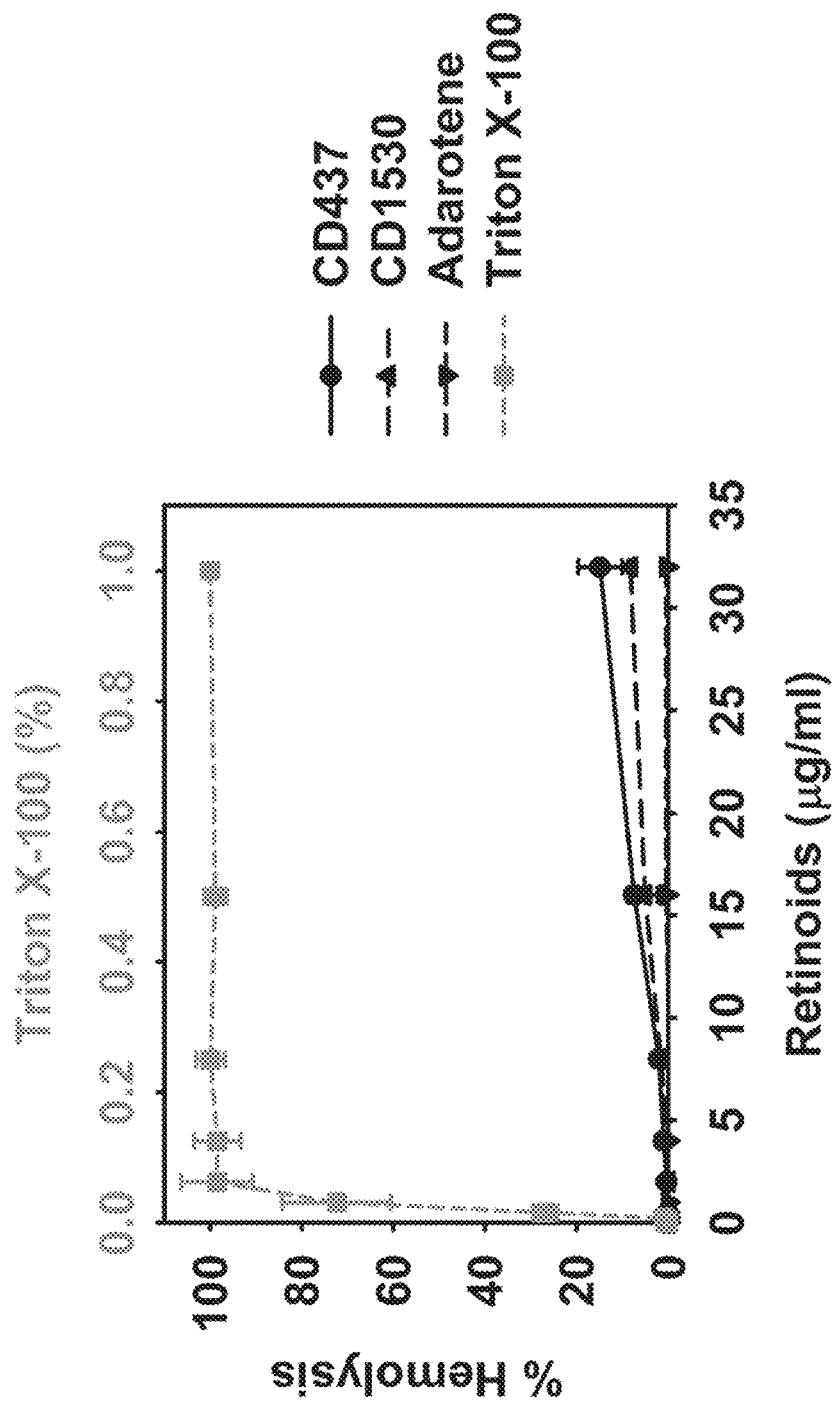
FIG. 30 is a line graph showing high selectivity of CD437, CD1530, and adarotene for bacterial membranes.

FIG. 30 shows that CD437, CD1530, and adarotene have high selectivity for bacterial membranes. 2% human erythrocytes were treated with two-fold serially diluted concentration of the retinoids for 1 h at 37° C. A sample treated with 1% Triton-X 100 was used as the control for 100% hemolysis. Results are shown as means±s.d.; n=3.

Figure 31:
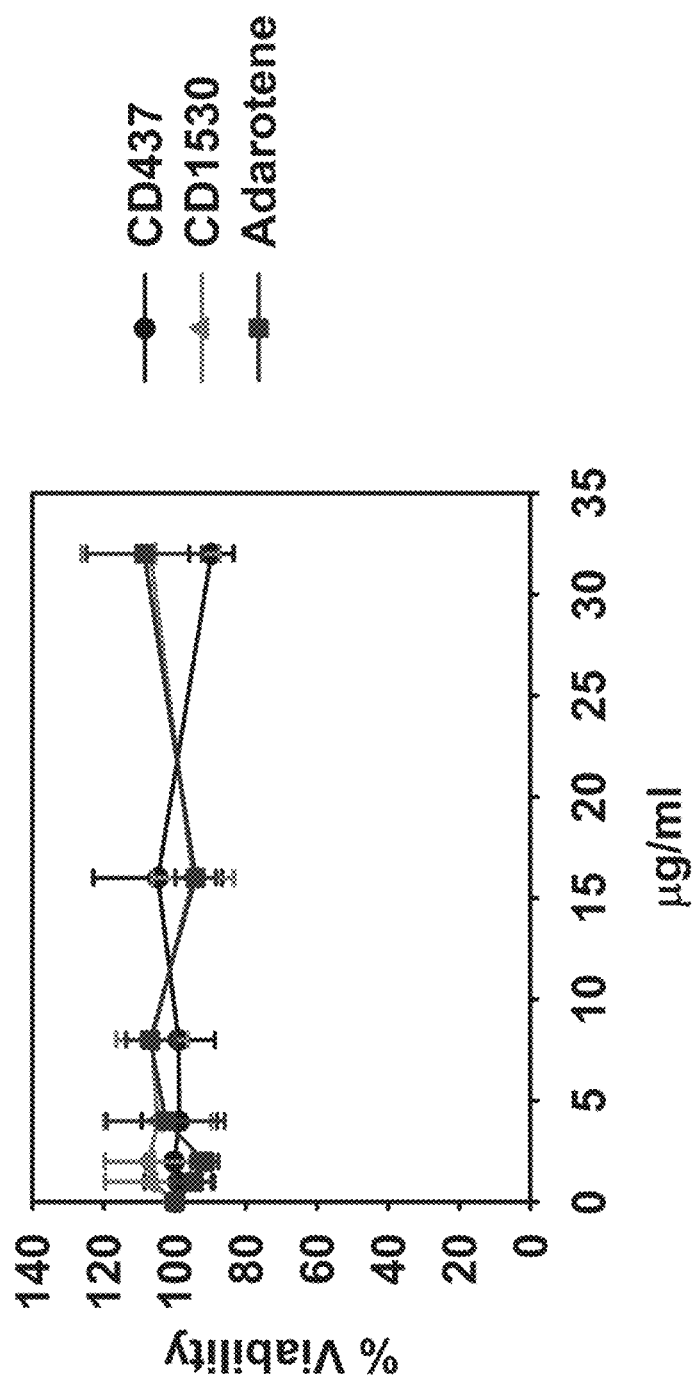
FIG. 31 is a line graph showing evaluation of hepatotoxic potentials of CD437, CD1530, and adarotene.

FIG. 31 shows evaluation of hepatotoxic potentials of CD437, CD1530, and adartotene. $0.4 \times 10^6$ primary human hepatocytes cultured in a collagen gel sandwich system were treated with a range of concentration of the synthetic retinoids for 24 h. Cell viability was calculated based on the absorbance readings at 450 nm at 4 h after adding WST-1 using the following equation: % viability=(Abs$_{sample}$−Abs$_{blank}$)/(Abs$_{non-treated}$−Abs$_{blank}$)×100. Results are shown as means±s.d.; n=3.

Figure 32:
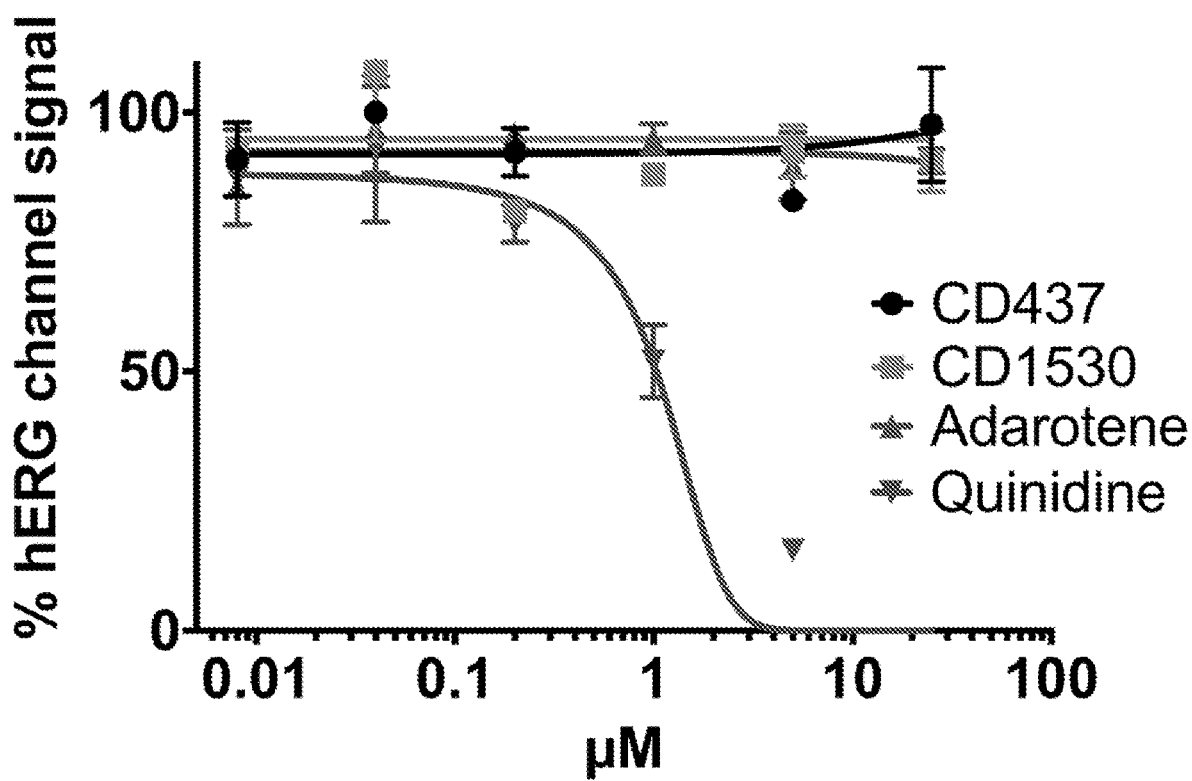
FIG. 32 is a line graph showing inhibitory potentials of CD437, CD1530, and adarotene on hERG potassium channels.
Figure 33A:
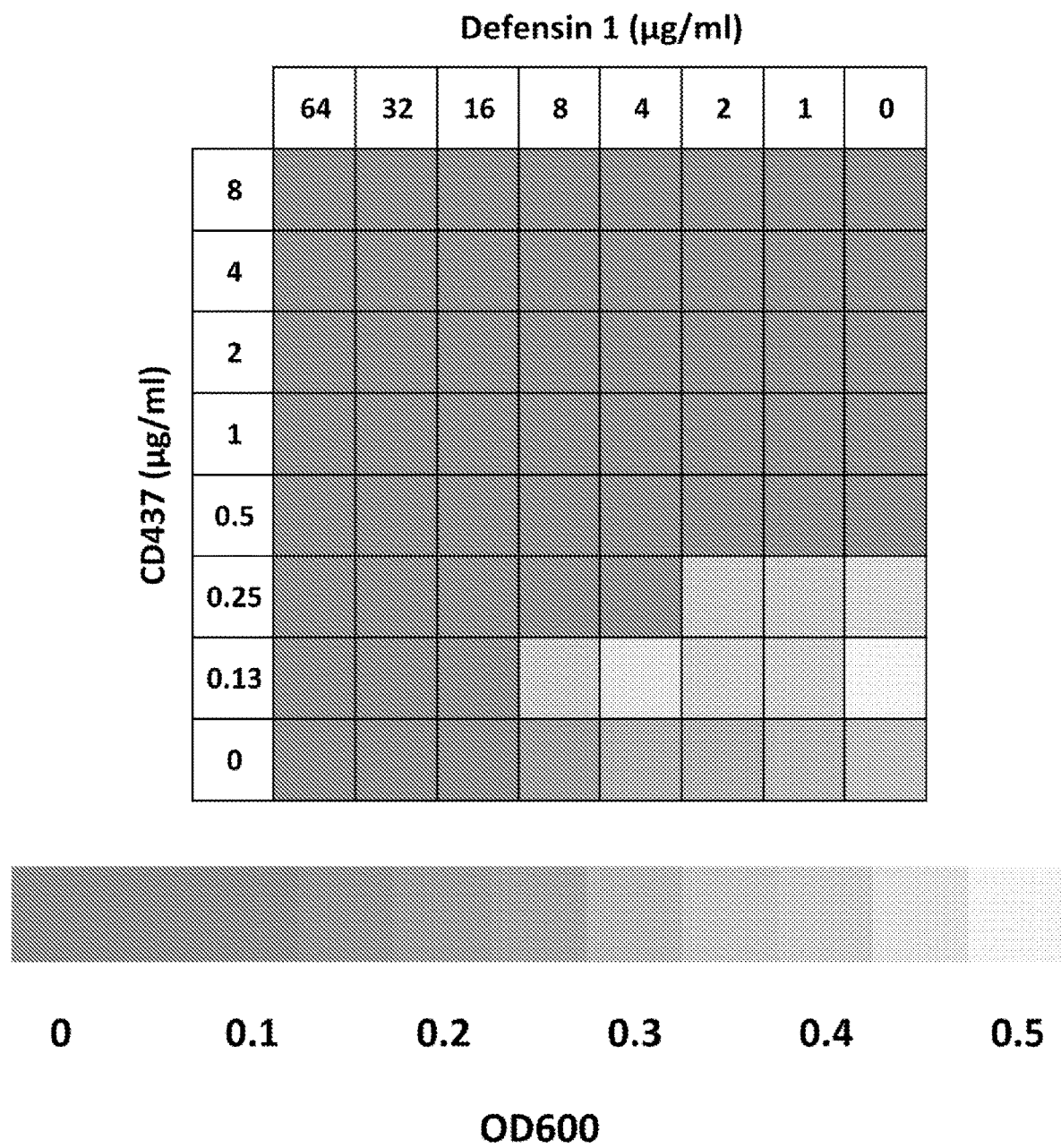
FIG. 33A is a plot showing antimicrobial synergism of CD437 with defensin 1 against MRSA strain MW2.
Figure 33B:
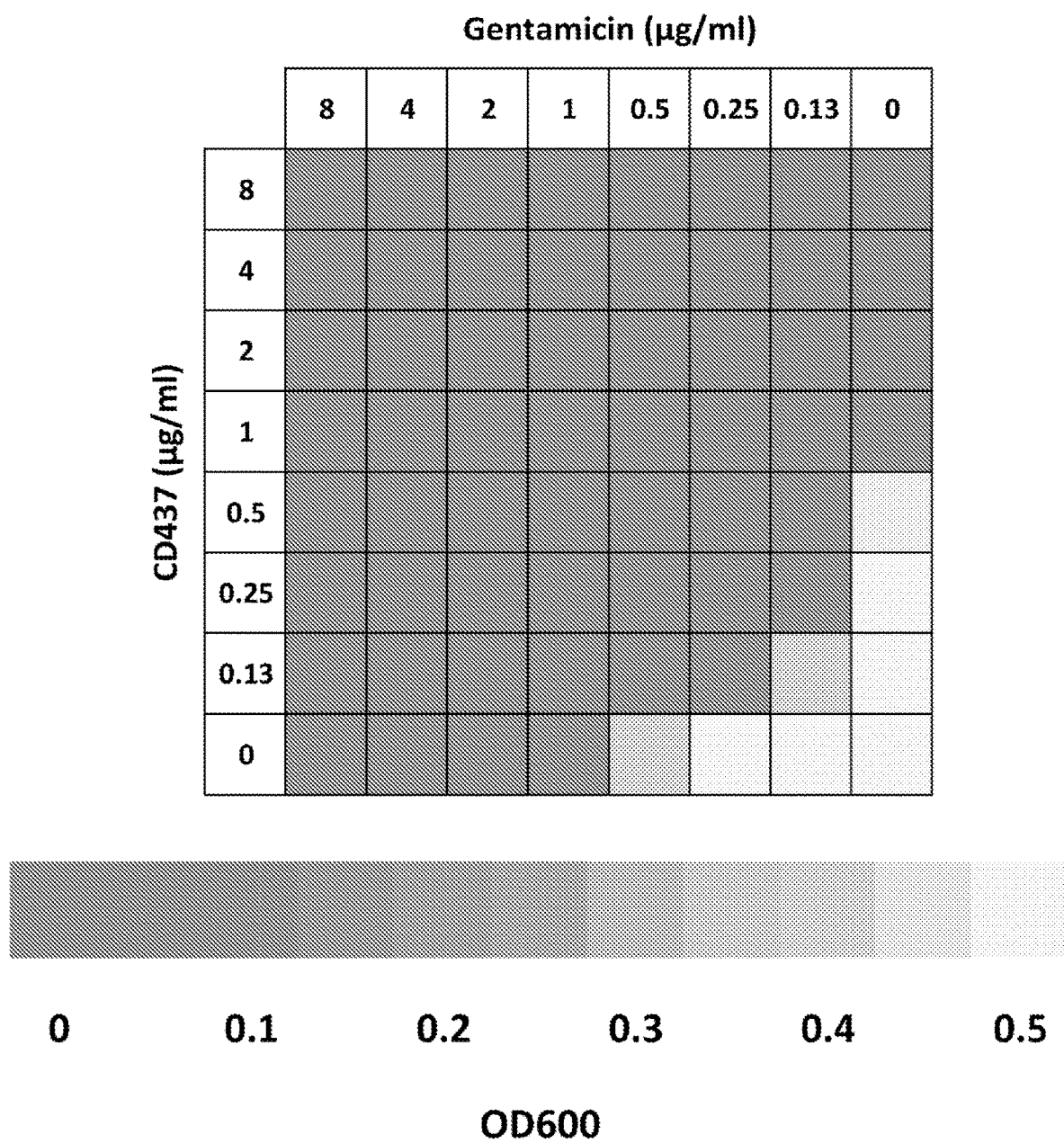
FIG. 33B is a plot showing antimicrobial synergism of CD437 with gentamicin against MRSA strain MW2.
Figure 33C:
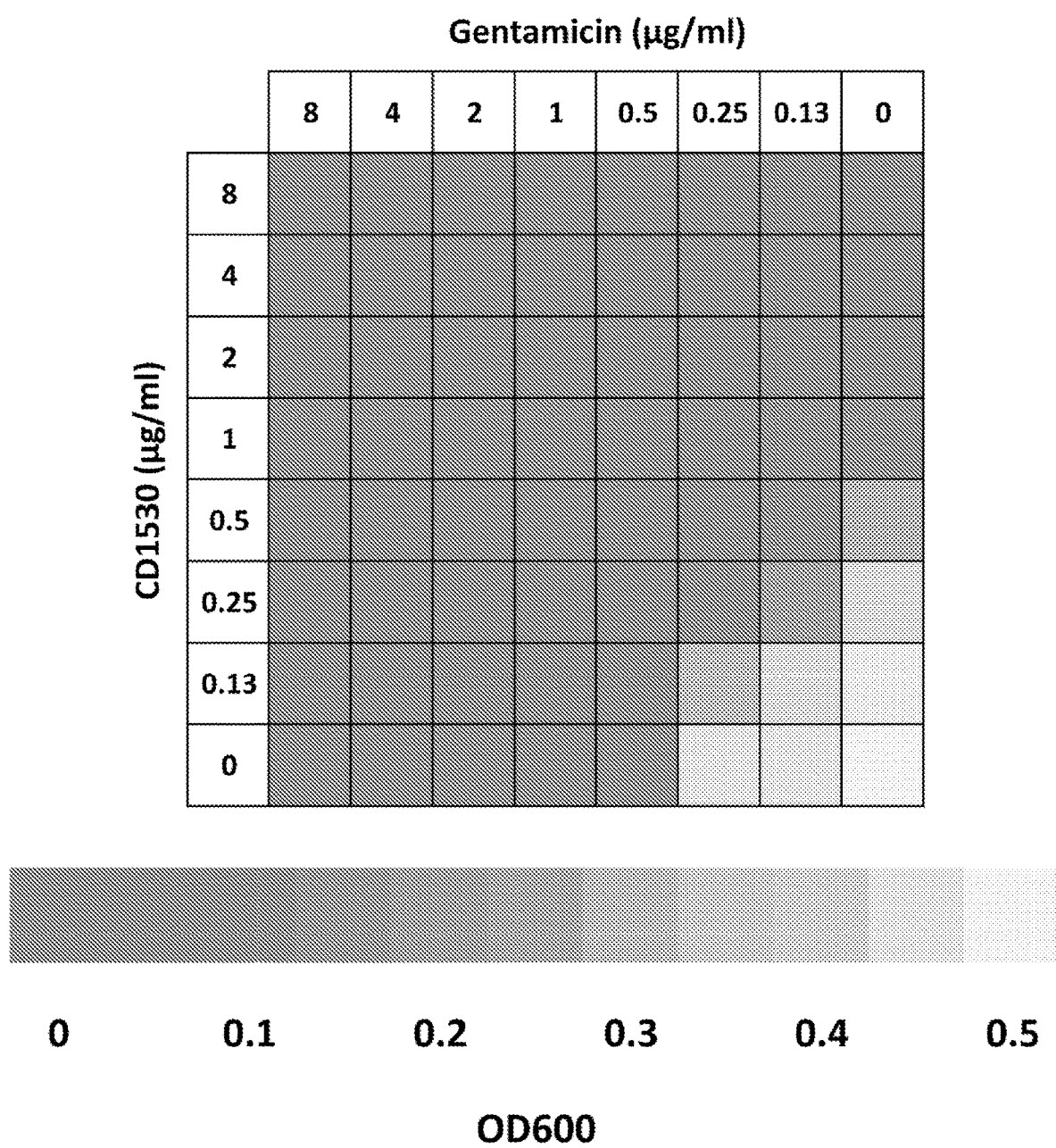
FIG. 33C is a plot showing antimicrobial synergism of CD1530 with gentamicin against MRSA strain MW2
Figure 33D:
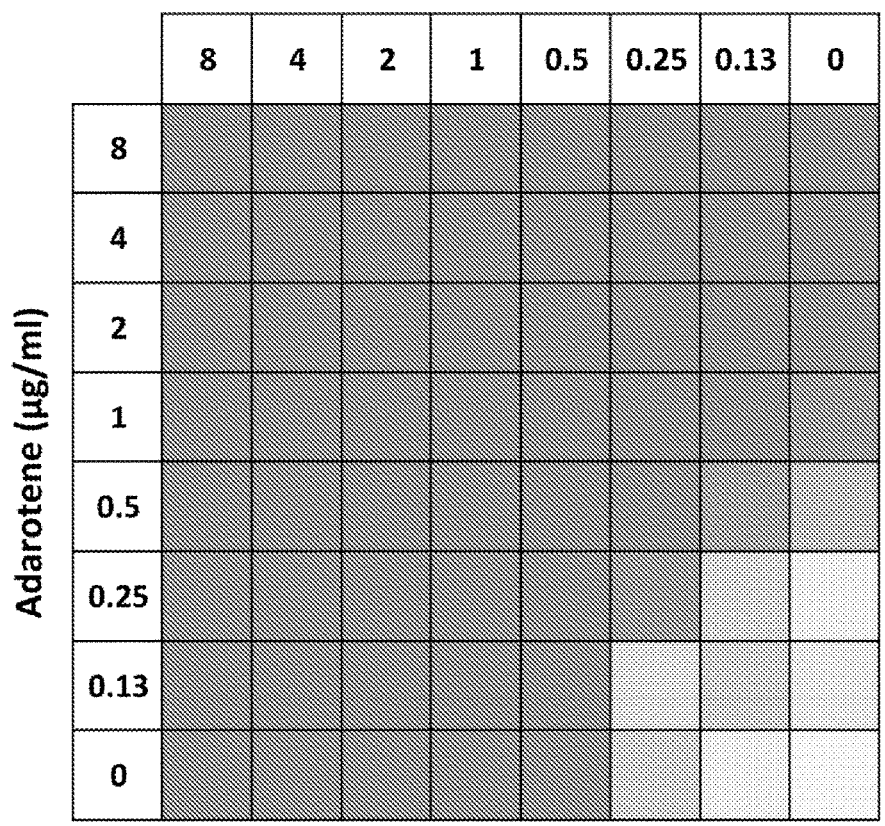
FIG. 33D is a plot showing antimicrobial synergism of adarotene with gentamicin against MRSA strain MW2
Figure 33D:
Figure 33D:

FIG. 32 shows evaluation of inhibitory potentials of CD437, CD1530, and adarotene on hERG potassium channels. Three synthetic retinoids and the positive control quinidine were tested for inhibition of the hERG potassium channel. Data are shown as means±s.d.; n=3 and are fitted to a standard inhibition curve.

Example 2b. Antimicrobial Activity of CD437, CD1530, and Adarotene in Combination Gentamicin and Defensin 1

CD437, CD1530, and adarotene showed significant synergistic antimicrobial activity with gentamicin, and CD437 showed synergism with defensin 1, a CAMP secreted by the host immune system (See, e.g., Rajamuthiah, R. et al. A defensin from the model beetle *Tribolium castaneum* acts synergistically with telavancin and daptomycin against multidrug resistant *Staphylococcus aureus*. PLoS ONE 10, e0128576 (2015)). See Table 2a and FIG. 33(A-D).

TABLE 2a

Fractional inhibitory concentration index (FICI)[1]

| | Defensin 1 | Gentamicin | Vancomycin | Ciprofloxacin | Rifampicin |
|---|---|---|---|---|---|
| CD437 | 0.5 | 0.375 | 1 | 0.625 | 0.625 |
| CD1530 | 1 | 0.5 | 1 | 0.75 | 0.75 |
| Adarotene | 1 | 0.5 | 1.016 | 0.75 | 1 |

[1]Synergy, FICI ≤ 0.5; no interaction, 0.5 < FICI ≤ 4; antagonism, FICI > 4

FIG. 33(A-D) shows antimicrobial synergism of retinoids with other antibiotics against MRSA strain MW2. Optical densities at 600 nm were measured after 18 h of incubation at 37° C. The results represent three independent experiments.

The minor hemolytic effect of CD437 in human erythrocytes compared to CD1530 and adarotene (See FIG. 30) might be mitigated by using a lower concentration of CD437 in combination with gentamicin and CAMPs. Although 4 µg/ml CD437 or CD1530 or 10 µg/ml gentamicin did not significantly affect the viability of MW2 persister cells (FIG. 22(E-F), FIG. 35(A-B)), the combination of either 4 µg/ml CD437 or CD1530 plus 10 µg/ml gentamicin completely eradicated the persisters within 3 h or 4 h for CD437 or CD1530, respectively (FIG. 35(A-B)).

Figure 35A:
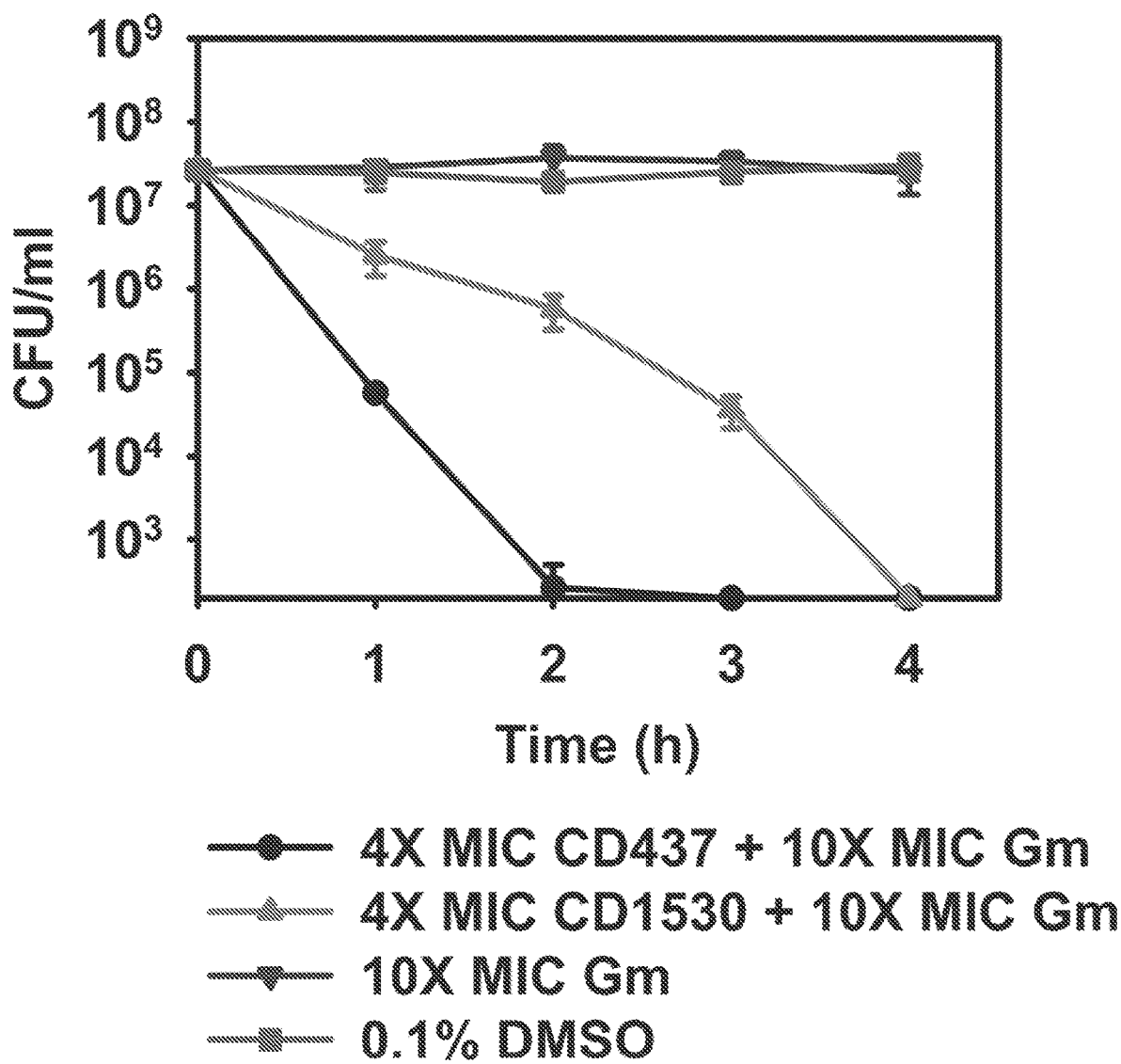
FIG. 35A is a line graph showing synergism of CD437 or CD1530 with gentamic in MRSA persisters treated in vitro with 4×MIC (4 µg/ml) of CD437 or CD1530 in combination with 1 OX MIC (10 µg/ml) of gentamicin (Gm).

FIG. 35A shows in vitro and in vivo synergism of CD437 or CD1530 with gentamicin. MRSA persisters were treated in vitro with 4×MIC (4 µg/ml) of CD437 or CD1530 in combination with 10×MIC (10 µg/ml) of gentamicin (Gm). Viability was measured by serial dilution and plating on TSA plates. The data points on the x-axis are below the level of detection ($2 \times 10^2$ CFU/ml). Results are shown as means±s.d.; n=3.

CD437 exhibited higher synergistic activity than CD 1530 against MRSA persisters, which is consistent with the fact that CD437 has a lower fractional inhibitory concentration index (FICI) than CD1530 against growing MRSA when combined with gentamicin (See Table 2a).

Clinically, gentamicin is used to treat severe MRSA infections (See, e.g., Liu, C. et al. Clinical practice guidelines by the Infectious Diseases Society of America for the treatment of methicillin-resistant *Staphylococcus aureus* infections in adults and children. Clin. Infect. Dis. 52, e18-e55 (2011).) Due to its nephrotoxicity, however, lowering the gentamicin dose is clinically important (See, e.g., Cosgrove, S. E. et al. Initial low-dose gentamicin for *Staphylococcus aureus* bacteremia and endocarditis is nephrotoxic. Clin. Infect. Dis. 48, 713-721 (2009); and Buchholtz, K. et al. Severity of gentamicin's nephrotoxic effect on patients with infective endocarditis: a prospective observational cohort study of 373 patients. Clin. Infect. Dis. 48, 65-71 (2009)). Combination of CD437 or CD1530 with gentamicin improves potency and reduces the toxicity in treating MRSA chronic persister-mediated infections.

Example 2c. Antimicrobial Activity of CD437, Alone or in Combination Gentamicin, in Mouse Thigh Infection Model Efficacy of CD437, as well as the combination of CD437 and gentamicin, was evaluated in an MW2 MRSA deep-seated mouse thigh infection model, which mimics human deep-seated chronic infections (see materials and methods). In a previous study (See Conlon, B. P. et al. Activated ClpP kills persisters and eradicates a chronic biofilm infection. Nature 503, 365-370 (2013)), vancomycin and gentamicin were unable to significantly reduce MRSA CFUs in the deep-seated mouse thigh infection model, suggesting that the infecting bacterial cells are persisters.

Figure 35B:
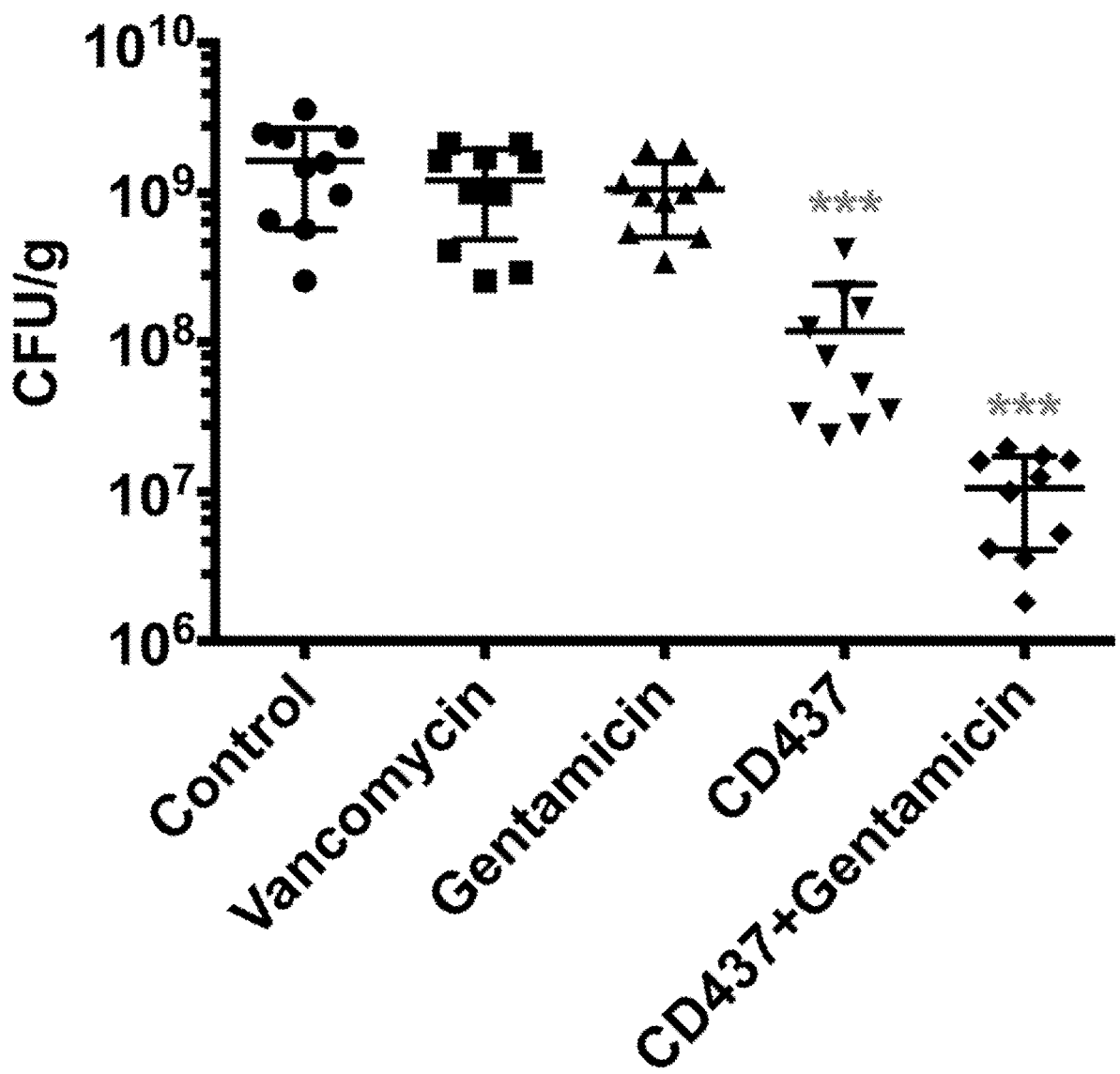
FIG. 35B in vivo efficacy of CD437 alone or in combination with gentamicin in a deep-seated mouse thigh infection model.

FIG. 35B shows in vivo efficacy of CD437 alone or in combination with gentamicin in a deep-seated mouse thigh infection model. Ten infected mice per group were treated with control (5% Killophor+5% ethanol, i.p.), vancomycin (25 mg/kg, i.p.), gentamicin (30 mg/kg, s.c.), CD437 (20 mg/kg, i.p.), or a combination of CD437 (20 mg/kg, i.p.) and gentamicin (30 mg/kg, s.c.) every 12 h for 3 days at 24 h post-infection. At 12 h after the last treatment, mice were euthanized and their thighs were excised and homogenized. CFU from each mouse thigh are plotted as individual points and error bars represent the standard deviation in each experiment group. Statistical differences between control and antibiotic treatment groups were analyzed by one-way ANOVA and post-hoc Tukey test (***p<0.001).

As shown in FIG. 35B, CD437 alone killed ~90% of the MRSA cells (p<0.001), and the combination of CD437 and gentamicin killed ~99% of the persisters (p<0.001). The hepatic and renal toxicity of CD437 in the animals used for the experiment shown in FIG. 35B were evaluated by measuring serum levels of alanine aminotransferase (ALT) and blood urea nitrogen (BUN). Mice treated with CD437 alone or CD437 in combination with gentamicin did not have elevated serum levels of ALT or BUN (See FIG. 34(A-B)), indicating that liver and renal functions were not impeded by the treatment course.

Figure 34A:
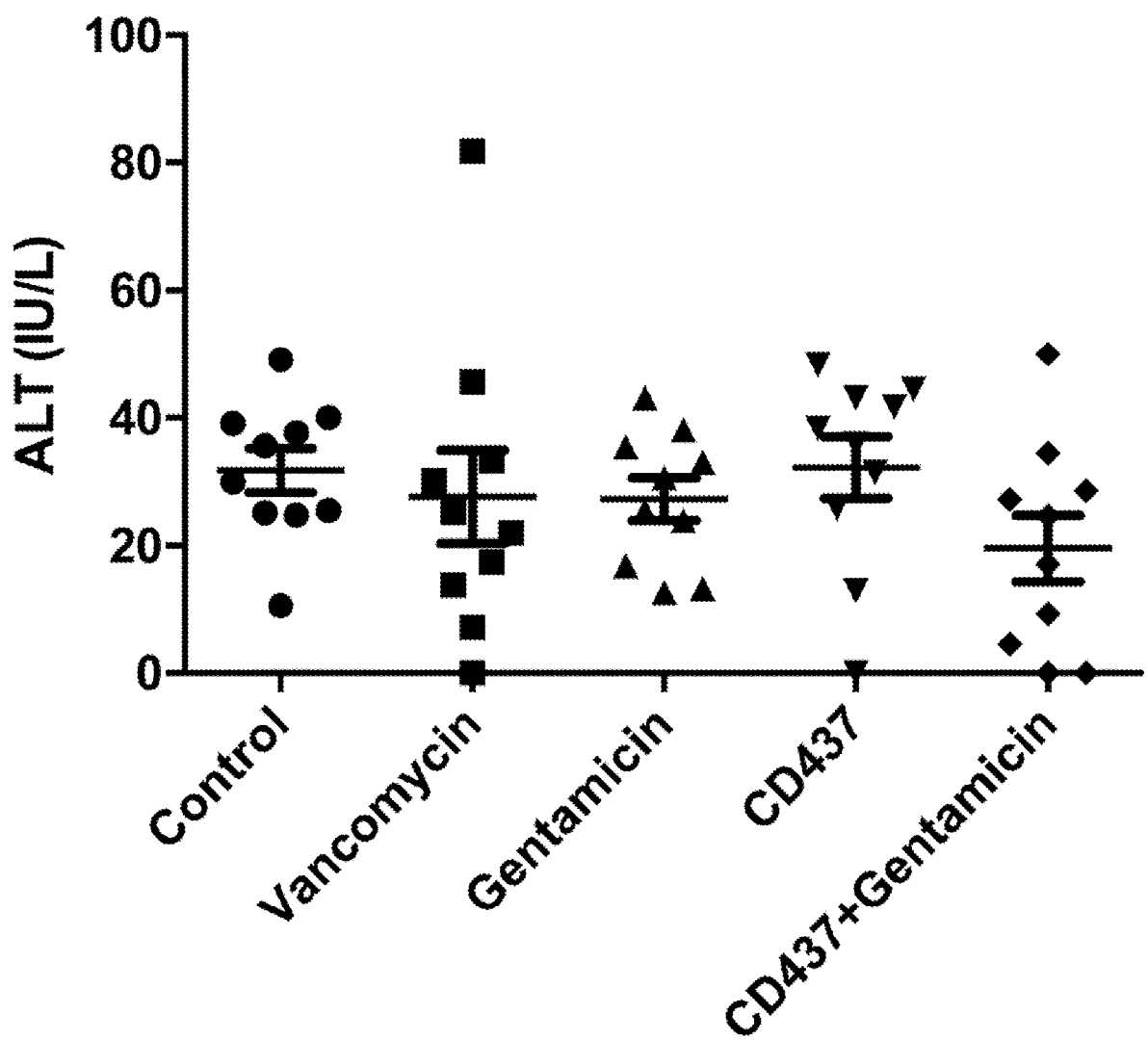
FIG. 34A is a plot showing International Units per Liter (IU/L) of alanine aminotransferase (ALT) for serum of each mouse treated with CD437 alone or in combination with gentamicin in a deep-seated mouse thigh infection model.
Figure 34B:
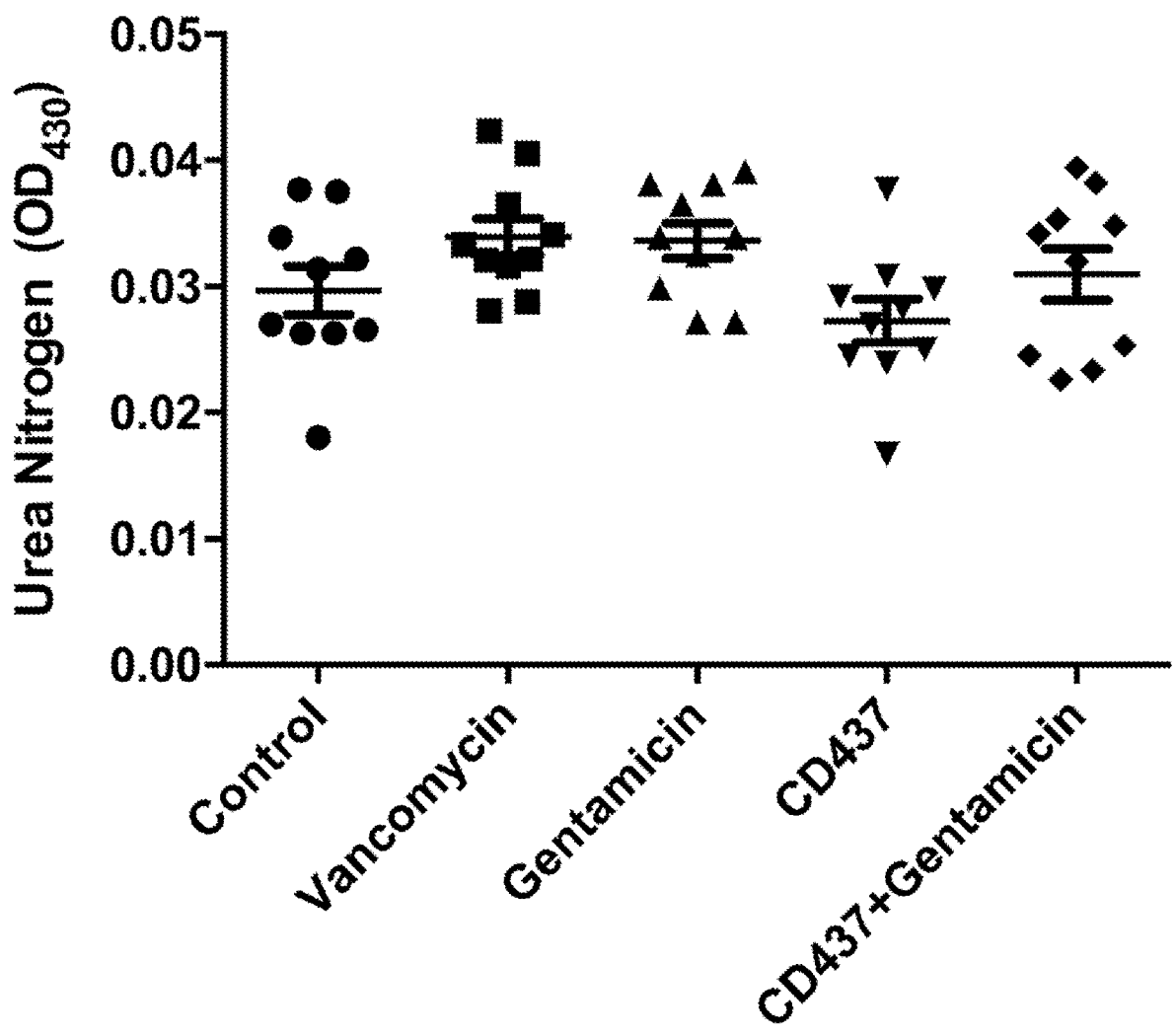
FIG. 34B is a plot showing absorbance at 430 nm of BUN urea nitrogen for serum of each mouse treated with CD437 alone or in combination with gentamicin in a deep-seated mouse thigh infection model.

FIG. 34(A-B) shows that CD437 alone or in combination with gentamicin have no toxicity in a deep-seated mouse thigh infection model. Ten infected mice per group were treated with control (5% Kolliphor+5% ethanol, i.p.), vancomycin (25 mg/kg, i.p.), gentamicin (30 mg/kg, s.c.), CD437 (20 mg/kg, i.p.), or a combination of CD437 (20 mg/kg, i.p.) and gentamicin (30 mg/kg, s.c.) every 12 h for 3 days at 24 h post-infection. At 12 h after the last treatment, mice were euthanized, blood was collected and analyzed for ALT and BUN. International Units per Liter (IU/L) of alanine aminotransferase (ALT) for each mouse serum (a) and absorbance at 430 nm of BUN urea nitrogen (b) are plotted as individual points and error bars represent the deviation in each experiment group. Control and antibiotic treatment were analyzed by one-way ANOVA and post-hoc Tukey test to confirm a lack of significant difference

Example 3. Antibacterial Activity of Z3060

Figure 5:
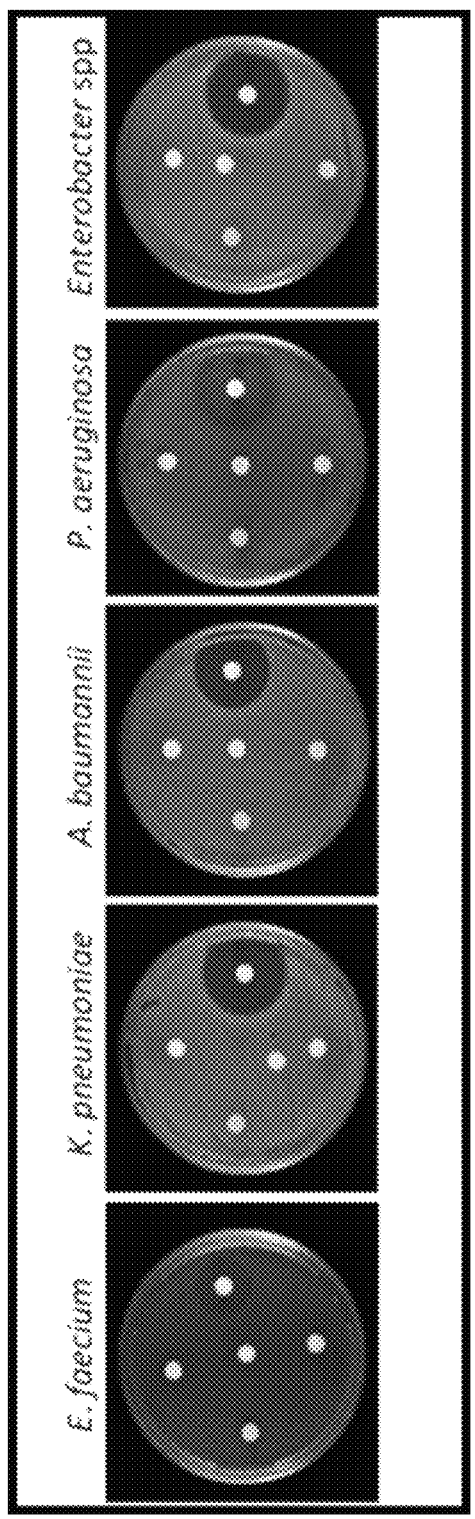
FIG. 5 is an image showing inhibition of bacterial strains by Z3060 (disc on right if each plate).

Compound Z3060 was identified using our in vivo *C. elegans*-based infection high throughput screening method as conferring antimicrobial activity The compound was evaluated to determine which bacterial pathogens were susceptible to Z3060. Using a disc clearing assay, we found that several types of bacteria were inhibited. FIG. 5 shows inhibition of bacterial strains by Z3060. The clearing on the right side of the plate shows the zone of inhibition induced by Z3060. Z3060 inhibited *S. aureus* with an MIC of 2 µg/ml.

Additional evaluation of the compound against a panel of ESKAPE pathogens showed that it exhibits inhibitory activity against the bacterial pathogens: *E. faecium, K. pneumoniae, A. baumannii, P aeruginosa*, and *E.* spp. (FIG. 5), generating a zone of inhibition on a lawn of bacteria. Further investigation of Z3060 with clinical isolates of *S. aureus* has shown that it maintains a low MIC (1-2 µg/ml), however, when tested with clinical isolates that are known to be drug resistant the MIC is increased.

Example 4. Toxicity Study of Z3060

Figure 6:
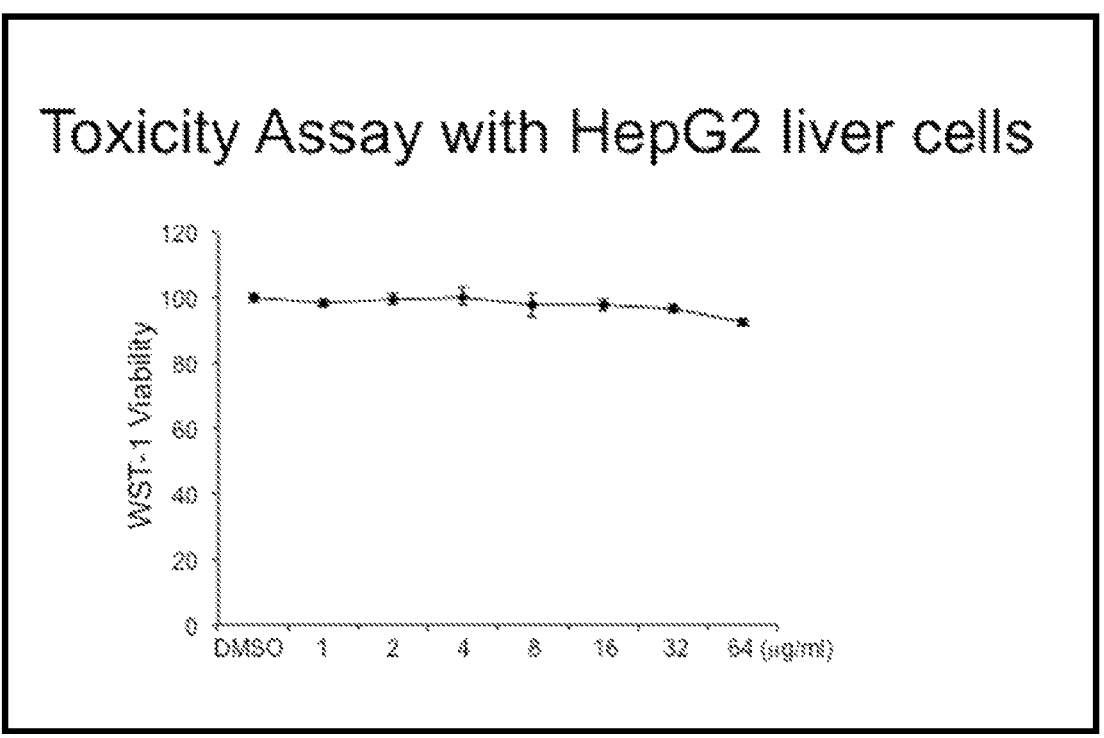
FIG. 6 is a line graph showing the results of a toxicity assay with HepG2 liver cells.

FIG. 6 shows toxicity assay with HepG2 liver cells. HepG2 cells were cultured in Dulbecco's modified Eagle medium (DMEM) containing 10% fetal bovine serum, 25 mM D-glucose, 2 mM L-glutamine, 1 mM sodium pyruvate and 1% penicillin/streptomycin and maintained at 37° C. in 5% $CO_2$. For the toxicity test, HepG2 were cultured at 70-80% confluence in 96-well plates in a volume of 100 µl/well culture medium. Serially diluted chemical compounds were incubated with the cells at 37° C. in 5% $CO_2$ for 24 hours. Ten microliters of 4-(3-(4-iodophenyl)-2-(4-nitrophenyl)-2H-5-tetrazolio)-1,3-benzene disulfonate (WST-1) solution were added per well for the last 4 hours of the 24 hours period. WST-1 reduction was detected using absorbance at 490 nm by a Vmax microplate reader. The percent fluorescence relative to that of the no-treatment control was calculated. The assay was done in triplicate.

Toxicity assay with HepG2 liver cells indicate that the cell viability are maintained in the presence of Z3060. Thus suggesting that Z3060 is not toxic to the liver cell line.

Z3060 did not exhibit lysis when tested with erythrocytes, again suggesting that it is not toxic to mammalian cells. The toxicity assay with erythrocytes is described in example 2a.

Example 5. Antifungal Activity of Auranofin Against *C. neoformans* and *C. albicans*

Figure 7A:
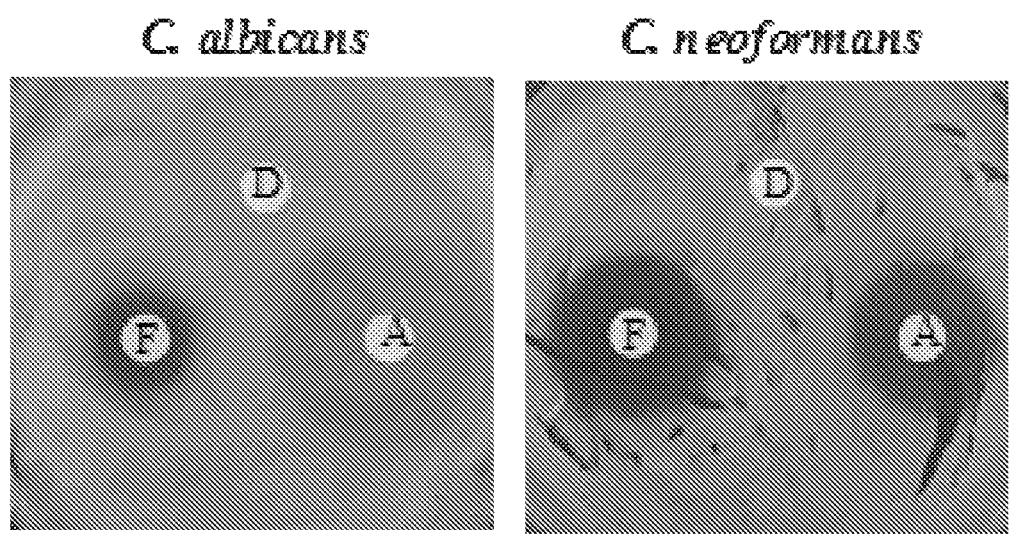
FIG. 7A is an image showing inhibition of *C. albicans* and *C. neoformans* by auranofin in a disk clearing assay.
Figure 7B:
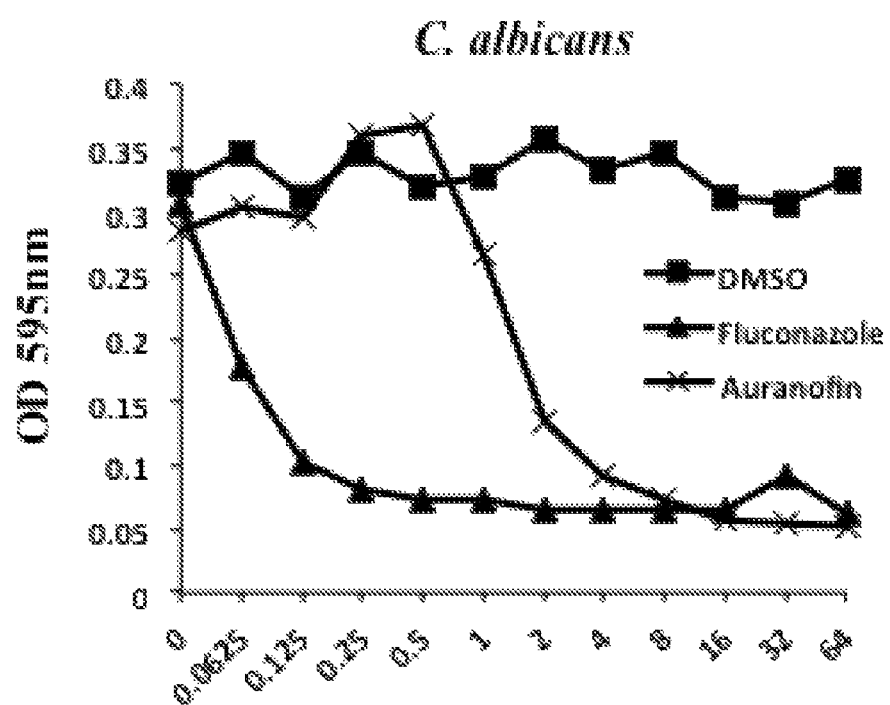
FIG. 7B is a line graph showing MIC of auranofon for inhibition of *C. albicans*.
Figure 7D:
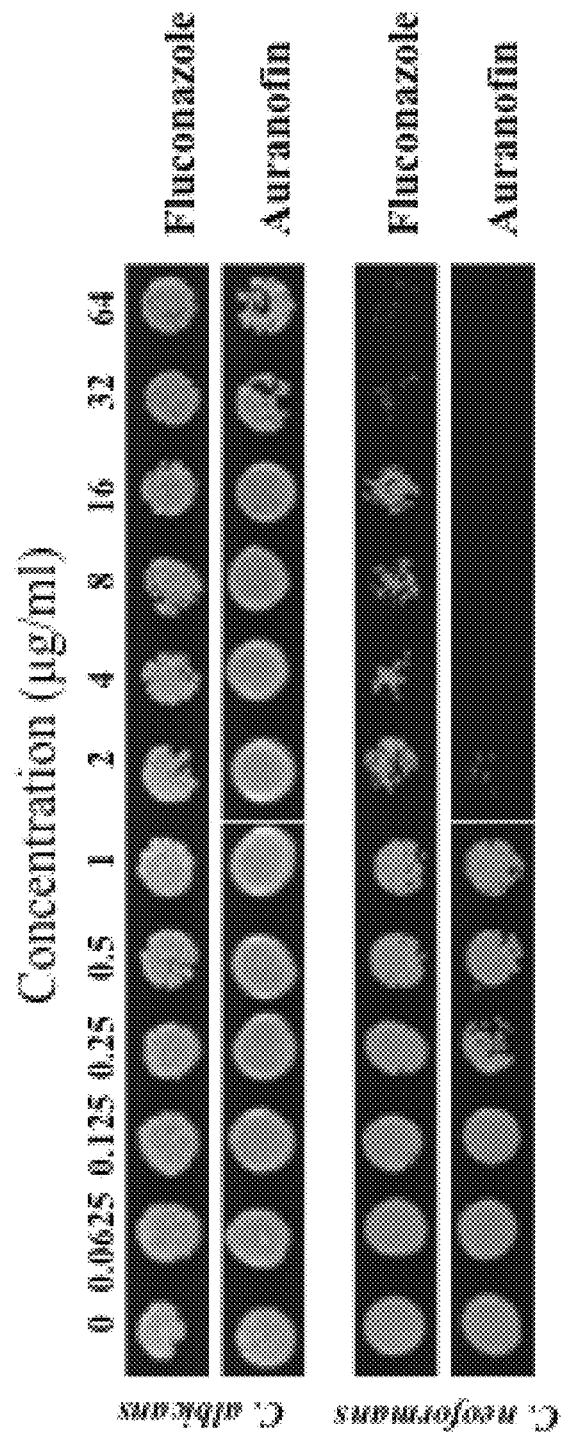
FIG. 7D is an image showing determination of static versus cidal nature of the inhibition of *C. albicans* and *C. neoformans* by auranofin.

A clearing assay with filters impregnated with auranofin exhibited clearing of *C. neoformans* (see FIG. 7A; A: auranofin, D: DMSO, F: fluconazole). The MIC for each of the pathogens was 8 µg/ml and 0.5 µg/ml, against *C. albicans* and *C. neoformans*, respectively (see FIG. 7(B-C)), as determined by testing the microdilutions of the compound in a liquid assay. The compounds exhibited fungistatic activity against *C. albicans*, however fungicidal activity was reached against *C. neoformans* at concentrations greater than 2 µg/ml (FIG. 7D).

Study of *C. neoformans* clinical isolates indicated that the inhibitory activity of auranofin was conserved among the 11 isolates tested, ranging from 2 to 8 µg/ml.

TABLE 2

Drug MIC for *C. neoformans* clinical isolates

| Isolate | Amphotericin B | Fluconazole | Auranofin |
|---|---|---|---|
| BF113 | 0.125 | 16 | 8 |
| BF114 | <0.0625 | 64 | 4 |
| 41291 | 0.125 | 8 | 4 |
| 41292 | 0.125 | 64 | 4 |
| 41294 | 0.125 | 8 | 2 |
| 41295 | 0.125 | 64 | 8 |
| 41296 | 0.125 | >64 | 4 |
| 41297 | 0.125 | 8 | 2 |
| 41298 | 0.125 | 8 | 2 |
| 41299 | 0.125 | 4 | 4 |
| 41300 | 0.125 | >64 | 4 |

Example 6. Antifungal Activity of Auranofin Against *C. glabrata*

Figure 8:
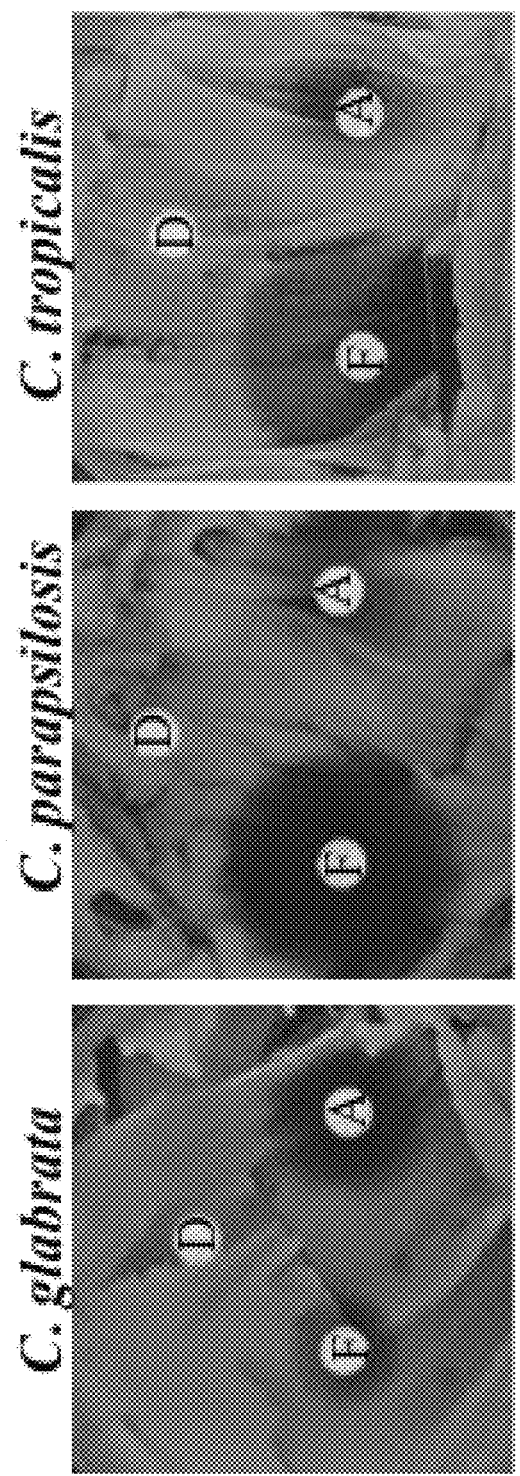
FIG. 8 is an image showing inhibition of non-*albicans Candida* strains by auranofin.

FIG. 8 (left, A: auranofin, D: DMSO, F: fluconazole) shows zones of inhibition when auranofin was tested against *C. glabrata*. Study of *C. glabrata* clinical isolates found an inhibition at 0.25 to 32 µg/ml.

Out of the 15 clinical isolates examined, 13 exhibited sensitivity to auranofin, but 2 isolates were resistant (Table 3).

TABLE 3

Drug MIC for *Candida glabrata* isolates

| Isolate | Isolate | Fluconazole | Amphotericin B | Auranofin |
|---|---|---|---|---|
| ATCC 90030 | Reference | 8 | 1 | 0.25 |
| 6891 | Clinical | 2 | 0.5 | 0.5 |
| 6922 | Clinical | 2 | 0.5 | 1 |
| 6927 | Clinical | 2 | 1 | 0.5 |
| 6930 | Clinical | 1 | 1 | 0.5 |
| 6931 | Clinical | 0.5 | 0.5 | 0.5 |
| 6932 | Clinical | 0.5 | 0.5 | 32 |
| 6943 | Clinical | 8 | 1 | 1 |
| 7110 | Clinical | 1 | 0.5 | 1 |
| 7117 | Clinical | 2 | 0.5 | 0.5 |
| 7221 | Clinical | 1 | 0.5 | 0.5 |
| 7255 | Clinical | 2 | 1 | 0.5 |
| 7815 | Clinical | 2 | 0.5 | 1 |
| 7869 | Clinical | 4 | 1 | 16 |
| 7871 | Clinical | 2 | 1 | 1 |
| 8066 | Clinical | 2 | 0.5 | 1 |

Concentrations are µg/ml.

Example 7. Antifungal Activity of Auranofin Against *C. tropicalis*

FIG. 8 (right, A: auranofin, D: DMSO, F: fluconazole) shows zones of inhibition when auranofin was tested against *C. glabrata, C. parapsilosis*, and *C. tropicalis*.

Further investigation of the reference strain and three *C. tropicalis* clinical isolates demonstrated MICs that ranged from 0.125 to 1 µg/ml, demonstrating the antifungal effect against this non-*albicans* strain (Table 4).

TABLE 4

Drug MIC for *Candida tropicalis* isolates

| Isolate | Isolate | Fluconazole | Amphotericin B | Auranofin |
|---|---|---|---|---|
| ATCC 13803 | Reference | 8 | 1 | 1 |
| 11 | Clinical | 0.5 | 0.5 | 0.125 |
| 85-S | Clinical | 1 | 0.125 | 0.125 |
| 172-S | Clinical | 2 | 0.5 | 0.5 |

Example 8. The Effect of Auranofin on Biofilm Growth

Figure 9A:
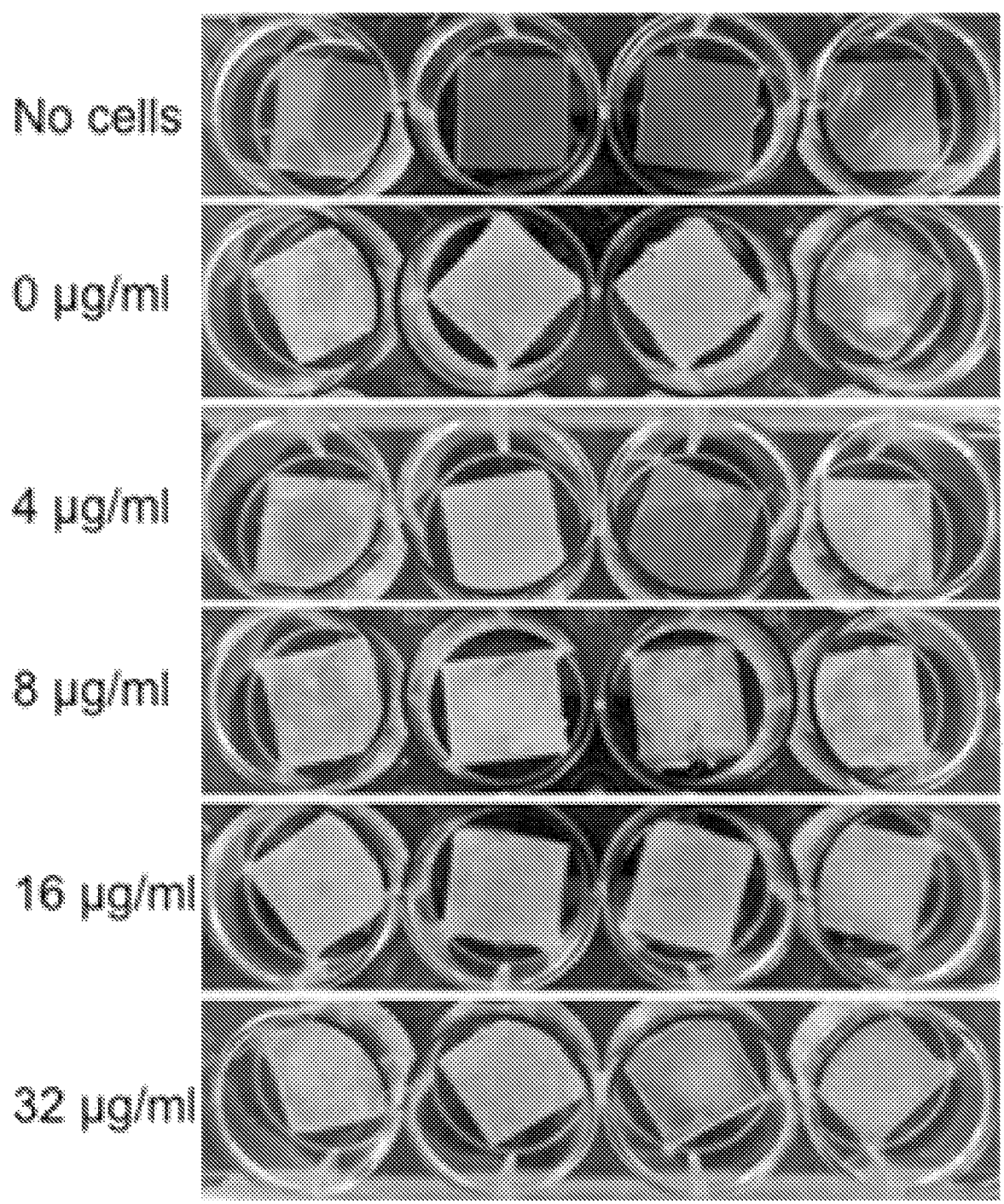
FIG. 9A is an image showing inhibition of *C. albicans* biofilm by auranofin.
Figure 9B:
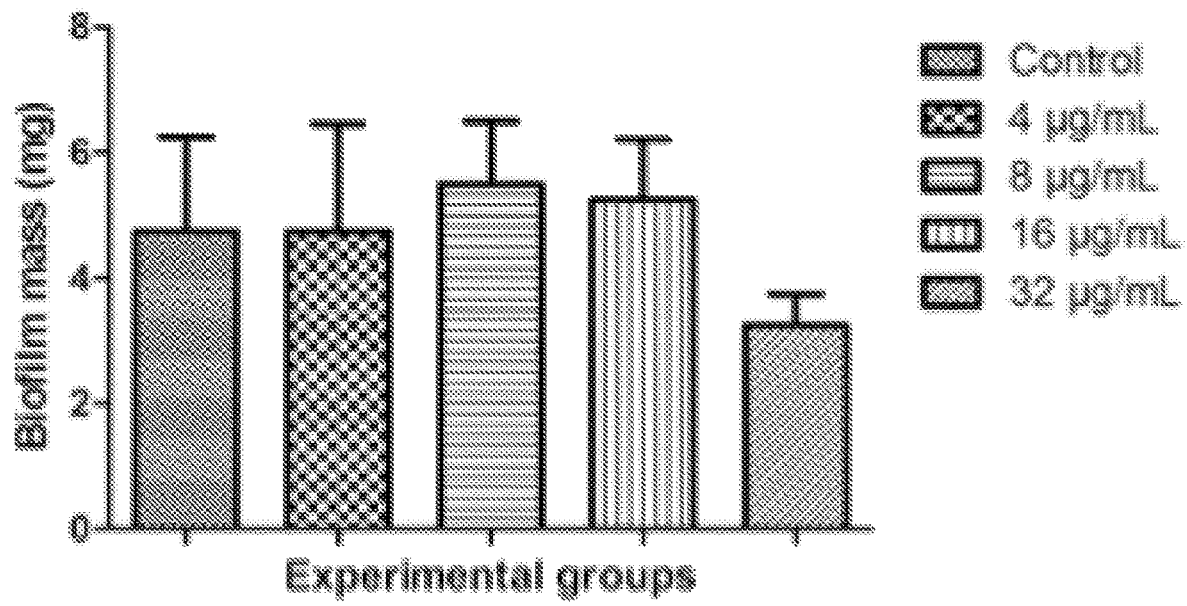
FIG. 9B is a bar graph showing reduction of *C. albicans* biofilm mass at different concentrations of auranofin.

*C. albicans* biofilm was generated to adhere to silicone pads testing increasing concentrations of auranofin 4-32 µg/ml (FIG. 9A) The biomass of the generated biofilm was assessed by weight to find that only the presence of 32 µg/ml induced a biofilm reduction, although not at a significant level (FIG. 9B).

*C. albicans* were grown in YPD medium overnight at 30° C., diluted to an $OD_{600}$ of 0.5 in 2 mL Spider medium, and added to a well of a sterile 12-well plate containing a silicone pad measuring 1.5×1.5 cm that had been pretreated overnight with bovine serum (Sigma-Aldrich). The inoculated 12-well plate was incubated with gentle agitation (150 rpm) for 90 min at 37° C. for adhesion to occur. The samples were washed with 2 ml PBS, and after the 90-min incubation, and PBS wash, auranofin was added to fresh media at 4 µg/ml (n=4), 8 µg/ml (n=4), 16 µg/ml (n=4), and 32 µg/ml (n=4).

Control groups were included that contained *C. albicans* alone in Spider medium without auranofin (n=4) and a negative control group of Spider medium without any fungal cells (n=4).

The silicone pads with biofilm were removed from the wells, dried overnight, and weighed the following day. The total biomass (mg) of each biofilm was calculated by subtracting the weight of the platform material prior to biofilm growth from the weight after the drying period and adjusting for the weight of a control pad exposed to no cells.

Statistical significance among the different groups was determined by the analysis of variance (ANOVA) and the Tukey test using the Graph Pad Prism Program.

*C. albicans* biofilm formation was not significantly reduced by auranofin. There was only reduction achieved with the addition of 32 µg/ml.

Figure 10:
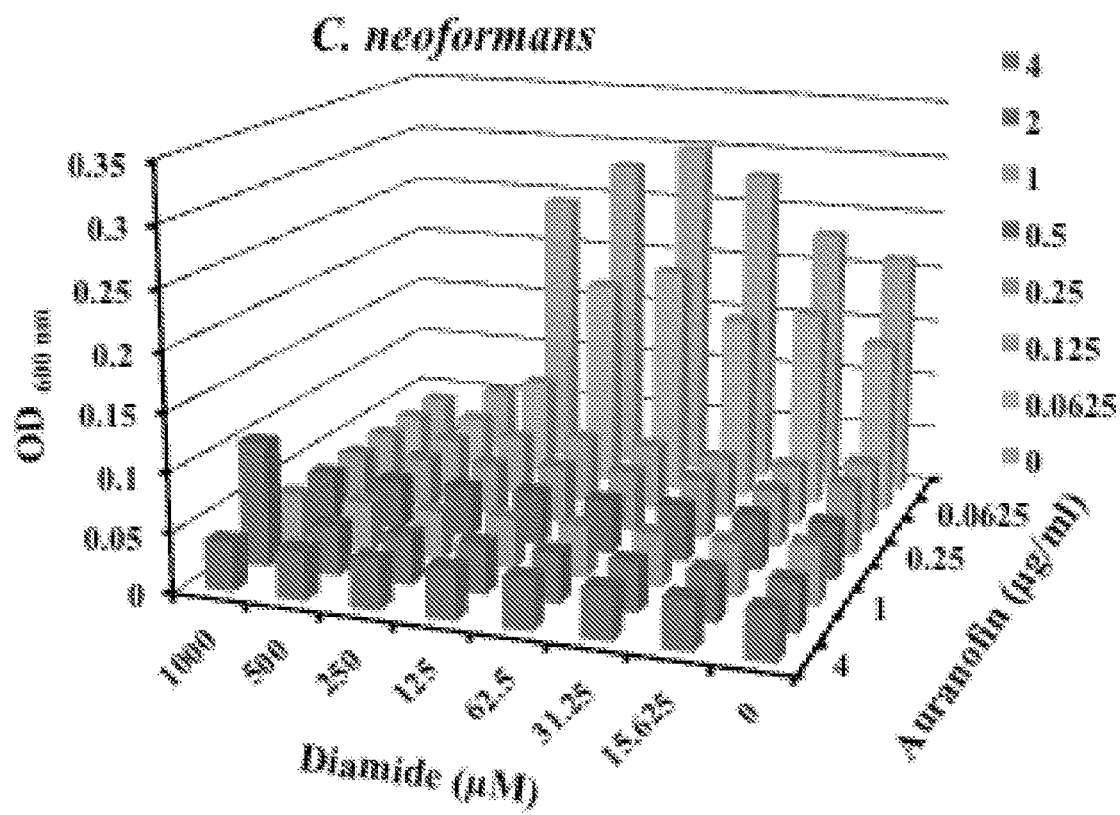
FIG. 10 is a bar graph showing reduction of auranofin MIC in combination with diamide.
Figure 11:
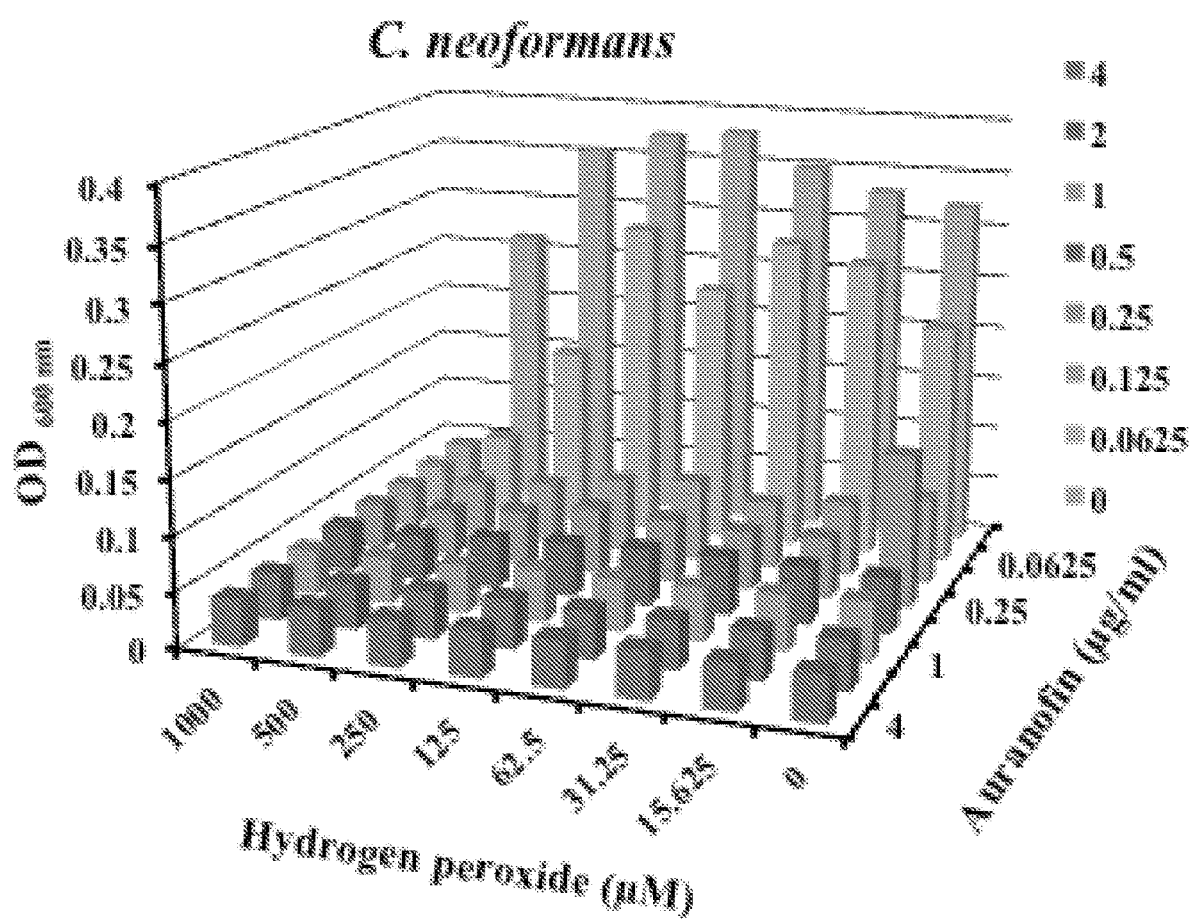
FIG. 11 is a bar graph showing reduction of auranofin MIC in combination with hydrogen peroxide.

Example 9. Antifungal Activity of Auranofin in Combination with Oxidizing Agents FIG. 10 shows auranofin was more effective at inhibiting *C. neoformans* in the presence of specific oxide stressors. In combination with diamide, a thiol oxidizing agent, the MIC was reduced. In FIG. 10, $OD_{600}$ at 4 µg/ml of Auranofin are shown in the front row, and $OD_{600}$ at 0.0625 µg/ml of Auranofin are shown in the back row. FIG. 11 shows the reduction of MIC when *C. neoformans* was treated with combination of auranofin and hydrogen peroxide as a different oxide stressor. In FIG. 11, $OD_{600}$ at 4 µg/ml of Auranofin are shown in the front row, and $OD_{600}$ at 0.0625 µg/ml of Auranofin are shown in the back row.

Using a checkerboard assay (FIGS. 10 and 11), we found the MIC of auranofin was reduced in the presence of diamide to 0.0625 µg/ml (lower than the MIC of 0.5 with auranofin alone), and in combination with hydrogen peroxide to 0.0325 µg/ml, but it did not constitute the level of synergism, only an additive effect.

There was no change in MIC in the presence of menadione, a superoxide stress agent.

Figure 12:
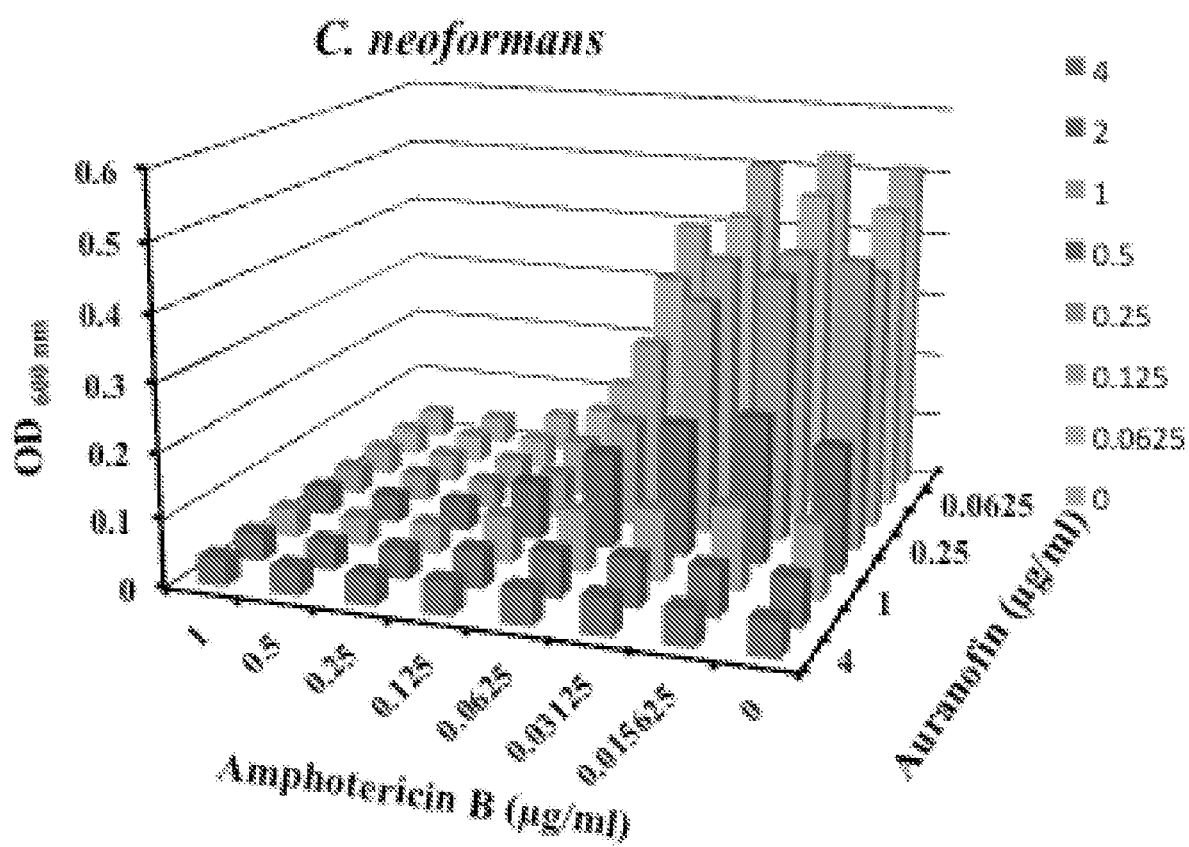
FIG. 12 is a bar graph showing additive effect of combination of auranofin with amphotericin B.
Figure 13:
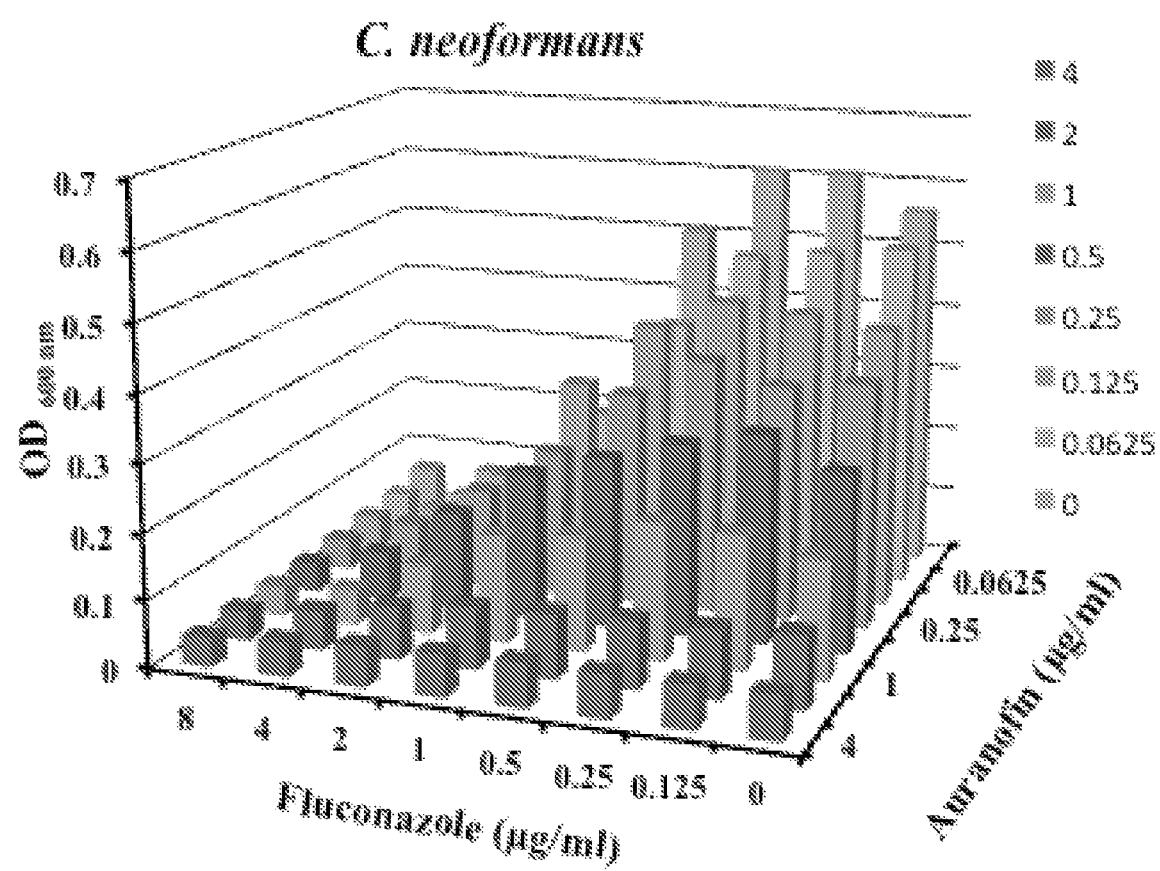
FIG. 13 shows additive effect of combination of auranofin with fluconazole.

Example 10. Antifungal Activity of Auranofin in Combination with Amphotericin B and Fluconazole A checkerboard assay was used to study synergistic activity of auranofin with amphotericin B and fluconazole. The ΣFICs for amphotericin and fluconazole in combination with auranofin were 1 and 2, respectively. FIGS. 12 and 13 show there were additive effects but not synergism. In FIGS. 12 and 13, $OD_{600}$ at 4 µg/ml of auranofin are shown in the front row, and $OD_{600}$ at 0.0625 µg/ml of auranofin are shown in the back row.

Example 11. Antibacterial Activity of Auranofin

Auranofin was able to produce a zone of inhibition against *S. aureus* and also *E. faecium*, and *A. baumannii*, affecting both Gram-positive and a Gram-negative bacteria. The MICs against these pathogens were 0.25 µg/ml, 0.5 µg/ml, and 32 µg/ml, respectively, and the inhibition of the bacterial strains was bacteriostatic at the MIC concentration but bactericidal at higher concentrations. Auranofin is effective against other medically important bacteria, in addition to *S. aureus*, and the MICs is lower for Gram-positive pathogens. Auranofin inhibits an array of clinical isolates, particularly MRSA strains. The MIC for auranofin for 11 clinical isolates are less than or equal to 0.5 µg/ml (Table 5).

TABLE 5

Drug MIC for *Staphylococcus aureus* clinical isolates

| Isolate | Vancomycin | Oxacillin | Auranofin |
|---------|------------|-----------|-----------|
| BF1 | 2 | >64 | 0.25 |
| BF2 | 2 | >64 | 0.25 |
| BF3 | 4 | 32 | 0.25 |
| BF4 | 2 | 16 | 0.25 |
| BF5 | 2 | >64 | 0.5 |
| BF6 | 2 | 1 | 0.25 |
| BF7 | 2 | >64 | 0.25 |
| BF8 | 2 | >64 | 0.5 |
| BF9 | 2 | 0.25 | 0.25 |
| BF10 | 2 | >64 | 0.5 |
| BF11 | 2 | >64 | 0.25 |

The MIC of auranofin against *E. faecium* was 0.5 µg/ml (reference strain) and 1 µg/ml against *E. faecium* clinical isolates, including strains that exhibited resistance to chloramphenicol and vancomycin (Table 6).

TABLE 6

Drug MIC for *Enterococcus faecium* clinical isolates

| Isolate | chloramphenicol | Oxacillin | Auranofin |
|---------|-----------------|-----------|-----------|
| C68 | 16 | >64 | 1 |
| D14 | 8 | 2 | 1 |
| D24 | 4 | 1 | 1 |
| D25 | 8 | 1 | 1 |
| D29 | 64 | 2 | 1 |
| W312 | 8 | >64 | 1 |
| WC176 | 16 | >64 | 1 |

Auranofin is able to inhibit multiple bacterial pathogens and the activity is not restricted to laboratory reference strains. Both *B. subtilis* and *E. faecalis* indicated clearing around the auranofin disc. The MIC of auranofin again *B. subtilis* is 0.5 µg/ml, and 1 µg/ml against *E. faecalis*.

Figure 19:
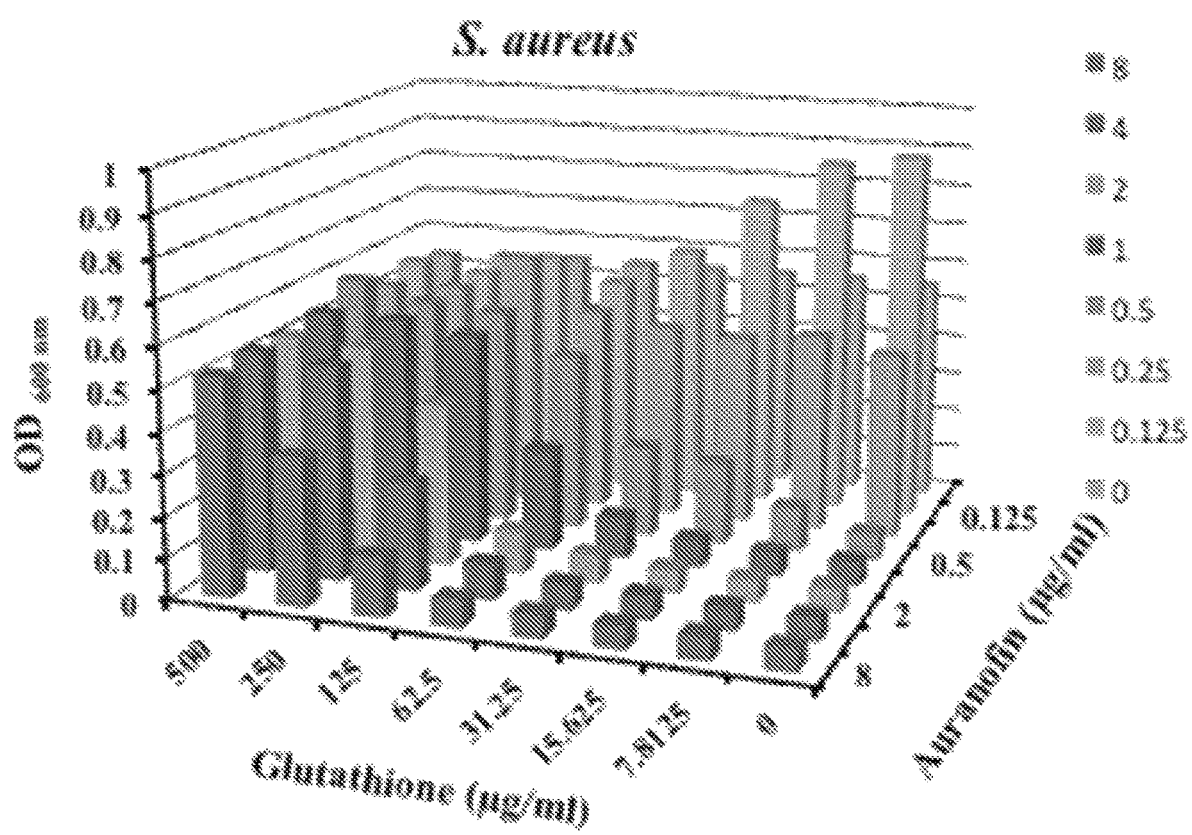
FIG. 19 is bar graph showing glutathione antagonism against auranofin (*S. aureus* inhibition).
Figure 20:
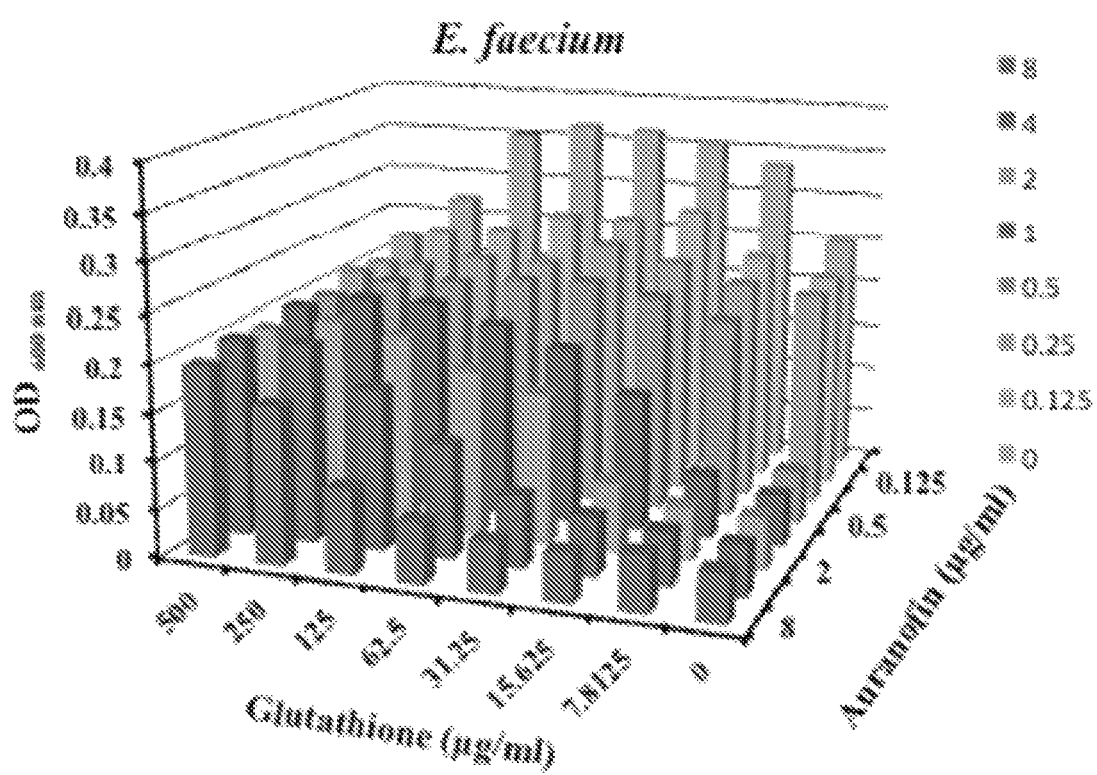
FIG. 20 is bar graph showing glutathione antagonism against auranofin (*E. faecium* inhibition).
Figure 21:
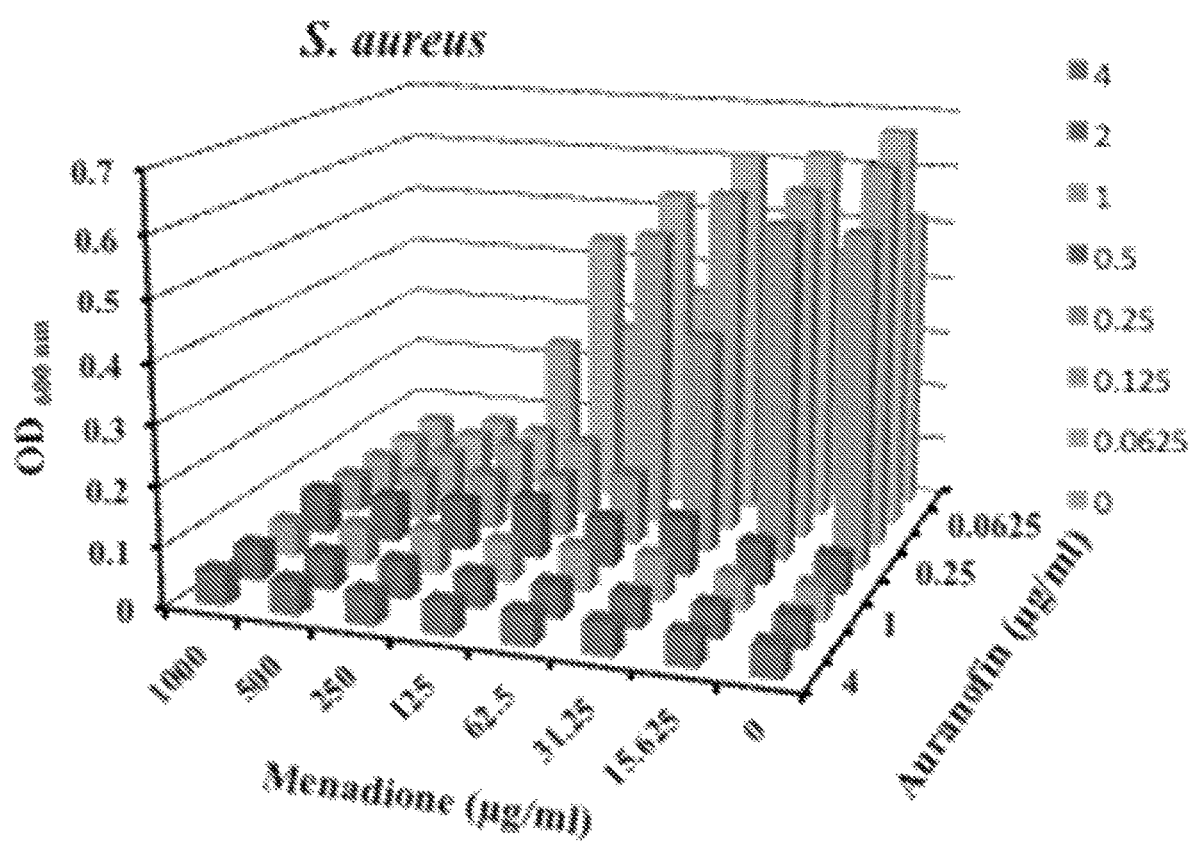
FIG. 21 is bar graph showing that in the presence of menadione *S. aureus* exhibited increased susceptibility to auranofin, lowering the MIC to 0.125 µg/ml.
Figure 22A:
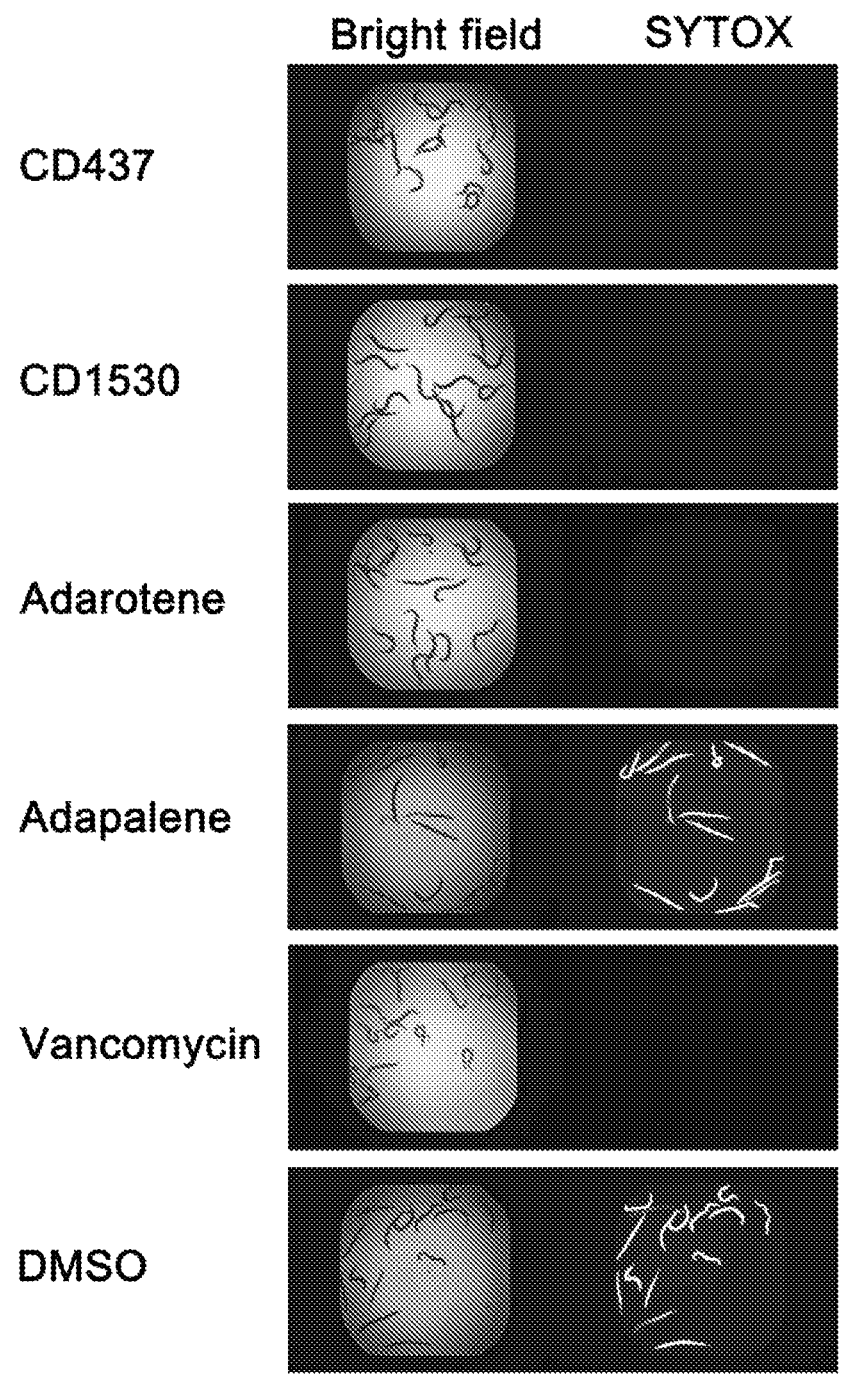
FIG. 22A contains brightfield and fluorescence microscopy images of MRSA-infected *C. elegans*.
Figure 22B:
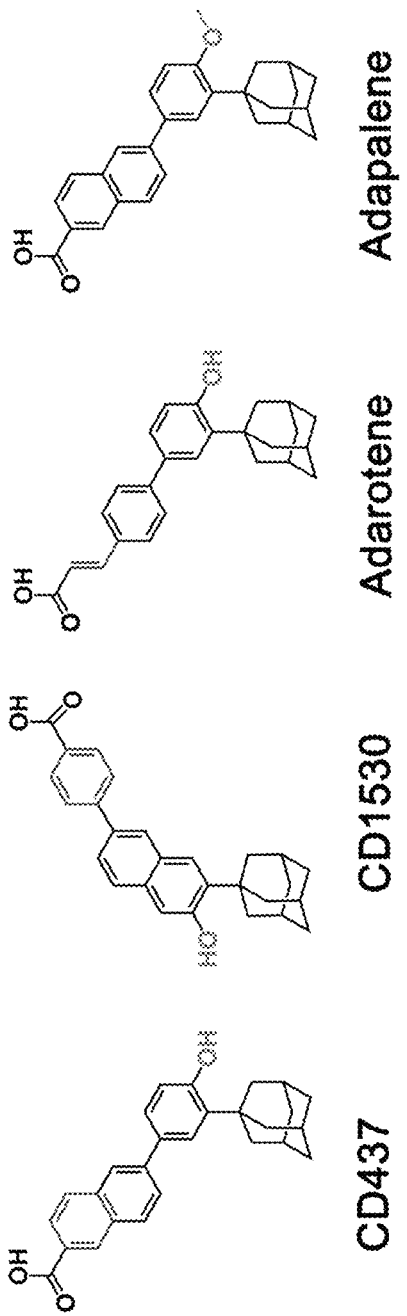
FIG. 22B contains chemical structures of synthetic retinoids CD437, CD1530, adarotene and adapalene.
Figure 22C:
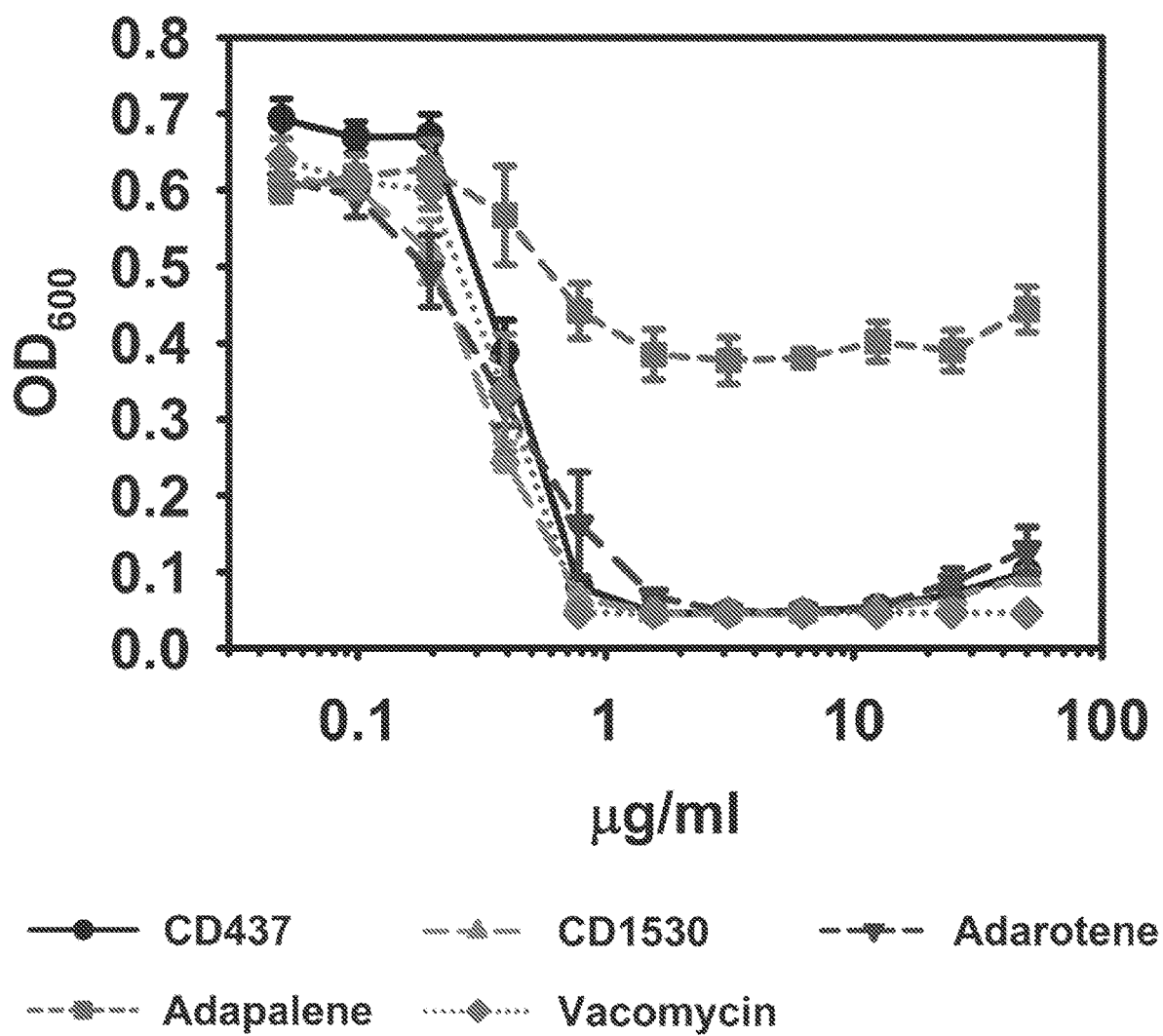
FIG. 22C is a line graph showing growth of MRSA strain MW2 exposed to the indicated concentrations of compounds was quantified by measuring OD600 after 18 h in tryptic soy broth (TSB).
Figure 22D:
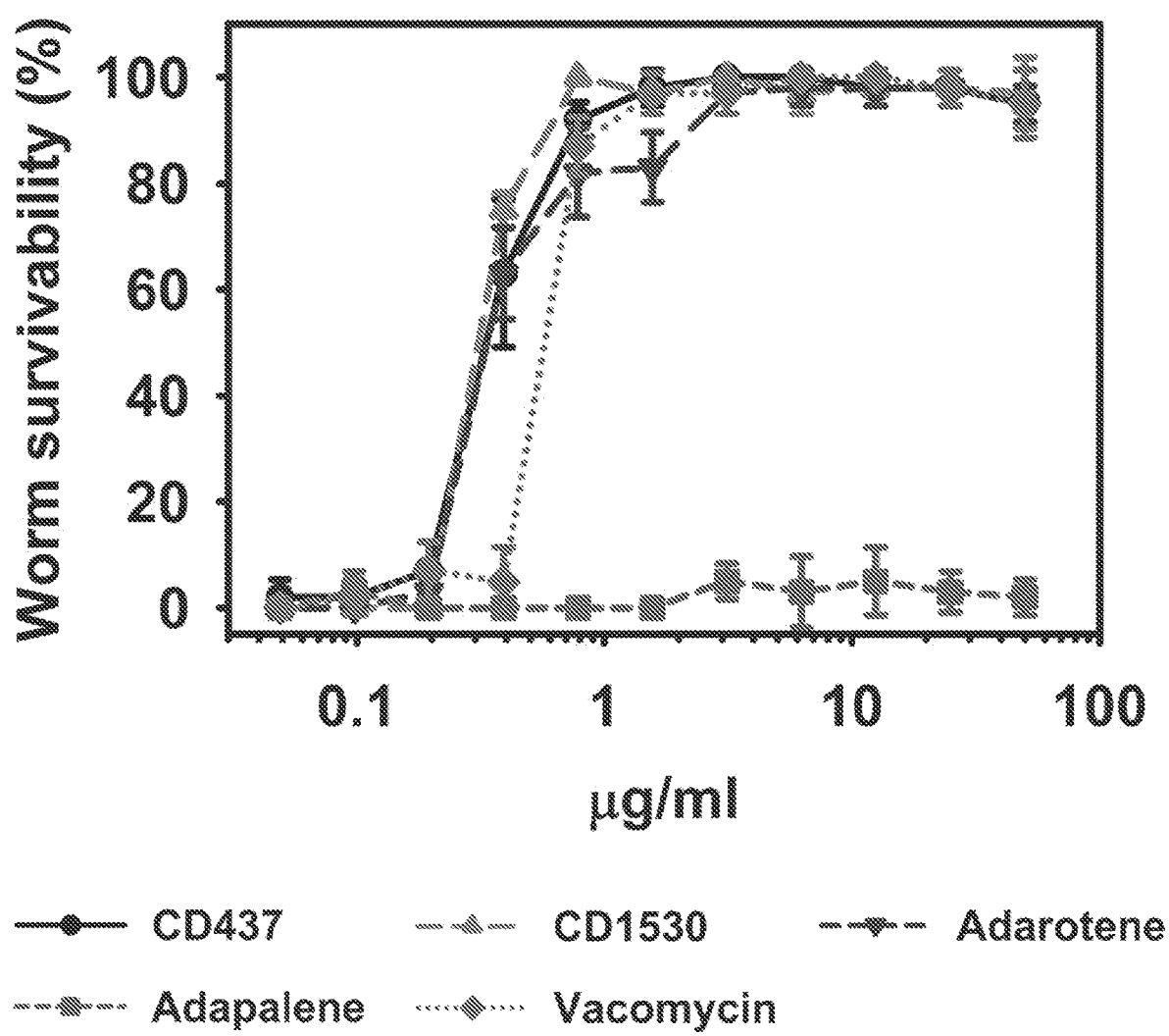
FIG. 22D is a line graph showing *C. elegans* infected with MRSA strain MW2 was treated with indicated concentrations of compounds. Percent survival of *C. elegans* was normalized to *C. elegans* treated with DMSO.
Figure 22E:
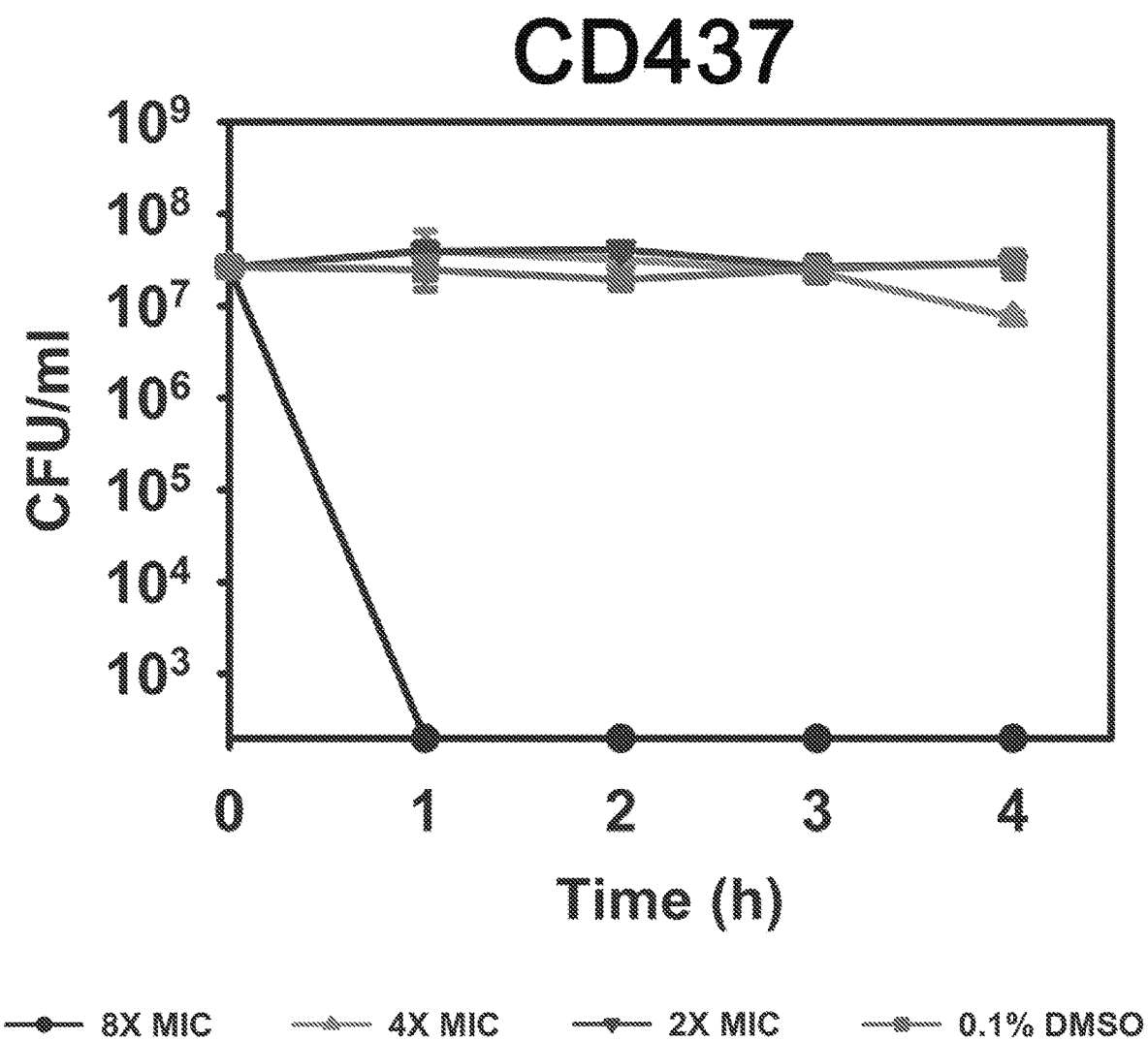
FIG. 22E is a line graph showing viability of MRSA persister cells after treatment with CD437 measured by serial dilution and plating on TSA plates. The data points on the x-axis are below the level of detection ($2 \times 10^2$ CFU/ml).
Figure 22F:
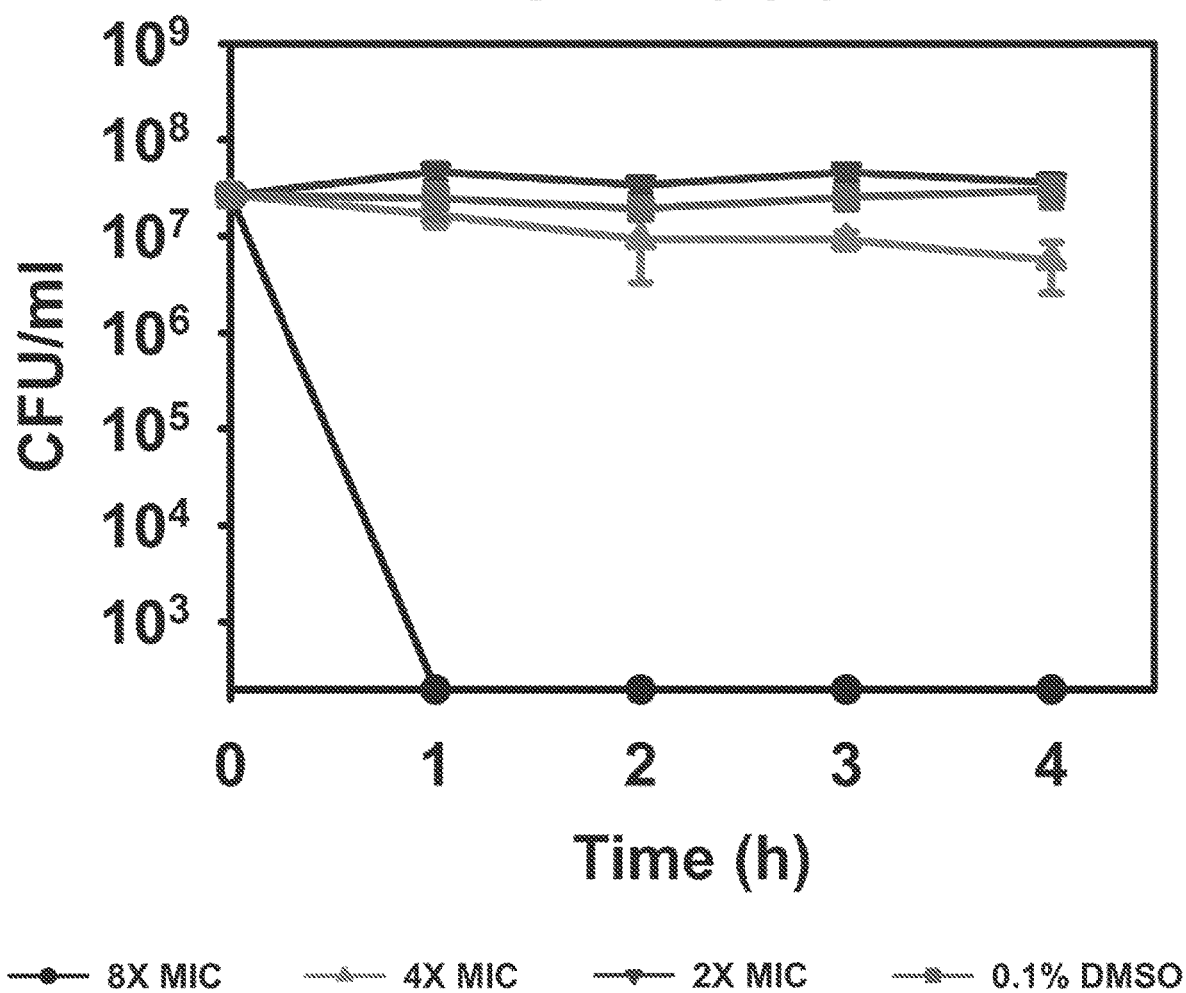
FIG. 22F is a line graph showing viability of MRSA persister cells after treatment with CD1530 measured by serial dilution and plating on TSA plates. The data points on the x-axis are below the level of detection ($2 \times 10^2$ CFU/ml).
Figure 22G:
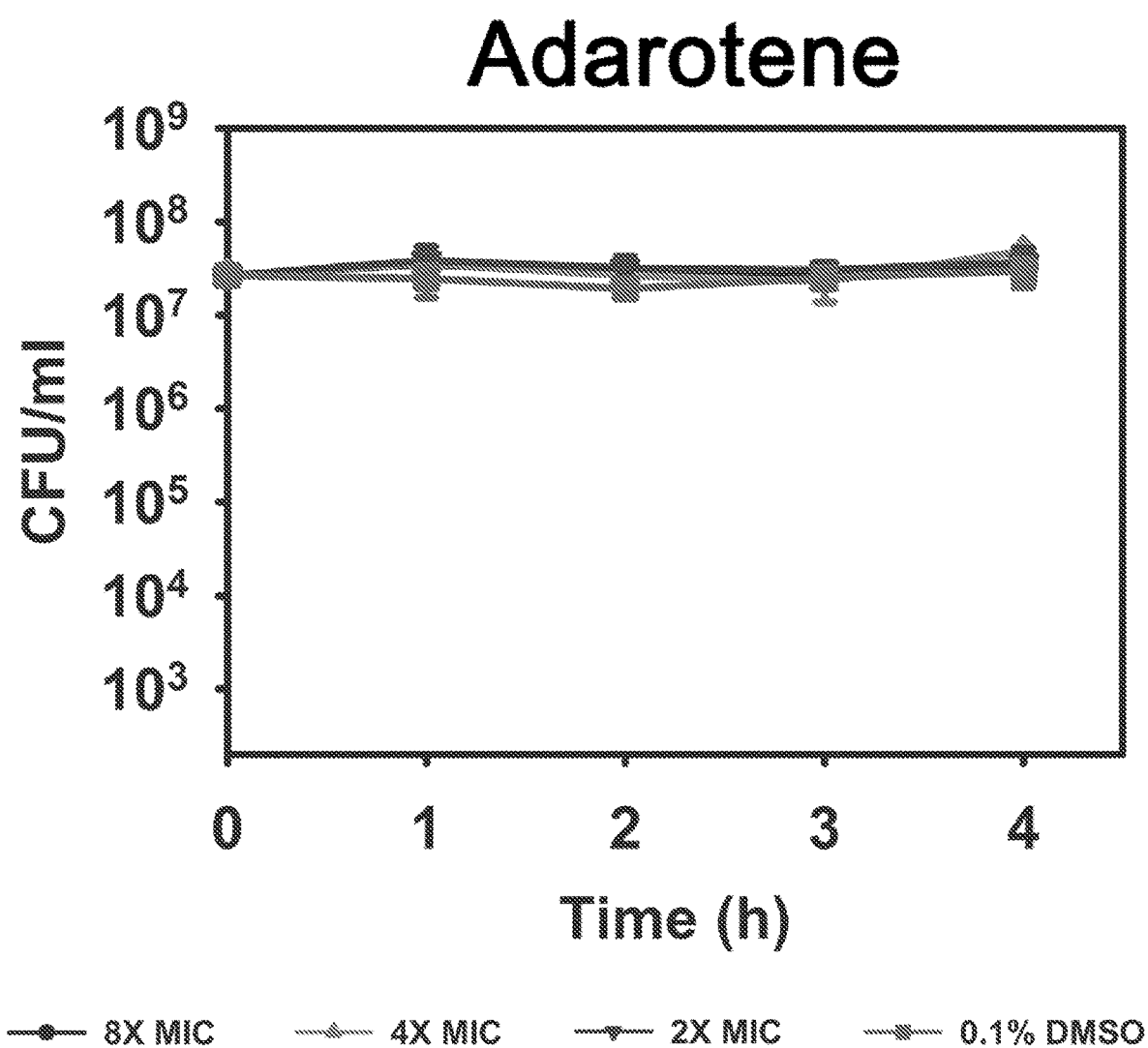
FIG. 22G is a line graph showing viability of MRSA persister cells after treatment with adarotene measured by serial dilution and plating on TSA plates. The data points on the x-axis are below the level of detection ($2 \times 10^2$ CFU/ml).

Auranofin is more active against Gram-positive bacteria that have a thioredoxin system, but are glutathione deficient. In both *S. aureus* and *E. faecium*, glutathione reduced the inhibitory effect of auranofin and resulted in higher MICs. FIG. 19 shows that the MIC of auranofin against *S. aureus* was 0.5 µg/ml but was increased to 1 µg/ml in the presence of 31.25 µg/ml of glutathione and even 8 µg/ml in the presence of 125 g/ml glutathione. *E. faecium* exhibited an MIC of 0.5 µg/ml in the absence of glutathione. The MIC increased to 8 µg/ml with the antagonistic effect of 125 µg/ml glutathione (FIG. 20). Glutathione alone did not inhibit either of the bacteria strains (suggesting antagonistic activity specific to auranofin, e.g., auranofin is targeting the thioredoxin system of *S. aureus* and *E. faeicium*). *S. aureus* was exposed to various oxide stresses in combination with auranofin. Hydrogen peroxide did not provide any synergistic activity to auranofin-mediated inhibition of *S. aureus*. The addition of diamide marginally reduced the MIC of auranofin from 0.5 µg/ml to 0.25 µg/ml in the presence of 1,000 µg/ml of diamide, a thiol oxidizing agent. Menadione, which generates superoxides, demonstrated synergistic activity with auranofin, with an FIC of 0.5, reducing the auranofin MIC from 0.5 to 0.125 µg/ml (FIG. 21). The data shows that compounds that elicits increases in superoxides function synergistically with auranofin.

Figure 14:
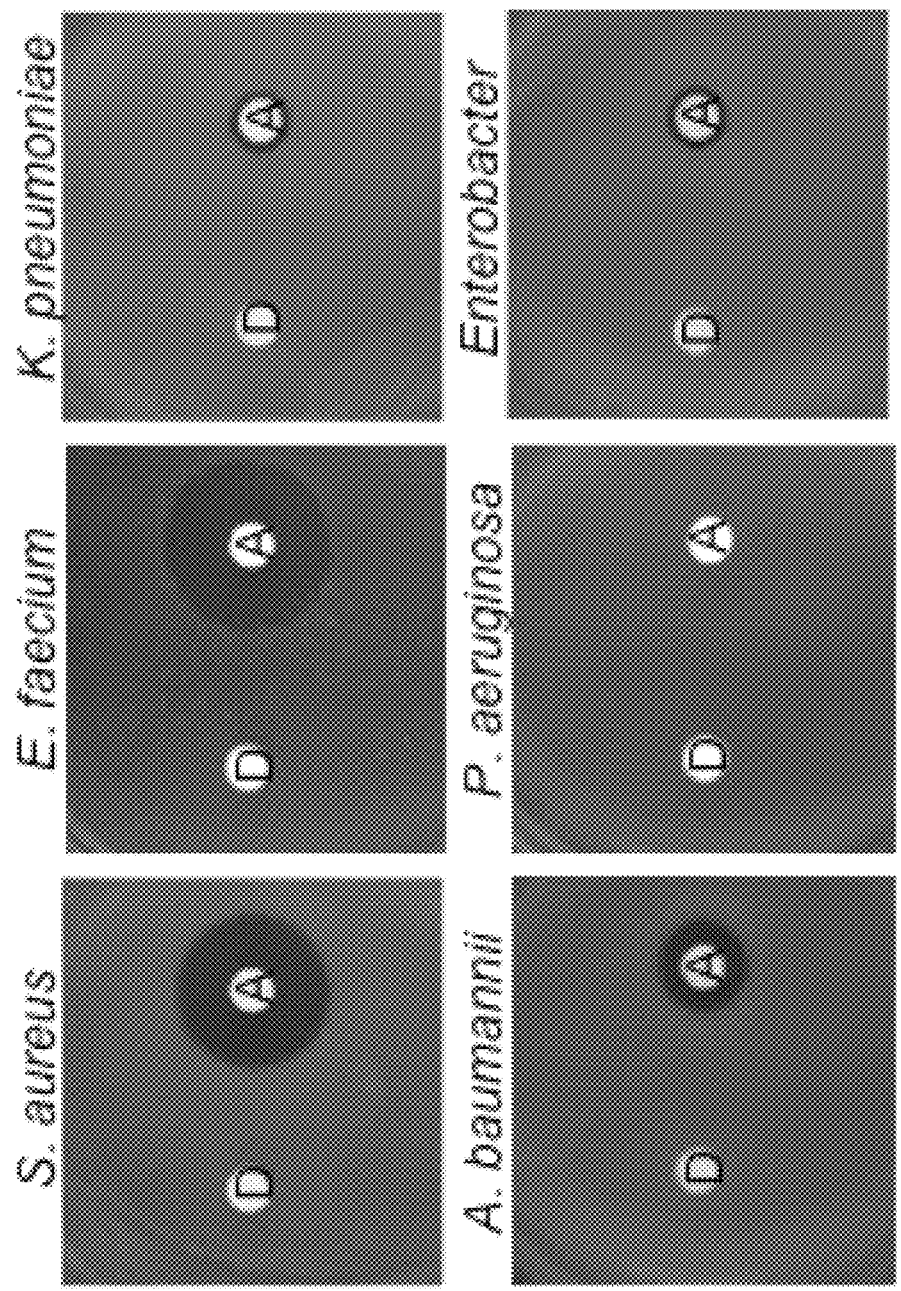
FIG. 14 is an image showing inhibition of 5 (five) bacterial pathogens *E. faeicium, K. pneumonia, A. baumannii, P. aeruginosa* and *Enterbacter.*
Figure 15A:
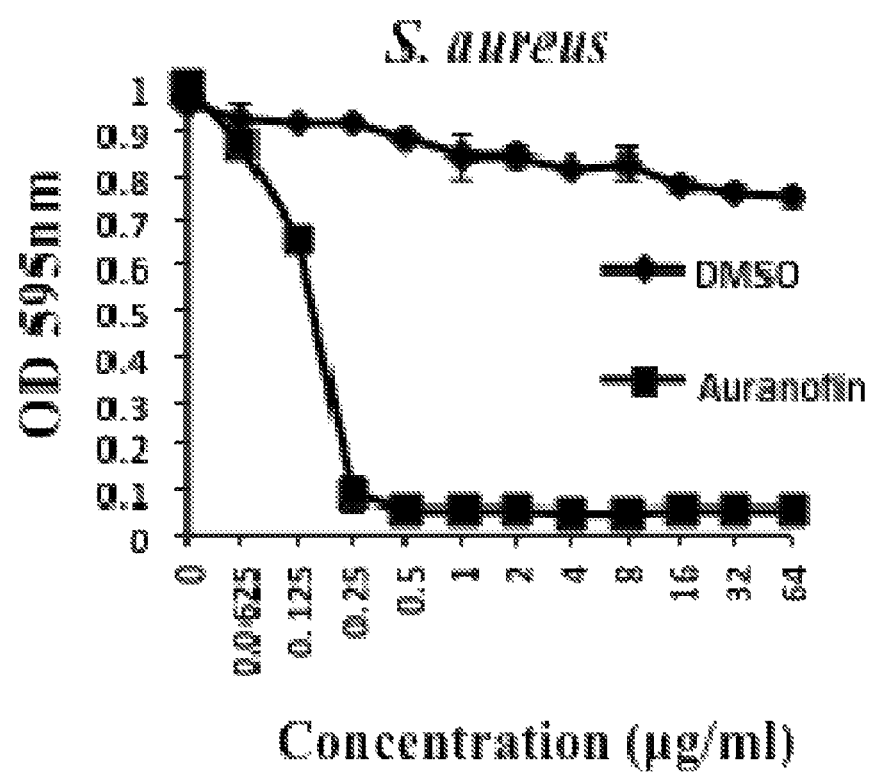
FIG. 15A is a line graph showing MIC determination for the bacteria that exhibited clearing round the auranofin impregnated disk: *S. aureus.*
Figure 15B:
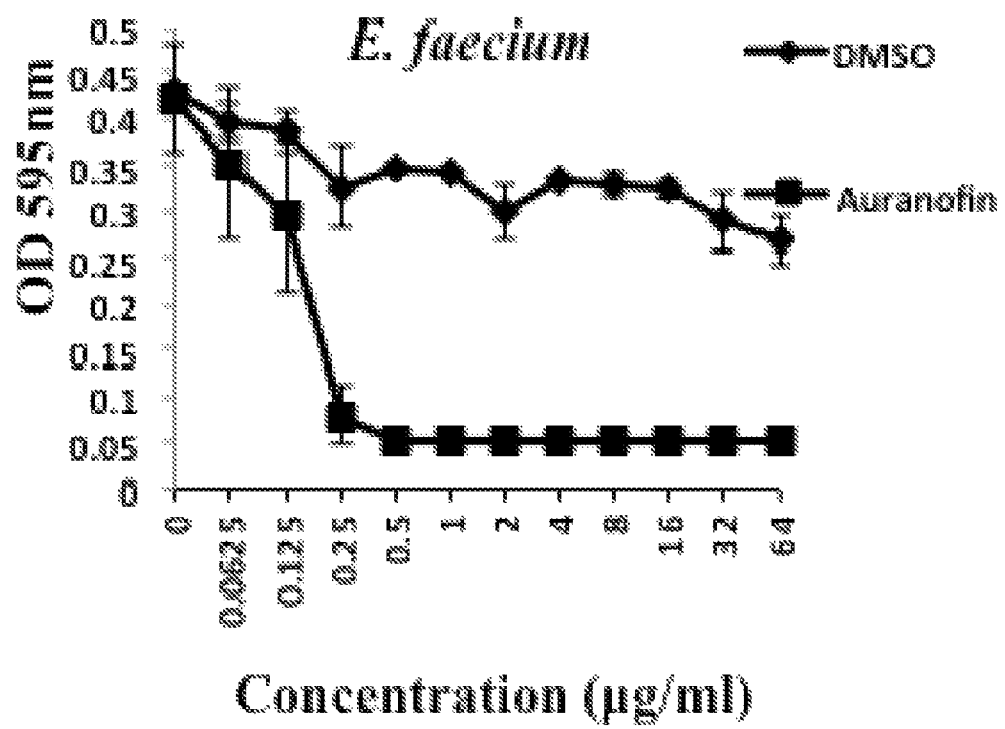
FIG. 15B is a line graph showing MIC determination for the bacteria that exhibited clearing round the auranofin impregnated disk: *E. faeicium*.
Figure 15C:
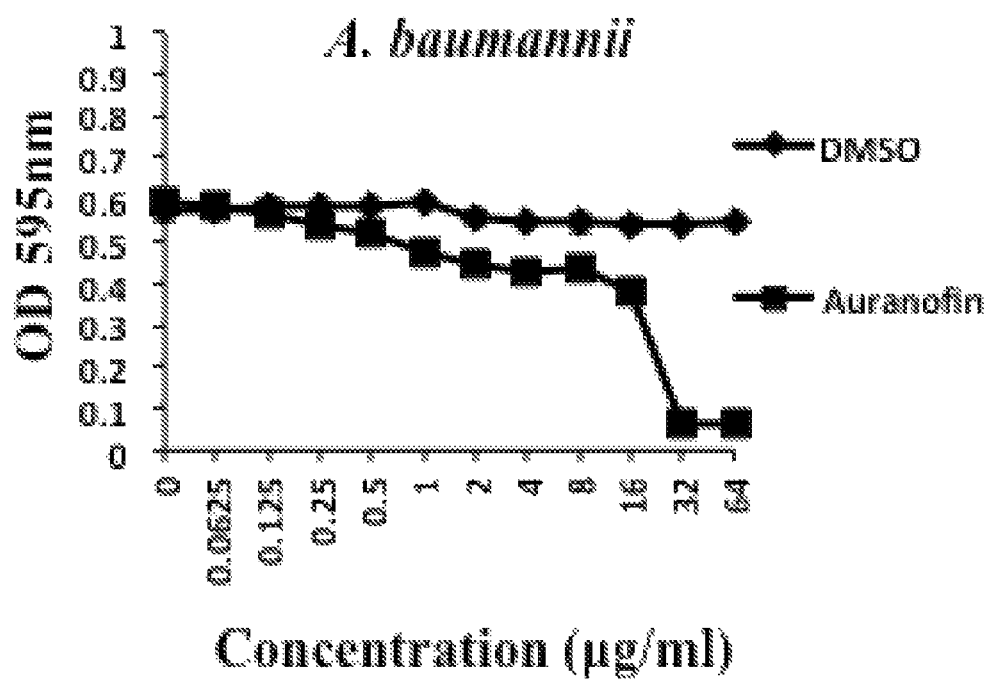
FIG. 15C is a line graph showing MIC determination for the bacteria that exhibited clearing round the auranofin impregnated disk: *A. baumannii*.
Figure 16:
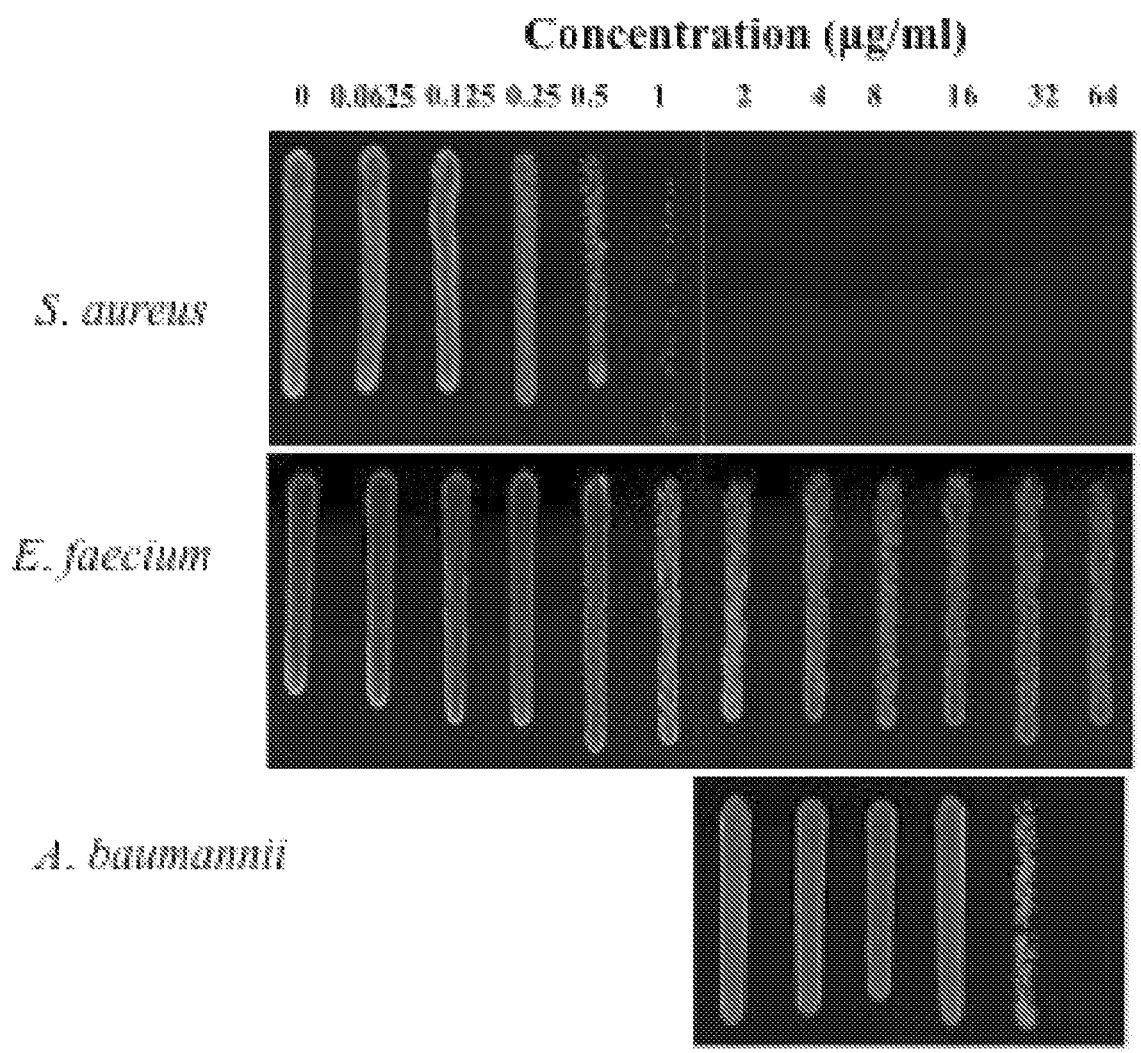
FIG. 16 is a photograph showing bactericidal nature of auranofin by plating cells that were exposed to various concentrations of auranofin.
Figure 17:
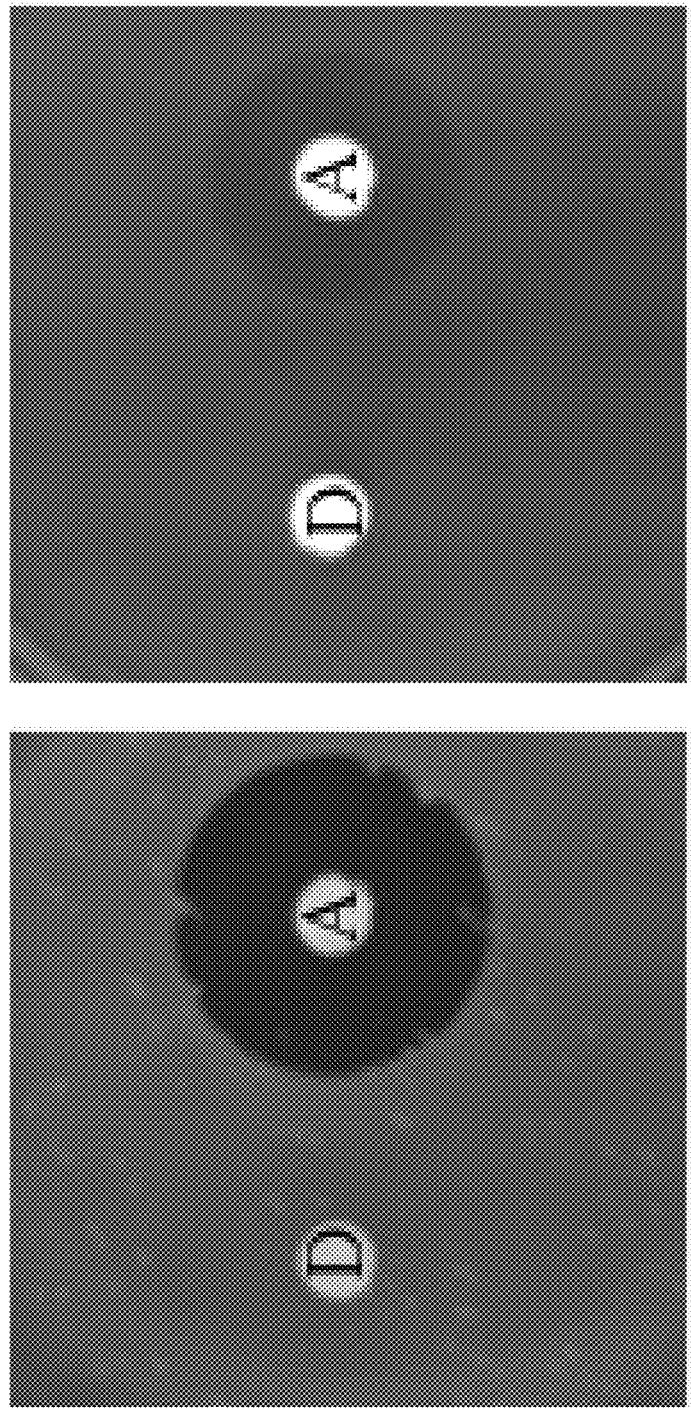
FIG. 17 is a photograph showing inhibition of growth of *B. subtilis* and *E. faecalis* by auranofin.
Figure 18A:
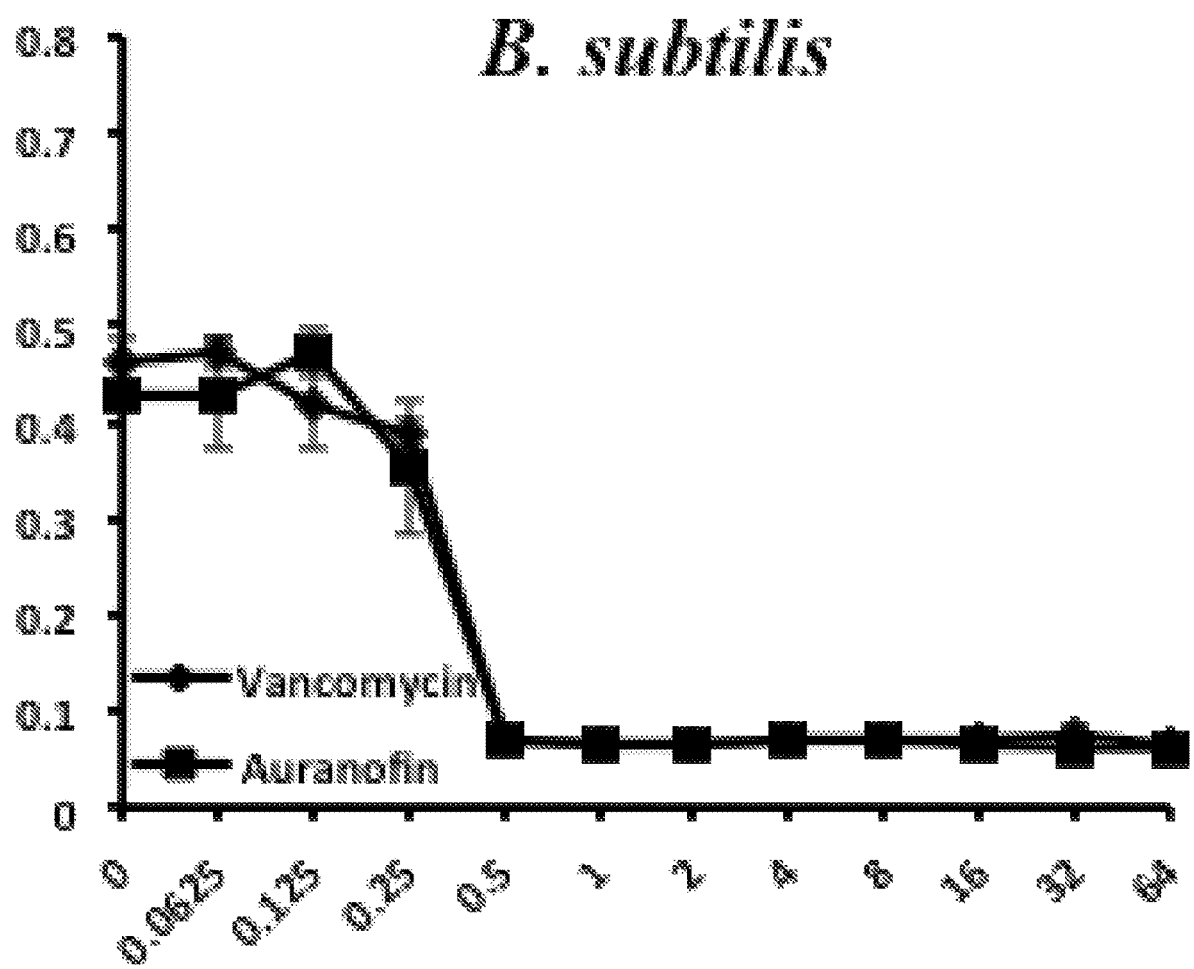
FIG. 18A is line graph showing MIC determination of auranofin against *B. subtilis*.
Figure 18B:
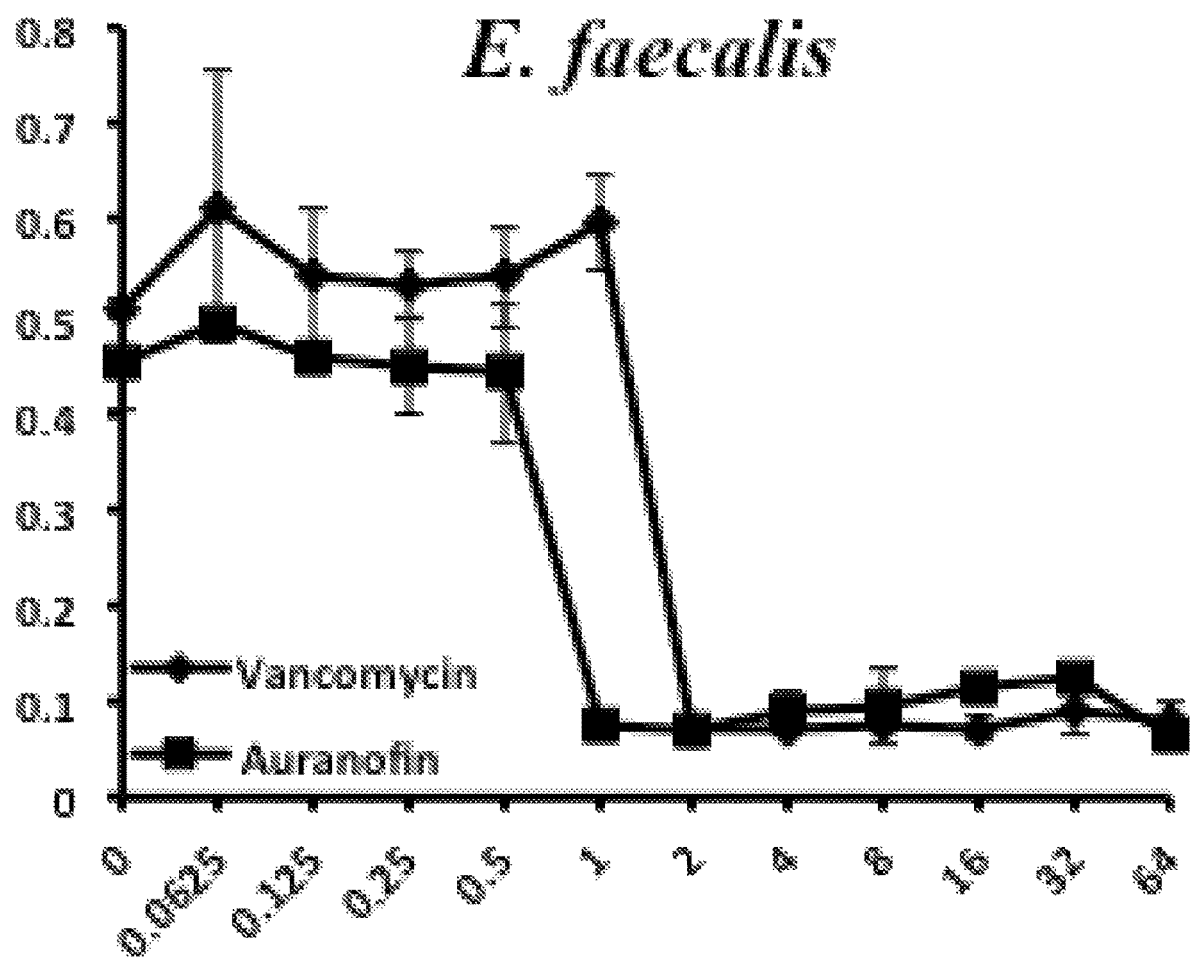
FIG. 18B is line graph showing MIC determination of auranofin against *E. faecalis*.

In FIG. 14 auranofin was examined for the ability to inhibit additional bacterial pathogens, examining 5 bacteria: *E. faecium*, *K. pneumoniae*, *A. baumannii*, *P aeruginosa*, and *Enterbacter*. Clearing around the disc indicates antimicrobial activity. In FIG. 15(A-C) MICs were determined for the bacteria that exhibited clearing around the auranofin impregnated disc: *S. aureus*, *E. faecium*, and *A. baumannii*. In FIG. 16 the static versus cidal nature of the inhibition was tested by plating out cells that were exposed to the various concentrations of auranofin. Growth at the MIC or higher indicated that auranofin was bacteriostatic. Lack of growth indicated that auranofin was bactericidal. (A: auranofin; D: DMSO). In FIG. 17 the bacteria *B. subtilis* and *E. faecalis* exhibited a zone of inhibition in the presence of auranofin. In FIG. 18(A-B), the MIC was determined to be 0.5 µg/ml against *B. subtilis* and 1 µg/ml against *E. faecalis*. (D: DMSO; A: auranofin). FIGS. 19-21 show that glutathione antagonizes auranofin inhibition and oxide stress is synergistic. *S. aureus* in inhibited by auranofin, however the MIC is increased in the presence of glutathione (FIG. 19). The same antagonism is found against auranofin that was found to inhibit *E. faeicium* (FIG. 20). In the presence of menadione, *S. aureus* exhibited increased susceptibility to auranofin, lowering the MIC to 0.125 µg/ml (FIG. 21).

In FIGS. 19 and 20, $OD_{600}$ at 8 µg/ml of auranofin are shown in the front row, and $OD_{600}$ at 0.125 µg/ml of auranofin are shown in the back row. In FIG. 21, $OD_{600}$ at 4 µg/ml of auranofin are shown in the front row, and $OD_{600}$ at 0.0625 µg/ml of auranofin are shown in the back row.

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method of killing or inhibiting growth of Gram-positive bacteria selected from the genus of *Staphylococcus, Enterococcus*, and *Bacillus*, which is resistant to one or more antibiotic agents, the method comprising contacting the bacteria with an effective amount of a compound selected from the group consisting of:

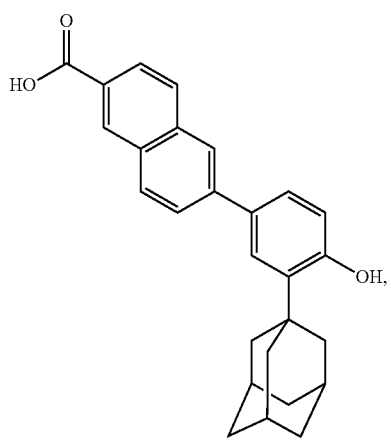

Ia

-continued

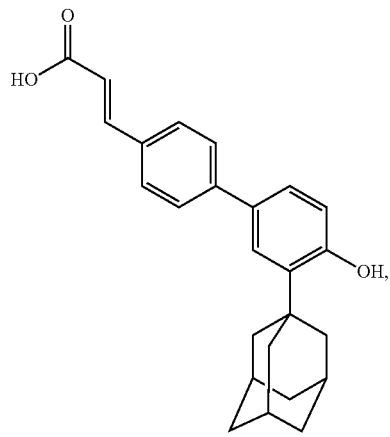

Ic or a pharmaceutically acceptable salt thereof.

2. The method of claim 1, wherein the bacteria is resistant to one or more antibiotic agents selected from methicillin, vancomycin, rifampicin, gentamicin and ciprofloxacin.

3. The method of claim 2, wherein the Gram-positive bacteria which is resistant to one or more other antibiotic agents is selected from the group consisting of methicillin-resistant *S. aureus* (MRSA) and vancomycin-resistant *S. aureus* (VRSA).

4. A method of treating a bacterial infection caused by Gram-positive bacteria of a genus selected from *Staphylococcus, Enterococcus*, and *Bacillus*, which is resistant to treatment with one or more antibiotic agents in a subject, the method comprising administering to the subject in need thereof a therapeutically effective amount of a compound selected from the group consisting of:

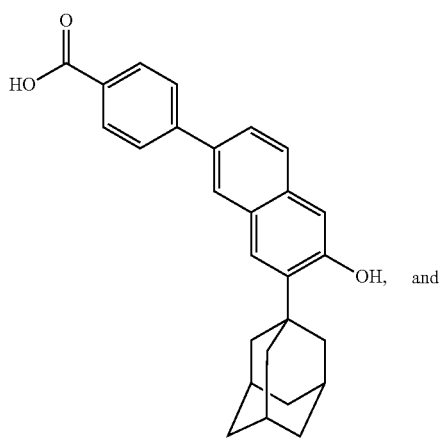

Ib and

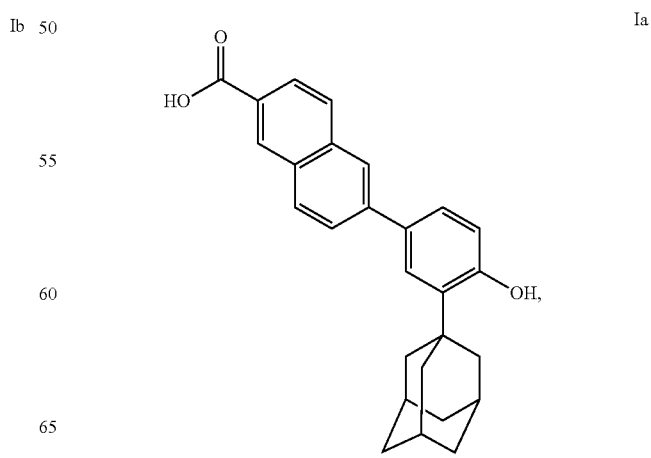

Ia

-continued

Ib

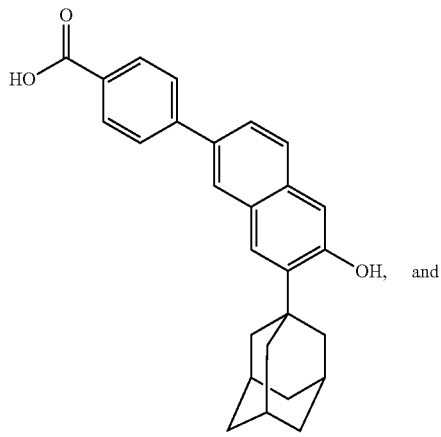

and

Ic

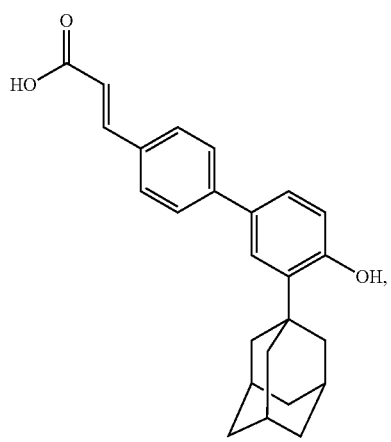

or a pharmaceutically acceptable salt thereof.

5. The method of claim 4, wherein the bacteria is resistant to one or more antibiotic agents selected from methicillin, vancomycin, rifampicin, gentamicin and ciprofloxacin.

6. The method of claim 5, wherein the bacterial infection is caused by methicillin-resistant *S. aureus* (MRSA) or vancomycin-resistant *S. aureus* (VRSA).

7. The method of claim 4, wherein the compound is administered to the subject in combination with an aminoglycoside antibiotic agent.

8. The method of claim 1, wherein the compound is:

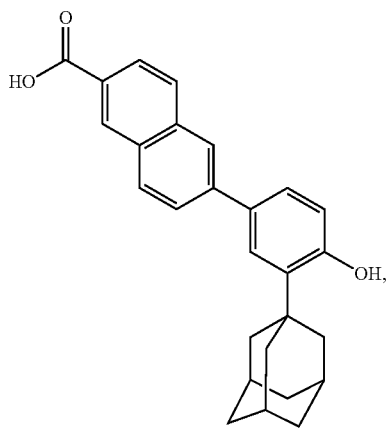 [SMILES: O=C(O)c1ccc2cc(-c3ccc(O)c(C45CC6CC(CC(C6)C4)C5)c3)ccc2c1]

or a pharmaceutically acceptable salt thereof.

9. The method of claim 1, wherein the compound is:

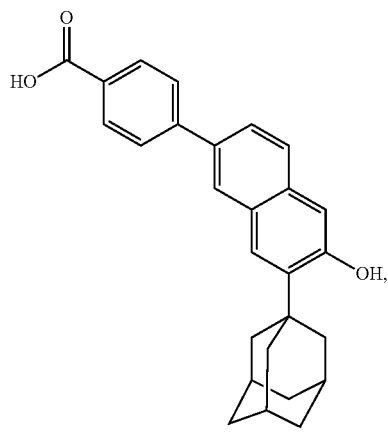 [SMILES: O=C(O)c1ccc(-c2ccc3cc(O)c(C45CC6CC(CC(C6)C4)C5)cc3c2)cc1]

or a pharmaceutically acceptable salt thereof.

10. The method of claim 1, wherein the compound is:

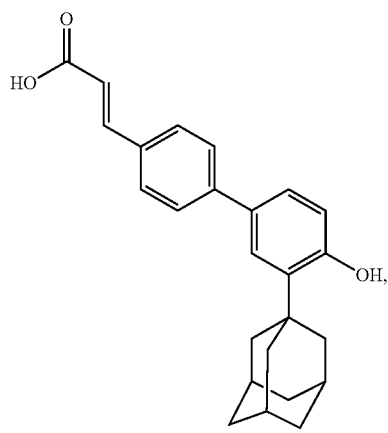 [SMILES: O=C(O)/C=C/c1ccc(-c2ccc(O)c(C34CC5CC(CC(C5)C3)C4)c2)cc1]

or a pharmaceutically acceptable salt thereof.

11. The method of claim 4, wherein the compound is:

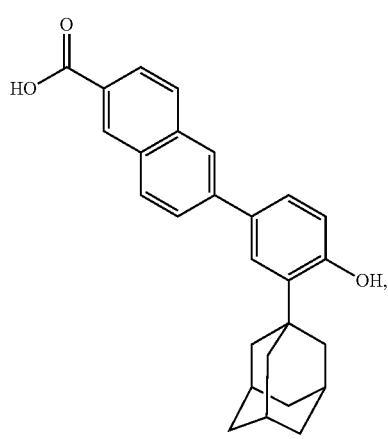 [SMILES: O=C(O)c1ccc2cc(-c3ccc(O)c(C45CC6CC(CC(C6)C4)C5)c3)ccc2c1]

or a pharmaceutically acceptable salt thereof.

12. The method of claim 4, wherein the compound is:
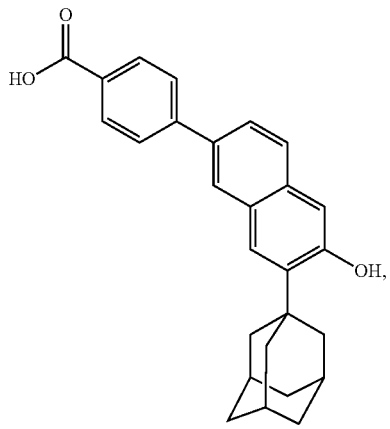 [SMILES: O=C(O)c1ccc(-c2ccc3cc(O)c(C45CC6CC(CC(C6)C4)C5)cc3c2)cc1]
or a pharmaceutically acceptable salt thereof.
13. The method of claim 4, wherein the compound is:
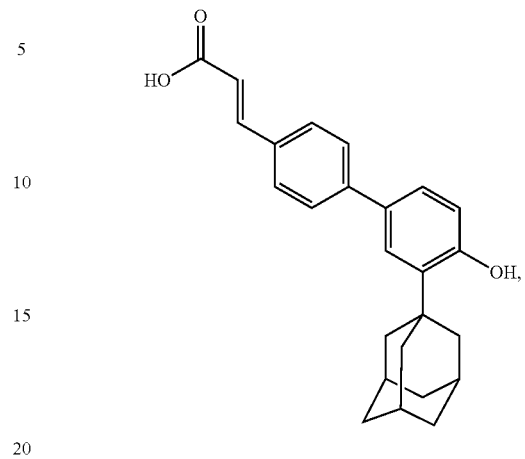
or a pharmaceutically acceptable salt thereof.
* * * * *

UNITED STATES PATENT AND TRADEMARK OFFICE
CERTIFICATE OF CORRECTION

| | | |
|---|---|---|
| PATENT NO. | : 11,707,442 B2 | Page 1 of 1 |
| APPLICATION NO. | : 15/763023 | |
| DATED | : July 25, 2023 | |
| INVENTOR(S) | : Fuchs et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 7 days.

Signed and Sealed this
Twelfth Day of November, 2024

Katherine Kelly Vidal
*Director of the United States Patent and Trademark Office*